United States Patent
Smith

(10) Patent No.: US 9,279,815 B2
(45) Date of Patent: Mar. 8, 2016

(54) **HUMAN *STREPTOCOCCUS PNEUMONIAE* ANTIBODIES AND USES THEREFOR**

(71) Applicant: Oklahoma Medical Research Foundation, Oklahoma City, OK (US)

(72) Inventor: Kenneth Smith, Oklahoma City, OK (US)

(73) Assignee: OKLAHOMA MEDICAL RESEARCH FOUNDATION, Oklahoma City, OK (US)

( * ) Notice: Subject to any disclaimer, the term of this patent is extended or adjusted under 35 U.S.C. 154(b) by 0 days.

(21) Appl. No.: 13/740,934

(22) Filed: Jan. 14, 2013

(65) Prior Publication Data

US 2013/0195876 A1 Aug. 1, 2013

Related U.S. Application Data

(60) Provisional application No. 61/593,654, filed on Feb. 1, 2012.

(51) Int. Cl.
*C07K 16/12* (2006.01)
*G01N 33/68* (2006.01)
*G01N 33/569* (2006.01)

(52) U.S. Cl.
CPC ........ *G01N 33/6854* (2013.01); *C07K 16/1275* (2013.01); *G01N 33/56944* (2013.01); *C07K 2317/21* (2013.01); *C07K 2317/33* (2013.01); *C07K 2317/92* (2013.01)

(58) Field of Classification Search
None
See application file for complete search history.

(56) References Cited

U.S. PATENT DOCUMENTS

2005/0014931 A1 1/2005 Pirofski et al.
2011/0053793 A1 3/2011 Monsterio et al.

OTHER PUBLICATIONS

Anttila et al. "Contribution of serotype-specific IgG concentration, IgG subclasses and relative antibody avidity to opsonophagocytic activity against *Streptococcus pneumonia*" *Clin Exp Immunol.*, (1999), pp. 402-407, vol. 118 No. 3.

Baxendale et al. "Correlation of molecular characteristics, isotype, and in vitro functional activity of human antipneumococcal monoclonal antibodies", *Infect Immun.*, (2006), pp. 1025-1031, vol. 74 No. 2.

Baxendale et al "Immunogenetic analysis of the immune response to pneumococcal polysaccharide" *Eur J Immunol.*, (2000), pp. 1214-1223, vol. 30 No. 3.

Chowdry et al. "Autoantibodies that bind glomeruli: cross-reactivity with bacterial antigen" *Arthritis Rheum.*, (2005), pp. 2403-2410, vol. 52 No. 8.

Clutterbuck et al. "The kinetics and phenotype of the human B-cell response following immunization with a heptavalent pneumococcal-CRM conjugate vaccine" *Immunology* (2006), pp. 328-337, vol. 119 No. 3.

Elkayam et al. "Pneumococcal vaccination of patients with systemic lupus erythematosus: effects on generation of autoantibodies" *Autoimmunity* (2005), pp. 493-496, vol. 38 No. 7.

Nieminen et al. "Circulating antibody secreting cell response to parenteral pneumococcal vaccines as an indicator of a salivary IgA antibody response" *Vaccine* (1998), pp. 313-319, vol. 16 No. 2-3.

Nieminen et al. "Pneumococcal conjugate vaccination in adults: circulating antibody secreting cell response and humoral antibody responses in saliva and in serum" *Vaccine* (1998), pp. 630-636, vol. 16 No. 6.

PCT International Search Report and Written Opinion issued in International Application No. (PCT/US13/21381), dated Jan. 14, 2013.

Smith et al. "Rapid generation of fully human monoclonal antibodies specific to a vaccinating antigen" *Nat. Protocol.*, (2009), pp. 372-384, vol. 4 No. 3; Especially Abstract p. 18 para 1.

Wrammert et al. "Rapid cloning of high-affinity human monoclonal antibodies against influenza virus" *Nature* (2008), pp. 667-671, vol. 453 No. 7195.

Zhou et al. "Recurrent variable region gene usage and somatic mutation in the human antibody response to the capsular polysaccharide of *Streptococcus pneumoniae* type 23F" *Infect Immunol.* (2002), pp. 4083-4091, vol. 70 No. 8.

Zhou et al. "Somatic hypermutation and diverse immunoglobulin gene usage in the human antibody response to the capsular polysaccharide of *Streptococcus pneumoniae* Type 6B" *Infect Immunol.* (2004), pp. 3505-3514, vol. 72 No. 6.

*Primary Examiner* — Nita M Minnifield
(74) *Attorney, Agent, or Firm* — Gilberto M. Villacorta; Jason Mock; Foley & Lardner LLP

(57) ABSTRACT

The present invention is directed to particular monoclonal antibodies and fragments thereof that find use in the detection, prevention and treatment of *Streptococcus pneumoniae* infections. In particular, these antibodies may kill *Streptococcus pneumoniae* or limit the replication of *Streptococcus pneumoniae*. Also disclosed are improved methods for producing such monoclonal antibodies.

15 Claims, 7 Drawing Sheets

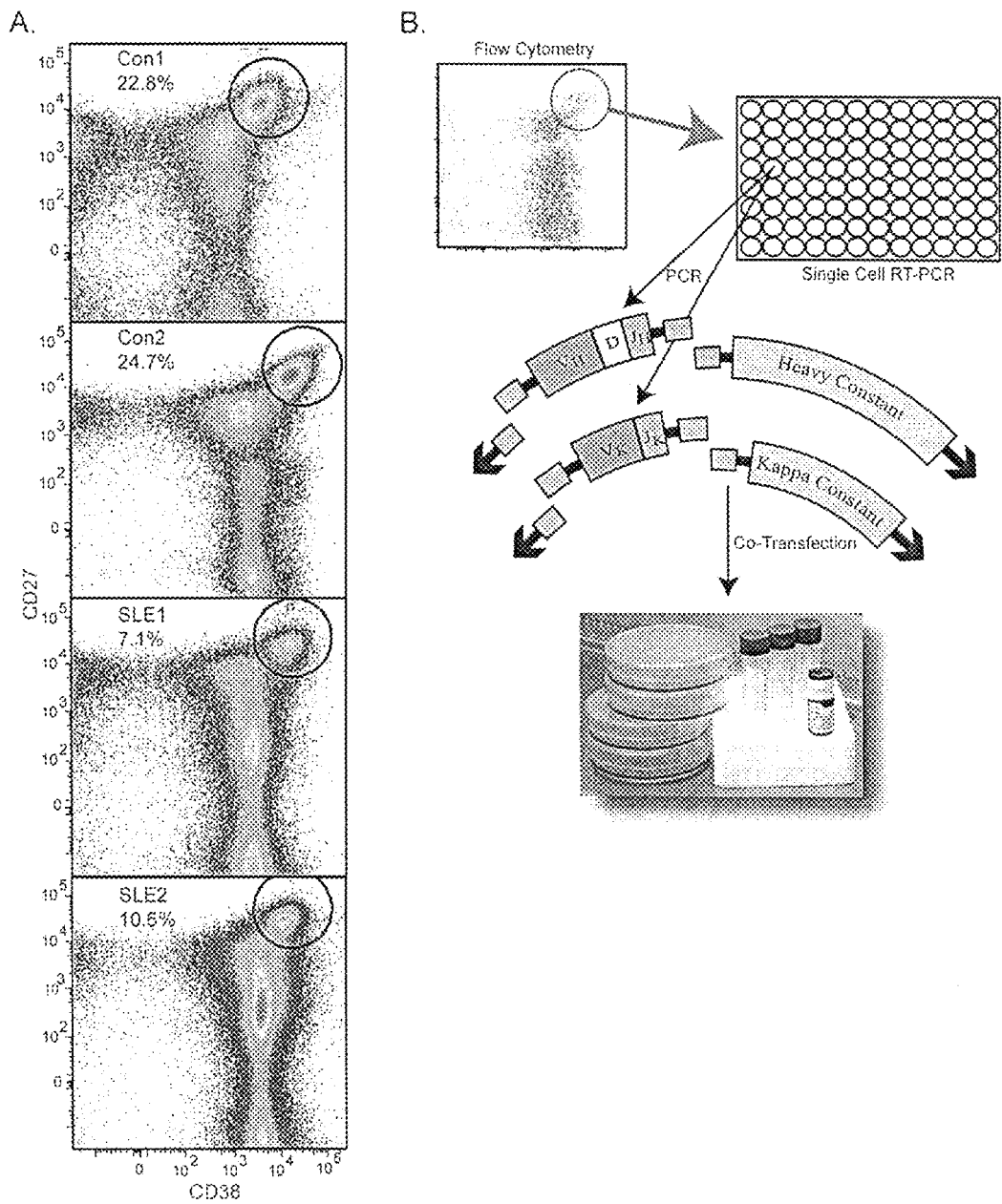
FIG. 1A-B

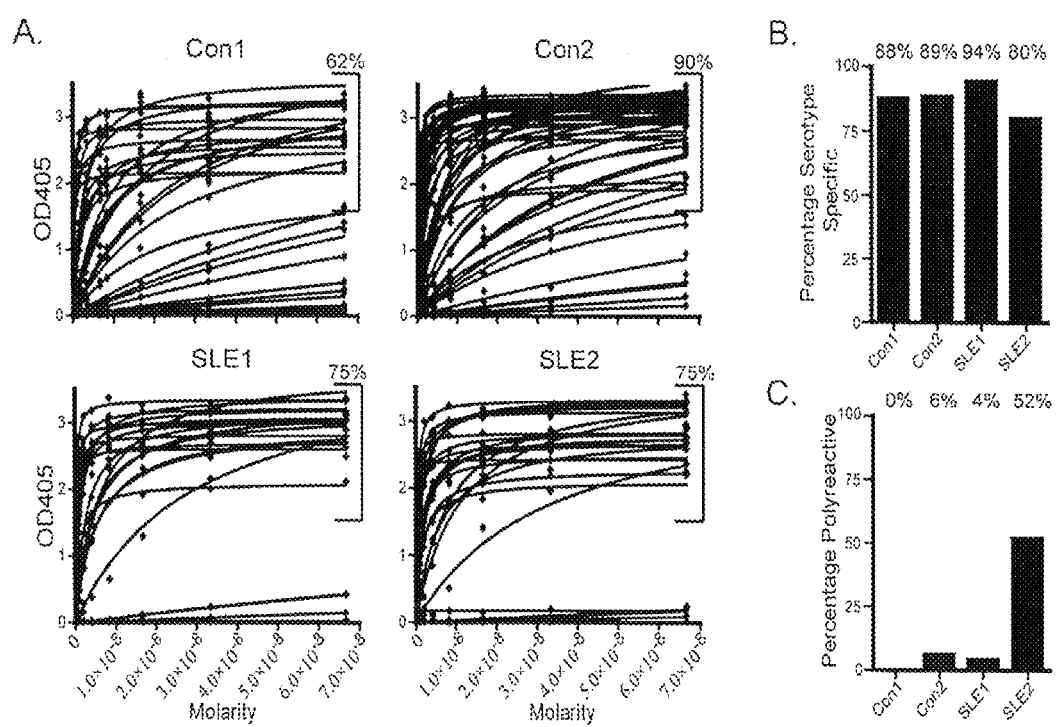
FIG. 2A-C

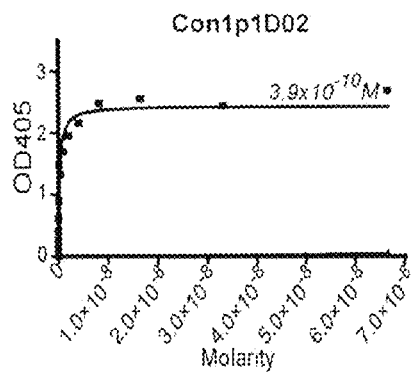
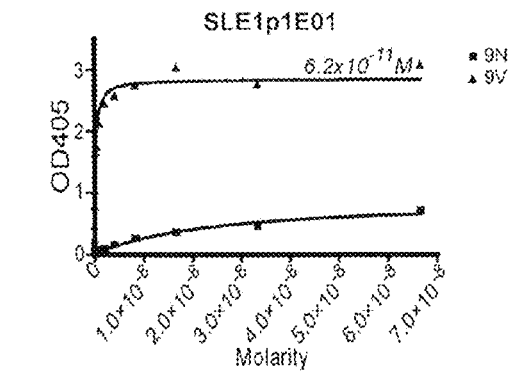
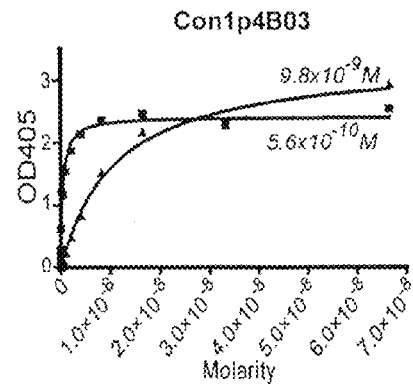
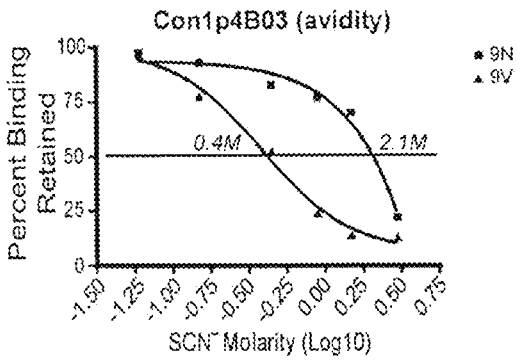
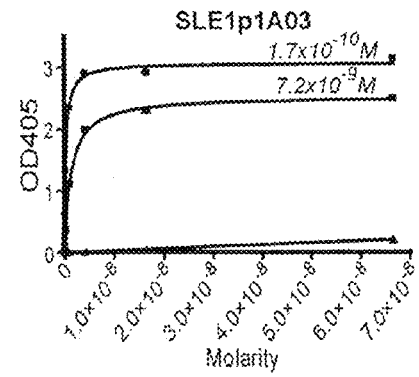
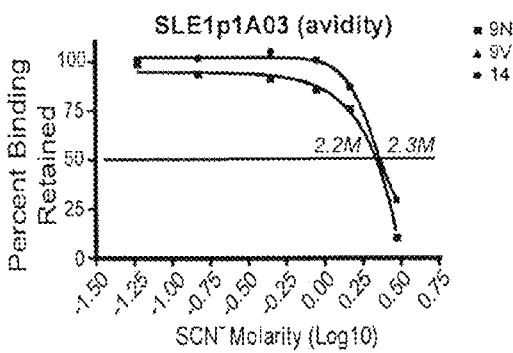
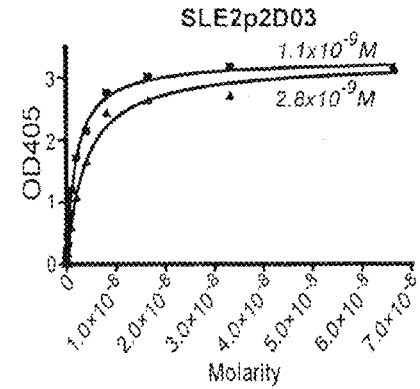
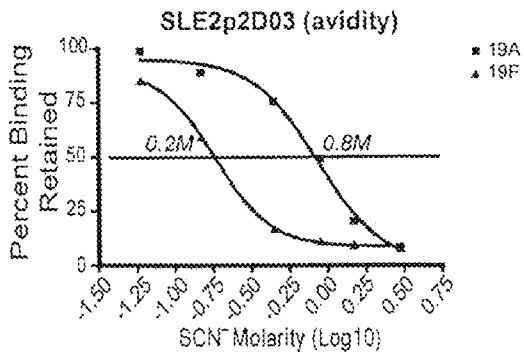
FIG. 3A-D

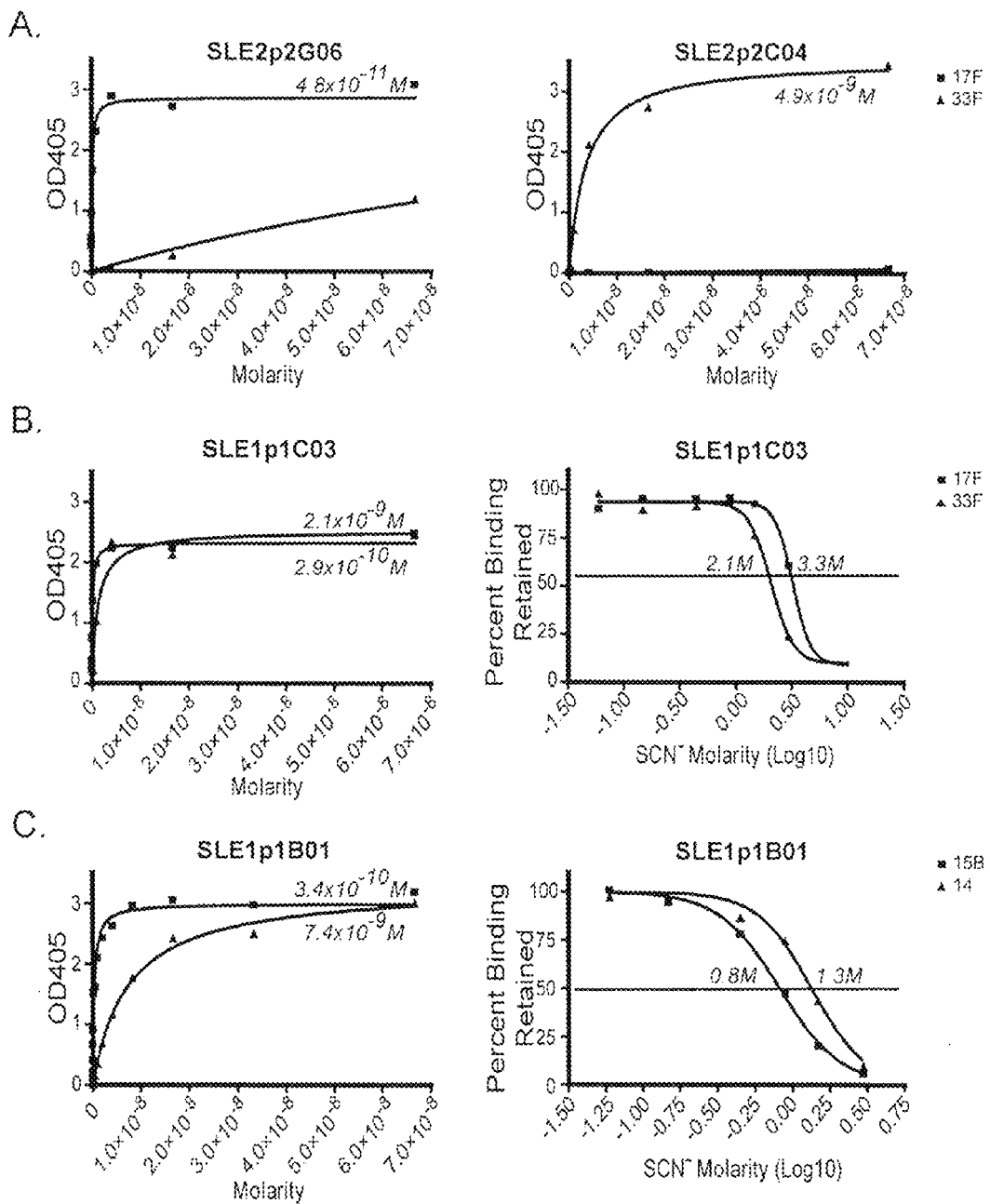
FIG. 4A-C

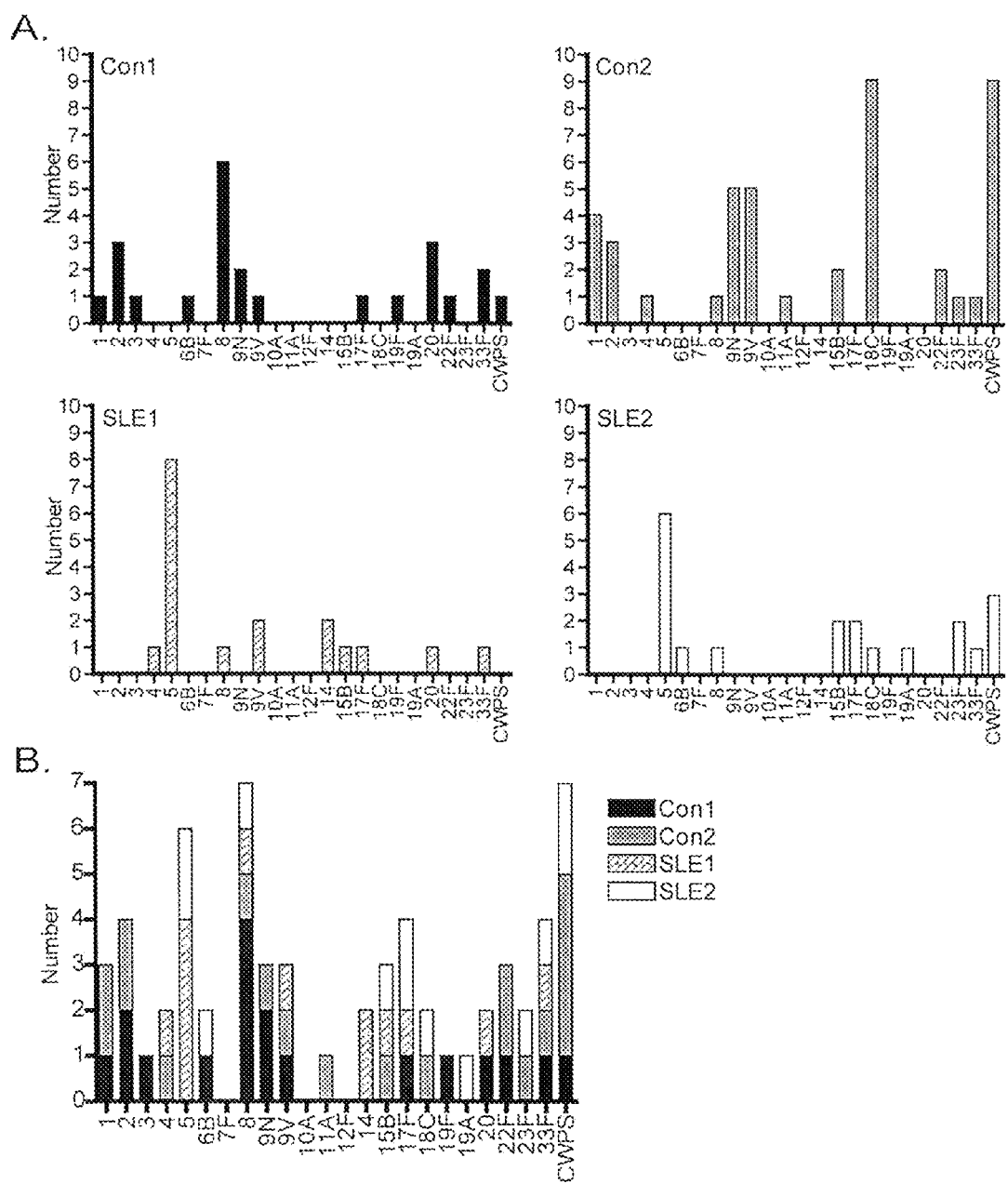
FIG. 6A-B

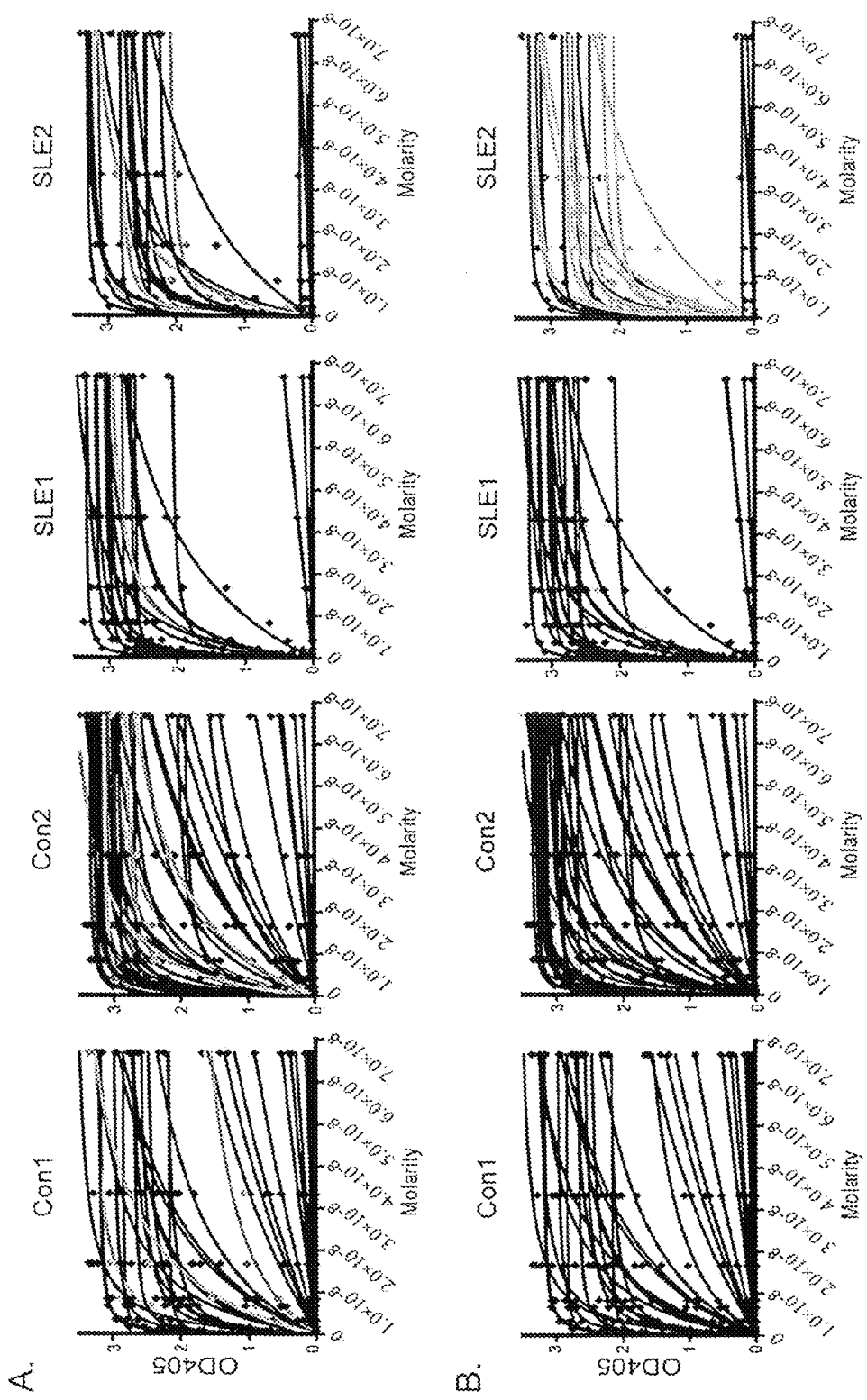
FIG. 7A-B

HUMAN *STREPTOCOCCUS PNEUMONIAE* ANTIBODIES AND USES THEREFOR

This application claims benefit of priority to U.S. Provisional Application Ser. No. 61/593,654, filed Feb. 1, 2012, the entire contents of which are hereby incorporated by reference.

The sequence listing that is contained in the file named "OMRFP0108US_ST25", which is ~91.8 KB and was created on Jan. 8, 2013, is filed herewith by electronic submission and is incorporate by reference herein.

This invention was made with government support under grant numbers P20RR015577, P20RR015577-10S1, P30RR031152, P30AR053483, and U19AI062629, and contract number HHSN266200500026C (N01-AI500026), awarded by the National Institutes of Health. The government has certain rights in the invention.

BACKGROUND OF THE INVENTION

1. Field of the Invention

The present invention relates generally to the fields of microbiology, immunology and pathology. More particularly, it concerns the development of human monoclonal antibodies for use in the diagnosis, prevention and therapy of *Streptococcus pneumoniae* infections.

2. Background of the Invention

*Streptococcus pneumoniae* is a ubiquitous human pathogen causing a range of clinical infections, such as otitis media, pneumonia, meningitis, and bacteremia. The more serious manifestations are especially virulent in immunocompromised and elderly individuals. Over 90 different *S. pneumoniae* serotypes have been characterized, each having a different capsular polysaccharide structure. These polysaccharides are immunogenic in adults, and the Pneumovax®23 vaccine consists of a cocktail of 23 of the most common and/or virulent *S. pneumoniae* strains. The vaccine is recommended for everyone over the age of sixty, as well as all immunocompromised individuals, to ensure seroprotection against these strains.

The serology of the response to Pneumovax®23, as well as the conjugate vaccine Prevnar® (used to immunize children), has been studied in depth with regard to the humoral polyclonal IgG and IgA responses in both sera and saliva (Anttila et al., 1999; Nieminen et al., 1998a; Nieminen et al., 1998b). The memory and antibody secreting cell (ASC) response to these vaccines has also been previously explored on a cellular level with B cell ELISpot assays and flow cytometry Nieminen et al., 1998b; Clutterbuck et al., 2006), and the presence of both responses after vaccination is now well established. However, utilizing ASCs to produce human monoclonal antibodies would provide a novel way to fully elucidate the recall response to pathogen serotypes after vaccination, and even provides a window to explore the evolution of past responses.

Antibodies that cross-react to two or more pneumococcal polysaccharides are present in sera both pre- and post-immunization (Lee et al., 1984; Soininen et al., 2000); however, whether this is due to single antibody specificities that are capable of cross-reacting or rather due to broad polyclonal antibody specificities is not known. Although it has been reported that immunization with Pneumovax®23 in patients with SLE does not induce new auto-specificities (Elkayam et al., 2005), one report has shown that kidney-binding antibodies in a patient with SLE also cross-reacted with pneumococcal polysaccharide (Chowdhry et al., 2005). Thus, it is possible that antibodies produced from B cells in SLE donors may show increased poly-reactivity or auto-reactivity. It is only possible to determine such per-antibody phenomenon by the characterization of human monoclonal antibodies from SLE donors.

SUMMARY OF THE INVENTION

Thus, in accordance with the present invention, there is provided a human monoclonal antibody panel comprising a plurality of antibodies, wherein antibodies in said panel bind to at least 15 serotypes of *Streptococcus pneumoniae*. The antibodies in said panel may bind to at least 18 *S. pneumoniae* serotypes or 21 *S. pneumoniae* serotypes. At least 15 antibodies may be serotype specific, at least 17 antibodies may be serotype specific, or 19 antibodies may be serotype specific. The antibody panel may be attached to a support, such as a bead, a dipstick, a filter, a membrane, a plate, or a chip. The serotypes may be selected from 1, 2, 3, 4, 5, 6B, 8, 9N, 9V, 11B, 14, 15B, 17F, 18C, 19A, 19F, 20, 22F, 23F, 33F and CWPS. The antibody panel may comprise an antibody that reacts with two serotypes.

In another embodiment, there is provided a method of assessing a *Streptococcus pneumoniae* in a subject comprising obtaining a first antibody-containing sample from said subject and assessing binding of antibodies in said sample to a human monoclonal antibody panel comprising a plurality of antibodies, wherein antibodies in said panel bind to at least 15 serotypes of *Streptococcus pneumoniae*. The antibodies in said panel may bind to at least 18 *S. pneumoniae* serotypes or 21 *S. pneumoniae* serotypes. At least 15 antibodies may be serotype specific, at least 17 antibodies may be serotype specific, or 19 antibodies may be serotype specific. The antibody panel may be attached to a support, such as a bead, a dipstick, a filter, a membrane, a plate, or a chip. The serotypes may be selected from 1, 2, 3, 4, 5, 6B, 8, 9N, 9V, 11B, 14, 15B, 17F, 18C, 19A, 19F, 20, 22F, 23F, 33F and CWPS. The antibody panel may comprise an antibody that reacts with two serotypes.

The subject may be immunocompromised and/or 60 years old or older. The subject may be suspected of having a *Streptococcus pneumoniae*. The method may further comprise treating said subject with an anti-*Streptococcus pneumoniae* therapy if said first antibody-containing sample is found to be positive for one or more serotypes. The method may further comprise treating said subject with vancomycin or levoflaxin if first said antibody-containing sample is found to be positive for serotype 19A and/or 19F. The first antibody-containing sample may be blood, serum, plasma, sputum, or saliva.

The method may further comprise obtaining a second antibody-containing sample from said subject and assessing binding of antibodies in said second sample to a human monoclonal antibody panel comprising a plurality of antibodies, wherein antibodies in said panel bind to at least 15 serotypes of *Streptococcus pneumoniae*. The second antibody-containing sample may be blood, serum, plasma, sputum, or saliva. The subject may have been treated with an anti-*Streptococcus pneumoniae* therapy after determining that said first antibody-containing sample was positive for one or more serotypes, and a reduction in antibody titer to serotypes from said first sample indicates that said anti-*Streptococcus pneumoniae* therapy is effective at treating *Streptococcus pneumoniae*. The subject may have been treated with an antibiotic after determining that said first antibody-containing sample was positive for one or more serotypes, and the absence of a reduction in antibody titer to serotypes from said first sample indicates that said anti-*Streptococcus pneumoniae* therapy is ineffective at treating *Streptococcus pneumonia*, and optionally the method may further comprise treating said subject with a different anti-*Streptococcus pneumoniae* therapy.

In yet another embodiment, there is provided an antibody that binds selectively to *Streptococcus pneumonia*, wherein said antibody has heavy and light chain CDRs selected from those set forth in Table 2. The antibody may be a single chain antibody, a single domain antibody, a chimeric antibody, a Fab fragment, or an IgG. The antibody may further comprise an antibiotic linked thereto, such as one linked to said antibody through a photolabile linker or through an enzymatically-cleaved linker. The antibody may be conjugated to a nanoparticle or a liposome.

In still yet another embodiment, there is provided a method of treating a *Streptococcus pneumoniae* infection in a subject comprising administering to said subject an antibody as described above. The method may further comprise administering to said subject a second anti-*Streptococcus pneumoniae* treatment, which can be given at the same time as said antibody or given before and/or after said antibody. The antibody may be a single chain antibody, a single domain antibody, a chimeric antibody, a Fab fragment or an IgG.

The antibody may further comprises an antibiotic linked thereto, such one linked to said antibody through a photolabile linker or through an enzymatically-cleaved linker. The antibody may be conjugated to a liposome or nanoparticle. Multiple anti-*Streptococcus pneumonia* antibodies are administered, such as multiple anti-*Streptococcus pneumonia* antibodies that bind to 2, 3, 4, 5, 6, 7, 8, 9, 10, 1, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95 or 100 *Streptococcus pneumonia* serotypes.

It is contemplated that any method or composition described herein can be implemented with respect to any other method or composition described herein.

The use of the word "a" or "an" when used in conjunction with the term "comprising" in the claims and/or the specification may mean "one," but it is also consistent with the meaning of "one or more," "at least one," and "one or more than one." The word "about" means plus or minus 5% of the stated number.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 1A-B. Pneumovax®23 causes a massive ASC burst which can be used as a source of high affinity anti-polysaccharide antibodies. (FIG. 1A) PBMCs were harvested from four donors 7 days after vaccination with Pneumovax®23. They were stained and sorted for cells which are CD3 and CD20 negative and CD19 intermediate. The dot plots presented indicate a large ASC burst in all four donors (CD27 high, CD38 high; circular gate). Averaging the percentage of ASCs from these four donors, designated as Con1, Con2, SLE1, and SLE2, 16.3% of total B cells in the peripheral blood are ASCs. (FIG. 1B) The ASCs indicated in A. are sorted into 96-well plates. RT-PCR and several rounds of nested PCR are performed to prepare the V regions for cloning. The DNA is then cloned into expression vectors, amplified, and transfected into the HEK293 human cell line.

FIGS. 2A-C. On average, 77% of antibodies produced after vaccination with Pneumovax®23 bind to a vaccine component. (FIG. 2A) An average of 77% (Con1, 62%; Con2, 90%; SLE1, 75%; SLE2, 75%) of the antibodies expressed bind to *S. pneumoniae* capsule or cell wall polysaccharide by ELISA. (FIG. 2B) While a significant percentage of antibodies are cross-reactive (12%), most of the antibodies produced are specific to a single serotype. (FIG. 2C) 52% of the antibodies from SLE2 are poly-reactive, binding to at least two of the following five antigens: Ro, La, Sm, nRNP, or cardiolipin.

FIGS. 3A-D. An individual can produce multiple antibodies to the same serotype, some of which are specific and others of which cross-react. (FIG. 3A.) Serotypes 9N and 9V have very similar structures, yet Con1p2D02 binds only 9N and SLE1p1E01 binds only 9V. (FIG. 3B) Conversely, Con1p4B03 binds to both 9N and 9V. As shown by both affinity and avidity measurements, the binding to 9N is stronger than to 9V. (FIG. 3C) SLE1p1A03 binds to 9N, but cross-reacts with 14 rather than 9V. Its affinity and avidity for both 9N and 14 are similar. (FIG. 3D) SLE2p2D03 binds to both 19A and 19F, which also share similar structures. The affinity to 19A and 19F is similar, however, the avidity to 19A is 4 times stronger than to 19F. Affinity ELISAs are performed by coating plates with a single purified polysaccharide using serial dilutions of the antibody. Affinities (Kd's) are expressed in molarity. Avidity chaotropic ELISAs are performed in the same manner, but a 15 minute elution step using various dilutions of ammonium thiocyanate is added. Avidity graphs are presented as percent binding retained ($OD_{405}$ with $SCN/OD_{405}$ without SCN*100) versus the log of the thiocyanate concentration. The avidity is equal to the concentration of ammonium thiocyanate causing a 50% reduction (or retention) of binding.

FIGS. 4A-C. B cells generate cross-reactive antibodies to serotypes 15B and 14, as well as 17F and 33F. (FIG. 4A) Two antibodies, SLE2p2G06 and SLE2p2C04 bind solely to 17F or 33F respectively. (FIG. 4B) SLE2p1C03, however, binds to both serotypes. The affinity for 33F is an order of magnitude better than the affinity for 17F, however, their avidities are similar. (FIG. 4C) SLE2p1B01 binds to both 15B and 14. Although the affinity is almost an order of magnitude higher for 15B, it actually shows two-fold higher avidity for 14.

FIGS. 6A-B. The specificity of ASCs induced by Pneumovax®23 is determined by a donor's memory response invoked by the vaccine. (FIG. 6A) The 'anamnestic fingerprint' from the four donors. None had previously received Pneumovax®23, thus the ASC 'recall' antibodies cloned resulted from memory due to previous exposure to *S. pneumoniae*. Each donor has a unique "fingerprint" of serotypes against which they have produced antibodies. (FIG. 6B) After eliminating members of clonal pools and combining all four graphs, the donors have very different 'pneumococcal fingerprints' with only three serotypes (9V, 15B and 17F) being represented from three donors, and only two from all four (8 and 33F).

FIGS. 7A-B. Cross-reactive and poly-reactive antibodies are shown from each donor. The ELISA curves from FIG. 2A are reproduced here also showing antibodies which are (FIG. 7A) cross-reactive in red and (FIG. 7B) poly-reactive in orange. Three of the four cross-reactive antibodies from SLE2 are also poly-reactive (but none from the other donors).

DESCRIPTION OF ILLUSTRATIVE EMBODIMENTS

Figure 5:
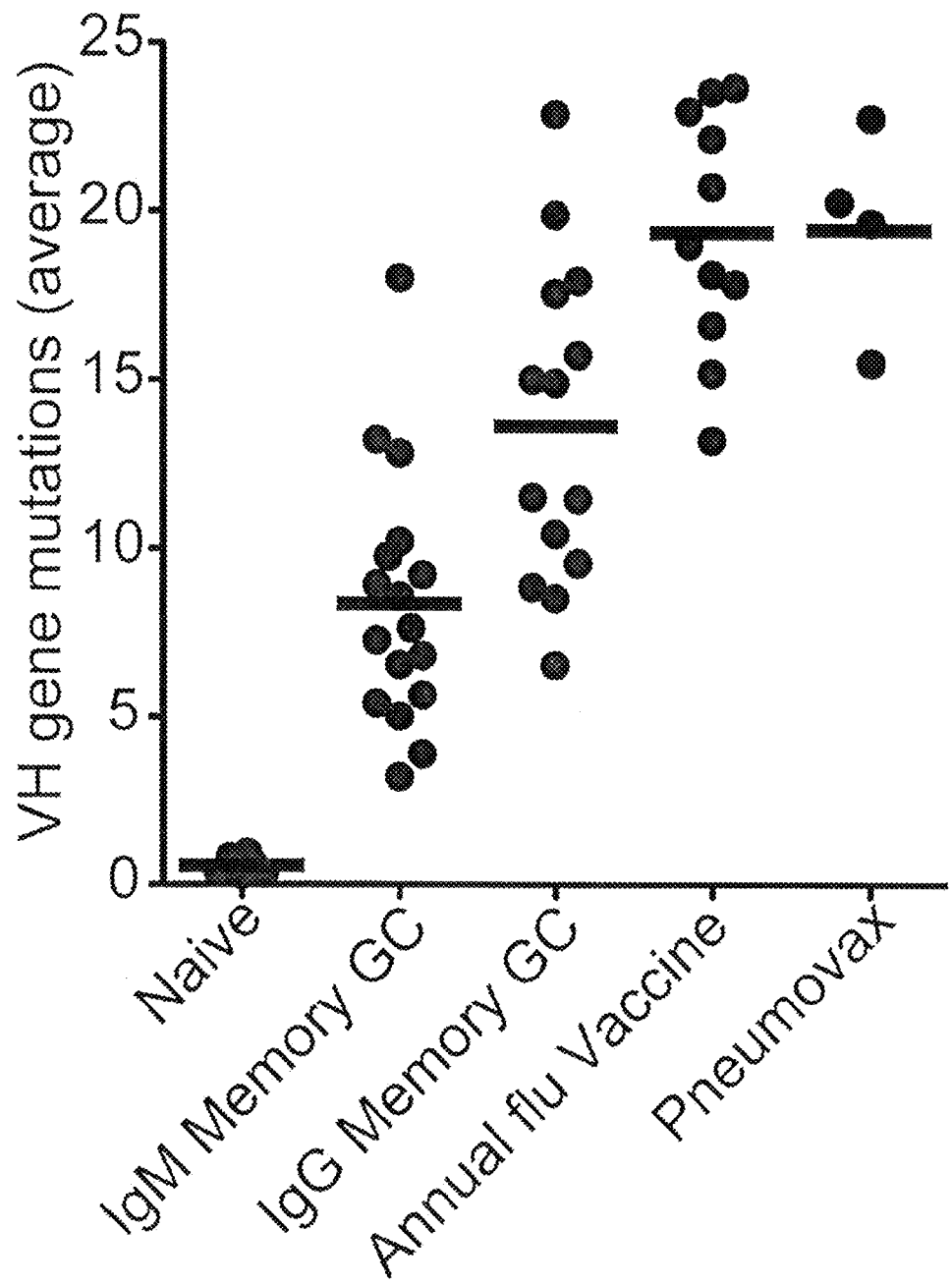
FIG. 5 ASCs resulting from vaccination with Pneumovax®23 produce antibodies which are highly mutated. Each data point is the average frequency of somatic mutations (nucleotide) per sequence from each donor (n values in Methods). On average, the anti-polysaccharide ASCs had accumulated a similar number of mutations as anti-influenza ASCs after seasonal influenza vaccination[14]. GC=germinal center populations.

To explore the antibody response generated by the Pneumovax®23 vaccine, the inventor generated and characterized large numbers of high affinity human monoclonal antibodies to the *S. pneumoniae* serotypes present in the vaccine from SLE patients and healthy controls. Although human monoclonal antibodies to *S. pneumoniae* have been made in the past (Baxendale and Goldblatt, 2006; Baxendale et al., 2000; Zhou et al., 2002; Zhou et al., 2004), these studies have been limited by two factors: one, they employed Fab expression library screens and two, they employed random production of hybridomas. In addition, previous studies have either focused on one serotype (6B and 23F) or have utilized vaccination with the conjugate vaccine Prevnar that consists of only seven capsular serotypes. In contrast, the inventor's technique provides cross-sectional characterization of the anti-polysaccharide response at one particular point in time, seven days post vaccination; thus, every cell used to clone an antibody has arisen from a memory response to this particular vaccination. This system will inform on a number of still unanswered questions in the field of polysaccharide immune responses and autoimmunity. In particular, the data here specifically address the percentage of human monoclonal polysaccharide antibodies that cross-react between different serotypes, how an individual's ASC response to Pneumovax®23 is a result of previous exposure to *S. pneumoniae*, and how this response differs in donors with SLE. As a result, there are now available a wide range of fully human monoclonal antibodies to *S. pneumoniae* that can be applied to diagnostic, theranostic and therapeutic applications. These and other aspects of the invention are described in detail below.

II. *Streptococcus pneumoniae*

A. General

*Streptococcus pneumoniae*, or pneumococcus, is Gram-positive, alpha-hemolytic, bile-soluble aerotolerant, anaerobic member of the genus *Streptococcus*. A significant human pathogenic bacterium, *S. pneumoniae* was recognized as a major cause of pneumonia in the late 19th century, and is the subject of many humoral immunity studies.

*S. pneumoniae* can be differentiated from *Streptococcus viridans*, some of which are also alpha-hemolytic, using an optochin test, as *S. pneumoniae* is optochin-sensitive. *S. pneumoniae* can also be distinguished based on its sensitivity to lysis by bile. The encapsulated, Gram-positive coccoid bacteria have a distinctive morphology on Gram stain, the so-called, "lancet-shaped" diplococci. They have a polysaccharide capsule that acts as a virulence factor for the organism; more than 90 different serotypes are known, and these types differ in virulence, prevalence, and extent of drug resistance.

The genome of *S. pneumoniae* is a closed, circular DNA structure that contains between 2.0 and 2.1 million basepairs, depending on the strain. It has a core set of 1553 genes, plus 154 genes in its virulome, which contribute to virulence, and 176 genes that maintain a noninvasive phenotype. Genetic information can vary up to 10% between strains.

*S. pneumoniae* is part of the normal upper respiratory tract flora, but, as with many natural flora, it can become pathogenic under the right conditions (e.g., if the immune system of the host is suppressed). Invasins, such as pneumolysin, an antiphagocytic capsule, various adhesins and immunogenic cell wall components are all major virulence factors.

Community-acquired pneumonia (CAP) is becoming more and more common, and represents an important cause of mortality and morbidity worldwide. While a number of different pathogens can give rise to CAP, *Streptococcus pneumoniae* is one of the most common. CAP is often acquired via inhalation or aspiration of pulmonary pathogenic organisms into a lung segment or lobe. Less commonly, CAP results from secondary bacteremia from a distant source.

Severe CAP normally develops in patients with cardiopulmonary disease, diminished splenic function, and/or pathogenic virulence, but even young and/or healthy hosts can develop severe CAP if the causative pathogen is sufficiently virulent. Complications in CAP depend on the infecting pathogen and patient health. Myocardial infarction can be precipitated by fever due to community-acquired pneumonia (CAP). Also, patients with CAP who have impaired splenic function may develop overwhelming pneumococcal sepsis, potentially leading to death within 12-24 hours, regardless of the antimicrobial regimen used.

CAP morbidity and mortality are highest in elderly patients and in immunocompromised hosts. Other factors that predict an increased risk of mortality in patients with CAP include the presence of significant comorbidities, an increased respiratory rate, hypotension, fever, multilobar involvement, anemia, and hypoxia.

B. Related Disease States

Despite the name, *S. pneumoniae* causes many types of pneumococcal infections other than pneumonia, including acute sinusitis, otitis media, meningitis, bacteremia, sepsis, osteomyelitis, septic arthritis, endocarditis, peritonitis, pericarditis, cellulitis, and brain abscess.

C. Multi-Drug Resistance

A growing concern in *S. pneumoniae* therapy is the resistance of strains many to penicillin and other beta-lactams (like amoxicillin), which is increasing worldwide. The major mechanism of resistance involves the introduction of mutations in genes encoding penicillin-binding proteins. This development complicates treatment immensely, and also adds unnecessary cost when therapies fail.

In 2000, Whitney et al. examined data on invasive pneumococcal disease in patients identified from 1995 to 1998 in the Active Bacterial Core Surveillance program of the Centers for Disease Control and Prevention. During 1998, 4013 cases of invasive *Streptococcus pneumoniae* disease were reported, and isolates were available for 3475 (87%). Overall, 24% of isolates from 1998 were resistant to penicillin. Penicillin-resistant isolates were more likely than susceptible isolates to have a high level of resistance to other antimicrobial agents. Serotypes included in the 7-valent conjugate and 23-valent pneumococcal polysaccharide vaccines accounted for 78% and 88% of penicillin-resistant strains, respectively. Between 1995 and 1998, the proportion of isolates that were resistant to three or more classes of drugs increased from 9% to 14%; there also were increases in the proportions of isolates that were resistant to penicillin (from 21% to 25%), cefotaxime (from 10% to 14%), meropenem (from 10% to 16%), erythromycin (from 11% to 15%), and trimethoprim-sulfamethoxazole (from 25% to 29%). These trends are like to continue, putting greater pressure on clinicians to resort to drugs such as vancomycin and levoflaxin.

D. Diagnosis

*S. pneumoniae* can be differentiated from other *Streptococcus* infections based on the alpha-hemolytic test. *Streptococcus viridans*, some of which are also alpha-hemolytic, can be distinguished using an optochin test, as *S. pneumoniae* is optochin-sensitive but *S. viridans* is not. *S. pneumoniae* can also be distinguished based on its sensitivity to lysis by bile. The encapsulated, Gram-positive coccoid bacteria have a distinctive morphology on Gram stain, the so-called, "lancet-shaped" diplococci. They have a polysaccharide capsule that acts as a virulence factor for the organism; more than 90 different serotypes are known, and these types differ in virulence, prevalence, and extent of drug resistance.

In terms of distinguishing serotypes, antibodies are currently available to serotypes 1, 3, 4, 5, 6B, 7F, 8, 9N, 9V, 12F, 14, 18C, 19F and 23F (ARUP Laboratories, Salt Lake City, Utah).

E. Treatments

Antibiotics are the treatment of choice for *S. pneumoniae* infects, with ventilation (oxygen supplement) as supportive therapy of bacterial pneumonia. The antibiotic choice depends on the microorganisms most commonly causing pneumonia in the geographical region, as well as nature of the specific organism, the immune status and underlying health of the individual, the severity of infection, and prior treatment history. In the United Kingdom, amoxicillin is used as first-line therapy in the vast majority of patients who acquire pneumonia in the community, sometimes with added clarithromycin. In North America, where the "atypical" forms of community-acquired pneumonia are becoming more common, clarithromycin, azithromycin, or fluoroquinolones as single therapy, have displaced the amoxicillin as first-line therapy. Local patterns of antibiotic-resistance should always be considered when initiating pharmacotherapy. In hospitalized individuals or those with immune deficiencies, local guidelines determine the selection of antibiotics. These antibiotics are typically given through an intravenous line. Specifically, *S. pneumoniae* is treated with amoxicillin (or erythromycin in patients allergic to penicillin), and with cefuroxime and erythromycin in severe cases.

III. Producing Monoclonal Antibodies

A. General Methods

It will be understood that monoclonal antibodies binding to *S. pneumoniae* will have utilities in several applications. These include the production of diagnostic kits for use in detecting and diagnosing disease. In these contexts, one may link such antibodies to diagnostic or therapeutic agents, or use them as capture agents or competitors in competitive assays. Means for preparing and characterizing antibodies are well known in the art (see, e.g., Antibodies: A Laboratory Manual, Cold Spring Harbor Laboratory, 1988; U.S. Pat. No. 4,196, 265).

The methods for generating monoclonal antibodies (MAbs) generally begin along the same lines as those for preparing polyclonal antibodies. The first step for both these methods is immunization of an appropriate host or identification of subjects who are immune due to prior natural infection. As is well known in the art, a given composition for immunization may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Means for conjugating a polypeptide to a carrier protein are well known in the art and include glutaraldehyde, m-maleimidobencoyl-N-hydroxysuccinimide ester, carbodiimyde and bis-biazotized benzidine. As also is well known in the art, the immunogenicity of a particular immunogen composition can be enhanced by the use of non-specific stimulators of the immune response, known as adjuvants. Exemplary and preferred adjuvants include complete Freund's adjuvant (a non-specific stimulator of the immune response containing killed *Mycobacterium tuberculosis*), incomplete Freund's adjuvants and aluminum hydroxide adjuvant.

The amount of immunogen composition used in the production of polyclonal antibodies varies upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization. A second, booster injection, also may be given. The process of boosting and titering is repeated until a suitable titer is achieved. When a desired level of immunogenicity is obtained, the immunized animal can be bled and the serum isolated and stored, and/or the animal can be used to generate MAbs.

In the case of human monoclonal antibodies, one may instead simply look for an individual already known to have generated an immune response, in this case, to have been exposed to *S. pneumoniae* or immunized with Pneumovax®23. In order to identify subjects with immunity to various *S. pneumoniae* strains, one could generally obtain blood from subjects and test them for *S. pneumoniae* antibodies. Many antibodies described in this invention were generated in this way using peripheral blood from otherwise healthy individuals previously infected with *S. pneumoniae*.

Following immunization or obtaining of cells from previously infected subjects as described above, somatic cells with the potential for producing antibodies, specifically B lymphocytes (B cells), are selected for use in the MAb generating protocol. These cells may be obtained from biopsied spleens or lymph nodes, or from circulating blood. The antibody-producing B lymphocytes from the immunized animal are then fused with cells of an immortal myeloma cell, generally one of the same species as the animal that was immunized or human or human/mouse chimeric cells. Myeloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas).

Any one of a number of myeloma cells may be used, as are known to those of skill in the art (Goding, pp. 65-66, 1986; Campbell, pp. 75-83, 1984). For example, where the immunized animal is a mouse, one may use P3-X63/Ag8, X63-Ag8.653, NS1/1.Ag 4 1, Sp210-Ag14, FO, NSO/U, MPC-11, MPC11-X45-GTG 1.7 and S194/5XX0 Bul; for rats, one may use R210.RCY3, Y3-Ag 1.2.3, IR983F and 4B210; and U-266, GM1500-GRG2, LICR-LON-HMy2 and UC729-6 are all useful in connection with human cell fusions. One particular murine myeloma cell is the NS-1 myeloma cell line (also termed P3-NS-1-Ag-4-1), which is readily available from the NIGMS Human Genetic Mutant Cell Repository by requesting cell line repository number GM3573. Another mouse myeloma cell line that may be used is the 8-azaguanine-resistant mouse murine myeloma SP2/0 non-producer cell line. More recently, additional fusion partner lines for use with human B cells have been described, including KR12 (ATCC CRL-8658; K6H6/B5 (ATCC CRL-1823 SHM-D33 (ATCC CRL-1668) and HMMA2.5 (Posner et al., 1987). The antibodies in this invention were generated using the HMMA2.5 line.

Methods for generating hybrids of antibody-producing spleen or lymph node cells and myeloma cells usually comprise mixing somatic cells with myeloma cells in a 2:1 proportion, though the proportion may vary from about 20:1 to about 1:1, respectively, in the presence of an agent or agents (chemical or electrical) that promote the fusion of cell membranes. Fusion methods using Sendai virus have been described by Kohler and Milstein (1975; 1976), and those using polyethylene glycol (PEG), such as 37% (v/v) PEG, by Gefter et al. (1977). The use of electrically induced fusion methods also is appropriate (Goding, pp. 71-74, 1986). The hybridomas secreting the influenza antibodies in this invention were obtained by electrofusion.

Fusion procedures usually produce viable hybrids at low frequencies, about $1 \times 10^{-6}$ to $1 \times 10^{-8}$. However, this does not pose a problem, as the viable, fused hybrids are differentiated from the parental, infused cells (particularly the infused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine. Ouabain is added if the B cell source is an Epstein Barr virus (EBV) transformed human B cell line, in order to eliminate EBV transformed lines that have not fused to the myeloma.

The preferred selection medium is HAT or HAT with ouabain. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B cells can operate this pathway, but they have a limited life span in culture and generally die within about two weeks. Therefore, the only cells that can survive in the selective media are those hybrids formed from myeloma and B cells. When the source of B cells used for fusion is a line of EBV-transformed B cells, as here, ouabain is also used for drug selection of hybrids as EBV-transformed B cells are susceptible to drug killing, whereas the myeloma partner used is chosen to be ouabain resistant.

Culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays dot immunobinding assays, and the like.

The selected hybridomas are then serially diluted or single-cell sorted by flow cytometric sorting and cloned into individual antibody-producing cell lines, which clones can then be propagated indefinitely to provide mAbs. The cell lines may be exploited for MAb production in two basic ways. A sample of the hybridoma can be injected (often into the peritoneal cavity) into an animal (e.g., a mouse). Optionally, the animals are primed with a hydrocarbon, especially oils such as pristane (tetramethylpentadecane) prior to injection. When human hybridomas are used in this way, it is optimal to inject immunocompromised mice, such as SCID mice, to prevent tumor rejection. The injected animal develops tumors secreting the specific monoclonal antibody produced by the fused cell hybrid. The body fluids of the animal, such as serum or ascites fluid, can then be tapped to provide MAbs in high concentration. The individual cell lines could also be cultured in vitro, where the MAbs are naturally secreted into the culture medium from which they can be readily obtained in high concentrations. Alternatively, human hybridoma cells lines can be used in vitro to produce immunoglobulins in cell supernatant. The cell lines can be adapted for growth in serum-free medium to optimize the ability to recover human monoclonal immunoglobulins of high purity.

MAbs produced by either means may be further purified, if desired, using filtration, centrifugation and various chromatographic methods such as FPLC or affinity chromatography. Fragments of the monoclonal antibodies of the invention can be obtained from the purified monoclonal antibodies by methods which include digestion with enzymes, such as pepsin or papain, and/or by cleavage of disulfide bonds by chemical reduction. Alternatively, monoclonal antibody fragments encompassed by the present invention can be synthesized using an automated peptide synthesizer.

It also is contemplated that a molecular cloning approach may be used to generate monoclonals. For this, RNA can be isolated from the hybridoma line and the antibody genes obtained by RT-PCR and cloned into an immunoglobulin expression vector. Alternatively, combinatorial immunoglobulin phagemid libraries are prepared from RNA isolated from the cell lines and phagemids expressing appropriate antibodies are selected by panning using viral antigens. The advantages of this approach over conventional hybridoma techniques are that approximately $10^4$ times as many antibodies can be produced and screened in a single round, and that new specificities are generated by H and L chain combination which further increases the chance of finding appropriate antibodies.

Other U.S. patents, each incorporated herein by reference, that teach the production of antibodies useful in the present invention include U.S. Pat. No. 5,565,332, which describes the production of chimeric antibodies using a combinatorial approach; U.S. Pat. No. 4,816,567 which describes recombinant immunoglobulin preparations; and U.S. Pat. No. 4,867,973 which describes antibody-therapeutic agent conjugates.

B. Antibodies of the Present Invention

Antibodies according to the present invention may be defined, in the first instance, by their binding specificity. Those of skill in the art, by assessing the binding affinity of a given antibody using techniques well known to those of skill in the art, can determine whether such antibodies fall within the scope of the instant claims.

In the context of the present invention, the antibody specificity relates to the *S. pneumoniae* serotype. There are 24 different serotypes represented by Pneumovax®23, represented by the following designations: 1, 2, 3, 4, 5, 6B, 7F, 8, 9N, 9V, 10A, 11A, 12F, 14, 15B, 17F, 18C, 19F, 19A, 20, 22F, 23F, 33F and CWPS. The CDR region sequences for representative antibodies are included in the appended sequence listing.

Another way of categorizing the antibodies of the present invention is by their activity. This could include the ability to neutralize or kill *Streptococcus pneumoniae* in the presence or absence of complement. Finally, the antibody may be defined in particular by reference to heavy/light chain variable region sequences. The present inventor provides the following antibodies that have demonstrated activity against *Streptococcus pneumoniae* in an opsonophagocytosis assay (OPA) that measures antibody mediated uptake of bacteria by a phagocytic cell line. The also can be presented by variable regions as set out in Table 2.

C. Engineering of Antibody Sequences

In various embodiments, one may choose to engineer sequences of the identified antibodies for a variety of reasons, such as improved expression, improved cross-reactivity or diminished off-target binding. The following is a general discussion of relevant techniques for antibody engineering.

Hybridomas may cultured, then cells lysed, and total RNA extracted. Random hexamers may be used with RT to generate cDNA copies of RNA, and then PCR performed using a multiplex mixture of PCR primers expected to amplify all human variable gene sequences. PCR product can be cloned into pGEM-T Easy® vector, then sequenced by automated DNA sequencing using standard vector primers. Assay of binding and neutralization may be performed using antibodies collected from hybridoma supernatants and purified by FPLC, using Protein G columns.

Recombinant full length IgG antibodies can generated by subcloning heavy and light chain Fv DNAs from the cloning vector into a second vector, such as a Lonza pConIgG1 or pConK2 plasmid vector, transfected into 293 Freestyle cells or Lonza CHO cells, and antibodies can then be collected and purified from the cell supernatants.

pCon Vectors™ are an easy way to re-express whole antibodies. The constant region vectors are a set of vectors offering a range of immunoglobulin constant region vectors cloned into the pEE vectors. These vectors offer easy construction of full length antibodies with human constant regions and the convenience of the GS System™.

Antibody molecules will comprise fragments (such as F(ab'), F(ab')$_2$) that are produced, for example, by the proteolytic cleavage of the mAbs, or single-chain immunoglobulins producible, for example, via recombinant means. Such antibody derivatives are monovalent. In one embodiment, such fragments can be combined with one another, or with other antibody fragments or receptor ligands to form "chimeric" binding molecules. Significantly, such chimeric molecules may contain substituents capable of binding to different epitopes of the same molecule.

In related embodiments, the antibody is a derivative of the disclosed antibodies, e.g., an antibody comprising the CDR sequences identical to those in the disclosed antibodies (e.g., a chimeric or CDR-grafted antibody). In yet a further embodiment, the antibody is a fully human recombinant antibody. Alternatively, one may wish to make more subtle modifications, such as introducing conservative changes into an antibody molecule. In making such changes, the hydropathic index of amino acids may be considered. The importance of the hydropathic amino acid index in conferring interactive biologic function on a protein is generally understood in the art (Kyte and Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

It also is understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: basic amino acids: arginine (+3.0), lysine (+3.0), and histidine (−0.5); acidic amino acids: aspartate (+3.0±1), glutamate (+3.0±1), asparagine (+0.2), and glutamine (+0.2); hydrophilic, nonionic amino acids: serine (+0.3), asparagine (+0.2), glutamine (+0.2), and threonine (−0.4), sulfur containing amino acids: cysteine (−1.0) and methionine (−1.3); hydrophobic, nonaromatic amino acids: valine (−1.5), leucine (−1.8), isoleucine (−1.8), proline (−0.5±1), alanine (−0.5), and glycine (0); hydrophobic, aromatic amino acids: tryptophan (−3.4), phenylalanine (−2.5), and tyrosine (−2.3).

It is understood that an amino acid can be substituted for another having a similar hydrophilicity and produce a biologically or immunologically modified protein. In such changes, the substitution of amino acids whose hydrophilicity values are within ±2 is preferred, those that are within ±1 are particularly preferred, and those within ±0.5 are even more particularly preferred.

As outlined above, amino acid substitutions generally are based on the relative similarity of the amino acid side-chain substituents, for example, their hydrophobicity, hydrophilicity, charge, size, and the like. Exemplary substitutions that take into consideration the various foregoing characteristics are well known to those of skill in the art and include: arginine and lysine; glutamate and aspartate; serine and threonine; glutamine and asparagine; and valine, leucine and isoleucine.

The present invention also contemplates isotype modification. By modifying the Fc region to have a different isotype, different functionalities can be achieved. For example, changing to IgG$_1$ can increase antibody dependent cell cytotoxicity, switching to class A can improve tissue distribution, and switching to class M can improve valency.

Modified antibodies may be made by any technique known to those of skill in the art, including expression through standard molecular biological techniques, or the chemical synthesis of polypeptides. Methods for recombinant expression are addressed elsewhere in this document.

D. Single Chain Antibodies

A Single Chain Variable Fragment (scFv) is a fusion of the variable regions of the heavy and light chains of immunoglobulins, linked together with a short (usually serine, glycine) linker. This chimeric molecule retains the specificity of the original immunoglobulin, despite removal of the constant regions and the introduction of a linker peptide. This modification usually leaves the specificity unaltered. These molecules were created historically to facilitate phage display where it is highly convenient to express the antigen binding domain as a single peptide. Alternatively, scFv can be created directly from subcloned heavy and light chains derived from a hybridoma. Single chain variable fragments lack the constant Fc region found in complete antibody molecules, and thus, the common binding sites (e.g., protein A/G) used to purify antibodies. These fragments can often be purified/immobilized using Protein L since Protein L interacts with the variable region of kappa light chains.

Flexible linkers generally are comprised of helix- and turn-promoting amino acid residues such as alaine, serine and glycine. However, other residues can function as well. Tang et al. (1996) used phage display as a means of rapidly selecting tailored linkers for single-chain antibodies (scFvs) from protein linker libraries. A random linker library was constructed in which the genes for the heavy and light chain variable domains were linked by a segment encoding an 18-amino acid polypeptide of variable composition. The scFv repertoire (approx. 5×10$^6$ different members) was displayed on filamentous phage and subjected to affinity selection with hapten.

The population of selected variants exhibited significant increases in binding activity but retained considerable sequence diversity. Screening 1054 individual variants subsequently yielded a catalytically active scFv that was produced efficiently in soluble form. Sequence analysis revealed a conserved proline in the linker two residues after the $V_H C$ terminus and an abundance of arginines and prolines at other positions as the only common features of the selected tethers.

The recombinant antibodies of the present invention may also involve sequences or moieties that permit dimerization or multimerization of the receptors. Such sequences include those derived from IgA, which permit formation of multimers in conjunction with the J-chain. Another multimerization domain is the Gal4 dimerization domain. In other embodiments, the chains may be modified with agents such as biotin/avidin, which permit the combination of two antibodies.

In a separate embodiment, a single-chain antibody can be created by joining receptor light and heavy chains using a non-peptide linker or chemical unit. Generally, the light and heavy chains will be produced in distinct cells, purified, and subsequently linked together in an appropriate fashion (i.e., the N-terminus of the heavy chain being attached to the C-terminus of the light chain via an appropriate chemical bridge).

Cross-linking reagents are used to form molecular bridges that tie functional groups of two different molecules, e.g., a stabilizing and coagulating agent. However, it is contemplated that dimers or multimers of the same analog or heteromeric complexes comprised of different analogs can be created. To link two different compounds in a step-wise manner, hetero-bifunctional cross-linkers can be used that eliminate unwanted homopolymer formation.

An exemplary hetero-bifunctional cross-linker contains two reactive groups: one reacting with primary amine group (e.g., N-hydroxy succinimide) and the other reacting with a thiol group (e.g., pyridyl disulfide, maleimides, halogens, etc.). Through the primary amine reactive group, the cross-linker may react with the lysine residue(s) of one protein (e.g., the selected antibody or fragment) and through the thiol reactive group, the cross-linker, already tied up to the first protein, reacts with the cysteine residue (free sulfhydryl group) of the other protein (e.g., the selective agent).

It is preferred that a cross-linker having reasonable stability in blood will be employed. Numerous types of disulfide-bond containing linkers are known that can be successfully employed to conjugate targeting and therapeutic/preventative agents. Linkers that contain a disulfide bond that is sterically hindered may prove to give greater stability in vivo, preventing release of the targeting peptide prior to reaching the site of action. These linkers are thus one group of linking agents.

Another cross-linking reagent is SMPT, which is a bifunctional cross-linker containing a disulfide bond that is "sterically hindered" by an adjacent benzene ring and methyl groups. It is believed that steric hindrance of the disulfide bond serves a function of protecting the bond from attack by thiolate anions such as glutathione which can be present in tissues and blood, and thereby help in preventing decoupling of the conjugate prior to the delivery of the attached agent to the target site.

The SMPT cross-linking reagent, as with many other known cross-linking reagents, lends the ability to cross-link functional groups such as the SH of cysteine or primary amines (e.g., the epsilon amino group of lysine). Another possible type of cross-linker includes the hetero-bifunctional photoreactive phenylazides containing a cleavable disulfide bond such as sulfosuccinimidyl-2-(p-azido salicylamido) ethyl-1,3'-dithiopropionate. The N-hydroxy-succinimidyl group reacts with primary amino groups and the phenylazide (upon photolysis) reacts non-selectively with any amino acid residue.

In addition to hindered cross-linkers, non-hindered linkers also can be employed in accordance herewith. Other useful cross-linkers, not considered to contain or generate a protected disulfide, include SATA, SPDP and 2-iminothiolane (Wawrzynczak & Thorpe, 1987). The use of such cross-linkers is well understood in the art. Another embodiment involves the use of flexible linkers.

U.S. Pat. No. 4,680,338, describes bifunctional linkers useful for producing conjugates of ligands with amine-containing polymers and/or proteins, especially for forming antibody conjugates with chelators, drugs, enzymes, detectable labels and the like. U.S. Pat. Nos. 5,141,648 and 5,563,250 disclose cleavable conjugates containing a labile bond that is cleavable under a variety of mild conditions. This linker is particularly useful in that the agent of interest may be bonded directly to the linker, with cleavage resulting in release of the active agent. Particular uses include adding a free amino or free sulfhydryl group to a protein, such as an antibody, or a drug.

U.S. Pat. No. 5,856,456 provides peptide linkers for use in connecting polypeptide constituents to make fusion proteins, e.g., single chain antibodies. The linker is up to about 50 amino acids in length, contains at least one occurrence of a charged amino acid (preferably arginine or lysine) followed by a proline, and is characterized by greater stability and reduced aggregation. U.S. Pat. No. 5,880,270 discloses aminooxy-containing linkers useful in a variety of immunodiagnostic and separative techniques.

In a particular embodiment, the antibody is a recombinant antibody that is suitable for action inside of a cell—such antibodies are known as "intrabodies." These antibodies may interfere with target function by a variety of mechanism, such as by altering intracellular protein trafficking, interfering with enzymatic function, and blocking protein-protein or protein-DNA interactions. In many ways, their structures mimic or parallel those of single chain and single domain antibodies, discussed above. Indeed, single-transcript/single-chain is an important feature that permits intracellular expression in a target cell, and also makes protein transit across cell membranes more feasible. However, additional features are required.

The two major issues impacting the implementation of intrabody therapeutic are delivery, including cell/tissue targeting, and stability. With respect to delivery, a variety of approaches have been employed, such as tissue-directed delivery, use of cell-type specific promoters, viral-based delivery and use of cell-permeability/membrane translocating peptides. With respect to the stability, the approach is generally to either screen by brute force, including methods that involve phage display and may include sequence maturation or development of consensus sequences, or more directed modifications such as insertion stabilizing sequences (e.g., Fc regions, chaperone protein sequences, leucine zippers) and disulfide replacement/modification.

An additional feature that intrabodies may require is a signal for intracellular targeting. Vectors that can target intrabodies (or other proteins) to subcellular regions such as the cytoplasm, nucleus, mitochondria and ER have been designed and are commercially available (Invitrogen Corp.; Persic et al., 1997).

By virtue of their ability to enter cells, intrabodies have additional uses that other types of antibodies may not achieve. In the case of the present antibodies, the ability to interact with the MUC1 cytoplasmic domain in a living cell may interfere with functions associated with the MUC1 CD, such as signaling functions (binding to other molecules) or oligomer formation. In particular, it is contemplated that such antibodies can be used to inhibit MUC1 dimer formation.

E. Purification

In certain embodiments, the antibodies of the present invention may be purified. The term "purified," as used herein, is intended to refer to a composition, isolatable from other components, wherein the protein is purified to any degree relative to its naturally-obtainable state. A purified protein therefore also refers to a protein, free from the environment in which it may naturally occur. Where the term "substantially purified" is used, this designation will refer to a composition in which the protein or peptide forms the major component of the composition, such as constituting about 50%, about 60%, about 70%, about 80%, about 90%, about 95% or more of the proteins in the composition.

Protein purification techniques are well known to those of skill in the art. These techniques involve, at one level, the crude fractionation of the cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a pure peptide are ion-exchange chromatography, exclusion chromatography; polyacrylamide gel electrophoresis; isoelectric focusing. Other methods for protein purification include, precipitation with ammonium sulfate, PEG, antibodies and the like or by heat denaturation, followed by centrifugation; gel filtration, reverse phase, hydroxylapatite and affinity chromatography; and combinations of such and other techniques.

In purifying an antibody of the present invention, it may be desirable to express the polypeptide in a prokaryotic or eukaryotic expression system and extract the protein using denaturing conditions. The polypeptide may be purified from other cellular components using an affinity column, which binds to a tagged portion of the polypeptide. As is generally known in the art, it is believed that the order of conducting the various purification steps may be changed, or that certain steps may be omitted, and still result in a suitable method for the preparation of a substantially purified protein or peptide.

Commonly, complete antibodies are fractionated utilizing agents (i.e., protein A) that bind the Fc portion of the antibody. Alternatively, antigens my be used to simultaneously purify and select appropriate antibodies. Such methods often utilize the selection agent bound to a support, such as a column, filter or bead. The antibodies is bound to a support, contaminants removed (e.g., washed away), and the antibodies released by applying conditions (salt, heat, etc.).

Various methods for quantifying the degree of purification of the protein or peptide will be known to those of skill in the art in light of the present disclosure. These include, for example, determining the specific activity of an active fraction, or assessing the amount of polypeptides within a fraction by SDS/PAGE analysis. Another method for assessing the purity of a fraction is to calculate the specific activity of the fraction, to compare it to the specific activity of the initial extract, and to thus calculate the degree of purity. The actual units used to represent the amount of activity will, of course, be dependent upon the particular assay technique chosen to follow the purification and whether or not the expressed protein or peptide exhibits a detectable activity.

It is known that the migration of a polypeptide can vary, sometimes significantly, with different conditions of SDS/PAGE (Capaldi et al., 1977). It will therefore be appreciated that under differing electrophoresis conditions, the apparent molecular weights of purified or partially purified expression products may vary.

IV. Passive Immunization and Treatment of *S. Pneumoniae* Infections

A. Formulation and Administration

Passive transfer of antibodies, known as artificially acquired passive immunity, generally will involve the use of intravenous or intramuscular injections. Such immunity generally lasts for only a short period of time, but provides immediate protection. The antibodies will be formulated in a carrier suitable for injection, i.e., sterile and syringeable. Thus, the present invention provides pharmaceutical compositions comprising anti-*S. pneumoniae* antibodies and antigens for generating the same. Such compositions comprise a prophylactically or therapeutically effective amount of an antibody or a fragment thereof, and a pharmaceutically acceptable carrier. In a specific embodiment, the term "pharmaceutically acceptable" means approved by a regulatory agency of the federal or a state government or listed in the U.S. Pharmacopeia or other generally recognized pharmacopeia for use in animals, and more particularly in humans. The term "carrier" refers to a diluent, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a particular carrier when the pharmaceutical composition is administered intravenously. Saline solutions and aqueous dextrose and glycerol solutions can also be employed as liquid carriers, particularly for injectable solutions. Other suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like.

The composition, if desired, can also contain minor amounts of wetting or emulsifying agents, or pH buffering agents. These compositions can take the form of solutions, suspensions, emulsion, tablets, pills, capsules, powders, sustained-release formulations and the like. Oral formulations can include standard carriers such as pharmaceutical grades of mannitol, lactose, starch, magnesium stearate, sodium saccharine, cellulose, magnesium carbonate, etc. Examples of suitable pharmaceutical agents are described in "Remington's Pharmaceutical Sciences." Such compositions will contain a prophylactically or therapeutically effective amount of the antibody or fragment thereof, preferably in purified form, together with a suitable amount of carrier so as to provide the form for proper administration to the patient. The formulation should suit the mode of administration, which can be oral, intravenous, intraarterial, intrabuccal, intranasal, nebulized, bronchial inhalation, or delivered by mechanical ventilation.

Generally, the ingredients of compositions of the invention are supplied either separately or mixed together in unit dosage form, for example, as a dry lyophilized powder or water-free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compositions of the invention can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

B. Combination Therapy

In order to increase the effectiveness of the antibody therapy of the present invention, it may be desirable to combine this treatment with other agents effective at treating or preventing *S. pneumonia* infections, e.g., antibiotics. This process may involve administering to the patient the antibody of the present invention and the other agent(s) at the same time. This may be achieved by use of a single pharmaceutical composition that includes both agents, or by administering two distinct compositions at the same time, wherein one composition includes the antibody of the present invention and the other includes the second agent(s).

The two therapies may be given in either order and may precede or follow the other treatment by intervals ranging from minutes to weeks. In embodiments where the other agents are applied separately, one would generally ensure that a significant period of time did not expire between the time of each delivery, such that the agents would still be able to exert an advantageously combined effect on the patient. In such instances, it is contemplated that one may administer both modalities within about 12-24 h of each other and, more preferably, within about 6-12 h of each other. In some situations, it may be desirable to extend the time period for treatment significantly, however, where several d (2, 3, 4, 5, 6 or 7) to several wk (1, 2, 3, 4, 5, 6, 7 or 8) lapse between the respective administrations.

Various combinations may be employed, the antibody treatment of the present invention is "A" and the secondary treatment is "B":

| | | | | |
|---|---|---|---|---|
| A/B/A B/A/B B/B/A | A/A/B A/B/B B/A/A | A/B/B/B | B/A/B/B |
| B/B/B/A | B/B/A/B | A/A/B/B | A/B/A/B | A/B/B/A | B/B/A/A |
| B/A/B/A | B/A/A/B | A/A/A/B | B/A/A/A | A/B/A/A | A/A/B/A |

Administration of the secondary agent will follow general protocols for that drug, taking into account the toxicity, if any. It is expected that the treatment cycles would be repeated as necessary.

1. Amoxicillin and Erythromycin

Amoxicillin.

Amoxicillin (INN), formerly amoxycillin (BAN), and abbreviated amox, is a moderate-spectrum, bacteriolytic, β-lactam antibiotic used to treat bacterial infections caused by susceptible microorganisms. It is usually the drug of choice within the class because it is better absorbed, following oral administration, than other β-lactam antibiotics. Amoxicillin is one of the most common antibiotics prescribed for children. This drug acts by inhibiting the synthesis of bacterial cell walls. It inhibits cross-linkage between the linear peptidoglycan polymer chains that make up a major component of the cell walls of both Gram-positive and Gram-negative bacteria.

It has two ionizable groups in the physiological range (the amino group in alpha-position to the amide carbonyl group and the carboxyl group). Amoxicillin is susceptible to degradation by β-lactamase-producing bacteria, which are resistant to a broad spectrum of β-lactam antibiotics, such as penicillin. For this reason, it is often combined with clavulanic acid, a β-lactamase inhibitor, and marketed under one name. This increases effectiveness by reducing its susceptibility to β-lactamase resistance.

Amoxicillin is used in the treatment of a number of infections including: acute otitis media, streptococcal pharyngitis, pneumonia, skin infections, urinary tract infections, salmonella, lyme disease, and chlamydia infections. It is used to prevent bacterial endocarditis in high risk people who are having dental work done, to prevent strep pneumococus infections in those without a spleen, and for both the prevention and treatment of anthrax. It is also a treatment for cystic acne. The UK however does not recommend its use for infectious endocarditis prophylaxis. These recommendations have not appeared to have changed the rates of infection.

Side-effects are as those for other beta-lactam antibiotics. Side-effects include nausea, vomiting, rashes, and antibiotic-associated colitis. Loose bowel movements (diarrhea) also may occur. Rarer, but patient-reported, side-effects include mental changes, lightheadedness, insomnia, confusion, anxiety, sensitivity to lights and sounds, and unclear thinking. Immediate medical care is required upon the first signs of these side-effects.

The onset of an allergic reaction to amoxicillin can be very sudden and intense—emergency medical attention must be sought as quickly as possible. The initial onset of such a reaction often starts with a change in mental state, skin rash with intense itching (often beginning in fingertips and around groin area and rapidly spreading), and sensations of fever, nausea, and vomiting. Any other symptoms that seem even remotely suspicious must be taken very seriously. However, more mild allergy symptoms, such as a rash, can occur at any time during treatment, even up to a week after treatment has ceased. For some people who are allergic to amoxicillin the side effects can be deadly. Use of the amoxicillin/clavulanic acid combination for more than one week has caused mild hepatitis in some patients. Young children having ingested acute overdoses of amoxicillin manifested lethargy, vomiting and renal dysfunction.

Amoxicillin in trihydrate form is available as capsules, chewable and dispersible tablets plus syrup and pediatric suspension for oral use, and as the sodium salt for intravenous administration (although the IV formulation is not available in the United States). Amoxicillin is most commonly taken orally. The liquid forms are helpful where the patient might find it difficult to take tablets or capsules.

Erythromycin.

Erythromycin is a macrolide antibiotic that has an antimicrobial spectrum similar to or slightly wider than that of penicillin, and is often used for people who have an allergy to penicillins. For respiratory tract infections, it has better coverage of atypical organisms, including mycoplasma and Legionellosis. It was first marketed by Eli Lilly and Company, and it is today commonly known as EES (erythromycin ethylsuccinate, an ester prodrug that is commonly administered).

In structure, this macrocyclic compound contains a 14-membered lactone ring with ten asymmetric centers and two sugars (L-cladinose and D-desosamine), making it a compound very difficult to produce via synthetic methods. Erythromycin is produced from a strain of the actinomycete *Saccharopolyspora erythraea*.

U.S. Pat. No. 2,653,899, which covers the drug, was granted in 1953. The product was launched commercially in 1952 under the brand name Ilosone (after the Philippine region of Iloilo where it was originally collected from). Erythromycin was formerly also called Ilotycin.

Over the years since the discovery of erythromycin A and its activity as an antimicrobial, many attempts have been made to synthesize it in the laboratory. However, the presence of ten stereospecific carbons and several points of distinct substitution has made the total synthesis of erythromycin A a formidable task. Complete syntheses of erythromycins' related structures and precursors such as 6-deoxyerythronolide B have been accomplished, giving way to possible syntheses of different erythromycins and other macrolide antimicrobials. However, Woodward and colleagues did successfully complete the synthesis of erythromycin A in 1981.

Erythromycin is available in enteric-coated tablets, slow-release capsules, oral suspensions, ophthalmic solutions, ointments, gels, and injections. Brand names include Robimycin, E-Mycin, E.E.S. Granules, E.E.S.-200, E.E.S.-400, E.E.S.-400 Filmtab, Erymax, Ery-Tab, Eryc, Ranbaxy, Erypar, EryPed, Eryped 200, Eryped 400, Erythrocin Stearate Filmtab, Erythrocot, E-Base, Erythroped, Ilosone, MY-E, Pediamycin, Zineryt, Abboticin, Abboticin-ES, Erycin, PCE Dispertab, Stiemycine, Acnasol and Tiloryth.

Gastrointestinal disturbances, such as diarrhea, nausea, abdominal pain, and vomiting, are very common because erythromycin is a motilin agonist. Because of this, erythromycin tends not to be prescribed as a first-line drug. However, erythromycin may be useful in treating gastroparesis due to this pro-motility effect. Intravenous erythromycin may also be used in endoscopy as an adjunct to clear gastric contents. More serious side-effects include arrhythmia with prolonged QTc intervals including Torsades-de-Pointe and reversible deafness. Allergic reactions range from urticaria to anaphylaxis. Cholestasis, Stevens-Johnson syndrome, and toxic epidermal necrolysis are some other rare side-effects that may occur.

Exposure to erythromycin (especially long courses at antimicrobial doses, and also through breastfeeding) has been linked to an increased probability of pyloric stenosis in young infants. Erythromycin used for feeding intolerance in young infants has not been associated with hypertrophic pyloric stenosis.

Erythromycin estolate has been associated with reversible hepatotoxicity in pregnant women in the form of elevated serum glutamic-oxaloacetic transaminase and is not recommended during pregnancy. Some evidence suggests similar hepatotoxicity in other populations.

It can also affect the central nervous system, causing psychotic reactions, nightmares and night sweats. It may also alter the effectiveness of combined oral contraceptive pills because of its effect on the gut flora. Erythromycin is an inhibitor of the cytochrome P450 system, which means that it can have a rapid effect on levels of other drugs metabolised by this system, e.g., warfarin.

Erythromycin displays bacteriocidal activity, especially at higher concentrations, but the mechanism is not fully understood. By binding to the 50S subunit of the bacterial 70s rRNA complex, protein synthesis and subsequent structure and function processes critical for life or replication are inhibited. Erythromycin interferes with aminoacyl translocation, preventing the transfer of the tRNA bound at the A site of the rRNA complex to the P site of the rRNA complex. Without this translocation, the A site remains occupied and, thus, the addition of an incoming tRNA and its attached amino acid to the nascent polypeptide chain is inhibited. This interferes with the production of functionally useful proteins, which is the basis of this antimicrobial action.

2. Clarithromycin, Azithromycin, Fluoroquinolones and Cefuroxime Clarithromycin.

Clarithromycin is a macrolide antibiotic used to treat pharyngitis, tonsillitis, acute maxillary sinusitis, acute bacterial exacerbation of chronic bronchitis, pneumonia (especially atypical pneumonias associated with *Chlamydia pneumoniae* or TWAR), skin and skin structure infections. In addition, it is sometimes used to treat Legionellosis, *Helicobacter pylori*, and lyme disease. Clarithromycin is available under several brand names, for example Crixan, Clarac, Biaxin, Klaricid, Klacid, Klaram, Klabax, Klacid, Claripen, Clarem, Claridar, Fromilid, Clacid, Clacee, Vikrol, Infex and Clariwin, Resclar.

Clarithromycin was invented by researchers at the Japanese drug company Taisho Pharmaceutical in the 1970s. The product emerged through efforts to develop a version of the antibiotic erythromycin that did not experience acid instability in the digestive tract, causing side effects, such as nausea and stomach ache. Taisho filed for patent protection for the drug around 1980 and subsequently introduced a branded version of its drug, called Clarith, to the Japanese market in 1991. In 1985 Taisho partnered with the American company Abbott Laboratories for the international rights, and Abbott also gained FDA approval for Biaxin in October 1991. The drug went generic in Europe in 2004 and in the US in mid-2005.

Antibacterial spectrum is the same as erythromycin but it is active against *Mycobacterium avium* complex (MAV), *M. leprae* and atypical mycobacteria.

Clarithromycin prevents bacteria from growing by interfering with their protein synthesis. Clarithromycin binds to the subunit 50S of the bacterial ribosome and thus inhibits the translation of peptides. Clarithromycin has similar antimicrobial spectrum as erythromycin but is more effective against certain gram-negative bacteria, particularly *Legionella pneumophila*. Besides this bacteriostatic effect, clarithromycin also has bactericidal effect on certain strains such as *Haemophilus influenzae, Streptococcus pneumoniae* and *Neisseria gonorrhoeae*.

Unlike erythromycin, clarithromycin is acid-stable and can therefore be taken orally without being protected from gastric acids. It is readily absorbed, and diffused into most tissues and phagocytes. Due to the high concentration in phagocytes, clarithromycin is actively transported to the site of infection. During active phagocytosis, large concentrations of clarithromycin are released. The concentration of clarithromycin in the tissues can be over 10 times higher than in plasma. Highest concentrations were found in liver and lung tissue.

Clarithromycin has a fairly rapid first-pass hepatic metabolism. However, 14-hydroxy clarithromycin, clarithromycin's metabolite, is almost twice as active and has a half life of 7 hours compared to clarithromycin's 5. Clarithromycin and its metabolites main routes of elimination are urinary and biliary excretion. Of all the drugs in its class, clarithromycin has the best bioavailability at 50%, which makes it amenable to oral administration.

Most common side-effects are gastrointestinal, including diarrhea, nausea, extreme irritability, abdominal pain and vomiting, facial swelling. Less common side-effects include headaches, hallucinations (auditory and visual), dizziness/motion sickness, rashes, alteration in senses of smell and taste, including a metallic taste that lasts the entire time one takes it. Dry mouth, panic and/or anxiety attacks and nightmares have also been reported albeit less frequently. In more serious cases it has been known to cause jaundice, cirrhosis, and kidney problems including renal failure. Uneven heartbeats, chest pain, and shortness of breath have also been reported while taking this drug.

Adverse effects of clarithromycin in the central nervous system include dizziness, ototoxicity and headaches, but delirium and mania are also uncommon side effects. When taken along with some statins, drugs used to reduce blood serum cholesterol levels, muscle pain may occur. There is also the risk of oral candidiasis, due to the increased yeast production in the body from the antibiotics.

Azithromycin.

Azithromycin is an azalide, a subclass of macrolide antibiotics. Azithromycin is one of the world's best-selling antibiotics, marketed in the United States under the name Zithromax, and under a variety of brand names and generic labels worldwide. It is derived from erythromycin; however, it differs in chemical structure from erythromycin in that a methyl-substituted nitrogen atom is incorporated into the lactone ring, thus making the lactone ring 15-membered.

Azithromycin is used to treat or prevent certain bacterial infections, most often those causing middle ear infections, strep throat, pneumonia, typhoid, and sinusitis. In recent years, it has been used primarily to prevent bacterial infections in infants and those with weaker immune systems. It is also effective against certain sexually transmitted infections, such as non-gonococcal urethritis, chlamydia, and cervicitis. Recent studies have indicated it also to be effective against late-onset asthma, but these findings are controversial and not widely accepted.

Azithromycin is used to treat many different infections including acute otitis media, streptococcal pharyngitis, gastrointestinal infections such as traveler's diarrhea, respiratory tract infections such as pneumonia, cellulitis, babesiosis, bartonella, chancroid, chlamydia, cholera, donovanosis, leptospirosis, lyme disease, malaria, mycobacterium avium complex, neisseria meningitis, pelvic inflammatory disease, pertussis, scrub typhus, syphilis, toxoplasmosis, and salmonella. It is used to prevent bacterial endocarditis and some sexually transmitted illnesses post sexual assault.

It has a similar antimicrobial spectrum as erythromycin, but is more effective against certain Gram-negative bacteria, in particular, *Haemophilus influenzae*. Azithromycin resistance has been described and is endemic in many areas. It is notably ineffective against MRSA. Azithromycin has been shown to be effective against malaria when used in combination with artesunate or quinine; the optimal dose for this is not yet known.

Most common side-effects are gastrointestinal: diarrhea (5%), nausea (3%), abdominal pain (3%), and vomiting. Fewer than 1% of patients stop taking the drug due to side-effects. Nervousness, dermatologic reactions, and anaphylaxis have been reported. As with all antimicrobial agents, pseudomembranous colitis can occur during and up to several weeks after azithromycin therapy. This drug may interfere with the effectiveness of birth control pills; other forms of contraception may be required during the treatment period. Azithromycin suspension has an objectionable taste, so can be difficult to administer to young children, i.e., 2-5 years, who may spit it out.

Occasional patients have developed cholestatic hepatitis or delirium. Accidental intravenous overdosage in an infant caused severe heart block, resulting in residual encephalopathy.

Azithromycin prevents bacteria from growing by interfering with their protein synthesis. Azithromycin binds to the 50S subunit of the bacterial ribosome, and thus inhibits translation of mRNA. Nucleic acid synthesis is not affected.

Unlike erythromycin, azithromycin is acid-stable and can therefore be taken orally with no need of protection from gastric acids. It is readily absorbed, but its absorption is greater on an empty stomach. Time to peak concentration in adults is 2.1 to 3.2 hours for oral dosage forms and one to two hours after a dose. Due to the high concentration in phagocytes, azithromycin is actively transported to the site of infection. During active phagocytosis, large concentrations of azithromycin are released. The concentration of azithromycin in the tissues can be over 50 times higher than in plasma. This is due to ion trapping and the high lipid solubility (Volume of distribution is too low).

Azithromycin's half-life allows a large single dose to be administered and yet maintain bacteriostatic levels in the infected tissue for several days. The new extended-release formulation of azithromycin "Zmax," A-Max is a liquid oral suspension that releases the drug in a single 2-g dose. With the macrolide technology of Zmax, this allows the drug to bypass the stomach, reducing gastrointestinal side-effects of high-dose azithromycin.

Azithromycin is commonly administered in tablet or oral suspension (a one-dose version was made available in 2005). It is also available for intravenous injection and in a 1% ophthalmic solution. Tablets come in doses of 250 mg and 500 mg. Oral suspension comes in strengths of 100 mg/5 mL and 200 mg/5 mL. The 250 mg tablets are often dispensed in packages of six and commonly referred to as a "Z-Pak," whereas the 500 mg tablets are commonly available commercially in a pack of three tablets, or "Tri-Pak," intended as a three-day treatment. A common dose of oral azithromycin therapy consists of a "double dose" of medication on the first day of treatment and subsequent treatment for four or five additional days. With the "Z-Pak," this means two 250 mg tablets (a total of 500 mg) on the first day and one 250 mg tablet once daily for the next four days.

Pfizer brand-name, i.e., Zithromax, azithromycin tablets are mottled pink, unscored, film-coated, modified-oval-shaped tablets containing azithromycin monohydrate and the following inactive ingredients: butylated hydroxytoluene, calcium phosphate, carmine, colloidal silicon dioxide, FD&C red #40 lake, FD&C yellow #6 lake, hypromellose (2910, 15cP), lactose monohydrate, magnesium stearate, pregelatinized starch, sodium lauryl sulfate, talc, titanium dioxide, and triacetin.

Fluoroquinolones.

The quinolones are a family of synthetic broad-spectrum antibiotics. The term quinolone(s) refers to potent synthetic chemotherapeutic antibacterials. The first generation of the quinolones begins with the introduction of nalidixic acid in 1962 for treatment of urinary tract infections in humans. Nalidixic acid was discovered by George Lesher and coworkers in a distillate during an attempt at chloroquine synthesis. They prevent bacterial DNA from unwinding and duplicating.

Quinolones, in comparison to other antibiotic classes, have the highest risk of causing colonization with MRSA and *Clostridium difficile*. For this reason, a general avoidance of fluoroquinolones is recommended based on the available evidence and clinical guidelines. The majority of quinolones in clinical use belong to the subset fluoroquinolones, which have a fluorine atom attached to the central ring system, typically at the 6-position or C-7 position. Debates are still taking place as to whether or not the effectiveness of fluoroquinolones for the treatment of respiratory disorders is similar to that of other antibiotic classes.

Fluoroquinolone use for pneumonia is increasing, and with it so is bacterial resistance to fluoroquinolones. The majority of the prescribing of fluoroquinolones is inappropriate, with less than four percent of people prescribed quinolones being appropriate according to clinical guidelines. Clinical guidelines in Canada recommend fluoroquinolones only for outpatient treatment of pneumonia in a small number of patients, such as those with certain comorbid conditions, e.g., patients with a history of COPD, or those with recent use of antibiotics. For severe forms of community-acquired pneumonia, the fluoroquinolones are associated with improved treatment rates, but with no differences found in mortality between other antibiotic classes.

Fluoroquinolones are not recommended as first-line antibiotics for acute sinusitis, as this condition is usually self-limiting, and the risks outweigh the benefits in comparison to other antibiotic classes.

Antibiotics including fluoroquinolones can be effective in some cases of bronchitis. However, only about 5-10% of bronchitis cases are caused by a bacterial infection; most cases of bronchitis are caused by a viral infection and are self-limiting and resolve themselves in a few weeks. It has been recommended that antibiotics are limited in most cases to those whose symptoms fail to resolve on their own.

Fluoroquinolones are often used for genitourinary infections; in general they are recommended only after other antibiotic regimens have failed. However, for serious acute cases of pyelonephritis or bacterial prostatitis where the patient may need to be hospitalised, fluoroquinolones are recommended as first-line therapy. Prostatitis has been termed "the waste basket of clinical ignorance" by prominent Stanford University urologist Dr. Thomas Stamey. Campbell's Urology, the urologist's most authoritative reference text, identifies only about 5% of all patients with prostatitis as having bacterial prostatitis, which can be "cured" at least in the short term by antibiotics. In other words, 95% of men with prostatitis have little hope for a cure with antibiotics alone, since they do not actually have any identifiable bacterial infection.

In general, fluoroquinolones are well tolerated, with most side effects being mild to moderate. On occasion, serious adverse effects occur. Some of the serious adverse effects that occur more commonly with fluoroquinolones than with other antibiotic drug classes include CNS and tendon toxicity. The currently marketed quinolones have safety profiles similar to those of other antimicrobial classes. Fluoroquinolones are sometimes associated with an QTc interval prolongation and cardiac arrhythmias, convulsions, tendon rupture, torsade de pointes and hypoglycemia.

These adverse reactions are a class effect of all quinolones; however, certain quinolones are more strongly associated with increased toxicity to certain organs. For example, moxifloxacin carries a higher risk of QTc prolongation, and gatifloxacin has been most frequently linked to disturbed blood sugar levels, although all quinolones carry these risks. Some quinolones were withdrawn from the market because of these adverse events (for example, sparfloxacin was associated with phototoxicity and QTc prolongation, thrombocytopenia and nephritis were seen with tosufloxacin, and hepatotoxicity with trovafloxacin). Simultaneous use of corticosteroids is present in almost one-third of quinolone-associated tendon rupture. The risk of adverse events is further increased if the dosage is not properly adjusted, for example if there is renal insufficiency.

The serious events may occur during therapeutic use at therapeutic dose levels or with acute overdose. At therapeutic doses, they include: CNS toxicity, cardiovascular toxicity, tendon/articular toxicity, and, rarely, hepatic toxicity. Caution is required in patients with liver disease. Events that may occur in acute overdose are rare, and include renal failure and seizure. Susceptible groups of patients, such as children and the elderly, are at greater risk of adverse reactions during therapeutic use. Adverse reactions may manifest during, as well as after fluoroquinolone therapy has been completed.

The CNS is an important target for fluoroquinolone-mediated neurotoxicity. Adverse event reporting in Italy by doctors showed fluoroquinolones among the top three prescribed drugs for causing adverse neurological and psychiatric effects. These neuropsychiatric effects included tremor, confusion, anxiety, insomnia, agitation, and, in severe cases, psychosis. Moxifloxacin came out worst among the quinolones for causing CNS toxicity.

The basic pharmacophore, or active structure, of the fluoroquinolone class is based upon the quinoline ring system. The addition of the fluorine atom at C6 is what distinguishes the successive-generation fluoroquinolones from the first-generation quinolones. The addition of the C6 fluorine atom has since been demonstrated to not be required for the antibacterial activity of this class (circa 1997).

Various substitutions made to the quinoline ring resulted in the development of numerous fluoroquinolone drugs available today. Each substitution is associated with a number of specific adverse reactions, as well as increased activity against bacterial infections, whereas the quinoline ring, in and of itself, has been associated with severe and even fatal adverse reactions.

Cefuroxime.

Cefuroxime is a second-generation cephalosporin antibiotic that has been widely available in the USA as Ceftin since 1977. GlaxoSmithKline sells the antibiotic in the United Kingdom (and other countries, such as Australia, Turkey, Israel, Bangladesh, Thailand, Hungary and Poland) under the name Zinnat.

As for the other cephalosporins, although as a second-generation it is less susceptible to beta-lactamase and so may have greater activity against *Haemophilus influenzae, Neisseria gonorrhoeae* and Lyme disease. Unlike other second generation cephalosporins, cefuroxime can cross the blood-brain-barrier.

Cefuroxime is generally well tolerated and side effects are usually transient. Cefuroxime, if ingested with food, is both better absorbed and less likely to cause its most common side effects of diarrhea, nausea, vomiting, headaches/migraines, dizziness and abdominal pain.

Although there is a widely quoted cross-allergy risk of 10% between cephalosporins and penicillin, recent assessments have shown no increased risk for cross-allergy for cefuroxime and several other $2^{nd}$ generation or later cephalosporins.

3. Vancomycin and Levoflaxin

Vancomycin.

Vancomycin (INN) is a glycopeptide antibiotic used in the prophylaxis and treatment of infections caused by Gram-positive bacteria. It has traditionally been reserved as a drug of "last resort," used only after treatment with other antibiotics had failed, although the emergence of vancomycin-resistant organisms means that it is increasingly being displaced from this role by linezolid (Zyvox) available PO and IV and daptomycin (Cubicin) IV and quinupristin/dalfopristin (Synercid) IV.

Vancomycin was first isolated in 1953 by Edmund Kornfeld (working at Eli Lilly) from a soil sample collected from the interior jungles of Borneo by a missionary. The organism that produced it was eventually named *Amycolatopsis orientalis*. The original indication for vancomycin was for the treatment of penicillin-resistant *Staphylococcus aureus*. One advantage that was quickly apparent is that staphylococci did not develop significant resistance despite serial passage in culture media containing vancomycin. The rapid development of penicillin resistance by staphylococci led to the compound's being fast-tracked for approval by the FDA in 1958. Eli Lilly first marketed vancomycin hydrochloride under the trade name Vancocin and as COVANC from Nucleus, India.

Vancomycin never became the first-line treatment for *Staphylococcus aureus* for several reasons. First, it possesses poor oral bioavailability. Also, it must be given intravenously for most infections. In addition, β-Lactamase-resistant semi-synthetic penicillins such as methicillin (and its successors, nafcillin and cloxacillin) were subsequently developed, which have better activity against non-MRSA staphylococci.

An oral form of vancomycin was originally approved by the FDA in 1986 for the treatment of *Clostridium difficile*-induced pseudomembranous colitis. It is not orally absorbed into the blood and remains in the gastrointestinal tract to eradicate *C. difficle*. This product is currently marketed by ViroPharma in the USA.

Vancomycin biosynthesis occurs via different nonribosomal protein synthases (NRPSs). The enzymes determine the amino acid sequence during its assembly through its 7 modules. Before Vancomycin is assembled through NRPS, the amino acids are first modified. L-tyrosine is modified to become the β-hydroxychlorotyrosine (β-hTyr) and 4-hydroxyphenylglycine (HPG) residues. On the other hand, acetate is used to derive the 3,5 dihydroxyphenylglycine ring (3,5-DPG).

Nonribosomal peptide synthesis occurs through distinct modules that can load and extend the protein by one amino acid through the amide bond formation at the contact sites of the activating domains. Each module typically consists of an adenylation (A) domain, a peptidyl carrier protein (PCP) domain, and a condensation (C) or elongation domain. In the A domain, the specific amino acid is activated by converting into an aminoacyl adenylate enzyme complex attached to a 4'phosphopantetheine cofactor by thioesterification. The complex is then transferred to the PCP domain with the expulsion of AMP. The PCP domain uses the attached 4'-phosphopantethein prosthetic group to load the growing peptide chain and their precursors. In the biosynthesis of Vancomycin, additional modification domains are present, such as the epimerization (E) domain, which is used isomerizes the amino acid from one stereochemistry to another, and a thioesterase domain (TE) is used as a catalyst for cyclization and releases of the molecule via a thioesterase scission.

After the linear heptapeptide molecule is synthesized, Vancomycin has to undergo further modifications, such as oxidative cross-linking and glycosylation, in trans, by distinct enzymes, referred to as tailoring enzymes, in order to become biologically active. To convert the linear heptapeptide, eight enzymes are used. With the help of these enzymes, β-hydroxyl groups are introduced onto tyrosine residues 2 and 6, and coupling occurs for rings 5 and 7, rings 4 and 6, and rings 4 and 2. In addition, a haloperoxidase is used to attach the chlorine atoms onto rings 2 and 6 via an oxidative process.

Vancomycin acts by inhibiting proper cell wall synthesis in Gram-positive bacteria. Due to the different mechanism by which Gram-negative bacteria produce their cell walls and the various factors related to entering the outer membrane of Gram-negative organisms, vancomycin is not active against Gram-negative bacteria (except some non-gonococcal species of *Neisseria*).

The large hydrophilic molecule is able to form hydrogen bond interactions with the terminal D-alanyl-D-alanine moieties of the NAM/NAG-peptides. Under normal circumstances, this is a five-point interaction. This binding of vancomycin to the D-Ala-D-Ala prevents cell wall synthesis in two ways. It prevents the synthesis of the log polymers of N-acetylmuramic acid (NAM) and N-acetylglucosamine (NAG) that form the backbone strands of the bacterial cell wall, and it prevents the backbone polymers that do manage to form from cross-linking with each other.

Although vancomycin levels are usually monitored, in an effort to reduce adverse events, the value of this is not beyond debate. Peak and trough levels are usually monitored, and, for research purposes, the area under the curve is also sometimes used. Toxicity is best monitored by looking at trough values. Common adverse drug reactions (≥1% of patients) associated with IV vancomycin include: local pain, which may be severe and/or thrombophlebitis.

Damage to the kidneys and to the hearing were a side-effect of the early impure versions of vancomycin, and these were prominent in the clinical trials conducted in the mid-1950s. Later trials using purer forms of vancomycin found that nephrotoxicity is an infrequent adverse effect (0.1-1% of patients), but that this is accentuated in the presence of aminoglycosides.

Rare adverse effects (<0.1% of patients) include: anaphylaxis, toxic epidermal necrolysis, erythema multiforme, red man syndrome (see below), superinfection, thrombocytopenia, neutropenia, leucopenia, tinnitus, dizziness and/or ototoxicity (see below).

It has recently been emphasized that vancomycin can induce platelet-reactive antibodies in the patient, leading to severe thrombocytopenia and bleeding with florid petechial hemorrhages, ecchymoses, and wet purpura.

Vancomycin must be given intravenously (IV) for systemic therapy, since it does not cross through the intestinal lining. It is a large hydrophilic molecule that partitions poorly across the gastrointestinal mucosa. The only indication for oral vancomycin therapy is in the treatment of pseudomembranous colitis, where it must be given orally to reach the site of infection in the colon. Following oral administration, the fecal concentration of vancomycin is around 500 μg/mL (sensitive strains of *C. difficile* have a mean inhibitory concentration of ≤2 g/mL)

Inhaled vancomycin has also been used (off-label), via nebulizer, for treatment of various infections of the upper and lower respiratory tract.

The caustic nature of vancomycin makes IV therapy using peripheral lines a risk for thrombophlebitis. Ideally, central lines, PICCs, or infusion ports should be used.

Vancomycin has traditionally been considered a nephrotoxic and ototoxic drug, based on observations by early investigators of elevated serum levels in renally impaired patients that had experienced ototoxicity, and subsequently through case reports in the medical literature. However, as the use of vancomycin increased with the spread of MRSA beginning in the 1970s, it was recognised that the previously reported rates of toxicity were not being observed. This was attributed to the removal of the impurities present in the earlier formulation of the drug, although those impurities were not specifically tested for toxicity.

Subsequent reviews of accumulated case reports of vancomycin-related nephrotoxicity found that many of the patients had also received other known nephrotoxins, in particular, aminoglycosides. Most of the rest had other confounding factors, or insufficient data regarding the possibility of such, that prohibited the clear association of vancomycin with the observed renal dysfunction. The most methodologically-sound investigations indicate that the actual incidence of vancomycin-induced nephrotoxicity is around 5-7%. To put this into context, similar rates of renal dysfunction have been reported for cefamandole and benzylpenicillin, two reputedly non-nephrotoxic antibiotics.

In addition, evidence to relate nephrotoxicity to vancomycin serum levels is inconsistent. Some studies have indicated an increased rate of nephrotoxicity when trough levels exceed 10 μg/mL, but others have not reproduced these results. Nephrotoxicity has also been observed with concentrations within the "therapeutic" range as well. In essence, the reputation of vancomycin as a nephrotoxin is over-stated, and it has not been demonstrated that maintaining vancomycin serum levels within certain ranges will prevent its nephrotoxic effects, when they do occur.

Attempts to establish rates of vancomycin-induced ototoxicity are even more difficult due to the scarcity of quality evidence. The current consensus is that clearly related cases of vancomycin ototoxicity are rare. The association between vancomycin serum levels and ototoxicity is also uncertain. While cases of ototoxicity have been reported in patients whose vancomycin serum level exceeded 80 μg/mL, cases have been reported in patients with therapeutic levels as well. Thus, it also remains unproven that therapeutic drug monitoring of vancomycin for the purpose of maintaining "therapeutic" levels will prevent ototoxicity.

Another area of controversy and uncertainty concerns the question of whether, and, if so, to what extent, vancomycin increases the toxicity of other nephrotoxins. Clinical studies have yielded variable results, but animal models indicate that there probably is some increased nephrotoxic effect when vancomycin is added to nephrotoxins such as aminoglycosides. However, a dose- or serum level-effect relationship has not been established.

Levofloxacin.

Levofloxacin is a synthetic chemotherapeutic antibiotic of the fluoroquinolone drug class and is used to treat severe or life-threatening bacterial infections or bacterial infections that have failed to respond to other antibiotic classes. It is sold under various brand names, such as Levaquin and Tavanic, the most common. In form of ophthalmic solutions it is known as Oftaquix, Quixin and Iquix.

Levofloxacin is a chiral fluorinated carboxyquinolone. Investigation of ofloxacin, an older drug that is the racemic mixture, found that the 1 form [the (−)-(S) enantiomer] is more active. This specific component is levofloxacin. Levofloxacin is available in tablet form, injection, oral solution, as well as used in prescription eye and ear drops.

Levofloxacin interacts with a number of other drugs, as well as a number of herbal and natural supplements. Such interactions increase the risk of cardiotoxicity and arrhythmias, anticoagulation, the formation of non-absorbable complexes, as well as increasing the risk of toxicity.

Levofloxacin is associated with a number of serious and life-threatening adverse reactions as well as spontaneous tendon ruptures and irreversible peripheral neuropathy. Such reactions may manifest long after therapy had been completed and in severe cases may result in life-long disabilities. Hepatoxicity has also been reported with the use of levofloxacin.

As of 2011 the FDA has added two Black box warnings for this drug in reference to spontaneous tendon ruptures and the fact that levofloxacin may cause worsening of myasthenia gravis symptoms, including muscle weakness and breathing problems. Such an adverse reaction is a potentially life-threatening event and may require ventilatory support.

Levofloxacin is used to treat a number of infections including: respiratory tract infections, cellulitis, urinary tract infections, prostatitis, anthrax, endocarditis, meningitis, pelvic inflammatory disease, and traveler's diarrhea.

In the adult population Oral and I.V. levofloxacin is limited to the treatment of proven serious and life-threatening bacterial infections such as Urinary Tract Infections, Community-acquired pneumonia, Skin and Skin Structure Infections, Nosocomial Pneumonia, Chronic bacterial prostatitis, Inhalational Anthrax, Acute Bacterial Sinusitis, Acute Bacterial Exacerbation of Chronic Bronchitis, and Acute Pyelonephritis.

Oral and I.V. Levaquin are not licensed by the FDA for use in children other than the exception (inhalational anthrax), due to the risk of reversible or irreversible injury to the musculoskeletal system. Although claimed to be effective, levofloxacin is not to be considered a first line agent for inhalational anthrax in the pediatric population due to severe adverse reactions involving the musculoskeletal system and other serious adverse reactions, including fatalities.

The CDC revoked its recommendation regarding the use of fluoroquinolones (ciprofloxacin) as a first-line agent in treating anthrax (in part) due to the risk of adverse reactions documented within the Antimicrobial Postexposure Prophylaxis for Anthrax study (aka Cipro 60-day study). However, the fluoroquinolones are licensed to treat lower respiratory infections in children with cystic fibrosis in the UK.

Serious adverse events occur more commonly with fluoroquinolones than with any other antibiotic drug classes. In most adverse reactions are mild to moderate; however, on occasion, serious adverse effects occur. There have been a number of regulatory actions taken as a result of such adverse reactions, which included published warnings, additional warnings and safety information added to the package inserts, which includes Black Box Warnings together with the issuance of "Dear Doctor Letters" concerning the recent addition of the Black Box Warnings.

In 2004, the FDA requested new warning labels to be added to all of the Fluoroquinolones, including levofloxacin, regarding peripheral neuropathy (irreversible nerve damage), tendon damage, heart problems (prolonged QT Interval/torsades de pointes), pseudomembranous colitis, rhabdomyolysis (muscle wasting), Stevens-Johnson Syndrome, as well as concurrent usage of NSAIDs contributing to the severity of these reactions. Subsequent to this, on Jun. 25, 2007, the FDA required the manufacturer to add an additional warning to the package inserts that stated that "Other serious and sometimes fatal events, some due to hypersensitivity, and some due to uncertain etiology, have been reported in patients receiving therapy with quinolones, including levofloxacin."

Serious visual complications have also been reported to occur with ophthalmic fluoroquinolone therapy, which may also occur with levofloxacin eye drops, especially corneal perforation, but also evisceration and enucleation. This increased incidents of corneal perforation may be due to fluoroquinolones causing alterations in stromal collagen, leading to a reduction in tectonic strength. As noted previously permanent double vision (diplopia) has also been reported.

Levofloxacin is the L-isomer of the racemate ofloxacin, a quinolone antimicrobial agent. In chemical terms, levofloxacin, a chiral fluorinated carboxyquinolone, is the pure (−)-(S)-enantiomer of the racemic drug substance ofloxacin. The chemical name is (−)-(S)-9-fluoro-2,3-dihydro-3-methyl-10-(4-methyl-1-piperazinyl)-7-oxo-7H-pyrido[1,2,3-de]-1,4-benzoxazine-6-carboxylic acid hemihydrate. The empirical formula is $C_{18}H_{20}FN_3O_4 \cdot \tfrac{1}{2}H_2O$, and the molecular weight is 370.38. Levofloxacin is a light-yellowish-white to yellow-white crystal or crystalline powder.

Levofloxacin pharmacokinetics are linear and predictable after single and multiple oral or IV dosing regimens. Levofloxacin is rapidly and, in essence, completely absorbed after oral administration. Peak plasma concentrations are usually attained one to two hours after oral dosing. The plasma concentration profile of levofloxacin after IV administration is similar and comparable in extent of exposure (AUC) to that observed for LEVAQUIN Tablets when equal doses (mg/mg) are administered. Levofloxacin is excreted largely as unchanged drug in the urine. The mean terminal plasma elimination half-life of levofloxacin ranges from approximately 6 to 8 hours following single or multiple doses of levofloxacin given orally or intravenously. Glucuronidation and hydroxylation have been cited as one of the major metabolic pathways for levofloxacin hydrochloride. However the drug card for levofloxacin (DB01137) states that the biotransformation information is not available. Specific information regarding biotransformation does not appear to be readily available within the package inserts.

Levofloxacin is a broad-spectrum antibiotic that is active against both Gram-positive and Gram-negative bacteria. It functions by inhibiting DNA gyrase, a type II topoisomerase, and topoisomerase iv, which is an enzyme necessary to separate replicated DNA, thereby inhibiting cell division.

The fluoroquinolones interfere with DNA replication by inhibiting an enzyme complex called DNA gyrase. This can also affect mammalian cell replication. In particular, some congeners of this drug family display high activity not only against bacterial topoisomerases but also against eukaryotic topoisomerases, and are toxic to cultured mammalian cells and in vivo tumor models. Although the quinolone is highly toxic to mammalian cells in culture, its mechanism of cytotoxic action is not known. Quinolone-induced DNA damage was first reported in 1986.

V. Antibody Conjugates

Antibodies of the present invention may be linked to at least one agent to form an antibody conjugate. In order to increase the efficacy of antibody molecules as diagnostic or therapeutic agents, it is conventional to link or covalently bind or complex at least one desired molecule or moiety. Such a molecule or moiety may be, but is not limited to, at least one effector or reporter molecule. Effector molecules comprise molecules having a desired activity, e.g., cytotoxic activity. Non-limiting examples of effector molecules which have been attached to antibodies include toxins, antibiotics, therapeutic enzymes, radionuclides, anti-cancer agents, antiviral agents, chelating agents, cytokines, growth factors, and oligo- or polynucleotides.

By contrast, a reporter molecule is defined as any moiety which may be detected using an assay. Non-limiting examples of reporter molecules which have been conjugated to antibodies include enzymes, radiolabels, haptens, fluorescent labels, phosphorescent molecules, chemiluminescent molecules, chromophores, photoaffinity molecules, colored particles or ligands, such as biotin.

Antibody conjugates are generally preferred for use as diagnostic agents. Antibody diagnostics generally fall within two classes, those for use in in vitro diagnostics, such as in a variety of immunoassays, and those for use in vivo diagnostic protocols, generally known as "antibody-directed imaging." Many appropriate imaging agents are known in the art, as are methods for their attachment to antibodies (see, for e.g., U.S. Pat. Nos. 5,021,236, 4,938,948, and 4,472,509). The imaging moieties used can be paramagnetic ions, radioactive isotopes, fluorochromes, NMR-detectable substances, and X-ray imaging agents.

In the case of paramagnetic ions, one might mention by way of example ions such as chromium (III), manganese (II), iron (II), iron (II), cobalt (II), nickel (II), copper (II), neodymium (III), samarium (III), ytterbium (III), gadolinium (III), vanadium (II), terbium (III), dysprosium (III), holmium (III) and/or erbium (III), with gadolinium being particularly preferred. Ions useful in other contexts, such as X-ray imaging, include but are not limited to lanthanum (III), gold (III), lead (II), and especially bismuth (III).

In the case of radioactive isotopes for therapeutic and/or diagnostic application, one might mention astatine$^{211}$, $^{14}$carbon, $^{51}$chromium, $^{36}$chlorine, $^{57}$cobalt, $^{58}$cobalt, copper$^{67}$, $^{152}$Eu, gallium$^{67}$, $^{3}$hydrogen, iodine$^{123}$, iodine$^{125}$, iodine$^{131}$, indium$^{111}$, $^{59}$iron, $^{32}$phosphorus, rhenium$^{186}$, rhenium$^{188}$, $^{75}$selenium, $^{35}$sulphur, technicium$^{99m}$ and/or yttrium$^{90}$. $^{125}$I is often being preferred for use in certain embodiments, and technicium$^{99m}$ and/or indium$^{111}$ are also often preferred due to their low energy and suitability for long range detection. Radioactively labeled monoclonal antibodies of the present invention may be produced according to well-known methods in the art. For instance, monoclonal antibodies can be iodinated by contact with sodium and/or potassium iodide and a chemical oxidizing agent such as sodium hypochlorite, or an enzymatic oxidizing agent, such as lactoperoxidase. Monoclonal antibodies according to the invention may be labeled with technetium$^{99m}$ by ligand exchange process, for example, by reducing pertechnate with stannous solution, chelating the reduced technetium onto a Sephadex column and applying the antibody to this column. Alternatively, direct labeling techniques may be used, e.g., by incubating pertechnate, a reducing agent such as SNCl$_2$, a buffer solution such as sodium-potassium phthalate solution, and the antibody. Intermediary functional groups which are often used to bind radioisotopes which exist as metallic ions to antibody are diethylenetriaminepentaacetic acid (DTPA) or ethylene diaminetetracetic acid (EDTA).

Among the fluorescent labels contemplated for use as conjugates include Alexa 350, Alexa 430, AMCA, BODIPY 630/650, BODIPY 650/665, BODIPY-FL, BODIPY-R6G, BODIPY-TMR, BODIPY-TRX, Cascade Blue, Cy3, Cy5,6-FAM, Fluorescein Isothiocyanate, HEX, 6-JOE, Oregon Green 488, Oregon Green 500, Oregon Green 514, Pacific Blue, REG, Rhodamine Green, Rhodamine Red, Renographin, ROX, TAMRA, TET, Tetramethylrhodamine, and/or Texas Red.

Another type of antibody conjugates contemplated in the present invention are those intended primarily for use in vitro, where the antibody is linked to a secondary binding ligand and/or to an enzyme (an enzyme tag) that will generate a colored product upon contact with a chromogenic substrate. Examples of suitable enzymes include urease, alkaline phosphatase, (horseradish) hydrogen peroxidase or glucose oxidase. Preferred secondary binding ligands are biotin and avidin and streptavidin compounds. The use of such labels is well known to those of skill in the art and are described, for example, in U.S. Pat. Nos. 3,817,837, 3,850,752, 3,939,350, 3,996,345, 4,277,437, 4,275,149 and 4,366,241.

Yet another known method of site-specific attachment of molecules to antibodies comprises the reaction of antibodies with hapten-based affinity labels. Essentially, hapten-based affinity labels react with amino acids in the antigen binding site, thereby destroying this site and blocking specific antigen reaction. However, this may not be advantageous since it results in loss of antigen binding by the antibody conjugate.

Molecules containing azido groups may also be used to form covalent bonds to proteins through reactive nitrene intermediates that are generated by low intensity ultraviolet light (Potter and Haley, 1983). In particular, 2- and 8-azido analogues of purine nucleotides have been used as site-directed photoprobes to identify nucleotide binding proteins in crude cell extracts (Owens & Haley, 1987; Atherton et al., 1985). The 2- and 8-azido nucleotides have also been used to map nucleotide binding domains of purified proteins (Khatoon et al., 1989; King et al., 1989; Dholakia et al., 1989) and may be used as antibody binding agents.

Several methods are known in the art for the attachment or conjugation of an antibody to its conjugate moiety. Some attachment methods involve the use of a metal chelate complex employing, for example, an organic chelating agent such a diethylenetriaminepentaacetic acid anhydride (DTPA); ethylenetriaminetetraacetic acid; N-chloro-p-toluenesulfonamide; and/or tetrachloro-3α-6α-diphenylglycouril-3 attached to the antibody (U.S. Pat. Nos. 4,472,509 and 4,938,948). Monoclonal antibodies may also be reacted with an enzyme in the presence of a coupling agent such as glutaraldehyde or periodate. Conjugates with fluorescein markers are prepared in the presence of these coupling agents or by reaction with an isothiocyanate. In U.S. Pat. No. 4,938,948, imaging of breast tumors is achieved using monoclonal antibodies and the detectable imaging moieties are bound to the antibody using linkers such as methyl-p-hydroxybenzimidate or N-succinimidyl-3-(4-hydroxyphenyl)propionate.

In other embodiments, derivatization of immunoglobulins by selectively introducing sulfhydryl groups in the Fc region of an immunoglobulin, using reaction conditions that do not alter the antibody combining site are contemplated. Antibody conjugates produced according to this methodology are disclosed to exhibit improved longevity, specificity and sensitivity (U.S. Pat. No. 5,196,066, incorporated herein by reference). Site-specific attachment of effector or reporter molecules, wherein the reporter or effector molecule is conjugated to a carbohydrate residue in the Fc region have also been disclosed in the literature (O'Shannessy et al., 1987). This approach has been reported to produce diagnostically and therapeutically promising antibodies which are currently in clinical evaluation.

VI. Immunodetection Methods

In still further embodiments, the present invention concerns immunodetection methods for binding, purifying, removing, quantifying and otherwise generally detecting *S. pneumonia*. While such methods can be applied in a traditional detection sense, a more specific use will involve the generation of a antibody panel that is capable of distinguishing a single *S. pneumoniae* serotype from most of the serotypes listed above. By identifying the specific serotype responsible for an infection, one can better assess the need and type of therapy. Also, protective immunity is primarily attributed to serotype-specific IgG. Measurement of specific pneumococcal antibodies are clinically useful in two settings: (1) to determine protective status of a patient, and (2) to assess B-cell functionality in a patient with recurrent infection. Use of antibodies in accordance with the present invention in a competitive format will facilitate this type of assay as well.

Some immunodetection methods include enzyme linked immunosorbent assay (ELISA), radioimmunoassay (RIA), immunoradiometric assay, fluoroimmunoassay, chemiluminescent assay, bioluminescent assay, and Western blot to mention a few. In particular, a competitive assay for the detection and quantitation of antibodies in samples also is provided. The steps of various useful immunodetection methods have been described in the scientific literature, such as, e.g., Doolittle and Ben-Zeev (1999), Gulbis and Galand (1993), De Jager et al. (1993), and Nakamura et al. (1987). In general, the immunobinding methods include obtaining a sample suspected of containing *S. pneumoniae*, and contacting the sample with a first antibody in accordance with the present invention, as the case may be, under conditions effective to allow the formation of immunocomplexes.

These methods include methods for purifying *S. pneumoniae* or related antigens from a sample. The antibody will preferably be linked to a solid support, such as in the form of a column matrix, and the sample suspected of containing the *S. pneumoniae* or antigenic component will be applied to the immobilized antibody. The unwanted components will be washed from the column, leaving the *S. pneumoniae* antigen immunocomplexed to the immobilized antibody, which is then collected by removing the organism or antigen from the column.

The immunobinding methods also include methods for detecting and quantifying the amount of *S. pneumoniae* or related components in a sample and the detection and quantification of any immune complexes formed during the binding process. Here, one would obtain a sample suspected of containing *S. pneumoniae* or its antigens, and contact the sample with an antibody that binds *S. pneumoniae* or components thereof, followed by detecting and quantifying the amount of immune complexes formed under the specific conditions. In terms of antigen detection, the biological sample analyzed may be any sample that is suspected of containing *S. pneumoniae* or *S. pneumoniae* antigen, such as a tissue section or specimen, a homogenized tissue extract, a biological fluid, including blood and serum, or a secretion, such as feces or urine.

Contacting the chosen biological sample with the antibody under effective conditions and for a period of time sufficient to allow the formation of immune complexes (primary immune complexes) is generally a matter of simply adding the antibody composition to the sample and incubating the mixture for a period of time long enough for the antibodies to form immune complexes with, i.e., to bind to *S. pneumoniae* or antigens present. After this time, the sample-antibody composition, such as a tissue section, ELISA plate, dot blot or Western blot, will generally be washed to remove any non-specifically bound antibody species, allowing only those antibodies specifically bound within the primary immune complexes to be detected.

In general, the detection of immunocomplex formation is well known in the art and may be achieved through the application of numerous approaches. These methods are generally based upon the detection of a label or marker, such as any of those radioactive, fluorescent, biological and enzymatic tags. Patents concerning the use of such labels include U.S. Pat. Nos. 3,817,837, 3,850,752, 3,939,350, 3,996,345, 4,277,437, 4,275,149 and 4,366,241. Of course, one may find additional advantages through the use of a secondary binding ligand such as a second antibody and/or a biotin/avidin ligand binding arrangement, as is known in the art.

The antibody employed in the detection may itself be linked to a detectable label, wherein one would then simply detect this label, thereby allowing the amount of the primary immune complexes in the composition to be determined. Alternatively, the first antibody that becomes bound within the primary immune complexes may be detected by means of a second binding ligand that has binding affinity for the antibody. In these cases, the second binding ligand may be linked to a detectable label. The second binding ligand is itself often an antibody, which may thus be termed a "secondary" antibody. The primary immune complexes are contacted with the labeled, secondary binding ligand, or antibody, under effective conditions and for a period of time sufficient to allow the formation of secondary immune complexes. The secondary immune complexes are then generally washed to remove any non-specifically bound labeled secondary antibodies or ligands, and the remaining label in the secondary immune complexes is then detected.

Further methods include the detection of primary immune complexes by a two step approach. A second binding ligand, such as an antibody that has binding affinity for the antibody, is used to form secondary immune complexes, as described above. After washing, the secondary immune complexes are contacted with a third binding ligand or antibody that has binding affinity for the second antibody, again under effective conditions and for a period of time sufficient to allow the formation of immune complexes (tertiary immune complexes). The third ligand or antibody is linked to a detectable label, allowing detection of the tertiary immune complexes thus formed. This system may provide for signal amplification if this is desired.

One method of immunodetection uses two different antibodies. A first biotinylated antibody is used to detect the target antigen, and a second antibody is then used to detect the biotin attached to the complexed biotin. In that method, the sample to be tested is first incubated in a solution containing the first step antibody. If the target antigen is present, some of the antibody binds to the antigen to form a biotinylated antibody/antigen complex. The antibody/antigen complex is then amplified by incubation in successive solutions of streptavidin (or avidin), biotinylated DNA, and/or complementary biotinylated DNA, with each step adding additional biotin sites to the antibody/antigen complex. The amplification steps are repeated until a suitable level of amplification is achieved, at which point the sample is incubated in a solution containing the second step antibody against biotin. This second step antibody is labeled, as for example with an enzyme that can be used to detect the presence of the antibody/antigen complex by histoenzymology using a chromogen substrate. With suitable amplification, a conjugate can be produced which is macroscopically visible.

Another known method of immunodetection takes advantage of the immuno-PCR (Polymerase Chain Reaction) methodology. The PCR method is similar to the Cantor method up to the incubation with biotinylated DNA, however, instead of using multiple rounds of streptavidin and biotinylated DNA incubation, the DNA/biotin/streptavidin/antibody complex is washed out with a low pH or high salt buffer that releases the antibody. The resulting wash solution is then used to carry out a PCR reaction with suitable primers with appropriate controls. At least in theory, the enormous amplification capability and specificity of PCR can be utilized to detect a single antigen molecule.

A. ELISAs

Immunoassays, in their most simple and direct sense, are binding assays. Certain preferred immunoassays are the various types of enzyme linked immunosorbent assays (ELISAs) and radioimmunoassays (RIA) known in the art. Immunohistochemical detection using tissue sections is also particularly useful. However, it will be readily appreciated that detection is not limited to such techniques, and western blotting, dot blotting, FACS analyses, and the like may also be used.

In one exemplary ELISA, the antibodies of the invention are immobilized onto a selected surface exhibiting protein affinity, such as a well in a polystyrene microtiter plate. Then, a test composition suspected of containing the *S. pneumoniae* or *S. pneumoniae* antigen is added to the wells. After binding and washing to remove non-specifically bound immune complexes, the bound antigen may be detected. Detection may be achieved by the addition of another anti-*S. pneumoniae* antibody that is linked to a detectable label. This type of ELISA is a simple "sandwich ELISA." Detection may also be achieved by the addition of a second anti-*S. pneumoniae* antibody, followed by the addition of a third antibody that has binding affinity for the second antibody, with the third antibody being linked to a detectable label.

In another exemplary ELISA, the samples suspected of containing the *S. pneumoniae* or *S. pneumoniae* antigen are immobilized onto the well surface and then contacted with the anti-*S. pneumoniae* antibodies of the invention. After binding and washing to remove non-specifically bound immune complexes, the bound anti-*S. pneumoniae* antibodies are detected. Where the initial anti-*S. pneumoniae* antibodies are linked to a detectable label, the immune complexes may be detected directly. Again, the immune complexes may be detected using a second antibody that has binding affinity for the first anti-*S. pneumoniae* antibody, with the second antibody being linked to a detectable label.

Irrespective of the format employed, ELISAs have certain features in common, such as coating, incubating and binding, washing to remove non-specifically bound species, and detecting the bound immune complexes. These are described below.

In coating a plate with either antigen or antibody, one will generally incubate the wells of the plate with a solution of the antigen or antibody, either overnight or for a specified period of hours. The wells of the plate will then be washed to remove incompletely adsorbed material. Any remaining available surfaces of the wells are then "coated" with a nonspecific protein that is antigenically neutral with regard to the test antisera. These include bovine serum albumin (BSA), casein or solutions of milk powder. The coating allows for blocking of nonspecific adsorption sites on the immobilizing surface and thus reduces the background caused by nonspecific binding of antisera onto the surface.

In ELISAs, it is probably more customary to use a secondary or tertiary detection means rather than a direct procedure. Thus, after binding of a protein or antibody to the well, coating with a non-reactive material to reduce background, and washing to remove unbound material, the immobilizing surface is contacted with the biological sample to be tested under conditions effective to allow immune complex (antigen/antibody) formation. Detection of the immune complex then requires a labeled secondary binding ligand or antibody, and a secondary binding ligand or antibody in conjunction with a labeled tertiary antibody or a third binding ligand.

"Under conditions effective to allow immune complex (antigen/antibody) formation" means that the conditions preferably include diluting the antigens and/or antibodies with solutions such as BSA, bovine gamma globulin (BGG) or phosphate buffered saline (PBS)/Tween. These added agents also tend to assist in the reduction of nonspecific background.

The "suitable" conditions also mean that the incubation is at a temperature or for a period of time sufficient to allow effective binding. Incubation steps are typically from about 1 to 2 to 4 hours or so, at temperatures preferably on the order of 25° C. to 27° C., or may be overnight at about 4° C. or so.

Following all incubation steps in an ELISA, the contacted surface is washed so as to remove non-complexed material. A preferred washing procedure includes washing with a solution such as PBS/Tween, or borate buffer. Following the formation of specific immune complexes between the test sample and the originally bound material, and subsequent washing, the occurrence of even minute amounts of immune complexes may be determined.

To provide a detecting means, the second or third antibody will have an associated label to allow detection. Preferably, this will be an enzyme that will generate color development upon incubating with an appropriate chromogenic substrate.

Thus, for example, one will desire to contact or incubate the first and second immune complex with a urease, glucose oxidase, alkaline phosphatase or hydrogen peroxidase-conjugated antibody for a period of time and under conditions that favor the development of further immune complex formation (e.g., incubation for 2 hours at room temperature in a PBS-containing solution such as PBS-Tween).

After incubation with the labeled antibody, and subsequent to washing to remove unbound material, the amount of label is quantified, e.g., by incubation with a chromogenic substrate such as urea, or bromocresol purple, or 2,2'-azino-di-(3-ethyl-benzthiazoline-6-sulfonic acid (ABTS), or $H_2O_2$, in the case of peroxidase as the enzyme label. Quantification is then achieved by measuring the degree of color generated, e.g., using a visible spectra spectrophotometer.

In another embodiment, the present invention contemplates the use of competitive formats. This is particularly useful in the detection of S. pneumoniae antibodies in sample. In competition based assays, an unknown amount of analyte or antibody is determined by its ability to displace a known amount of labeled antibody or analyte. Thus, the quantifiable loss of a signal is an indication of the amount of unknown antibody or analyte in a sample.

Here, the inventor proposes the use of labeled S. pneumoniae monoclonal antibodies to determine the amount of S. pneumoniae antibodies in a sample. The basic format would include contacting a known amount of S. pneumoniae monoclonal antibody (linked to a detectable label) with S. pneumoniae antigen or particle. The S. pneumoniae antigen or organism is preferably attached to a support. After binding of the labeled monoclonal antibody to the support, the sample is added and incubated under conditions permitting any unlabeled antibody in the sample to compete with, and hence displace, the labeled monoclonal antibody. By measuring either the lost label or the label remaining (and subtracting that from the original amount of bound label), one can determine how much non-labeled antibody is bound to the support, and thus how much antibody was present in the sample.

B. Western Blot

The Western blot (alternatively, protein immunoblot) is an analytical technique used to detect specific proteins in a given sample of tissue homogenate or extract. It uses gel electrophoresis to separate native or denatured proteins by the length of the polypeptide (denaturing conditions) or by the 3-D structure of the protein (native/non-denaturing conditions). The proteins are then transferred to a membrane (typically nitrocellulose or PVDF), where they are probed (detected) using antibodies specific to the target protein.

Samples may be taken from whole tissue or from cell culture. In most cases, solid tissues are first broken down mechanically using a blender (for larger sample volumes), using a homogenizer (smaller volumes), or by sonication. Cells may also be broken open by one of the above mechanical methods. However, it should be noted that bacteria or environmental samples can be the source of protein and thus Western blotting is not restricted to cellular studies only. Assorted detergents, salts, and buffers may be employed to encourage lysis of cells and to solubilize proteins. Protease and phosphatase inhibitors are often added to prevent the digestion of the sample by its own enzymes. Tissue preparation is often done at cold temperatures to avoid protein denaturing.

The proteins of the sample are separated using gel electrophoresis. Separation of proteins may be by isoelectric point (pI), molecular weight, electric charge, or a combination of these factors. The nature of the separation depends on the treatment of the sample and the nature of the gel. This is a very useful way to determine a protein. It is also possible to use a two-dimensional (2-D) gel which spreads the proteins from a single sample out in two dimensions. Proteins are separated according to isoelectric point (pH at which they have neutral net charge) in the first dimension, and according to their molecular weight in the second dimension.

In order to make the proteins accessible to antibody detection, they are moved from within the gel onto a membrane made of nitrocellulose or polyvinylidene difluoride (PVDF). The membrane is placed on top of the gel, and a stack of filter papers placed on top of that. The entire stack is placed in a buffer solution which moves up the paper by capillary action, bringing the proteins with it. Another method for transferring the proteins is called electroblotting and uses an electric current to pull proteins from the gel into the PVDF or nitrocellulose membrane. The proteins move from within the gel onto the membrane while maintaining the organization they had within the gel. As a result of this blotting process, the proteins are exposed on a thin surface layer for detection (see below). Both varieties of membrane are chosen for their non-specific protein binding properties (i.e., binds all proteins equally well). Protein binding is based upon hydrophobic interactions, as well as charged interactions between the membrane and protein. Nitrocellulose membranes are cheaper than PVDF, but are far more fragile and do not stand up well to repeated probings. The uniformity and overall effectiveness of transfer of protein from the gel to the membrane can be checked by staining the membrane with Coomassie Brilliant Blue or Ponceau S dyes. Once transferred, proteins are detected using labeled primary antibodies, or unlabeled primary antibodies followed by indirect detection using labeled protein A or secondary labeled antibodies binding to the Fc region of the primary antibodies.

C. immunodetection Kits

In still further embodiments, the present invention concerns immunodetection kits for use with the immunodetection methods described above. As the S. pneumoniae antibodies are generally used to detect S. pneumoniae or S. pneumoniae antigens, the antibodies will be included in the kit. The immunodetection kits will thus comprise, in suitable container means, a first antibody that binds to S. pneumoniae or S. pneumoniae antigen, and optionally an immunodetection reagent.

In certain embodiments, the antibody may be pre-bound to a solid support, such as a column matrix, dipstick, membrane, particle (e.g., bead or nanoparticle) or well of a microtitre plate. The immunodetection reagents of the kit may take any one of a variety of forms, including those detectable labels that are associated with or linked to the given antibody. Detectable labels that are associated with or attached to a secondary binding ligand are also contemplated. Exemplary secondary ligands are those secondary antibodies that have binding affinity for the first antibody.

Further suitable immunodetection reagents for use in the present kits include the two-component reagent that comprises a secondary antibody that has binding affinity for the first antibody, along with a third antibody that has binding affinity for the second antibody, the third antibody being linked to a detectable label. As noted above, a number of exemplary labels are known in the art and all such labels may be employed in connection with the present invention.

The kits may further comprise a suitably aliquoted composition of the S. pneumoniae or S. pneumoniae antigens, whether labeled or unlabeled, as may be used to prepare a standard curve for a detection assay. The kits may contain antibody-label conjugates either in fully conjugated form, in the form of intermediates, or as separate moieties to be conjugated by the user of the kit. The components of the kits may be packaged either in aqueous media or in lyophilized form.

The container means of the kits will generally include at least one vial, test tube, flask, bottle, syringe or other container means, into which the antibody may be placed, or preferably, suitably aliquoted. The kits of the present invention will also typically include a means for containing the antibody, antigen, and any other reagent containers in close confinement for commercial sale. Such containers may include injection or blow-molded plastic containers into which the desired vials are retained.

VII. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Materials and Methods

Immunization and Donors.

Donors received Pneumovax®23 (Merck, Whitehouse Station, N.J.) as standard of care vaccination based upon their age or SLE status. Healthy donors Con1 and Con2 were both Caucasian, age 62 and 61 respectively. Lupus donor SLE1 was an African American, age 47, SLE2 was a Caucasian, age 45. All protocols were approved by the IRB and patients consented to participate in this study. Blood was drawn (~40-60 ml) into ACD tubes (BD, Franklin Lakes, N.J.) by venipuncture seven days post vaccination and were stored no longer than 18 hours before processing.

Cell Isolation and Flow Cytometry.

Peripheral blood mononuclear cells (PBMC) were isolated from fresh blood using lymphocyte separation medium (Cellgro, Manassas, Va.) and suspended in 2% inactivated fetal calf serum in PBS. Cells were then counted and stained within two hours of the isolation. Antibodies used for the staining were anti-CD3 and anti-CD20 conjugated to FITC, anti-CD38 conjugated to APC-Cy5.5, anti-CD27 conjugated to PE, anti-CD19 conjugated to PE-Alexa610 (all from invitrogen/Caltag, Carlsbad, Calif.), anti-IgG conjugated to APC (BD Biosciences, San Jose Calif.), and anti-IgM conjugated to biotin (Southern Biotech, Birmingham, Ala.) followed by streptavidin-PE-Cy7 (Invitrogen/Caltag). The B cells were bulk sorted (CD3/CD20$^{neg}$, CD19$^{low}$, CD38$^{high}$, CD27$^{very\ high}$, IgG$^{positive}$) using a Becton-Dickinson FACS Aria cytometer (BD Biosciences, San Jose, Calif.) and then single cell sorted into 96-well PCR plates with a Cytomation MoFlo cytometer (Dako, Carpinteria, Calif.).

Single Cell RT-PCR and PCR of Antibody Variable Region Genes.

As detailed in prior studies (Smith et al., 2009; Wrammert et al., 2008), the plates receiving the single cells sorted above contain 10 microliters of a hypotonic buffer consisting of 10 mM Tris-HCl with 40 U/μl of RNase inhibitor (Promega, Madison, Wis.) in each well. After the sort, plates were immediately frozen on dry ice and stored at −80° C. A One-Step RT-PCR kit (Qiagen, Valencia, Calif.) was used to amplify $V_H$ and $V_K$ message using a cocktail of sense primers to the leader regions of each of the gene families and antisense primers to the constant regions of the heavy and kappa chains. One microliter of the RT-PCR mixture was then amplified in separate heavy and kappa chain PCR reactions to first obtain sequences, and another microliter was used for the final PCR reactions to incorporate restriction sites for further cloning. The variable regions were then cloned into expression vectors (containing full length IgG$_1$ heavy or kappa constant regions), maxi-prepped (Roche, Indianapolis Ind.), and co-transfected into the HEK293A cell line using polyethyleneimine (PEI) (Polysciences, Warrington, Pa.). The transfected cells were allowed to secrete antibodies into serum-free DMEM supplemented with 1% Nutridoma (Roche, Indianapolis, Ind.) for five days. The antibodies were then purified using protein A-agarose beads (Pierce, Rockford, Ill.). Antibody purity and integrity were verified by SDS-PAGE and concentrations were obtained with a Nanodrop spectrophotometer (Fisher, Pittsburgh, Pa.).

Polysaccharide Affinity and Avidity ELISAs.

To screen for binding, ELISAs were first performed by coating plates with cocktails of five or six *S. pneumoniae* polysaccharides, screening all 23 (ATCC, Manassas, Va.) in this manner. Positive binders in this cocktail assay were then re-screened against each of the individual polysaccharides. As cell wall polysaccharide (CWPS) is an impurity in nearly all of the coat polysaccharides (Xu et al., 2005), antibodies that bound to all four groups were further tested on purified cell wall polysaccharide (CWPS) (Miravista Labs, Indianapolis, Ind.) to confirm CWPS binding. Wells were coated with gig of each polysaccharide (or total mixed polysaccharide), blocked with 20% FCS and developed with anti-human IgG-HRP (Jackson ImmunoResearch, West Grove, Pa.) and Super Aqua Blue substrate (EBiosciences, San Diego Calif.). The absorbance was measured at 405 nm on a microplate reader (Molecular Devices, Sunnyvale, Calif.). Antibody affinities (Kd) were calculated by curve fitting analysis of individual ELISA curves plotted from a dilution series of 16 two-fold dilutions of antibody beginning at 10 μg/ml. For avidity ELISAs, one concentration of antibody was used (1 μg/ml) and an elution step was added before the addition of the conjugate. This elution step used varying concentrations of ammonium thiocyanate (3M to 0.06M, 8 total dilutions) in PBS, as well as PBS alone. The percent of binding retained was calculated for each dilution of ammonium thiocyanate. These values were graphed versus thiocyanate concentration and the concentration of thiocyanate which caused 50% retention (or loss) of binding was calculated by fitting the data with a dose-response/sigmoidal curve with hillslope correction.

Autoantigen ELISAs.

All antibodies were also tested for binding to five autoantigens, Ro, La, Sm, nRNP, and cardiolipin. For each, except cardiolipin, 1 unit of antigen (ImmunoVision, Springdale, Ark.) was coated per well on high bind plates. Plates were blocked with 0.1% BSA in PBS, antibodies were added at 1 μg/ml and developed as per polysaccharide ELISAs above. For anti-cardiolipin ELISAs, cardiolipin solution at ~5 mg/ml (Sigma, St. Louis, Mo.) was diluted 1 to 1000 in ethanol and 50 μl/well was allowed to evaporate in medium bind plates. Plates were blocked with 0.5% adult bovine serum in PBS and antibodies were screened at 10 μg/ml and developed as above.

Analysis of Sequences and Curve Fitting.

All curve fitting was performed using the GraphPad Prism software, with background subtraction or percent retention values calculated and averaged using Excel. Variable region sequences were analyzed using the International Immunogenetics Information System (IMGT, Montpellier, France), as well as with in-house software and/or Vector NTI (Invitrogen, Carlsbad, Calif.). Clonally related antibodies were defined as those having the same VDJ/VJ usage in the heavy and light chains respectively, as well as highly related $V_HD_H$, $D_HJ_H$, and $V_KJ_K$ junctions. Average nucleotide somatic hypermutation values were obtain by analyzing sequences (using IMGT) for the number of nucleotide changes from germline in each antibody sequence. Resulting per-antibody values were then averaged to obtain average mutation rates per donor. The n value for these analyses included: naïve cells from six donors (n=18, 42, 21, 34, 15, 36); IgM germinal center/memory cells from 17 donors (n=56, 158, 18, 91, 17, 10, 16, 30, 19, 28, 11, 36, 29, 13, 22, 20, 64); IgG germinal center/memory cells from 13 donors (n=110, 37, 19, 28, 174, 40, 25, 15, 21, 18, 22, 24, 19, 71); anti-influenza ASCs from 11 donors (n=63, 18, 33, 46, 49, 11, 36, 11, 30, 35, 25). These donors were previously described in (Wrammert et al., 2008). The anti-polysaccharide ASC sequences are from the four donors in this study (Con1, 39; Con2, 49; SLE1, 24; SLE2, 25).

Example 2

Results

Pneumovax®23 Induces a Strong ASC Response which is More Robust in Healthy Controls as Compared to SLE Patients.

Four individuals were immunized with Pneumovax®23. Blood was drawn seven days post vaccination and PBMCs were isolated by Ficoll gradient. The cells were then stained and CD38$^{high}$/CD27$^{very\ high}$ cells were enumerated. The inventor's previous results using these techniques after influenza vaccination (Wrammert et al., 2008) showed an ASC burst ranging from 1% to 16% of total peripheral blood B cells at day seven (average 6.4%). Pneumovax®23 induces an even more robust ASC response (FIG. 1A), with the two healthy donors having ASCs representing 22.8% to 24.7% of their total peripheral blood B cells, especially as this is a primary vaccination for each donor. Although both SLE donors had half as many ASCs as the healthy donors, the overall percentages (10.6% and 7.1%) are still quite high. This strong anamnestic response is likely due to the fact that *S. pneumoniae* is a ubiquitous organism that causes both clinical and subclinical disease among the general population. FIG. 1B shows a schematic representation of the process for making human monoclonal antibodies from antibody secreting cells. This technique has been previously described in detail (Smith et al., 2009; Wrammert et al., 2008). In total, including non-binding antibodies, 137 antibodies were produced and characterized (Con1, n=39; Con2, n=49; SLE1, n=24; SLE2, n=25).

A Large Majority of Polysaccharide Antibodies Produced from the ASCs Bind to a Single Serotype.

Polysaccharide ELISA curves are shown in FIG. 2A, where each curve represents one antibody. A cutoff of an $OD_{405}$ of 1.5 was used as an arbitrary separation between high to moderate affinity antibodies and low to non-binding antibodies. Percentages were calculated using this cutoff as a means to determine which antibodies had significant binding. Averaged across the four donors, 76% of the antibodies (Con1, 62%; Con2, 90%; SLE1 75%; SLE2, 75%) bound to *S. pneumoniae* serotype polysaccharide or cell wall polysaccharide from the vaccine. Of the hmAbs generated, SLE donors showed no significant difference in the number of high-affinity antibodies isolated. A list of all antibodies with positive binding is shown in Table 1, which details serotype bound, number of total clonal siblings characterized, as well as $V_H$ and $V_K$ usage. Of the antibodies which bound to polysaccharide (76% of the total), an average of 88% of the antibodies characterized from the four donors are serotype specific (FIG. 2B) (Con1, 88%; Con2, 90%; SLE1 94%; SLE2, 80%). The observation that 88% of the antibodies currently in the serum bind to carbohydrate epitopes in a manner specific even among very closely related structures reinforces the well known specificity of the antibody repertoire.

TABLE 1

Summary of anti-*S. pneumoniae* antibodies (SEQ ID NOS: 1 through 126)

| Ab | # of Clones | Serotype(s) | Kd(M)* | OPA** | VH gene | JH gene | Heavy CDR3 | VK gene | JK gene | Kappa CDR3 |
|---|---|---|---|---|---|---|---|---|---|---|
| Con1p2 C01 | 3 | 20 | 1.1E-08 | 512 | VH3-66 | JH6 | AKGVTSFDY | VK3-20 | JK4 | QQFGSSPPDT |
| Con1p2 C04 | 1 | 1 | 2.2E-10 | none | VH3-23 | JH4 | ARDPGIRNGMGV | VK2-30 | JK1 | MQVTHWPRT |
| Con1p2 D02 | 1 | 9N | 3.9E-10 | 256 | VH3-23 | JH4 | AKAHRGDWNNFFDY | VK3-11 | JH4 | QQSGDWPLT |
| Con1p2 D03 | 1 | 19F/19A | 1.2E-08 | 1024/none | VH4-59 | JH3 | AREWSGFDF | VK3-20 | JK1 | QQYGSLPRT |
| Con1p2 E01 | 3 | 8 | 7.7E-11 | 512 | VH3-7 | JH4 | ARGQWLAF | VK2-30 | JK2 | MQGTHWPYT |
| Con1p3 C02 | 1 | 2 | 1.4E-10 | 4096 | VH3-7 | JH4 | ARGRNNFRH | VK1-33 | JK3 | QQFESFPRT |
| Con1p3 C03 | 1 | 22F | 1.8E-10 | 32 | VH3-66 | JH4 | ARELGVFHSGGDQWLGPLDC | VK3-15 | JK3 | HQYKNWPPMGT |
| Con1p3 G01 | 2 | 2 | 1.4E-10 | 2048 | VH3-49 | JH4 | RWTGGVSFGAY | VK1-5 | JK1 | QQYDIYLT |
| Con1p3 G06 | 1 | 8 | 2.1E-08 | 16 | VH3-74 | JH4 | ARDYYHSVDY | VK2-30 | JK2 | MQGTHWPYT |
| Con1p4 B01 | 2 | 33F | 4.0E-08 | 256 | VH4-59 | JH4 | ARGPDAHKTGY | VK4-1 | JK1 | QQYAATPWT |
| Con1p4 B03 | 1 | 9N/9V | 5.6E-10 | 128/128 | VH3-74 | JH4 | ARDSYTSPDY | VK2-30 | JK4 | MQGSHWPLT |

TABLE 1-continued

Summary of anti-*S. pneumoniae* antibodies (SEQ ID NOS: 1 through 126)

| Ab | # of Clones | Serotype(s) | Kd(M)* | OPA ** | VH gene | JH gene | Heavy CDR3 | VK gene | JK gene | Kappa CDR3 |
|---|---|---|---|---|---|---|---|---|---|---|
| Con1p4 C01 | 1 | 8 | 9.5E-10 | 128 | VH3-15 | JH3 | TTDNGVKAFDI | VK4-1 | JK3 | HQYYTTPFA |
| Con1p4 G01 | 1 | 6B | 3.1E-10 | 256 | VH3-74 | JH4 | TRGGSGATINY | VK1-39 | JK4 | QQSHSSPLT |
| Con1p6 C01 | 1 | 9V | 3.0E-08 | 256 | VH4-61 | JH4 | ARDRAGIDGYNYYFDY | VK1-5 | JK2 | QQYYSFYT |
| Con1p6 D04 | 1 | CWPS | 4.2E-08 | none | VH1-46 | JH4 | AREVAAEGKAFDY | VK4-1 | JK4 | QQYYTPPLT |
| Con1p6 E03 | 1 | 3 | 8.9E-10 | 128 | VH3-7 | JH3 | ARGQSYPGI | VK3-15 | JK1 | QQYNNWPRT |
| Con1p6 E06 | 1 | 17F/33F | 9.4E-09 | 8/none | VH4-59 | JH4 | AGRAYSSGYYYLIDY | VK3-15 | JK2 | QHYHNWPPT |
| Con2p3 C04 | 3 | CWPS | 7.9E-11 | none | VH3-30 | JH4 | AKGCSNGGNCFLIDY | VK4-1 | JK4 | QQYYNAPLT |
| Con2p3 C05 | 1 | 4 | 1.8E-10 | 256 | VH3-23 | JH3 | AKGGYYESGTMRAFDI | VK3-11 | JK4 | QQRSNWPAT |
| Con2p3 F03 | 2 | 2 | 1.5E-10 | 4096 | VH3-7 | JH4 | ARGESNFRY | VK1-33 | JK3 | QQFVSFPRT |
| Con2p3 G05 | 9 | 18C | 2.8E-10 | 64 | VH3-7 | JH4 | ARDSTSPARFGY | VK3-20 | JK2 | QHYGTSPPRYT |
| Con2p4 B03 | 1 | 1 | 3.4E-08 | none | VH3-53 | JH4 | ATGGMTSSWYGY | VK4-1 | JK2 | QQYYSTPYT |
| Con2p4 C02 | 5 | 9N/9V | 2.7E-10 | 512/8 | VH1-46 | JH4 | SMGPPYCTGGSCYSACDF | VK3-20 | JK2 | QRYGNSPPYT |
| Con2p4 D06 | 5 | 9V | 2.6E-10 | 2048 | VH3-15 | JH5 | TTDIGKGWYTHYPDL | VK4-1 | JK4 | LQYRSAPFT |
| Con2p5 A06 | 2 | CWPS | 5.1E-10 | none | VH3-30 | JH4 | VKEYSWGYYRTADY | VK1-5 | JK1 | QQYSTYPWT |
| Con2p5 B06 | 3 | 1 | 1.4E-10 | none | VH3-74 | JH4 | ARSPGGYFDY | VK3-15 | JK1 | QQYSTWLWT |
| Con2p5 C04 | 1 | 8 | 2.3E-08 | 32 | VH3-15 | JH4 | TTDDLKN | VK1-39 | JK2 | QQRYRIPYS |
| Con2p5 E05 | 1 | 2 | 2.8E-10 | 2048 | VH3-48 | JH6 | ARGRDCYGGNCVIYFHYYGLDV | VK2-28 | JK2 | MRALQTPYT |
| Con2p6 B03 | 3 | CWPS | 6.4E-11 | none | VH3-30 | JH4 | VKESATGWYRTADY | VK1-5 | JK1 | HQYNKYPWT |
| Con2p6 C05 | 1 | 33F | 3.3E-09 | none | VH3-66 | JH3 | ARDIPTTFGIGEAFDI | VK1-5 | JK1 | QQYYSWGT |
| Con2p6 G04 | 1 | 22F | 4.4E-10 | 128 | VH1-46 | JH4 | ARDDSAFDY | VK2-24 | JK1 | MQASQSTWT |
| Con2p7 D03 | 1 | CWPS | 1.8E-09 | none | VH3-30 | JH6 | AKGCSGENCFYMDD | VK4-1 | JK4 | QQCYNAPLT |
| Con2p8 B01 | 1 | 22F | 2.3E-08 | none | VH1-46 | JH4 | TREIGAVVVDATSLGWLGYFDY | VK3-15 | JK1 | QQYNNWPPVT |
| Con2p8 B05 | 2 | 15B | 1.7E-10 | none | VH3-7 | JH4 | AGWGRTQD | VK2-30 | JK2 | MQYTFWPHT |
| Con2p8 E03 | 1 | 23F | 3.3E-08 | none | VH3-30 | JH3 | TKEGAPPGKYAFDI | VK3-11 | JK3 | QHRGEWPPGAT |
| Con2p8 F05 | 1 | 11A | 1.8E-10 | none | VK3-72 | JH3 | LKDSSQYSFDA | VK1-9 | JK4 | QQFKGYPLT |
| SLE1p1 A02 | 3 | 5 5. | 1E-10 | 1024 | VH4-59 | JH4 | ARGDGYNFF | VK1-9 | JK2 | QQINSYPRT |
| SLE1p1 A03 | 1 | 14/9N | 1.7E-10 | 512/32 | VH3-30 | JH5 | AKCGAEDSTTVWLNWFDP | VK3-11 | JK4 | QQRADWPLT |
| SLE1p1 B05 | 3 | 5 | 9.5E-10 | none | VH3-23 | JH4 | AKPNYFGSGSPDY | VK3-11 | JK2 | LQCSNWPMYT |
| SLE1p1 C04 | 1 | 5 | 2.8E-10 | 2048 | VH4-59 | JH4 | VKEQDYGYYRTADH | VK1-6 | JK2 | QQYDKYPWT |
| SLE1p1 E01 | 2 | 9V/9N | 6.2E-11 | 512/256 | VH3-20 | JH3 | VRVAVPAATYTRGNDAFDI | VK1-17 | JK1 | LQHSSFPWT |

TABLE 1-continued

Summary of anti-*S. pneumoniae* antibodies (SEQ ID NOS: 1 through 126)

| Ab | # of Clones | Serotype(s) | Kd(M)* | OPA ** | VH gene | JH gene | Heavy CDR3 | VK gene | JK gene | Kappa CDR3 |
|---|---|---|---|---|---|---|---|---|---|---|
| SLE1p1 F02 | 1 | 14 | 1.0E-09 | none | VH3-15 | JH4 | TTAHGPVGDH | VK4-1 | JK5 | QQYYTTPSIT |
| SLE1p1 G05 | 1 | 158 | 1.6E-10 | none | VH3-7 | JH4 | ARAGGCSSTRCHTTPGFDY | VK4-1 | JK5 | QQYYTTPPIT |
| SLE1p2 A02 | 1 | 5 | 1.4E-10 | 512 | VH4-39 | JH3 | ASLSGTNAFDI | VK3-11 | JK1 | QQRSSGRT |
| SLE1p2 D04 | 1 | 8 | 7.4E-09 | 256 | VH3-23 | JH4 | AKPRGYSYGYFDY | VK3D-20 | JK2 | QQYGISPRT |
| SLE1p3 A02 | 1 | 17F | 2.7E-09 | none | VH3-7 | JH4 | APPARRLDY | VK2-29 | JK1 | MQGTHHPWT |
| SLE1p3 A04 | 1 | 4 3. | 8E-08 | none | VH3-74 | JH4 | ARSNAGHEA | VK4-1 | JK4 | QQYYSTPLT |
| SLE1p3 B03 | 1 | 20 | 1.5E-09 | none | VH1-46 | JH4 | ARDIPHANLDY | VK1-17 | JK1 | LQHTTFPWT |
| SLE1p3 C03 | 1 | 33F | 1.1E-09 | 128 | VH3-23 | JH4 | VKDRVPPGDVPGDF | VK3-11 | JK5 | QQRRTWPPLT |
| SLE2p1 A01 | 2 | 23F | 2.5E-09 | none | VH3-48 | JH6 | ATLLLRDNQLDV | VK2-30 | JK1 | MQGTHWRT |
| SLE2p1 A06 | 1 | CWPS | 7.9E-10 | none | VH3-33 | JH4 | VKEQGFGYYRTADY | VK1-5 | JK1 | HQYDKYPWT |
| SLE2p1 B01 | 2 | 15B/14 | 2.0E-10 | 256/256 | VH4-59 | JH3 | ARRNDFNI | VK3-20 | JK3 | QQYGSSPFT |
| SLE2p1 C03 | 1 | 17F/33F | 2.9E-10 | none | VH3-23 | JH4 | SIWWGTSVQYPLVLDY | VK3D-15 | JK5 | QQYSKWPPIT |
| SLE2p1 C04 | 1 | CWPS | 2.0E-09 | none | VH3-30 | JH5 | VKEQDYYYRTADH | VK1-5 | JK1 | QQYDKYPWT |
| SLE2p1 D02 | 5 | 5 | 2.0E-10 | none | VH4-61 | JH4 | ARGHGFNAY | VK3-20 | JK1 | QQYGNSPRT |
| SLE2p1 D04 | 1 | 6B | 8.8E-11 | 512 | VH3-15 | JH4 | TTVRNMADLSLNH | VK3-20 | JK1 | QQYDDSRWT |
| SLE2p2 A01 | 1 | 18C | 4.2E-09 | none | VH3-48 | JH4 | ATGNRGSLPRR | VK2D-28 | JK2 | MQALRSPYT |
| SLE2p2 C04 | 1 | 33F | 4.9E-09 | none | VH3-7 | JH4 | VRDGWDTFFDS | VK2-30 | JK2 | MQGRYWPYT |
| SLE2p2 D03 | 1 | 19A/19F | 1.1E-09 | none/8192 | VH3-74 | JH4 | VNFQLG | VK3-20 | JK1 | QQYGNSPRT |
| SLE2p2 E04 | 1 | 8 | 5.1E-10 | 1024 | VH3-30-3 | JH5 | ARAEYCSPGDCFLIDT | VK2-30 | JK1 | MQGTHWRT |
| SLE2p2 F01 | 1 | CWPS | 9.6E-10 | none | VH3-33 | JH4 | LRGNPPSSPTDY | VK1-16 | JK4 | QQYNSYPLT |
| SLE2p2 G01 | 1 | 5 | 1.4E-09 | none | VH3-23 | JH6 | AKVVYSRPPMDV | VK1D-39 | JK1 | QQSYSTPWT |
| SLE2p2 G06 | 1 | 17F | 4.8E-11 | 128 | VH3-7 | JH4 | ARASRETGEPY | VK2-30 | JK1 | MQATHWPWT |

*Calculated ELISA affinities, averaged for the clonal family. The affinity listed from cross-reactive antibodies is for the serotype which is most strongly bound (the serotype listed first in the serotype column).
** Opsonophagocytosis assay (OPA) measures antibody mediated uptake of bacteria; values 4 or less are considered negative ("none").
The number of clones indicates the total number of members of the clonal family

TABLE 2

Selected Heavy and Light Chain Sequences from Antibodies of Table 1 (SEQ ID NOS. 127-252)

| Con1 Heavy | Seq ID No: | |
|---|---|---|
| Con1p2-c01h | 127 | GAGGTGCAGCTGTTGGAGTCGGGGGAGGCTTGGTACAGCCTGGGGGGTCCCTGAGAGTCTCCTGTGCAGC<br>CTCTGGATTCACCTTTAGCAACTCTGGCATGAGTTGGGTCCGCCAGGCTCCAGGGAAGGGGCTGGAGTGGGT<br>CTCAGGTATTGGTGGTGGTGGTAGTGCATACTACGCAGACTCCGTGAAGGGCCGGTTCACCATCTCCAG<br>AGACAATTCCAAGAACACGCTGTATCTACAAATGAACAATTTGAGAGCCGAGGACACGGCCGTATACTACT<br>GTGCGAAAGGAGTTACCAGTTTTGACTACTGGGGCCAGGGAATCCTGGTCACCGTCTCCTCA |
| Con1p2-c04h | 128 | GAGGTGCAGCTGGTGGAGTCTGGGGGAGGCTTGGTCCAGCCTGGGGGGTCCCTGAGACTCTCCTGTGCAGCC<br>TCTGGATTCACCGTCAGTAGCGACTATATGAGTTGGGTCCGCCAGGCTCCAGGGAAGGGGCTGGAGTGGGTC |

TABLE 2-continued

Selected Heavy and Light Chain Sequences from Antibodies of Table 1 (SEQ ID NOS. 127-252)

|  |  |  |
|---|---|---|
|  |  | TCAGTTATGTATAGCGGGGGTAGCACATACTACGCAGACGCCGTGAAGGACAGATTCACCATCTCCAGAGA<br>CAATTCCAAGAAATATACTGTATCTTCAAATGAACAGCCTGAGAGCCGAGGACACGGCCGTTTATTACTGTGC<br>GAGAGATCCCGGGATAAGGAACGGTATGGGCGTCTGGGGCCAAGGGACCACGGTCACCGTCTCCTCA |
| Con1p2-d02h | 129 | GAGGTGCAGCTGTTGGAGTGGGGGAGCCTTGGTACAGCCGGGGGGTCCCTGAGACTTTCCTGTGCAGCC<br>TCTGGATTCACCTTTACCAGCTTTGCCCATGGGCTGGGTCCGCCAGGCTCCAGGGAAGGGGCTGGAGTGGGTC<br>TCAGCTGTGACTGGCAGTGGTTATTACAAAAACTATGCAGATTCCGTGAAGGGCCGGTTCACCATCTCCCAGA<br>GACAATTCCGACAATACTCTCTATCATGCAAATGAACAGCCTGAGAGGCGACGACACGGCCCTATATTACTGT<br>GCGAAAGCACATAGAGGTGACTGGAATAACTTCTTTGACTATTGGGGCCAGGGAACCCTGGTCACCGTCTCC<br>TCA |
| Con1p2-d03h | 130 | CAGGTGCAGCTGCAGGAGTCGGGCCCAGGACTAGTGAAGCCTTCGGAGACCCTGTCCCTCACCTGCTCTGTG<br>TCTGCTGACTCCTTCAGTCCTTACAAGTGGAGCTGGATCCGGCAGCCCCCAGGGAAGGGACTGGAATGGATT<br>GGATATATCTATTCCAGTGGGAACACCAACTACAACCCCCCCCTCAAGAGTCGAGTCACCATATCACTGGAC<br>ACGTCCAAGAATCAGGTCTCCCTGAGGCTGAGCTCTGTGACCGCTGCGGACACGGCCATGTATTACTGTGCG<br>AGAGAGTGGAGTGGTTTTGATTTCTGGGGCCAAGGAACAATGGTCACCGTCTCTTCA |
| Con1p2-e01h | 131 | GAGGTGCAGCTGGTGGAGTCTGGGGGAGGCTTGGTCCAGCCTGGGGGGTCCCTGAGACTCTCCTGTGCAGCC<br>TCTGGATTCACCTTTACTAACTATTGGATGAGCTGGGTCCGCCAGGCTCCAGGGAAGGGGCTGGAGTGGGTG<br>GCCAACATAAAGCAAGATGGACGTGAGACATACTATGTGGACTCTGTGAAGGGCCGATTCACCATCTCCAG<br>AGACAACGCCAAGAACTCAGTGTCTCTACAGATGAGTAGCCTGAGAGCCGAGGACACGGCCGTGTATTACT<br>GTGCGCGAGGGCAGTGGCTGGCCTTCCGGGGCCAGGGAACCCTGGTCACCGTCTCCTCA |
| Con1p3-c02h | 132 | GAGGTGCAGCTGGTGGAGTCTGGGGGAGGCTTGGTCCAGATTGGGGGGTCCCTGAGACTCTCCTGTGCAGCC<br>TCTGGATTCACCTTTAGTACCTATTGGATGAGCTGGGTCCGCCAGGCTCCAGGGAAGGGGCTGGAGTGCGTG<br>GCCAGCATAAAGGAGGATGGAAGTGAGAGATACTATGTGGACTCTGTGAAGGGCCGATTCACCATCTCCAG<br>AGACAACGCCAAGAACTCACTGCATCTGCAGATGGACAGCCTGAGAGCCGCGGACACGGCTGTGTATTTCT<br>GTGCGAGAGGCCGGAACAACTTCCGACACTGGGGCCAGGGAACCCTGGTCACCGTCTCCTCA |
| Con1p3-c03h | 133 | GAGGTGCAGCTGGTGGAGTCTGGGGGAGGCTTGGTCCAGCCTGGGGGGTCCCTGAGACTCTCCTGTGCAGCC<br>TCTGGATTCGCCATCAGTGGTAACTACATGAGTTGGGTCCGCCAGGCTCCAGGGAAGGGGCTGGAGTGGGTC<br>TCACTTATTTATTGGACTGATGACACAGTCTACGCAGACTCCGTGAAGGGCAGATTCACCATCTCCAGGGAC<br>GTCTCCAAGAACATGGTGCATCTTCAAATGAGCAGCCTGAGAGTCGAGGACACGGCTGTTTATTACTGTGCG<br>AGAGAATTAGGTGTTTTTCATTCAGGGGGGGACCAGTGGCTGGGCCCTTTAGACTGCTGGGGCCAGGGAACC<br>CTGGTCACCGTCTCCTCA |
| Con1p3-g01h | 134 | GAGGTGCAGCTGGTGGAGTCTGGGGGAGGCTTGGTGCAGCCAGGGCAGTCCCTGAGACTTTCCTGTACAGTT<br>TCTGGATTCAGCGTAGAAGACCATGGTCTGAACTGGGTCCGCCAGGCTCCAGGGAAGGGGCTGGAGTGGGT<br>AGGGTTCATTAGAAGGAAAAGTTCTGGTGGGACAGAATACGCCGCGTCTGTGAAAGGCCGATTCACCATCTC<br>AAGAGATGATTCCAAGAGCGCCGTCTATCTGCAAATGAACAGCCTGAAGATGGAGGACACAGGCGTATATT<br>ATTGTCTTCGCTGGACGGGTGGAGTGAGTTTTGGTGCCTACTGGGGCCAGGGAACCCTGGTCACCGTCTCCT<br>CA |
| Con1p3-g06h | 135 | GAGGTGCAGCTGGTGGAGTCCGGGGGAGGCTTAGTTCAGCCTGGGGGGTCCCTGAGACTCTCCTGTGCAGCC<br>TCTGGATTCACCTTCACTAGCTGGATGCACTGGGTCCGCCAAGCTCCAGGGAAGGGGCTGGTGTGGGTCTCA<br>CATATTAATACTGATGGGAGTAGCACAAGCTACGCCGGACTCCGTGAAGGGCCGATTCACCATCTCCAGAGAC<br>AACGCCAAGAACACGCTGTATCTGCAAATGAACAGTCTGAGAGCCGAGGACACGGCTGTGTATTACTGTGC<br>AAGAGATTATTACCACTCCGTTGACTACTGGGGCCAGGGAACCCTGGTCACCGTCTCCTCA |
| Con1p4-b01h | 136 | CAGGTCAGCTGCAGGAGTCGGGCCCAGGAATGGTGAAGCCTTCGGAGACCCTGTCCCTCATCTGCAGTGTC<br>TCTGGTGCCTCCGTCAGTCGTGACCACTGGAGCTGGATCCGCCAGTCCCCAGGGAAGGGACTGGAGTGGATT<br>GTCTATATATATAACAGTGAGAGCATCGAATACAATCCCTCCCTCAAGAGTCGAGTCACCATATCCGTAGAC<br>ACGTCCAAGAACCAGGTCTCCCTGACAGTGACTTCTGTGACCGCTGCAGACACGGCCTTCTATTACTGTGCG<br>CGAGGGCCAGATGCCCACAAAACTGGCTACTGGGGCCCGGGAACCCTGGTCACCGTCTCCTCA |
| Con1p4-b03h | 137 | GAGGTGCAGCTGGTGGAGTCCGGGGGAGGCTTAGTTCAGCCTGGGGGGTCGCTGAGACTCTCCTGCGCAGC<br>CTCTGGATTCACCTTCAGTAACTTCTGGATGTACTGGGTCCGCCAAGTTCCAGGGAAGGGGCTGGTGTGCGT<br>CTCACGTATTAATAGAGATGGGAGTATCACATTGTACGCGGACTCCGTGAGGGGCCGATTCACCATCTCCAG<br>AGACAACGCCAAGAACACGCTGTATCTGCAAATGAACAGTCTGAGAGTCGAGGACACGGCTGTGTATTACT<br>GTGCAAGAGATTCCTATACCAGCCCTGACTACTGGGGCCAGGGGACCCTGGTCACCGTCTCCTCA |
| Con1p4c01h | 138 | GAGGTGCAGCTGGTGGAGTCTGGGGGAGGCTTGGTAAAGCCGGGGAGTCCCTTAGACTCTCCTGTGCGAC<br>CTCAGGATTAACTTTCAGTAACGTATGGATGAGCTGGGTCCGCCAGGCTCCAGGGAAGGGGCTGGAGTGGG<br>TTGGGCGTCTTAAAAACAAGCCTGATGTGGAACAACAGACTACGCAGCACCCGTGAAGGGCAGATTCACC<br>ATCTCAAGAGATGATTCAAAAACCACGCTGTATCTGGAAATGAACAGCCTGAAGTCGAGGACACAGCCGT<br>GTATTACTGTACCACAGATAACGGAGTCAAGGCTTTTGATATCTGGGGCCAAGGGACAATGGTCACCGTCTC<br>TTCA |
| Con1p4-g01h | 139 | GAGGTGCAGCTGGTGGAGTCCGGGGGAGGCTTAGTTCAGCCTGGGGGGTCCCTGAGACTCTCCTGTGCAGCC<br>TCTGGATTCACCTTCAGTACCTACTGGATGCACTGGGTCCGCCAAACTCCGGAGAAGGGGCTGGTATGGGTC<br>TCACGTATTCATCCTGATGGAGTAACACAGCTACGCGGACTCCGTGAAGGGCCGATTCACCATCTCCAGA<br>GACAACGCCAAGAACACGCTGTATCTGCAAATGAATAGTCTGAGAGTCGAGGACACGGCTTTTATTATTGT<br>ACAAGAGGGGGTTCCGGGCTACGATCAATTACTGGGGCCAGGGAATCCTGGTCACCGTCTCCTCA |
| Con1p6-c01h | 140 | CAGGTGCAGCTGCAGGAGTCGGGCCCAGGGCTGGTGAAGCCTTCACAGACCCTGTCCCTCACCTGCACTGTC<br>TCTGGTGGCTCCATCAGCGGTGGTACTTACTCCTGGACCTGGATCCGGCAGCCCGCCGGGAAGGGACTGGAG<br>TGGATTGGGCGTATTTTTGCTAGTGGGAGCACCAACTACAATTCCTCCCTCAAGAGTCGAGTCACCATTTAG<br>TAGACACGTCCAAGAACCTGTTCTCCCTGAGCCTGAGCTCTGTGACCGCCGCAGACACGGCCATGTATTACT |

TABLE 2-continued

Selected Heavy and Light Chain Sequences from Antibodies of Table 1 (SEQ ID NOS. 127-252)

| | | |
|---|---|---|
| | | GTGCGAGAGATCGAGCCGGTATAGATGGCTACAATTACTACTTTGACTACTCTGGGGCCAGGGAACCCTGGTCA<br>CCGTCTCCTCA |
| Con1p6-d04h | 141 | AGGTGCAGCTGGTGCAGTCTGGGGCTGAGGTGAAGAAGCCTGGGGCCTCAGTGAAGGTTTCCTGCAAGACA<br>TCTGGATACACCCTCACCAGTTACTATATGCACTGGGTGCGACAGGCCCCTGGACAAGGGCTTGAGTGGCTG<br>GGAGTGATCAGGCCTACGGACGCTAGCACAAGGTCCGCACAGAGATTCCAGGGCAGAATCACCATGACCAG<br>GGACACGTCCACGAGCACACTCTACATGGAGCTGAGTGAGCCTGAGATCTGAAGACACGGCCGTGTACTATTG<br>TGCGAGAGAAGTGGCAGCAGAAGGTAAAGCTTTCGACTACTGGGGCCAGGGAACCCTGGTCACCGTCTCCT<br>CA |
| Con1p6-e03h | 142 | GAGGTGCAGCTGGTGGAGTCTGGGGGAGGCTTGGTCCAGCCTGGGGGGTCCCTGAGACTCTCCTGTGCAGCC<br>TCTGGATTCACCTTTAGTAGCTATTGGATGAGCTGGGTCCGCCAGGCTCCAGGGAAGGGACTGGAGTGGGTG<br>GGCAAAATAAAGGAAGCGGAAGTGAGAAATACTATGTGGACTCTGTGAAGGGCCGATTCGCCATCTCCAG<br>AGACAACGCCAAGAACTCCCTGTCTCTGCAAATGAACAGCCTGAGAGCCGAGGACACGGCCGTCGTATTACT<br>GTGCGAGAGGTCAATCATATCCGGGAATTTGGGGCAAGGGACAATGGTCACCGTCTCTTCA |
| Con1p6-e06h | 143 | CAGGTGCAGCTGCAGGAGTCGGGCCCAGGACTGGTGAAGCCTTCGGAGACCCTGTCCCTCACCTGCACTGTC<br>TCTGGTGGCTCCATCACTAATTACTACTGGGGCTGGATCCGGCAGCCCCCAGGGGAGGGACTGGAGTGGATT<br>GGCTATATCTATTACAGTGGAAGCACCAACTACAACCCCTCCCTCAAGAGTCGAGTCACCATATCAGTAGAC<br>ACGTCCAAGAACCAGTTCTCCCTAAAGCTGACCTCTGTAACCGCCGCAGACACGGCCGTGTATTACTGTGCG<br>GGTCGGGCTTACAGTAGTGGTTACTACTACCTAATTGACTACTGGGGCCAGGGAACCCTGGTCACCGTCTCC<br>TCA |

| Con1 Kappa | Seq ID No. | |
|---|---|---|
| Con1p2-c01k | 144 | GAAATTGTGTTGACGCAGTCTCCAGGCACCCTGTCTTTGTCTCCAGGGGAAAGAGCCACCCTCTCCTGCAGG<br>GCCAGTCAGAGTGTTACCTACTTAGCCTGGTACCAGCAGAAACCTGGCCAGGCTCCCAGGCTCCTCTTCTAT<br>GGTACATCCAGCAGGGCCACTGGCATCCCAGACAGGTTCAGTGGCAGTGGGTCTGGGACAGACTTCACTCTC<br>ACCATCAGCAGAGTGGAGCCTGAAGATTTTGCAGTGTATTACTGTCAGCAGTTTGGCAGCTCACCTCCGGAC<br>ACTTTCGGCGGAGGGACCAAGGTGGAAATCAAA |
| Con1p2-c04k2 | 145 | TTGTGATGACTCAGTCTCCACTCTCCCTGCCCGTCACCCTTGGACAGCCGGCCTCCATCCTGCAGGGCTAG<br>TCAAGGCCTCGAACACAGTGATGGAAACACCTACTTGAGTTGGTTTCAGCAGAGGCCAGGCCGATCTCCCCG<br>GCGCCTAATTTATAAGGTTTCTAACCGGGACTCTGGGGTCCCAGACAGATTCAGTGGCAGTGGGTCAGGCAC<br>TGATTTCACACTGGAAATCACCAGGGTGGAGGCTGAGGATGTTGGAGTTTATTACTGCATGCAAGTTACACA<br>CTGGCCGAGGACGTTCGGCCAAGGGACCAAGGTGGAAATCAAA |
| Con1p2-d02k | 146 | GAAATTGTGTTGACACAGTCTCCAGGCACCCTGTCGTTGTCTCCAGGGGAAAGAGCCACCCTCTCCTGCAGG<br>GCCAGTCAGAGTATTAGTCCCCACTTGGCCTGGTACCAACAGAAACCTGGCCAGTCTCCCAGGCTCCTCATA<br>TATGATGCATCCAACAGGGCCACTGGCATCCCAGCCAGGTTCAGTGGCAGTGAGTCTGGGACAGACTTCACT<br>CTCAGCATCAGCAGCCTAGAGCCTGAAGATTTTGCAGTTTATTACTGTCAGCAGAGTGGCGACTGGCCTCTC<br>ACTTTCGGCGGAGGGACCAAGGTGGAGATCAAA |
| Con1p2-d03k3 | 147 | GAAATTGTGTTGACGCAGTCTCCAGGCACCCTGTCTTTGTCTCCAGGGGAAAGAGCCACCCTCTCCTGCAGG<br>GCCAGTCAGAGTGTTTACAGCATCTACTTCGCCTGGTACCAGCAGAAACCCGGCCAGGCTCCCAGGCCCCTC<br>ATTTATGGTGTCTCCAACAGGGCCACTGGCATCCCAGACAGGTTCAGTGGCAGTGGGTCTGGGACAGACTTC<br>ACTCTCACCATCAGCAGACTGGAGCCAGAAGATTTTGCAGTGTATTACTGTCAGCAGTATGGTAGTTTACCT<br>CGGACGTTCGGCCAAGGGACCAAGGTGGAAATCAAA |
| Con1p2-e01k | 148 | TTGTGATGACTCAGTCTCCACTCTCCCTGCCCGTCACCCTTGGACAGCCGGCCTCCATCTCCTGCAGGTCTAG<br>TCGAAGCCTCGTATACAGTGATGGAGGCACCTACTTGAATTGGTTTCAGCAGAGGCCAGGCCAATCTCCAAG<br>GCGCCTAATTTGGCACGTTTCTAACCGGGACTCTGGGGTCCCAGACAGATTCAGCGGCAGTGGGTCAGGCAC<br>TGATTTCACACTGAAAATCAGCAGGGTGGAGGCTGAGGATGTTGGGGTTTATTACTGCATGCAAGGTACACA<br>CTGGCCTTACACTTTTGGCCAGGGGACCAAGGTGGAAATCAAA |
| Con1p3-c02k | 149 | GACATCCAGATGACCCAGTCTCCATCTTCCCTGTCTGCATCTGTAGGAGACAGAGTCACCATCACTTGCCAG<br>GCGAGTCAGGACATTAGGAAGCTTTTAAATTGGTATCAGCAGAGACCAGGGAAAGCCCCTAACCTCCTGATC<br>TACGATGCATCCAATTTGGAAACAGGGGTCCCATCAAGGTTCAGTGGAAGTGGATCTGGGACACATTTTAGT<br>TTCACCATCACCAGCCTGCAGCCTGAAGATATTGCAACATATTACTGTCAACAGTTTGAAAGTTTCCCTCGCA<br>CCTTCGGCCCTGGGACCAAAGTGGATATCAAA |
| Con1p3-c03k | 150 | GAAATAGTGATGACGCAGTCTCCAGCCACCCTGTCTGTGTCTCCAGGGGAAAGAGCCACCCTCTCCTGCAGG<br>GCCAGTCAGAGTGTTAACAGCTTCTTAGCCTGGTACCAGCAGAAACCTGGCCAGGCTCCCAGGCTCCTCATC<br>TATGCTGCATCCACCAGGGCCACTGGTGTCCCAGCCAGGTTCAGTGGCAGTGGGTCTGGGACAGAGTTCACT<br>CTCACCATCAGCAGCCTGCAGTCTGAAGATTTTGCAGTTTACTACTGTCACCAGTATAAAAACTGGCCTCCG<br>ATGGGCACTTTCGGCCCTGGGACCAAAGTGGATATCAAA |
| Con1p3-g01k | 151 | GACATCCAGATGACCCAGTCTCCTTCCACCCTGTCTTCTTCTGTCGGAGACAGAGTCACTATCACTTGCCGGG<br>CCAGTCAGAATATTGGTGTCTCCTTGGCCTGGTATCAGCAGAAACCAGGGAAAGCCCCTAACCTCCTGATCT<br>ATAAGGCGTCTTATTTAGAAACGGGGGTCCCATCAAGGTTCAGCGGCAGTGGATCTGGGACAGAATTCACTC<br>TCACCATCAGCAGCCTACAGCCTGATGATTTTGCAACTTATTATTGCCAACAGTATGATATTTATTTGACATT<br>CGGCCAAGGGACCAAGGTGGAAATCAAA |
| Con1p3-g06k | 152 | TTGTGATGACTCAGTCTCCACTCTCCCTGCCCGTCACCCTTGGACAGCCGGCCTCCATCCTGCAGGTCTAG<br>TCAAAGTCTCGCACACAGTGATGGAAATACCTACTTGAATTGGTTTCAGCAGAGGCCAGGCCAATCTCCAAG<br>GCGCCTAATTTATAAGGTTTCTAACCGGGACTCTGGGGTCCCAGACAGATTCAGCGGCAGTGGGTCAGGCAC<br>TGATTTCACACTGAAAATCAGCAGGGTGGAGGCTGAGGATGTTGGGGTTTATTACTGCATGCAAGGTACACA<br>CTGGCCGTACACTTTTGGCCAGGGGACCAAGGTGGAAATCAAA |

TABLE 2-continued

Selected Heavy and Light Chain Sequences from Antibodies of Table 1 (SEQ ID NOS. 127-252)

| | | |
|---|---|---|
| Con1p4-b01k | 153 | GACATCGTGATGACCCAGTCTCCAGACTCCCTGGCTGTGTCTCTGGGCGAGAGGGCCACCATCAACTGCAAG<br>TCCAGCCAGAGTGTTTTATACAGCTCCAACAATAAGAATTACTTAGCTTGGTTCCAGCAGAAGCCAGGACAG<br>CCTCCTAAATTACTCATTTACTGGGCATCTATCCGGGACTCCGGGGTCCCTGACCGATTCAGTGGCAGCGGGT<br>CTGGGACAGATTTCACTCTCACCGTCAGCAGTCTGCAGGCTGACGATGTGGCAGTTTATTACTGTCAGCAAT<br>ATGCTGCTACTCCGTGGACGTTCGGCCAAGGGACCAAGGTGGAAATCAAA |
| Con1p4-b03k2 | 154 | TTGTGATGACTCAGTCTCCACTCTCCCTGCCCGTCACCCTTGGACAGCCGGCCTCCATCCTGCAGTTCTAG<br>TCAAAGCCTCGTATACAGTGATGGAAACACCTACTTGAGTTGGTTTCAGCAGAGGCCAGGCCAATCTCCCG<br>GCGCCTAATTTATAAGGTTTCTAACCGGGACTCTGGGGTCCCAGACAGATTCAGCGGCAGTGGGTCAGGCAC<br>TGATTTCACACTGAGAATCAGCAGGGTGGAGGCTGAGGATGTTGGGGTTTATTACTGCATGCAAGGTTCACA<br>CTGGCCGCTCACTTTCGGCGGAGGGACCAAGGTGGAGATCAAA |
| Con1p4-c01k | 155 | GACATCGTGATGACCCAGTCTCCAGACTCCCTGGCTGTGTCTCTGGGCGAGAGGGCCACCATCAACTGCAAG<br>TCCAGCCTGAGTGTTTTATCCAGCTCCAATAATGAGAACTACTTAGCTTGGTACCAGCAGAAACCAGGACAG<br>CCTCCTAAGCTGCTCATTTACTGGGCATCTACCCGGGGATCCCGGGTCCCTGGCCGATTCAGTGGCAGCGGG<br>TCTGGGACAGATTTCACTCTCACCATCAGCAGCCTGCAGGCTGAAGATGTGGCAGTTTATTACTGTCACCAA<br>TATTATACTACTCCCTTCGCTTTCGGCCCTGGGACCAAAGTGGATATCAAA |
| Con1p4-g01k | 156 | GACATCCAGATGACCCAGTCTCCGTCCTCCCTGTCTGCATCTGTGGGAGACAGTGTCACCATCACTTGCCGG<br>GCAAGTCAGAGCATTAGCAGCTATTTAAATTGGTATCACCAAAAACCAGGGAAAGCCCCTAAACTCCTGATC<br>TATGGTGCATCCACTTTGCAAAGTGGGGTCCCATCAAGGTTCGGTGGCAGTGGATCTGGGACAGATTTCACT<br>CTCACCATCAGCAGTCTGCAACCTGACGATTTTGCAACTTACTACTGTCAACAGAGTCACAGTTCCCTCTCA<br>CTTTCGGCGGAGGGACCAAGGTGGAGATCAAA |
| Con1p6-c01k | 157 | GACATCCAGATGACCCAGTCTCCTTCCACCCTGTCTGCCTCTGTAGGAGACAGAGTCACCATCACTTGTCGG<br>GCCAGTCGGAGTCTTGGTAGCGTTGGCCTGGTATCAGCAGAGCCCAGGGAAAGCCCCTAAGCTCCTGATC<br>TATAAGGCGTCTACTTTAGAAAGTGGGGTCCCATCACGGTTCAGCGGCAGTGGATCTGGGACAGAATTCACT<br>CTCACCATCAGCAGCCTGCAGCCTGATGATTTTGCAACTTATTACTGCCAACAGTATTATAGCTTACACTT<br>TTGGCCAGGGGACCAAGGTGGAAATCAAA |
| Con1p6-d04k | 158 | GACATCGTGATGACCCAGTCTGCAGACTCCCTGGCTGTGTCTCTGGGCGAGAGGGCCACCATCAACTGCAAG<br>TCCAGCCAGAGTCTTTTCTACAGTTCCAACAAGAAGAACTACTTAGCTTGGTACCAGCAGAAGCCAGGACAG<br>CCTCCTAAACTGATCATTTACTGGGCATCTACCCGGGAATCCGGGGTCCCTGACCGATTCAGTGGCAGCGCGGG<br>TCTGGGACAGATTTCACTCTCACCATCACCAGCCTGCGGGCTGAAGATGTGGCAGTTTATTACTGTCAGCAA<br>TATTATACTCCTCCTCTCACATTCGGCGGAGGGACCAAGGTGGAAATCAAA |
| Con1p6-e03k | 159 | GAAATAGTGATGACGCAGTCTCCAGCCACCCTGTCTGTGTCTCCAGGGGAAAGAGCCACCCTCTCCTGCAGG<br>GCCAGTCAGAGTGTTAGCGGCGACTTAGTCTGGTACCAGCAGAAACCTGGCCAGGCTCCCAGGCTCCTCATC<br>TATGGTGCCACCACCAGGGCCTCTGGTGTCCCAGCCAGGTTCAGTGGCAGTGGGTCTGGGACAGAGTTCACT<br>CTCACCATCAGCAGCCTGCAGTCTGAAGATTTTGCAATTTATTACTGTCAGCAGTATAATAACTGGCCCCGG<br>ACGTTCGGCCAAGGGACCAAGGTGGAAATCAAA |
| Con1p6-e06k | 160 | GAAATAGTGATGACGCAGTCTCCAGCCACCCTGTCTGTGTCTCCAGGGGAAAGAGCCACCCTCTCCTGCAGG<br>GCCAGTCAGAGTGTTGGCAACAACTTAGCCTGGTTTCAGCAGAAACCTGGCCAGGCTCCCAGGCTCCTCATC<br>TATGGTGCATCCACCAGGGCCACTGGTATCCCAGCCAGGTTCAGTGGCAGTGGGTCTGGGACAGAGTTCACT<br>CTCACCATCAGCAGCCTGCAGTCTGAAGATTTTGCAGTTTATCACTGTCAACACTATCATAACTGGCCTCCCA<br>CTTTTGGCCAGGGGACCAAGGTGGAAATCAA |

| Con2 Heavy | Seq ID No. | |
|---|---|---|
| Con2p3-c04h | 161 | CAGGTGCAGCTGGTGGAGTCTGGGGGAGGCGTGGTCCAGCCTGGGAGGTCCCTGAGACTCTCCTGTGCAGCC<br>TCTGGATTCACCTTCAGCAACCATGGCATGCACTGGCTCCGCCAGACTCCAGGCAAGGGGCTGGAGTGGGTG<br>GCAGTCATTTCATATGATGGAAGTACCAAATACTATGCAGACTCCGTGAAGGGCCGATGCACCCTCTCCAGA<br>GACAATTCCAAGGAAACGGTGTTTCTGCAAATGAACAGCCTGAGACCTGAGGACACGGCTGTGTATTATTGT<br>GCGAAAGGGTGTTCTAATGGTGGTAACTGCTTTTTGATTGACTACTGGGGCCCGGGAACCCTGGTCACCGTC<br>TCCTCA |
| Con2p3-c05h | 162 | GAGGTGCAGCTGTTGGAGTCGGGGGGAGACTTGGTGCAGCCTGGGGGGTCCCTGAGACTCTCCTGTGCAGCC<br>TCTGGATTCGACTTCAGTATTTATGGCATGAACTGGGTCCGCCAGGCTCCAGGGAAGGGGCTTGAATGGGTC<br>TCAGTTATTAGTGGTGATGGCACTATCATATACTACGCAGACTCCGTGAAGGGCCGGTTCACTATCTCCAGA<br>GACAATTCCAAGAACACACTGTTTTTGCAAGTGAACAGCGTGAGAGCCGAGGACACGGCCGTATATTACTGT<br>GCGAAGGGGGGCTACTATGAATCGGGGACTATGCGGCTTTTGATATCTGGGGCCAAGGGACAATGGTCAC<br>CGTCTCTTCA |
| Con2p3-f03h | 163 | GAGGTGCAGCTGGTGGAGGAGTCTGGGGGAGGCTTGGTCCAGCCTGGGGGGTCCCTGAGACTCTCCTGTGC<br>AGCCTCTGGATACACCTTTAGTAGTTATTCAATGAGTTGGGTCCGCCAGGCTCCAGGGAAGGGGCTGGAGTG<br>GGTGGCCAGCATTAAGCCAGAAGGAAGTGAGAAATTCTATGTGGACTCTGTGAAGGGCCGATTCACTATCTC<br>CAGAGACAACGCCAAGAACTCACTGTATCTGCAAATGAACAGCCTGAGAGGCGAGGACACGGCTGTCTACT<br>ACTGTGCGAGAGGGAATCTAATTTCCGATACTGGCACCAGGGAACCCTGGTCACCGTCTCCTCA |
| Con2p3-g05h | 164 | GAGGTGCAGCTGGTGGAGTCTGGGGGAGCCTTGGTCCAGCCTGGGGGGTCCCTGAGACTCTCCTGTGCAGCC<br>TCTGGATTCATCTTCAGTAACTCTTGGATGGGCTGGTTCCGCCAGGCTCCAGGGAAGCGGCCGGAGTTCGTG<br>GCCAACATAAAACCAGATGGAAGTGAGAAATTCTATGGACTCTGTGAAGGGCCGATTCACCATCTCCAG<br>AGACAACGCCGAGAACTCACTGTATCTGCTGATGAACAGCCTGAGAGCGAGGACACGGCTGTCTATTACTG<br>CGCGAGAGATAGCACTTCCCGGCCCGTTTGGGTACTGGGGCCAGGGAACCCTGGTCACCGTCTCCTCA |
| Con2p4-b03h | 165 | GAGGTGCAGCTGGTGGAGACTGGAGGAGGCTTGATCCAGCCTGGGGGGTCCCTGAGGCTCTCCTGTGCACGC<br>CTCTGGGTTAAACGTCAATAGTTACTACATGAACTGGGTCCGCCAGGCTCCAGGGAAGGGGCTGGAGTGGGT |

TABLE 2-continued

Selected Heavy and Light Chain Sequences from Antibodies of Table 1 (SEQ ID NOS. 127-252)

| | | |
|---|---|---|
| | | CTCAGTTATTTATAGCGGTGGTGGCACAAACTACGCAGACTCCGTGAGGGGCCGATTCATCATCTCCAGAGA<br>CAATTCCAGGAACGCGCTTTATCTTCAAATGAACAGCCTGAGAGCCGAGGACACGGCCGTGTATTACTGTGC<br>GACGGGCGGGATGACCAGTAGTTGGTACGGCTACTGGGGCCAGGGAACCCTGGTCACCGTCTCCTCA |
| Con2p4-c02h | 166 | AGGTGCAGCTGGTGCAGTCTGGGGCCGAGGTGAAGAAGCCTGGGGCCTCAGTGAAGGTTTCCTGCAAGGCA<br>TCTGGAATACACTTTCATCAACTACCTTGTGTTCTGGGTGCGACAGGCCCCTGGACAAGGGCTTGAGTGGATG<br>GGAGAAATGAACCCCACTCGTGGGAGCAAGCTACGCACAGAAGTTCCAGGGCAGAGTCACCATGACCAG<br>GGACACGTCCACGAGCACAGTCTACATGGAGTTGAGCAGCCTGAGATCTGACGACACGGCCGTTTATTACTG<br>CTCCATGGGTCCGCCTATTGTACTGGTGGAAGCTGTTACTCCGCCTGTGATTTCTGGGGCCCGGGAACCCTG<br>GTCACCGTCTCCTCA |
| Con2p4-d06h | 167 | GAGGTGCAGCTGGTGGAGTCTGGGGCAGGCTTGATGAAACCTGGGGGGTCCCTTAGACTCTCCTGTGCAGTC<br>TCTGGGTTCACTTTCACTAACGCCTGGCTGAGCTGGGTCCGCCAGCCTCCAGGGAAGGGGCTGGAGTGGGTT<br>GGCCGTGCTTACAGCAGTTCTGGCGGTTGGACAATGGACTACTCTTCACCCGTGAGGGGCAGATTCACCATC<br>ACAAGAGACGATTCAAAAAACACTGTATCTGCAAATGAACAACCTGAAAACCGAGGACACAGCCGTGTA<br>TTACTGTACCACAGATATTGGCAAAGGCTGGTACACGCACTATCCTGACCTCTGGGGCCAGGGAACCCTGGT<br>CACCGTCTCCTCA |
| Con2p5-a06h | 168 | CAGGTGCAGCTGGTGGAGTCTGGGGGAGGCGTGGTCCAGCCTGGGAAGTCCCTCAGACTCTCCTGTGTAGCC<br>TCTGGATTCACCTTAAGTACCTGTGGCATGCACTGGGTCCGCCAGGCTCCAGGCAAGGGGCTGGAGTGGGTG<br>GCAGTTACAACATATGATGGAGATCGTAAATAATGTAGACTCCGTGAAGGGCCGATTCACCATCTCCAGA<br>GACAATTCCAAGAACACGGTGTATCTGCAAATGGACGGCCTCAAAGCCGAGGACACGGCTGTGTATCACTG<br>TGTGAAAGAATATAGTTGGGGTTACTACAGAACTGCGGACTACTGGGGCCAGGGAACCCTGGTCACCGTCTC<br>CTCA |
| Con2p5-b06h | 169 | GAGGTGCAGCTGGTGGAGTCCGGGGGAGGCTTAGTTCAGCCGGGGGGGTCCCTGAGACTCTCCTGTGTAGCC<br>TCTGGATTCACCTTCAGTACTTACTGGATGCACTGGGTCCGCCAACCTCCGGGGAAGGGGCTGGTGTGGGTC<br>TCACGTATTAATCCTGATGGCAGTAGCACAAACTACGCGGACTCCGTGAACGGCCGATTCACCATCTCCAGA<br>GACAACGCCAAGAACACGCTGTATCTTGAAATGAACAGTTTGAGAGTCGAGGACACAGCTCTCTATTACTGT<br>GCAAGAAGTCCTGGGGGTTACTTTGACTACTGGGGCCACAGCACCCTGGTCACCGTCTCCTCA |
| Con2p5-c04h | 170 | GAGGTGCAGCTGGTGGAGTCTGGGGGAGGCTTGGTGAAGCCTGGGGGGTCCCTTACACTCTCCTGTGCAGTC<br>TCTGGATTCACTTTCAGTACCGGCTGGATGAGCTGGGTCCGCCAGGCTCCAGGGAAGGGGCTGGACTGGGTT<br>GGCCGTATTAAAAGCAAAACTGCTGGTGGGACAACAGACTATGCTGCACCCGTGAAAGACAGATTCACCAT<br>CTCAAGAGATGATTCAAAAAACACGCTGTATCTGCAACTGAGCAGCCTTAAAACCGAGGACACAGCCGTGT<br>ATTACTGTACCACAGATGACCTGAAAAACTGGGGCCAGGGAACCCTGGTCACCGTCTCCTCA |
| Con2p5-e05h | 171 | GAGGTGCAGCTGGTGGAGTCTGGGGGAGGCTTGGTGCAGCCGGGGGGGTCCCTGAGACTCTCCTGTGCAGC<br>CTCTGGATTCACCTTCAGTAGTTATAGCATGAACTGGGTCCGCCAGGTCCCGGGAAAGGGGCTGGAGTGGGT<br>CTCATACACAAGTACTAAAAGTGATATCAAATACTACGCGACTCTGTGGAAGGCCGATTCACCATTTCCAG<br>AGACAATGCCAAGAACTCATTGTATCTGCAAATGAACAGCCTGAGAGACGAAGACACGGCTGTCTATTATTG<br>TGCGAGAGGACGAGATTGTTATGGGGGTAACTGCGTCATCTACTTCCACTACTACGGTTTGGACGTCTGGGG<br>CCAAGGGACCACGGTCACCGTCTCCTCA |
| Con2p6-b03h | 172 | CAGGTGCAGCTGGTGGAGTCTGGGGGAGGCGTGGTCCAGCCTGGGGGGTCCCTGAGACTCTCCTGTGTAGTC<br>TCTGGATTCACCCTCAGTTCCTGTGGCATGCATTGGGTCCGCCAGTCTCCAGGCAAGGGGCTGGAGTGGCTG<br>TCAGTTAGCACCTATGATGGAGATGGCAATCAGAAATACTATGCGGCCTCCGTGAAGGGCCGATTCCTCATC<br>TCCAGACACTTCGAAGAACACGGTGTATCTCCATATGAACAGCCTGACAGCTGAGGACACGGCTCTATAT<br>TATTGTGTGAAAGAGAGTGCCACTGGCTGGTATCGCACCGCTGATTACTGGGGCCAGGGAACCCTGGTCACC<br>GTCTCCTCA |
| Con2p6-c05h | 173 | GAGGTGCAGCTGGTGGAGTCTGGGGGAGGCTTGGTCCAGCCTGGGGGGTCCTTGAGACTCTCCTGTGCAGCC<br>TCTGGATTCACCGTCAGTAGCATATTCATGAGCTGGGTCCGCCAGGCTCCAGGGCAGGGGCTGGAGTGGGTC<br>TCAGTCATCTATACCGATGGAAAAACATATTATGCACACTCCGTGGAGGGCCGATTCACCATCTCCAGAGAC<br>GATTCCAAGAATATGGTGTATCTTCAATTGAGCAGCCTGAGAACTGAGGACACGGCTGTTTATTACTGTGCG<br>AGAGATATTCCAACGACATTTGGAATAGGTGAAGCTTTTGATATCTGGGGCCAGGGGACAATGGTCACCGTC<br>TCTTCA |
| Con2p6-g04h | 174 | AGGTGCAGCTGGTGCAGTCTGGGGCTGAGGTGAAGAAGCCTGGGGCCTCAGTGAAGCTTTCCTGCAAGACA<br>TCTGGATACTCCTTCACCAGCAACTATTTGCACTGGGTGCGACAGGCCCCTGGACAAGGACTTGAGTGGATG<br>GGAATGGTCTACCCAAATGATGGTACTACAACCTACGCTCAGAAGTTTCAGGGCAGAGTCACCATGACCAGT<br>GAGACGTCCACAACCACAATTTACATGGACCTGAGCGGCCTGACATCTGAGGACACGGCCATATATTACTGT<br>GCTAGAGACGATTCGGCCTTTGACTACTGGGGCCAGGGAACCCTGGTCACCGTCTCCTCA |
| Con2p7-d03h | 175 | CAGGTGCAGCTGGTGGAGTCTGGGGGAGGCGTGGTCCAGCCTGGGAGGTCCCTGAGACTCTCCTGTGAAGC<br>CTCTGGATTCATCTTCAGTAGCAATGGCATGCACTGGGTCCGCCAGGCTCCAGGCAAGGGCTGGAGTGGGA<br>GGCAGTTATATCATCTGATGGAAGTAGGAGATACTATGCAGATCCAATGAAGGGCCGATTCACCATCTCCAG<br>AGACAACTCCAAGAACACGCTGTATCTGCAATTGAACAGCCTGAGAGCTGACGACACGGCCGTCTATTACTG<br>TGCGAAAGGCTGTAGTGTGAAAATTGCTTCTATATGGACGACTGGGGCAAAGGGACCACGGTCACCGTCTCC<br>TCA |
| Con2p8-b01h | 176 | AGGTGCAGCTGGTGCAGTCTGGGGCTGAGGTGAAGAAGCCTGGGGCCTCACTGAAGGTCTCCTGCAAGGCA<br>TCTGGATACACCTTCAGACAGAACTATTTCCACTGGGTGCGACAGGCCCCTGGACAAGGGCTTGAGTGGATG<br>GGAGTAATCAACCCGAGTGATGTAGTACAAAGTTCGCACAGAAGTTCCAGGGCAGAGTCAGCATGACCAG<br>GGACACGTCCACGAGCACAGTTTACATGGACCTGAGCAGTCTGACATCTGAGGACACGGCCGTCTATTATTG<br>TACGAGAGAGATCGGCGCAGTGGTAGTAGATGCTACGTCGTTGGGGTGGTTGGGCTACTTTTGACTACTGGGG<br>CCAGGGAACCCTGGTCACCGTCTCCTCA |

TABLE 2-continued

Selected Heavy and Light Chain Sequences from Antibodies of Table 1 (SEQ ID NOS. 127-252)

| | | |
|---|---|---|
| Con2p8-b05h | 177 | GAGGTGCAGCTGGTGGAGTCTGGGGGAGGCTTGGTCCAGCCGGGGGGGTCCCTGAGTCTCTCCTGTGAAGCC<br>TCTGGATTAACCTTCAGTGGCTACTGGATGAACTGGGTCCGCCAGGCTCCAGGGAAGGGGCTGGAGTGGGTG<br>GCCAACATAAATCCAGAAGGAAGTGAGAGGAGATACGTGGAGTCTGTGCAGGGCCGATTCACCGTCTCCAG<br>AGACAACCCGAAGAACACCCTGTATTTGCAAATGAACAGCCTGAGAGTCGAGGACACGGCTCTGTATTACT<br>GTGCGGGCTGGGGGAGAACCCAGGACTGGGGCCAGGGAGCCCTGGTCACCGTCTCCTCA |
| Con2p8-e03h | 178 | CAGGTGCAGCTGGTGGAGTCTGGGGGAGGCGTGGTCCAGCCTGGGAGGTCCCTGAGACTCTCCTGTGCAGCC<br>TCTGGACTCACCTTCAGCAATTATGGCATGCACTGGGTCCGCCAGGCTCCAGGGAAGGGGCTGGAGTGGGTT<br>GCAGTTGTGTCGGCAAGGGGAGGAACTACATATTATGCAGACTCCGTGAAGGGCCGATTCACCATCTCCAGA<br>GACAATTCCAAGAACACGATGTCTCTGCAAATGAACGGCCTGAGACCTGACGACACGGCTGTGTATTTTTGT<br>ACGAAAGAAGGAGCACCACCTGGAAAATATGCTTTTGATATCTGGGGCCAAGGGACAATGGTCACCGTCTC<br>TTCA |
| Con2p8-f05h | 179 | GAGGTGCAGCTGGTGGAGTCTGGGGGAGGCTTGGTCCAGCCTGGAGGATCCCTGAGACTCTCCTGCGCAGCC<br>TCCGGATTCACCTTCAGTGACTACCGCATGGACTGGGTCCGCCAGGCTCCAGGGAAGGGGGCTGGAGTGGATT<br>GCCCGTATTAGACACAGAGATGCAGGCTATAGCACAGAATACGCCGCGTCTGTGAGGGGCAGATTCACCGT<br>CTCAAGAGATGACTCACAGAGTACACTGTACCTGCAGATGAACAGCTTGAAAGCCGACGACACGGCCGTGT<br>ATATTTGTCTTAAAGATTCTTCGCAATACTCTTTTGATGCGTGGGGCCAAGGGACAATGGTCACCGTCTCTTC<br>A |
| Con2 Kappa | Seq ID No. | |
| Con2p3-c04k | 180 | GACATCGTGATGACCCAGTCTCCAGACTCCCTGGCTGTGTCTCTGGGCGAGAGGGCCACCATCAACTGCAAG<br>TCCAGTCAGAGTATTTTATCCAGATCCAACAATAAGAACTACTTAGCCTGGTACCAGCAGAAACCAGGACAG<br>CCTCCTAAATTGCTCCTTTATTGGGCATCTACCCGGGAATCCGGGGTCCCTGACCGATTCAGTGTCAGCGGGT<br>CTGGGTCAGATTTCACTCTCACCATCAGTAGCCTGCAGGCTGAGGATGTGGCAGTTTATTACTGTCAGCAGT<br>ATTATAATGCTCCCCTCACTTTCGGCGGAGGGACCAAGGTGGAGATCAAA |
| Con2p3-c05k | 181 | GAAATTGTGTTGACACAGTCTCCAGCCACCCTGTCTTTGTCTCCAGGGGAAAGGGCCACCCTCTCCTGCAGG<br>GCCAGTCAGACTGTTAGCAGGTACTTAGCCTGGTACCAACAAAAGCCTGGCCAGGCTCCCAGGCTCCTCATC<br>TATGCTGCATCCAACAGGGCCACTGGCATCCCAACCAGGTTCAGTGGCAGTGGGTCTGGGACAGACTTCACT<br>CTCACCATCAGCAGCTAGAGCCTGAAGATTTTGCATTTTATTACTGTCAGCAGCGTAGCAACTGGCCTGCC<br>ACTTTCGGCGGAGGGACCAAGGTGGAGATCAAA |
| Con2p3-f03k | 182 | GACATCCAGATGACCCAGTCTCCTTCCTCCCTGTCTGCATCTGTAGGAGACAGTGTCACCATCACTTGCCAGG<br>CGAGTCAGGACATTAGAGACCGTTTAAATTGGTATCAGCAGAAGCCAGGGAAAGCCCCTAACCTCCTGATCT<br>ACGATGCATCAAGTTTGGAAACAGGGGTCCCATCAAGGTTCAGAGGAAGTGGATCTGGGACAGATTTTACTT<br>TCACCATCAGCAGCCTGCAGCCTGAAGATATTGCAACATATTACTGTCAACAGTTTGTTAGTTTCCCTCGAAC<br>TTTCGGCCCGGGGACCAAAGTGGATATCAAA |
| Con2p3-g05k | 183 | GAAATTGTGTTGACGCAGTCTCTCAGGCATCCTGTCTTTGTCTCCAGGGGAAAGAGCCACCCTCTCCTGCAGG<br>GCCAGTCAGAGTGTTAGCAGCAGGTCCTTGTCCTGGTACCAGCAGAGACCTGGCCTGGCTCCCAGGCTCCTC<br>ATCTATGCTGCATCCAGCAGGGCCGCTGTCACCCCAGACAGGTTCACTGCCAGCGGGTCTGGGACAGACTTC<br>ACTCTCACCATCAGCAGTCTGGAGCCTGAAGATTTTGCAGTGTATTACTGTCAGCACTATGGTACCTCACCTC<br>CGAGGTACACTTTTGGGCAGGGGACCAAGGTGGAGATCAAA |
| Con2p4-b03k | 184 | GACATCGTGATGACCCAGTCCCCAGACTCCCTGGCTGTGTCTCTGGGCGAGAGGGCCACCATCAACTGCAAG<br>TCCAGCCAGAGTGTTTTACACAGCTCCAACAATAAGAACTACTTGCTTGGTACCAGCAGAAACCAGGACAG<br>CCTCCTAAGCTGCTCATTCACTGGGCATCTACCCGGGCATCCGGGGTCCCTGACCGATTCAGTGGCAGCGGG<br>TCTGGGACAGATTTCACTCTCACCATCAGCAGCCTGCAGGCTGAAGATGTGACAATTTATTACTGTCAGCAA<br>TATTATAGTACTCCGTACACTTTTGGCCAGGGGACCAAGGTGGAAATCAAA |
| Con2p4-c02k | 185 | GAAATTGTGTTGACGCAGTCTCCAGGCACCCTGTCTTTGTCTCCAGGGGAAAGAGCCACCCTCTCCTGCAGG<br>GCCAGTCCGAGTCTTGACAGCGCCTACTTAGCCTGGTACCAGCAGAAGCCTGGCCAGGCTCCCAGGCTCCTC<br>ATCTATGGTGCATCCTCCAGGGTCACTGGCATCCCAGATAGGTTCAGTGGCAGTGCGTCAGGGACAGACTTC<br>ACTCTCACCATCAGCAGACTGGAGCCTGAAGATTTTGCAGTGTACTACTGTCAGCGGTATGGTAACTCACCT<br>CCGTACACTTTTGGCCAGGGGACCAAGGTGGAGATCAAA |
| Con2p4-d06k | 186 | GACATCGTGATGACCCAGTCTCCAGACTCCCTGGCTGTGTCTCTGGGCGAGAGGGCCACCATCAGCTGCAAG<br>TCCAGCCAGAGTCTTTTATACAGTTCCAGCAATAAGAACTACCTAGCTTGGTTCCAGCAGAAACCAGGACAG<br>GCTCCTAAGTTGCTCATTTACTGGGCATCTACCCGGGAATCCGGGGTCCCTGACCGATTCAGTGGCAGCGGG<br>TCTGGGACAGATTTCACTCTCACCATCAGCAGCCTGCAGACTGAAGATGTGGCAGTTTATTATTGTCTGCAAT<br>ATCGTAGTGCTCCGTTCACTTTCGGCGGAGGGACCAAGGTGGAGATCAAA |
| Con2p5-a06k | 187 | GACATCCAGATGACCCAGTCTCCTTCCACCCAGTCTGCATCTGTAGGAGACAGAGTCACCATCACTTGCCGG<br>GCCAGTCAGAGTATTAGTAGTTGGTTGGCCTGGTATCAGCAGAAACCAGGGAAAGCCCCTAAGGTCCTGATC<br>TATGCGGTGTCTAGTTTAGAAAGTGGGGTCCCATCAAGGTTCAGCGGCAGTGGATCTGGGACAGAATTCACT<br>CTCACCATCAGCAGCCTGCAGCCTGAGGATTTTGCAACTTATTACTGCCAACAATATAGTACTTATCCCTGGA<br>CGTTCGGCCCAGGGACCAAGGTGGAAATCAAA |
| Con2p5-b06k | 188 | GAAATAGTGATGACGCAGTCTCCAGCCTCCCTGTCTGTGTCTCCAGGGGAAACAGCCACCCTCTCCTGCAGG<br>GCCAGTCAGAGTGTTGGCAGCACCTTAGCCTGGTACCAGCAGAAGCCCGGCCAGGCTCCCAGGCTCCTCATC<br>TATAATGTATTCACCAGGGCCGCTGGTGTCCCAGCCAGGTTCAGTGGCAGTGGGTCTAGGACGGAGTTCACT<br>CTCACCATCAGCAGCCTGCAGTCTGAAGATTTTGCAGTTTATTACTGTCAGCAGTATAGTACCTGGCTGTGGA<br>CGTTCGGCCAAGGGACCAAGGTGGAAATCAAA |
| Con2p5-c04k | 189 | GACATCCAGATGACCCAGTCTCCATCCTCCCTGTCTGCATCTGTAGGAGACAGAGTCACCATCACTTGCCGG<br>GCAAGTCAGCGCATTAGCAGCTACTTGAATTGGTATCAGCAGAAACCAGGGAAAGCCCCTAACCTCCTGATC |

TABLE 2-continued

Selected Heavy and Light Chain Sequences from Antibodies of Table 1 (SEQ ID NOS. 127-252)

| | | |
|---|---|---|
| | | TACGCTGCAGCCAGTTTGCATGATGGGGTCCCATCAAGGTTCAGTGGCAGTGGATCTGGGACAGATTTCACT<br>CTCACCATCAGCAGTCTGCAACCTGAAGATTTTGCAACTTATTATTGTCAACAGCGTTACAGAATCCCGTACA<br>GTTTTGGCCCGGGGACCAAGGTGGAGATCAAA |
| Con2p5-e05k | 190 | GATATTGTGATGACTCAGTCTCCACTCTCCCTGTCCGTCACCCCTGGAGAGCCGGCCTCCATCTCCTGCAGGT<br>CTAGTCAGAGCCTCCTTCAGGGTAATGGACACAACTATTTGGATTGGTACCTGCAGAAGCCAGGACAGTCTC<br>CACAACTCCTGATCTATTTGGGTTCTATTCGGGCCTCCGGGGTCCCTGACAGGTTCAGTGGCAGTGGATCAG<br>GCACAGATTTATACTGAAATCAGCAGAGTGGAGGCTGAGGATGTTGGGGTTTATTACTGCATGCAAGCTC<br>TACAAACTCCGTACACTTTTGGCCAGGGGACCAAGGTGGAAATCAAA |
| Con2p6-b03k | 191 | GACATCCAGATGACCCAGTCGCCTTCCACCCTGTCTGCATCTGTTGGAGACAGAGTCACCCTCACTTGTCGG<br>GCCAGTCAGAGACTCTTAATAACTGGTTGGCCTGGTTTCAGCAAAAGCCAGGGAAAGCCCCTACCCTCCTGATC<br>TATGAGGCGTCTAGTTTAGAAAGTGGAGTCCCATCAAGGTTCAGCGGCAGTGGATCTGGGACAGACTTCGCT<br>CTCACCATCAGCAGCCTGCAGCCCGATGATTTTGCAACTTATTATTGCCACCAGTATAATAAATACCCGTGG<br>ACGTTCGGCCAAGGGACCAAGGTGGAGATCAAA |
| Con2p6-c05k | 192 | GACATCCAGATGACCCAGTCTCCTTCCACCTTGTCTGCATCTGTAGGAGACAGAGTCACCATCACTTGTCGG<br>GCCAGTCAGAGTATTAGTGGCTGGTTGGCCTGGTATCAGCAGAAAGCAGGGAAAGCCCCTAAGCTCCTGATC<br>TATAAGGCGTCTAGTTTAGAAAGTGGGGTCCCATCAAGGTTCAGCGGCAGTGGATCTGGGACAGAGTTCACT<br>CTCACCATCAGCAGCCTGCAGCCTGATGATTTTGCAACTTATTACTGCCAGCAGTATTATAGTTGGGGAACGT<br>TCGGCCAAGGGACCAAGGTGGAGATCAAA |
| Con2p6-g04k | 193 | GATATTGTGATGACCCAGACTCCACTCTCCTTACCTGTCACCCTTGGACAGCCGGCCTCCATCTCCTGCATAT<br>CTAGTCAAAGCCTCGTACACAGTGATGGAAACACCTACTTGAGTTGGCTTCAGCAGAGGCCAGGCCAGCCTC<br>CAAGACTCCTGATTTATAAGATTTCTAACCGGTTCTCTGGGGTCCCAGACAGATTCAGTGGCAGTGGGGCAG<br>GGACAGATTTCACACTGAAAATCAGCAGGGTGGAAGCTGAGGATGTCGGGGTTTATTACTGCATGCAAGCTT<br>CACAATCTACGTGGACGCTCGGCCAAGGGACCAAGGTGGAGATCAAA |
| Con2p7-d03k | 194 | GACATCGTGATGACCCAGTCTCCAGACTCCCTGGCTGTGCCTCTGGGCGAGAGGGCCACCATCAACTGCACG<br>TCCAGCCAGACTGTTTTATCCAGTTCCAACAATAAGAACTACTTAGTTTGGTACCAGCAGAAACCAGGACAG<br>CCTCCTAAGTTGCTCCTTTACTGGGCGTCTACCCGGGCATCCGGGGTCCCTGACCGATTCAGTGGGAGCGGG<br>TCTGGGACAGATTTCACTCTCACCATTAGCAGTCTGCAGGCTGAAGATGTGGCAGTTTATTACTGTCAGCAAT<br>GTTATAATGCTCCGCTCTCACTTTCGGCCGAGGGACCAAGGTGGAGATCAAA |
| Con2p8-b01ka | 195 | GAAATAGTGATGACGCAGTCTCCAGCCACCCTGTCTGTGTTTCCAGGGGAAGGAGTCACCCTCTCCTGCAGG<br>GCCAGTCAGAGTATTAGCAACAACTTGGCCTGGTACCAGCAGAAACCTGGCCAGGCTCCCAGGCTCCTCATG<br>TATGATGCATCCACCAGGGCCACTGGTATCCCAGCCAGGTTCAGTGGCAGTGGGTCTGGGACAGAGTTCACT<br>CTCACCATCAGCAGCCTGCAGTCTGAAGATTTCGCAGTTTATTACTGTCAGCAGTATAATAACTGGCCTCCGG<br>TCACGTTCGGCCAAGGGACCAAGGTGGAAATCAAA |
| Con2p8-b05k | 196 | TTGTGATGACTCAGTCTCCACTCTCCCTGCCCGTCACCCTTGGACAGTCGGCCTCCTGTCTCCTGCAGGTCAAG<br>TCAAAGCCTCGGCCCCAGTGACGGAAGCACCCGCTTGGATTGGTTTCAACAGAGGCCAGGCCAATCTCCAAG<br>GCGCCTAATTTATGCGGTTTCTAACCGGGACTCTGGGGTCCCAGACAGATTCAGCGGCAGCGGGTCAGGCAG<br>TGATTTCACACTGAGAATCAGCAGAGTGGAGGCTGAGGATGTTGGGGTTTATTACTGCATGCAATATACATA<br>CTGGCCTCACACTTTTGGCCAGGGGACCAAGGTGGAAATCAAA |
| Con2p8-e03k | 197 | GAAATTGTGTTGACACAGTCTCCAGCCACCCTGTCTTTGTCTCCAGGGGAAAGAGCCACCCTCTCCTGCAGG<br>GCCAGTCAGAGTGTTAGCAGTTCCTTAGCCTGGTACCAACAAAAACCTGGCCAGGCTCCCAGGCTCCTCATC<br>TATGATGCATCCAAGAGGGCCACTGACATCCCAGCCAGGTTCAGTGGCAGTGGGTCTGGGACAGACTTCACT<br>CTCACCATCAGCTAGAGCCTGAAGATTTTGCGGTTTATTACTGTCAGCACCGGGGGGAGTGGCCTCCG<br>GGGGCCACTTTCGGCCCTGGGACCAAAGTGGATATCAAA |
| Con2p8-f05k | 198 | GACATCCAGTTGACCCAGTCTCCATCCTTCCTGTCTGCATCTGTAGGAGACAGAGTCACCATCACTTGCCGGG<br>CCAGTCAGGGCATTGATACTCGTTTGATCTGGTATCAACAGAAGCCAGGGGAAGCCCCTAAGCTCCTGATCT<br>ATGAAGCATCCACTTTGCAAAGTGGGGCCCCATCAAGGTTCAGCGGCAGTGATTCGGGACAGAATTCACTC<br>TCACAATCAGCAGTCTGCAGCCTGAAGACTTTGCAACTTATTACTGTCAACAGTTTAAAGGTTACCCGCTCAC<br>TTTCGGCGGGGGGACCAAGGTGGAGATCAAA |
| SLE1 Heavy | Seq ID No. | |
| SLE1p1-a02h | 199 | CAGGTGCAGCTGCAGGAGTCGGGCCCAGGACTGGTGAAGCCTTCGGAGACCCTGTCCCTCACCTGCACTGTC<br>TCTGGTGGCTCCATCAGTAGTCACTACTGGAGCTGGATCCGGCAGCCCCCAGCGAAGGGACTGGAGTGGATT<br>GGGTATATCTATACAGTGGGATGACCAACTACAACCCCTCCCTCAAGAGTCGAGTCACCATATCAATAGAC<br>ACGTCCAAGAACCAGTTCTCCCTGAAGTTGAGCTCTGTGACCGCTGCGGACACGGCCGTGTATTACTGTGCG<br>AGAGGTGATGGCTACAATTTCTTCTGGGGCCAGGGAACGCTGGTCACCGTCTCCTCA |
| SLE1p1-a03h | 200 | CAGGTGCAGCTGGTGGAGTCTGGGGGAGGCGTGGTCCAGCCTGGGGGGTCCCTGAGACTCTCCTGTGCAGC<br>GTCTGGACTCACGTTCAGTAACCAAGATTTCCACTGGGTCCGCCAGGCTCCAGGCAAGGGGCTGGAAGGGT<br>GGCATTTATACGTTATGATGGAGGTTTTAAAAACTATGCAGACTCCGTGAAGGGCCGATTCACCATCTCCAG<br>AGACAATTCCCAGAACACGCTGTATCTGCAAATGGACAGCCTGAGAGTTGAAGACACGGCTGTGTATTACTG<br>TGCGAAGTGCGCGCAGAGGACTCTACTACTGTCTGGCTGAATTGGTTCGACCCCTGGGGCCAGGGAACCCT<br>GGTCACCGTCTCCTCA |
| SLE1p1-b05h | 201 | GAGGTGCAGCTGTTGGAGTCTGGGGGAGGCTTGGTAGAGCCTGGGGGGTCCCTGAGACTCTCCTGTGCAGCC<br>TCTGGATTCACCTTTAGCAGCTATGCCATGAGCTGGGTCCGCCAGGCTCCAGGGAAGGGGCTGGAGTGGGTC<br>TCAGCTATTAGTGACAGTGGTGGTAGCACATACTACGCAGACTCCGTGAAGGGCCGGTTCACCATCTCCAGA |

TABLE 2-continued

Selected Heavy and Light Chain Sequences from Antibodies of Table 1 (SEQ ID NOS. 127-252)

| | | |
|---|---|---|
| | | GACAAGTCCAAGAACACGCTGTATCTGCAAATGAACAGCCTGAGAGCCGAGGACACGGCCGTATATTACTG TGCGAAACCGAATTACTTTGGTTCGGGGAGTCCCGACTACTGGGGCCAGGGAACGCTGGTCACCGTCTCCTC A |
| SLE1p1-c04h | 202 | CAGGTGCAGCTGCAGGAGTCGGGCCCAGGACTGGTGAAGCCTTCGGAGACCCTGTCCCTCACCTGCACTGTC TCTGGTGCCTCCATCAGTAGTCACTACTGGAGCTGGATCCGGCAGCCCCCAGGGAAGGGACTGGAGTGGATT GGGTATATCTATACAGTGGGATTACCAACTACAACCCCTCCCTCAAGAGTCGAGTCACCATATCAATAGAC ACGTCCAAGAACCAGTACTCCCTGAAGCTGAGCTCTGTGACCGCTGCGGACACGGCCGTGTATTACTGTGCG AGAGGTGATGGCTACAATTTCTACTGGGGCCAGGGAACGCTGGTCACCGTCTCCTCA |
| SLE1p1-e01h | 203 | GAGGTGCAGCTGGTGGAGTCTGGGGGAGGTGTGGTACGGCCTGGGGGGTCCCTGAGACTCTCCTGTGCAGC CTCTGGATTCACCTTTGATGATTATGGCATGACCTGGGTCCGCCAAGCTCCAGGGAAGGGGCTGGAGTGGAT CTCTGGTATTTGTTGCAACGGTGGTTGCTCAGGTTATGCAGACTCTGTGAAGGGCCGATTCACCATCTCCAGA GACAACGCCAAGAAGTCCCTGTTTCTGGTCATGAACAGTCTGAGAGCCGAGGACACGGCCTTGTATTACTGT GTGAGAGTGGCAGTACCAGCTGCTACATACACCCGAGGGAATGATGCTTTTGATATTTGGGGCCAAGGGAC AATGGTCACCGTCTCTTCA |
| SLE1p1-f02h | 204 | GAGGTGCAGCTGGTGGAGTCTGGGGGAGGCTTGGTAGAGCCTGGGGGGTCCCTCAGACTCTCCTGTGCAGTC TCTGGTTTCACTTTCACGACGCCTGGATGACCTGGGTCCGCCAGGCTCCAGGGAAGGGGCTAGATTGGGTT GGCCATGTAAAAAGTAAATATGATGGTGCGACAACAGAGTACGCTGCACCCGTGCAAGGCAGATTCACCAT CTCAAGAGATGATTCAAAGAAGACAATATATCTGCAAATGAACAGCCTGAACACCGAGGACACAGGCGTCT ATTTTTGTACCACAGCTCATGGCCCGGTGGGTGACCATTGGGGCCAGGGAACACTGGTCACCGTCTCCTCA |
| SLE1p1-g05h | 205 | GAGGTGCAGCTGGTGGAGTCTGGGGGAGGCTTGGTCCAGCCGGGGGGGTCCCTGAGACTCTCCTGTGCAGC CTCTGGATTCAGCTTTGATACCTCTTGGATGACCTGGGTCCGCCAGGCTCCAGGGAAGGGGCTGGAGTGGGT GGCCACCATAAACCAGGGTGGAAGTGACAAATACTATGTGGACTCTGTGAAGGGCCGATTCACCATCTCCA GAGACAACGCCAAGAACTCACTGTATCTGCAAATGAACAGCTGCGAGCCGAGGACACGGCTGTATATTAC TGTGCGAGAGCGGGCGGGTGTAGCTCTACCAGATGCCATACAACCCCGGGATTTGACTACTGGGGCCAGGG AGCGCTGGTCACCGTCTCCTCA |
| SLE1p2-a02h | 206 | TGCAGCTGCAGGAGTCGGGCCCAGGACTGGTGAAGCCTTCGGAGACCCTGTCCCTCACCTGCACTGTCTCTG GTAGCTCCATCAGCAGTAGTAGTTACTACTGGGGCTGGGTCCGCCAGTCCCCAGGGAAGGGACTGGAGTGG ATTGGGAGTATCTATACAGTGGGACCATCTACTACAACCCGTCCCTCAGGAGTCGAGTCACCATATCCGTA GACACGTCCAAGAACCAGTTCTCCCTGAAGCTGAACTCTGTGACCGCCGCAGACACGGCTGTTTATTACTGT GCGAGTCTTAGTGGCACAAATGCTTTTGATATCTGGGGCCAAGGGACAATGGTCACCGTCTCTTCA |
| SLE1p2-d04h | 207 | GAGGTGCAGCTGTTGGAGTCTGGGGGGGCTTGGTACAGCCTGGGGGGTCCCTGAGACTCTCCTGTGCAGCC TCTGGATTCACCTTTAGCAGCCATGACATGAGTTGGGTCCGCCTGGCTCCAGGGAAGGGGCCGGAGTGGGTC TCAGCTCTTGGTGCTGGAGATGCTTGGACACACTACGCAAACTCCGTGAGGGCCGGTTCACCATCTCCAGA GACGATTCCAAGAACACGCTGTATCTGCAAATGAACAGCCTGAGAGCCGAGGACACGGCCGTGTATTTCTGT GCGAAACCCCGTGGATACTCCTATGGCTACTTTGACTACTGGGGCCAAGGGAACGCTGGTCACCGTCTCCTCA |
| SLE1p3-a02h | 208 | GAGGTGCAGCTGGTGGAGTCTGGGGGAGGCTTGGTCCAGCCTGGGGGGTCCCTGAGACTCTCCTGTGGAGCC TCTGGATTCACCTTTAGTACCTATTGGATGACCTGGGTCCGCCAGGCTCCAGGGAAGGGGCTGGAGTGGGTG GCCAATATAAACCAAGATGGAAGTGAGAAACAATATGTGGACTCTGTGAAGGGCCGATTCACCATCTCCAG AGACAACGCCAAGAACTCACTGTATCTGCAGATGAACAGCCTGAGAGTCGAGGATACGGCTATTTATTACTG TGCGAGACCCCCAGCTCGCCGACTTGACTACTGGGGCCAGGGATCGCTGGTCACCGTCTCCTCA |
| SLE1p3-a04h | 209 | GAGGTGCAGCTGGTGGAGTCCGGGGGAGGCTTAGTTCAGCCTGGGGGGTCCCTGAGACTCTCCTGTGCAGCC TCTGAATTCACCTTCAGTGACTGGATGCACTGGGTCCGCCAAGCTCCAGGGAAGGGGCTGGTCTGGGTC TCACGTATTAATACTGACGGGAGTACCACAACCTACGCGGACTCCGTGAAGGGCCGATTCACCATCTCCAGA GACAACGCCAAGAACACGCTGTATCTACAAATGAACAGTCTGAGGGCCGAGGACACGGCTGTGTATTACTG TGCAAGATCTAATGCGGGGCACGAAGCGTGGGGCCAGGGAACGCTGGTCACCGTCTCCTCA |
| SLE1p3-b03h | 210 | AGGTGCAGCTGGTGCAGTCTGGGGCTGAGGTGAAGAAGCCTGGGGCCTCAGTGAGGGTTTCCTGCAAGGCA TCTGGATACACCTTCACCAACTACTGGATACACTGGGTGCGACAGGCCCCTGGACAAGGGCTTGAGTGGATG GGAATGATCGCCCCTAAGGAAGGTTACACATTCTACGCACAGCAATTACAGGGCAGAGTCACCGTGACCAG GGACACGTCGACGAGCGCGGTTTACATGGAGCTGAACAGCCTGAGATCTGAGGACACGGCCGTATATTTCTG TGCGAGAGACATTCCCCACGCTAATTTGGACTATTGGGGCCAGGGGACGCTGGTCACCGTCTCCTCA |
| SLE1p3-c03h | 211 | GAGGTGCAGCTGTTGGAGTCTGGGGGAGGATTGGTACAGCCTGGGGGGTCCCTGAGACTCTCCTGTGCAGCC TCTGGATTCACCTTTAGCGATTATACCATGAATTGGGCCCGCCAGGCTCCAGGGAAGGGGCTGGAGTGGGTC TCAGTATTAGAGAGTGGTGACAGCACATACTACGCAGACTCCGTGACGGGCCGGTTCACCATCTCCAGG GACAATTCCAGAAACACACTTTATCTGCACATGAACAGCCTGAGAGCCGAGGACACGGCCATGTATTTTGT GTGAAAGACAGGGTGCCGCCGGGTGACGTGCCGGGTGACTTCTGGGGCCCGGGAACGCTGGTCACCGTCTC CTCA |

| SLE1 Kappa | Seq ID No. | |
|---|---|---|
| SLE1p1-a02k | 212 | GACATCCAGTTGACCCAGTCTCCATCCTTCCTGTCTGCATCTGTAGGAGACAGAGTCACCATCACTTGCCGGG CCAGTCAGGACATGACCCATTCTTTAGCCTGGTATCAGCAAAAACCAGGGAAAGCCCCTAACCTCCTGATCT ATAATGCATACACTTTGCAAAGTGGGGTCCCATCAAGGTTCAGCGGCAGTGGATCTGGGACAGAATTCACTC TCACCATCAGCAGCCTGCAGCCTGAAGATTTTGCAACTTATTACTGTCAACAGATTAATAGTTACCCTCGAA CTTTTGGCCAGGGGACCAAGGTGGAGATCAAA |
| SLE1p1-a03k | 213 | GAAATTGTGTTGACACAGTCTCCAGGCACCCTGTCTTTGTCTCCAGGGGAAAGAGCCACTCTCTCCTGCAGG GCCAGTCAGAATATTGGCACCGCCTTAGCCTGGTACCAACAGAAACCTGGCCAGGCTCCCAGACTCATCATC TATGAAACATCCAACAGGGCCACTGACGTCCCAGCCAGGTTCAGTGGCAGTGGGTCTGGGACAGACTTCACT |

TABLE 2-continued

Selected Heavy and Light Chain Sequences from Antibodies of Table 1 (SEQ ID NOS. 127-252)

| | | |
|---|---|---|
| | | CTCACCATCAGCAGCCTGGAGCGTGAAGATTTTGCCCTTTATTACTGTCAACAGCGTGCCGACTGGCCGCTC<br>ACTTTCGGCGGAGGGACCAAGGTGGAGATCAAA |
| SLE1p1-b05k | 214 | GAAATTGTGTTGACACAGTCTCCAGCCACCCTGTCTTTGTCTCCAGGGGAAAGAGCCACCCTCTCCTGCAGG<br>GCCAGTCAGAGTGTTAGCAGCTACTTAGCCTGGTACCAACAGAGACCTGGCCAGGCTCCCAGGCTCGTCATC<br>TATGCTGCATCCAACAGGGCCACTGGCATCCCAGCCAGGTTCAGTGGCAGTGGGTCTGGGACAGACTTCACT<br>CTCACCATCAGCAGCCTAGAGCCTGAAGATTTTGCAGTTTATTACTGTCTGCAGTGTAGCAACTGGCCCATGT<br>ACACTTTTGGCCAGGGGACCAAGGTGGAGATCAAA |
| SLE1p1-c04k | 215 | GACATCCAGTTGACCCAGTCTCCATCCTTCCTGTCTGCATCTGTAGGGGACAGAGTCACCATCACTTGCCGGG<br>CCAGTCAGGACATTACCGATTCTTTAGCCTGGTATCAGCAAAAACCAGGGAAAGCCCCTAACCTCCTGATCT<br>ATACTGCATCCACTTTGCAAAGTGGGGTCCCATCAAGGTTCAGCGGCAGTGGATCTGGGACAGAATTCACTC<br>TCACAATCAGCAGCCTGCAGCCTGAAGATTTTACAACTTATTACTGTCAACAGATTAATAGTTACCCTGAA<br>CTTTTGGCCAGGGGACCAAGGTGGAGATCAAA |
| SLE1p1-e01k | 216 | GACATCCAGATGACCCAGTCTCCATCCTCCCTGTCTGCATCTGTAGGAGACAGAGTCACCATCACTTGCCGG<br>GCAAGTCAGGGCATTAGAAATGATTTAGGCTGGTATCAGCAGAAACCAGGGAAAGCCCCTAAGCGCCTGAT<br>CTATGCTGCATCCAGTTTGCAAAGTGGGGTCCCATCAAGGTTCAGCGGCAGTGGATCTGGGACAGAATTCAC<br>TCTCACAATCAGCAGCCTGCAGCCTGAAGATTTTGCAAGTTATTACTGTCTACAGCATAGTAGTTTCCCGTGG<br>ACGTTCGGCCAGGGGACCAAGGTGGAAATCAAA |
| SLE1p1-f02k | 217 | GACATCGTGATGACCCAGTCTCCAGACTCCCTGGCTGTGTCTCTGGGCGAGAGGGCCGCCATCAACTGCAAG<br>TCCAGCCAGAGTGTCTTAGACAGCTCCAACATGAAGAGGTACTTAGCCTGGTATCAGCTGAAAGCAGGACA<br>GCCTCCTAGGTTGCTCATTTACTTGGCTTCCACCCGGGAATCCGGGGTCCCGGACCGATTCAGTGGCAGCGG<br>GTCCGGGACAGATTTCAATCTCACTATCAGCAGCCTGCAGGCTGAAGATGTGGCAGTTTATTACTGTCAGCA<br>AATATTATACAACCCCTTCGATCACCTTCGGCCAAGGGACACGACTGGAGATTAAA |
| SLE1p1-g05k | 218 | GACATCGTGATGACCCAGTCTCCAGACTCCCTGGCTGTGTCTCTGGGCGAGAGGGCCACCATCAACTGCAAG<br>TCCAGCCAGAGTGTTTTATACAGCTCCAACAATAAGAACTACTTAGCTTGGTACCAGCAGAAACCAGGTCAG<br>CCTCCTAAGATGCTCATTTACTGGGCATCTACCCGGGAGTCCGGGGTCCCTGACCGATTCAGTGGCAGCGGG<br>TCTGGGACAGATTTCACTCTCACCATCAGCAGCCTGCAGGCTGAAGATGTGGCAGTTTATTACTGTCAGCAA<br>TATTATACTACTCCTCCCATCACCTTCGGCCAAGGGACACGACTGGAGATTAAA |
| SLE1p2-a02k | 219 | GAAATTGTGTTGACACAGTCTCCAGCCACCCTGTCTTTGTCTCCAGGGGAAAGAGCCACCCTCTCCTGCAGG<br>GCCAGTCAGAGTGTTAGTATCTACTTAGCCTGGTACCAACAGAAACCTGGCCAGGCTCCCAGGCTCCTCATC<br>TATGATTCATCCAACAGGGCCACTGGCATCCCAGCCAGGTTCAGTGGCAGTGGGTCTGGGACAGACTTCACT<br>CTCACCATCAGCAGCCTAGAGCCCGAAGATTTTGCGGTTTATTACTGTCAGCAGCTAGCAGCGGGCGAACG<br>TTCGGCCAAGGGACCAAGGTGGAGATCAAA |
| SLE1p2-d04k | 220 | GAAATTGTGTTGACGCAGTCTCCAGGCACCCTGTCTTTGTCTCCAGGGGAAAGAGCCACCCTCTCCTGCAGG<br>GCCAGTCAGACTGTTACCAACAACTACTTAGCCTGGTACCAACACAAACCTGGCCTGGCGCCCAGGCTCCTC<br>ATCTTTGATGCATCCATCAGGGCCACTGGCATCCCAGACAGGTTCAGTGGCAGTGGGTCTGGGGCAGACTTC<br>ACTCTCACCATCAGCAGACTGGAGCCTGAAGATTTTACATTCTATTACTGTCAGCAATATGGTATTTCACCTC<br>GAACTTTTGGCCAGGGGACCAAGGTGGAGATCAAA |
| SLE1p3-a02k | 221 | GATATTGTGATGACCCAGACTCCACTCTCTCTGTCCGTCACCCCTGGACAGCCGGCCTCCATCTCCTGCAAGT<br>CTAGTCAGAGTCTCCTGGATAGTGATGAAGGACCCTATTTCTTTTGGTATTTGCAGAAGCCAGGCCAGTCTCC<br>ACAACTCCTGATCTATGAAGTTTCCAACCGGTTCTCTGGAGTGCCAGATAGGTTCAGTGGCAGCGGGTCAGG<br>GACAGATTTCACACTGAAAATCAGCCGGGTGGAGTCTGAAGATGTTGGGGTTTATTACTGCATGCAAGGTAC<br>ACACCATCCGTGGACGTTCGGCCAAGGGACCAAGGTGGAAATCAAA |
| SLE1p3-a04k | 222 | GACATCGTGACCCAGTCTCCAGACTCCCTGGCTGTGTCTCTGGGCGAGAGGGCCACCGTCAACTGCAAG<br>TCCAGCCAGAGTGTTTTATACAGCTCCAACAGTAAGAACTACTTAGCTTGGTACCAGCAGAAACCAGGACAG<br>CCTCCTAAGCTGCTCATTTACTGGGCATCTACCCGGGAATCCGGGGTCCCTGACCGATTCAGTGGCAGCGGG<br>TCTGGGACAGATTTCACTCTCACCATCAGCAGCCTGCAGGCTGAAGATGTGGCAGTGTATTACTGTCAGCAA<br>TATTATAGTACTCCTCTCACTTTCGGCGGAGGGACCAAGGTGGAGATCAAAC |
| SLE1p3-b03k | 223 | GACATCCAGATGACCCAGTCTCCATCCTCCCTGTCTGCATCTGTGGGAGACAGAGTCACCATCACTTGCCGG<br>GCAAGTCAGGGCATTGGAATGATTTAGGCTGGTATCAGCATGAACCAGGGAAAGCCCCTAAGCGCCTGAT<br>CTATGCAGCATCCAGTTTGCAAAGTGGGGTCCCATCGAGGTTCAGCGGCAGTGCATCTGGGACAGAATTCAC<br>TCTCACAATCACCAGCCTGCAGCCTGAAGATTTTGCAACTTATTACTGTCTACAACATACTACTTTCCCGTGG<br>ACGTTCGGCCAAGGGACCAAGGTGGAAATCAAAC |
| SLE1p3-c03k | 224 | GAAATTGTGTTGACACAGTCTCCAGCCACCCTGTCTTTGTCTCCAGGGGAAAGAGCCACCCTCTCCTGCAGG<br>GCCAGTCAGAGTGTTGGCAGTCACTTCGCCTGGTACCAACAGAAACCTGGCCAGGCTCCCAGGCTCCTCATC<br>TATGGTGCATCCAACAGGGCCCCTGGCATCCCCACCTAGGTTCAGTGCCAGTGGATCTGGGACAGACTTCACT<br>CTCACCATCAGCAGCCTAGAGCCTGAAGATTTTGCAATTTATTACTGTCAACAGCTAGGACCTGGCCTCCG<br>CTAACCTTCGGCCAAGGGACACGACTGGAGATTAAAC |
| SLE2 Heavy | Seq ID No. | |
| SLE2p1-a01h | 225 | GAGGTGCAGCTGGTGGAGTCTGGGGGAGGCTTGGTACAGCCTGGAGGGTCCCTGAGACTCTCCTGTGTAGCC<br>TCTGGATTCAGTTTCAGTGGTCATGAAATGAACTGGGTCCGCCAGCCTCCAGGGAAGGGGCTGGAGTGGGTT<br>TCACACATTGGCAGTGGTGGTGATTATATAGGTTACGCAGACTCTGTGAAGGGCCGATTCACCGTCTCTAGA<br>GACAACGCCAAGAATTTACTCTATCTGCAAATGAACAGCCTGAGAGCCGACGACACGGCTGTTTATTACTGT<br>GCGACCTTGCTTTTGCGAGACAACCAACTGGACGTCTGGGGCCAAGGGACCACGGTCACCGTCTCCTCA |

TABLE 2-continued

Selected Heavy and Light Chain Sequences from Antibodies of Table 1 (SEQ ID NOS. 127-252)

| | | |
|---|---|---|
| SLEp1-a06h | 226 | CAGGTGCAGCTGGTGGAGTCTGGGGGAGGCGTGGTCCAGCCAGGGAGGTCCCTAAGACTCTCCTGTGCAGC<br>CTCTGGATTCACCCTCAGTAGTTGTGGCATGCACTGGATCCGCCAGGCTCCAGGCAAGGGGCTGGAGTGGGT<br>GGCAGTTATAACATATGATGGACGAAGTCACTTCAACGCAGACGCCGTGAAGGGCCGATTCACCATCTCCAG<br>AGACAGATCCATGAACCGGTGTCTCTGCAAATGGACAGCCTGAGACCCGAGGACACGGCTGTTTATTACTG<br>TGTCAAAGAACAAGGCTTTGGTTACTACCGGACCGCCGACTACTGGGGCCAGGGAACCCTGGTCACCGTCTC<br>CTCA |
| SLE2p1-b01h | 227 | CAGGTGCAGCTGCAGGAGTCGGGCCCAGGACTGGTGAGGCCTTCGGAGACCCTGTCCCTCACCTGCACTGTC<br>TCTGGTGGCTCCATCAGTAGTGACCACTGGAGTTGGATCCGGCAGCCCCCAGGCAAGGGACTGGAGTGGATT<br>GGGAATGTCTATTACAGTGGGCGCACCTACTACAACCCCTCCTTCAAGAGTCGAGTCACCATATCAGTAGCC<br>ACGTCCAAGAACCAGTTCTCCCTGAAGGTGACCTCTGTGACCGCCGCAGACACGGCCATTTATTACTGTGCG<br>AGGCGAAATGATTTTAATATCTGGGGCCAGGGGACAATGGTCACCGTCTCTTCA |
| SLE2p1-c03h | 228 | GAGGTGCAGCTGTTGGAGTCTGGGGGAGGCTTGGTACAGCCTGGGGGGTCCCTGAGACTCTCCTGTGCAGCC<br>TCTGGATTCACCTTTAGTAAATATGCCGTGAGCTGGGTCCGCCAGGCTCCAGGGAAGGGGCTGGAGTGGGTC<br>TCAGCTGTCAGTGGTAATGGTGACTCCACATACTACGCAGACCCCGTGAGGGCCGGTTCACCATCTCCAGA<br>GACAATTCCAAGAACACCCTGTATCTGCAAATGAACAGCCTGAGAGCCGAGGACACGGCCTATATTACTGT<br>TCGATCTGGTGGGGGACTTCAGTACAGTACCCATTGGTGCTCGACTACTGGGGCCTGGGAACCCTGGTCACC<br>GTCTCCTCA |
| SLE2p1-c04h | 229 | CAGGTGCAGCTGGTGGAGTCGGGGGAGGCGTGGTCCAGCCTGGGAGGTCCCTAAGACTCCTGTGTGCAGC<br>CTCTGGATTCACCCTCAGTACTTGTGGCATGCACTGGATCCGCCAGATCCTGGCAAGGGGCTGGAGTGGGT<br>GGCAGTTAAAACATATGACGAAGAGAGGAGTTCTACGCAGACTCCGTGAAGGGCCGATTCACCATTTCCA<br>GAGACGAGTCCATGAACACGCTGTCTTTGCAGATGAACAGCCTGAGACCTGAAGACACGGCTGTATATTACT<br>GTGTCAAAGAACAAGACTACGGTTACTACCGGACCGCCGACCACTGGGGCCAGGGAACCCTGGTCACCGTC<br>TCCTCA |
| SLE2p1-d02h | 230 | CAGGTGCAGCTGCAGGAGGCGGGCCCAGGACTGGTGAAGCCTTCACAGACCCTGTCCCTCACCTGCACTGTC<br>TCTGGTGGCTCCATCAGCAGTGGTGGTTACTACTGGAGCTGGATCCGCCAGCACCCAGGGAAGGGCCTGGAG<br>TGGATTGGGTACATCTATTACAGTGGGAGCACCTACTACAACCCGTCCCTCAAGAGTCGAGTCACCATATCA<br>GTAGACACGTCCAAGAACCAGTATTCCCTGAAGCTGAGTTCTGTGACCGCCGCAGACACGGCCGTATATTAC<br>TGTGCGAGAGGGCATGGCTTCAACGCCTACTGGGGCCAGGGAACCCTGGTCACCGTCTCCTCA |
| SLE2p1-d04h | 231 | GAGGTGCAGCTGGTGGAGTCCGGGGGAGGCTTGGTAAAGCCGGGGAGTCCCTTAGACTCTCGTGTGCAAC<br>CTCTGGAGTCAACTTCAACATCGCCTGGATGACCTGGGTCCGCCAGGCTCCAGGGAAGGGGACTGGAGTGGGT<br>TGGCCGTATTAAAAGCAAATTGGTGGTGGGACAACAGACTATGCTGCACCCGTGAAAGGCAGATTCACCA<br>TGTCAATAGATGATTCAAAAAANTACCCTATATCTGCAAATGAACAGCCTGAAAACCGAGGACACAGCCGTG<br>TATTATTGTACCACAGTCCGCAATATGGCCGACTTGTCCCTTAATCACTGGGGCCAGGGAACCCTGGTCACC<br>GTCTCCTCA |
| SLE2p2-a01h | 232 | GAGGTGCAGCTGGTGGAGTCTGGGGGAGGCTTGGTACAGCCTGGAGCGTCCCTGACACTGTCATGTGTAGTC<br>TCTGGATTCACCTTCATTGGCACTGAAATGACCTGGATTCGCCAGGCTCCAGGGAAGGGGCTGGAGGGACTT<br>TCGTACATCAGTGGGAGTGGCGGACAACATACTACGCAGAGTCTGTGAGGGGCCGATTCACCATCTCCAG<br>AGACAACGCCAAGAAGTCACTGTTTCTGCAAATGACCAGCCTGACAGCCGAGGACACGGCTGTTTACTACTG<br>TGCGACAGGCAACCGGGGATCACTTCCTCGCCGCTGGGGCCAGGGAACCCTGGTCACCGTCTCCTCA |
| SLE2p2-c04h | 233 | GAGGTGCAGCTGGTGGAGTTTGGGGGAGGCTTGGTCCAGCCTGGGGGGTCCCTGAGACTCTCCTGTGTAGCC<br>TCTGGATTCACCTTTAGTTCCTCTTGGATGAGTTGGGTCCGCCAGGCTCCAGGGAAGGGGCTGGAGTGCGTG<br>GGCAACATAAAGCCGGATGCAAGTTTGGTGTCCTATGTGGACTCTGTGAAGGGCCGAGTCACCATCTCCAGA<br>GACAACGCCAAGAATTCACTGTTTCTGGATATGAGCAGCCTGAGAGTCGAGGACACGCCGTCTACTACTGT<br>GTGAGAGACGGGTGGGACACCTTCTTTGACTCCTGGGGCCAGGGAACCCTGGTCACCGTCTCCTCA |
| SLE2p2-d03h | 234 | GAGGTGCAGCTGGTGGAGTCCGGGGGAGGCTTAGTTCAGCGGGGGGGTCCCTGAGACTCTCCTGTCAGC<br>CTCTGGATTCACCTTTAGTAACTACTGGATGAGGTGGGTCCGCCAATCTCAGGGAAGGGGCTGGTGTGGGT<br>CTCACATATTAACCTGATGGGAGTTTTACAAACTACGCAGACTCCGTGAAGGGCCGATTCACCATCTCCAG<br>AGACAACACCAAGAACACACTGTATCTGCAAATGAACAGTCTGAGAGCCGAGGACACGGCTGTCGTATTACT<br>GTGTGAATTTTCAACTGGGGTGGGGCCAGGGAACCCTGGTCACCGTCTCCTCA |
| SLE2p2-e04h | 235 | CAGGTGCAGCTGGTGGAGTCTGGGGGAGGCGTAGTCCAGCCTGGGAGGTCCCTGAAACTCTCCTGTGCAGTC<br>GCTGGATTCACCTTCAGGACCTATGCTATGCACTGGGTCCGCCAGGCTCCAGGCAGGGGCTGGAGTGGGTG<br>GCACTTATATCAAATGATGGAACCAAAAATACTCCGCAGACTCCGTGAGGGCCACTTCACCATCTCCAGA<br>GACAATTCCAAGGACACGCTGTATCTGCAAATGAACAGCCTGCGACCTGACGACACGGCTGTCTATTACTGT<br>GCGAGAGCGGAGTATTGTAGTCCTGGTGACTGCTTCCTTATTGACACCTGGGGCCAGGGAACCCTGGTCACC<br>GTCTCCTCA |
| SLE2p2-f01h | 236 | CAGGTGCAGCTGGTGGAGTCTGGGGGAGGCGTGGTCCAGCCTGGGAGGTCCCTGAGACTCTCCTGTGCAGTG<br>TCTGGATTCACCTTCAGTAGATACGGCATGCACTGGGTCCGCCAGGCTCCAGGCAAGGGGCTGGAGTGGGTG<br>GTAGTTATATGGCATGATGGAAGTAATACATACTATGCAGACTCCGTGAAGGGCCGATTCACCATCTCCAGA<br>GACGACTCCAAGAACACGGTGTATCTGCAAATGAACAGCCTGAGAGTCGAGGACACGGCTATGTATTACTGT<br>CTGAGAGGCAACCCCACCTAGCAGCCCCACCGACTACTGGGGCCAGGGAACCCTGGTCACCGTCTCCTCA |
| SLE2p2-g01h | 237 | GAGGTGCAGCTGTTGGAGTCTGGGGGAGGCTTGGTACAGCCTGGGGGGTCCCTGAGACTCTCCTGTGAAGTC<br>TCTGGATTCATCTTTAGCAACTATGCCATGACCTGGGTCCGCCAGGCTCCAGGGAAGGGGCTGCAGTGGGTC<br>TCAGCTATTGGCACTAGTGGTGGTGACACACACTACGCAGACTCCGTGAAGGGCCGGTTCACCATCTCCAGA<br>CACAATTCCCAGAACACCCTGTATCTGCAGATGAACAGCCTGAGAGCCGAGGACACGGCCATATATTACTGT<br>GCGAAAGTCGTTTATAGCAGGCCTCCTATGGACGTCTGGGGCCAAGGGACCACGGTCACCGTCTCCTCA |

TABLE 2-continued

Selected Heavy and Light Chain Sequences from Antibodies of Table 1 (SEQ ID NOS. 127-252)

| | | |
|---|---|---|
| SLE2p2-g06h | 238 | GAGGTGCAGCTGGTGGAGTCTGGGGGAGGCTTGGTCCAGCCTGGGGGGTCCCTGAGACTCTCCTGTGCAGCC<br>TCTGGATTCACCTTTAGTAATCGTTGGATGAGTTGGGTCCGCCAGGCTCCAGGGAAGGGGCTGGAATGGGTG<br>GCCAACATAAACGAAGATGGAAGTCAGAAACACTATGTGGACTCTGTGAGGGGCCGATTCACCATCTCCAG<br>AGACAACGCCAAGAACTCACTGTCTCTGCAAATGGACAGCCTGAGAGTCGAGGATACGGCCGTGTATTATTG<br>CGCGAGAGCATCGAGGGAGACCGGTGAACCTTACTGGGGCCAGGGAACCCTGGTCACCGTCTCCTCA |

| SLE2 Kappa | Seq ID No. | |
|---|---|---|
| SLE2p1-a01k | 239 | TTGTGATGACTCAGTCTCCACTCTCCCTGCCCGTCACCCTTGGACAGTCGGCCTCCATCTCCTGCAGGTCTAG<br>TCGAAGCCTCGTATTCAGTGATGGAAACACCTACTTGAATTGGTTTCAGCAGAGGCCAGGCCGATCTCCAAG<br>GCGCCTAATTTATAAGGTTTCTAAGCGGGACTCTGGGGTCCCAGACAGATTCAGCGGCAGTGGGTCAGACAC<br>TGATTTCACACTGAAAATCAGCAGGGTGGAGGCTGAGGATGTTGGGGTTTATTACTGCATGCAAGGTACACA<br>CTGGCGGACGTTCGGCCAAGGGACCAAGGTGGAGATCAAA |
| SLE2p1-a06k | 240 | GACATCCAGATGACCCAGTCTCCTTCCACACTGTCTGCATCTGTGGGAGACAGAGTCACCATCACTTGCCGG<br>GCCAGTCAGAGTATTAATTCCTGGTTGGCCTGGTATCAGCGGAAACCAGGGAAAACCCCTAAACTCCTCATC<br>TATGAGGCGTCCAGTTTAGAAAGTGGGGTCCCATCAAGGTTCAGCGGCAGTAGATCTGGGACAGAGTTCACC<br>CTCACCATCAGCAGCCTGCAGGCTGATGATTTTGCAACTTATTACTGCCACCAGTATGATAAATATCCGTGG<br>ACGTTCGGCCAAGGGACCAAGGTGGAGATCAAA |
| SLE2p1-b01k | 241 | GAAATTGTGTTGACGCAGTCTCCAGGCACCCTGTCTTTGTCTCCAGGGGAAAGAGCCACCCTCTCCTGCAGG<br>GCCAGTCAGAGTGTGACCAACAACTATTTGGTCTGGCACCAGCAGAAACCTGGCCAGGCTCCCAGGCTCCTC<br>ATTTCTGATGCATCCAACAGGGCCACTGGCATCCCAGACAGGTTCAGTGGCAGTGGGTCTGGGACAGACTTC<br>ACTCTCACCATCAACAGACTGGAGCCTGAAGATTTCGCAGTGTATTACTGTCAGCAATACGGTAGCTCACCT<br>TTCACTTTCGGCCCTGGGACCAAAGTGGATATCAAA |
| SLE2p1-c03k | 242 | GAAATAGTGATGACGCAGTCTCCAGCCACCCTGTCTGTGTCTCCAGGGGAAAGAGTCACCCTCTCCTGCAGG<br>GCCAGTCAGAGTATTGGCAGCAGCTTAGCTGGTACCTGCAGAAACCTGGCCAGGCTCCCAGAGTCCTCATC<br>TATGGTGCATCCACCAGGACCCCTGGCACCCCAGCCAGGTTCAGTGGCAGTGGGTCTGGGACAGAGTTCACT<br>CTCACCATCAGCAGCCTGCAGCTGAAGATCTTGCAGATTATTATTGTCAACAGTATAGTAAGTGGCCTCCGA<br>TCACCTTCGGCCAAGGGACACGACTGGAGATTAAA |
| SLE2p1-c04k | 243 | GACATCCAGATGACCCAGTCTCCCTCCATCCTGTCTGCATCTGTAGGAGACAGAGTCACCATCAATTGCCGG<br>GCCAGTCAGAGTATTAATGCCTGGTTGGCCTGGTATCAGCAGAAACCAGGGAAAGCCCCTAAATTCCTAATT<br>TATAAGGCGTCTAGTTTAGAAAGTGGGGTCTCGTCAAGGTTCAGCGGCAGTGGATCTGGGACAGAATTCACC<br>CTCATCATCAGCAGCCTGCAGCCTGATGATTTTGCAACTTATTACTGCCAACAGTATGATAAATATCCGTGGA<br>CGTTCGGCCGGGGGACCAAGGTGGAGATCAAA |
| SLE2p1-d02k | 244 | GAAATTGTGTTGACGCAGTCTCCAGGCACCCTGTCTTTCTCTCCAGGGGATAGAGCCACCCTCTCCTGCAGG<br>GCCAGTCAGAGTGTTAGCAGCAGCTCCTTAGCCTGGTACCAGCAGCAGACCTGGCCAGGCTCCCAGCCTCCTC<br>ATCTATGGTGCATCCAGCAGGGCCACTGGCATCCCAGACAGGTTCAGTGGCAGTGGGTCTGGGACAGACTTC<br>ACTCTCACCATCAGCAGACTGGAGCCTGAAGATTTTGCAGTGTATTACTGTCAGCAGTATGGTAACTCACCT<br>CGGACGTTCGGCCAAGGGACCAAGGTGGAGATCAAA |
| SLE2p1-d04k | 245 | GAAATTGTGTTGACGCAGTCTCCAGGCACCCTGTCTTTGTCTCCAGGGGAAAGAGCCACCCTCTCCTGCAGG<br>GCCAGTCAGAGTGTCAGCAGCACCTACTTAAACTGGTACCAGCAGAAGCCTGGCCAGGCTCCCAGGCTCCTC<br>ATCTATGGTGCGTCCACCAGGGCCACTGGCATCCCAGACAGGTTCAGTGGCAGTGGGTCTGGGGCAGACTTC<br>ACTCTAACCATCAGCAGACTGGAGCCTGAAGACTTTGCAGTGTACTACTGTCAGCAATATGATGACTCACGG<br>TGGACGTTCGGCCAAGGGACCAAGGTGGAAATCAAA |
| SLE2p2-a01kb | 246 | GATATTGTGATGACTCAGTCTCCACTCTCCCTGCCCGTCACCCCTGGAGAGCCGGCCTCCATCTCCTGCAGGT<br>CTGGTCAGAGCCTCCTGTATAGTGATGGAAACAACTATTTGGATTGGTATCTGCAGAAGCCAGGGCAGTCTC<br>CACAGCTCCTGATCTATTTGGGTTCAATCGGGCCTCCGGGGTCCCTGACAGGTTCAGTGGCAGTGAATCAG<br>GCACAGATTTTACACTGAAAATCAGCAGAGTGGAGGCTGGGGATGTTGGGATTTATTACTGCATGCAAGCTC<br>TACGAAGTCCGTACACTTTTGGCCAGGGGACCAAGGTGGAGATCAAA |
| SLE2p2-c04k | 247 | TTGTGATGACTCAGTCTCCACTCTCCCTGCCCGTCACCCTTGGACAGCCGGCCTCCATCTCCTGCAGGTCTAG<br>TCAAAGCCCCGTATACAGTGATGGAAACACCTACCTGAATTGGTTTCAGCAGAGGCCAGGCCAATCTCCAAG<br>GCGCCTAATTTATAAGGTTTCTAACCGGGACTCCGGGGTCCCAGACAGATTCAGCGGCAGTGGGTCAGGCAC<br>TGATTTCACACTGAATATCAGCGGGGTGGAGGCTGAGGACGTTGGGGTTTATTACTGCATGCAAGGTAGATA<br>CTGGCCGTACACTTTTGGCCAGGGGACCAAGGTGGAGATCAAA |
| SLE2p2-d03k | 248 | GAAATTGTGTTGACGCAGTCTCCAGGCACCCTGTCTTTCTCTCCAGGGGATAGAGCCACCCTCTCCTGCAGG<br>GCCAGTCAGAGTGTAAGCAGCAGCGCCTTAGCCTGGTACCAGCAGAAACCTGGCCAGGCTCCCAGCCTCCTC<br>ATCTATGGTGCATCCAGCAGGGCCACTGGCATCCCAGACAGGTTCAGTGGCAGTGGGTCTGGGACAGACTTC<br>ACTCTCACCATCAGCAGACTGGAGCCTGAAGATTTTGCAGTGTATTACTGTCAGCAGTATGGTAACTCACCT<br>CGGACGTTCGGCCAAGGGACCAAGGTGGAAATCAAA |
| SLE2p2-e04k | 249 | TTGTGATGACTCAGTCTCCACTCTCCCTGCCCGTCACCCTTGGACAGTCGGCCTCCATCTCCTGCAGGTCTAG<br>TCGAAGCCTCGTATTCAGTGATGGAAACACCTACTTGAATTGGTTTCAGCAGAGGCCAGGCCGATCTCCAAG<br>GCGCCTAATTTATAAGGTTTCTAAGCGGGACTCTGGGGTCCCAGACAGATTCAGCGGCAGTGGGTCAGACAC<br>TGATTTCACACTGAAAATCAGCAGGGTGGAGGCTGAGGATGTTGGGGTTTATTACTGCATGCAAGGTACACA<br>CTGGCGGACGTTCGGCCAAGGGACCAAGGTGGAAATCAAAC |
| SLE2p2-f01k | 250 | GACATCCAGATGACCCAGTCTCCTTCCTCACTGTCTGCATCTGTAGGGGACAGAATCACCATCACTTGTCGG<br>GCGAGTCAGGGCATTAACAATTATTTAGCCTGGTTTCAGCAGAAGCCAGGGAAAGCCCCTAAGACCCTGATC |

TABLE 2-continued

Selected Heavy and Light Chain Sequences from Antibodies of Table 1 (SEQ ID NOS. 127-252)

| | | |
|---|---|---|
| | | TACTCTACATCCACTTTGCAAAGTGGGGTCCCATCAAAGTTCAGCGGCAGTGGATCTGGGACAGTTTTCACT<br>CTCACCATCAGCAACCTGCAGCCTGAAGATTTTGCAACTTATTACTGTCAACAATATAATAGTTACCCGCTCA<br>CTTTCGGCGGAGGGACCAAGGTGGAGATCAAA |
| SLE2p2-g01k | 251 | GACATCCAGATGACCCAGTCTCCATCCTCCCTGTCTGCATCTGTAGGAGACAGAGTCACCATCACTTGCCGG<br>GCAAGTCAGACCATTAGCAACTATTTAAATTGGTTTCAGCAGAAACCAGGGAAAGCCCCTAGGCTCCTGATC<br>TATGCTGCATCGAGTTTGCAAAGTGGGGTCCCATCAAGGTTCAGTGGCAGTGGATCTGTGACAGATTTCACT<br>CTCACCATCAGCAGTCTGCAACCTGAAGATTTTGCAACTTACTTCTGTCAACAGAGTTACAGCACCCCGTGG<br>ACGTTCGGCCAAGGGACCAAGGTGGAAATCAAA |
| SLE2p2-g06k | 252 | TTGTGATGACTCAGTCTCCATTCTCCCTGCCCGTCACCCTTGGACAGCCGGCCTCCATCTCCTGCAGGTCTAG<br>TCAAAGCCTCGTATACAGTGATGGAAACACCTACTTGAATTGGTTTCAGCAGAGGCCAGGCCAATCTCCAAG<br>GCGCCTGATTTATAAGCTTTCTAACCGGGACTCTGGGGTCCCAGACAGATTCAGCGGCAGTGGGTCAGGCAC<br>TGATTTCACACTGAAAATCAGCAGGGTGGAGGCTGAGGATGTTGGGGTTTATTACTGCATGCAAGCTACACA<br>CTGGCCTTGGACGTTCGGCCAAGGGACCAAGGTGGAAATCAAA |

Antibodies were also tested for binding against five common lupus autoantigens: Ro, La, Sm, nRNP, and cardiolipin. Antibodies which bound to at least two of these five antigens were classified as poly-reactive (whether or not they bind polysaccharide). FIG. 2C shows the percentage of poly-reactive antibodies from each donor. SLE2 shows a remarkable 52% of antibodies showing polyreactivity. Graphs similar to those in FIG. 2A, but highlighting cross-reactive or poly-reactive antibodies from each donor are shown in FIGS. 7A-B.

A Small but Significant Percentage of Anti-Polysaccharide Antibodies Produced from ASCs Bind to the Polysaccharides of Two Distinct Serotypes.

Although most of the antibodies are serotype specific, 12% of the antibodies characterized bind two serotypes. Of the antibodies that bind two serotypes, one pair of polysaccharides, 9N and 9V, were dually bound by several antibodies. These two carbohydrates have very similar non-branched structures with one of four D-Glc in a 9N chain repeat being replaced by a D-Gal in 9V. Thus, it is not unexpected that some antibodies will cross-react with both serotypes. However, the inventor observed a wide variety of 9N and 9V binding antibodies, some of which cross-react and some that do not. For example, Con1p2D02 and SLE1p1E01 antibodies are mono-specific to 9N and 9V respectively (FIG. 3A), showing little to no cross-reactivity. Con1p4B03, however, binds to both serotypes, favoring 9N by an order of magnitude in affinity and by 5-times in avidity (FIG. 3B). One antibody to 9N, SLE1p1A03, does not bind to 9V, but rather cross-reacts to serotype 14 polysaccharide (FIG. 3C), with similar affinity and avidity, an observation which is difficult to explain examining only the carbohydrate sequence. Several of these cross-reacting antibodies are from the same donor, demonstrating a variety of antibodies to a certain serotype within a single individual. Serotypes 19A and 19F also have very similar structures with 19F having a D-Glc with a 1-2 linkage and 19A having a 1-3 linkage. The antibody SLE2p2D03 binds to both 19A and 19F with nearly equivalent affinities (FIG. 3D), although four-fold different avidities (favoring 19A).

The inventor also detected cross-reactivity between serotypes 15B and 14 (FIG. 4C), as well as 17F and 33F (FIGS. 4A and 4B). The antibody SLE2p1B01 slightly favors serotype 14 over serotype 15B in avidity, although not in affinity. While SLE2p2G06 and SLE2p2C04 are mono-specific for 17F and 33F respectively (FIG. 4A), SLE2p1C03 (from the same donor; FIG. 4B) cross-reacts to both serotypes with similar avidity. Overall, it is evident that although serum may cross-react between two serotypes, 85% of the actual antibodies making up this response are specific to only one polysaccharide. The inventor encountered no antibodies that reacted with more than two serotypes with a measurable affinity/avidity.

A High Frequency of Somatic Hypermutation in these Antibodies Indicates Frequent Anamnestic Anti-Polysaccharide Responses.

As previously reported, the ASC recall response to the influenza vaccine is highly mutated, even more so than in the typical IgG germinal center memory cell. The inventor hypothesized that this was due to the repeated nature of the annual vaccine, as well as frequent exposure to various influenza strains. The antibodies obtained in this study have a similar mutation frequency (see FIG. 5). This is particularly interesting because for each donor, this was a primary vaccination. If the donors were truly naïve to these polysaccharide antigens, the ASC response would have been smaller and the sequences of the antibodies would show less mutation. Thus, this vaccine is producing an anamnestic response which can only arise from previous infection or exposure to S. pneumoniae strains.

Each Donor Displays a Unique Anamnestic Fingerprint of Antibody Serotype Specificities.

Each of the four donors showed a remarkably different antibody response, as demonstrated by the number of antibodies produced against each serotype or cell wall polysaccharide (FIG. 6A, non-binding antibodies not shown; antibodies that cross-react are counted in the bin of the serotype with the strongest affinity). A response to certain serotypes seems to predominate in each donor. Donor Con1 shows a strong response to serotype 8 (six total antibodies, three of which are clonal), Con2 shows a strong response to serotype 18C (nine antibodies, all clonal), SLE1 and SLE2 both exhibit a strong response to serotype 5 (six antibodies, two of which are clonal and six antibodies, four of which are clonal, respectively). The inventor hypothesizes that this is due to an infection (clinically evident or not) by that serotype at some point in that donor's lifetime.

The inventor's previous study of the immune response to influenza vaccination (Wrammert et al., 2008) highlighted the strong clonality of the ASC response to that vaccine, and this is also the case after immunization with Pneumovax®23. Thus, several of the antibodies the inventor characterized are clonally related, but show very similar binding characteristics (see Table 1 to compare affinities). When displaying all four donors on a single histogram graph and reducing clonally related antibodies to a count of 1 (FIG. 6B), it is quite evident that the hmAbs isolated from each donor create a unique fingerprint with three donors binding 9V, 15B, 17F, and only serotypes 8 and 33F being bound by all four donors. Also, no subject in the study produced an antibody that bound to serotypes 7F, 10A, or 12F. Although it is difficult to mathematically show that the histograms from each donor are unique, the inventor is confident that producing 44 antibodies from Con2 gives a representative distribution of the serotypes to which this individual is having an anamnestic response and that this differs from donor to donor.

Example 3

Discussion

This is the first comprehensive analysis of the human immune response to Pneumovax®23 immunization, on a per antibody basis, utilizing antibody secreting cells (ASCs) that emerge seven days post vaccination as a source for the production of monoclonal antibodies. An analysis of these polysaccharide specific monoclonal antibodies allowed a detailed study of the human antibody repertoire to this vaccine. It also provided insight into the specificities of each antibody and surprisingly revealed an "anamnestic fingerprint" that the inventor interprets to reflect the prior infection history of each participant.

In an earlier study (Wrammert et al., 2008), the inventor found that the magnitude of the anamnestic response after influenza vaccination was such that an average of 6% of total B cells were ASCs, yet some donors made poor to non-existent responses. Using these same techniques, some vaccines (notably Anthrax AVA) routinely result in a very poor induction of a protective response (Crowe et al., 2010). Here, the inventor reports that Pneumovax®23 invoked a two- to four-fold more robust response than the strongest responses induced in some of the influenza donors, suggesting that these polysaccharides are exceptionally efficient at triggering a memory response. Earlier studies (2-4) also detected antibody secreting cells seven days post vaccination with both the polysaccharide and conjugate vaccines, averaging over 100 serotype specific cells per million PBMCs. The inventor's own ELISpot results were similar to these previous reports (data not shown), but the overall magnitude of the IgG ASC response as determined by flow cytometry was still surprising. Interestingly, one of the SLE donors, SLE2 also participated in the previous influenza study and did not make a response to the influenza vaccine, yet produced an impressive ASC response to the polysaccharide vaccine. This provides a direct comparison, albeit with a small sample size, of the vast difference in potential immune response to vaccines, especially in immunocompromised individuals.

There are several interesting differences in this study between the SLE donors and healthy controls. As discussed above, the percentage of ASCs that arose from the vaccination was considerably smaller in SLE1 and SLE2 (8.8% on average, as compared to 23.8% for Con1 and Con2). Although the percentage of high affinity antibodies generated from these donors was not different, the antibodies generated from SLE2 do appear to be quite poly-reactive against non-carbohydrate antigens. It is also important to note that three of the four cross-reactive antibodies from SLE2 are also poly-reactive (see FIGS. 7A-B). It is remarkable that although they bind to multiple self-antigens, they are still specific for only one or two polysaccharide structures. These results likely indicate a defect in B cell tolerance in this donor which is allowing cross- and poly-reactive B cells, which would otherwise be deleted or anergized, to mature and secrete antibody. Although it is unknown if this manner of poly-reactive antibody has physiological effects, it is likely that any vaccination in this individual will result such poly-reactive antibodies.

This study has greatly increased the number of reported human monoclonal antibodies to S. pneumoniae that have been characterized both in terms of binding and repertoire usage. These anti-polysaccharide antibodies are as highly mutated as antibodies which arise from repeated seasonal influenza vaccination. In comparing V gene usage in these antibodies to the previous reports, the inventor observes similar trends. For example, Baxendale (Baxendale and Goldblatt, 2006; Baxendale et al., 2000) suggests that VH3-48 likely contributes to an antigen binding domain that prefers epitopes from serotypes 23F and 18C, as the two VH3-48 family antibodies they characterized bound those two serotypes and Zhou found VH3-48 in the 23F study (Zhou et al., 2002), but not the 6B study (Zhou et al., 2004). Similarly, three of four VH3-48 antibodies (Table 1) characterized in this study also bind these two serotypes. The inventor have also characterized a VH3-48 which binds serotype 2 (Con2p5E05), a case of a VH3-48 binding a different serotype. They have also observed remarkable similarity in the antibodies characterized which bind cell wall polysaccharide (CWPS). Comparing two unique donors, these antibodies use either VH3-30 or closely related VH3-33. The CDR3s even show remarkable similarity, (Con2p6B03, VKESATGWYRTADY (SEQ ID NO:57); Con2p5A06, VKEYSWGYYRTADY (SEQ ID NO:49); SLE2p1A06, VKEQGFGYYRTADY (SEQ ID NO:101); SLE2p1C04, VKEQDYGYYRTADH (SEQ ID NO:107)). Thus, the chemical simplicity of repeated polysaccharide sequences seems to induce similar V gene family usage even in distinct individuals.

Although avidity has been shown to be an important correlate with protection (Anttila et al., 1999; Harris et al., 2007; Usinger and Lucas, 1999), thiocyanate ELISA is not commonly performed on monoclonal antibodies. The inventor utilizes it here because there are several complications in determining affinity by fitting simple ELISA curves. These include the magnified effects of small antibody concentration errors on affinities, uncertainty whether or not the antigen binding interaction is univalent or bivalent, and coating plates with large units of repeating epitopes. It is also possible that poly-reactive antibodies from SLE donors (and occasionally healthy controls) may interact with antigens outside of the binding site. All of these effects are minimized in the thiocyanate avidity ELISA system. FIGS. 3D and 4C both represent an antibody for which affinity and avidity ELISA binding measurements do not correlate. Both of these antibodies are from SLE2 and both antibodies are poly-reactive. The inventor is currently exploring interesting antibodies such as these in more detail, but in these cases, thiocyanate avidity is a more reliable measure of the antibody-carbohydrate interaction.

Serum cross-reactivity is typically determined by depleting the serum with a particular serotype carbohydrate and then observing binding of the serotypes still present in the serum. Soininen et al. (2000), for example, found remarkable cross-reactivity in the serum, especially in unvaccinated individuals. However, these assays require careful calibration, as well as pre-adsorption of CWPS and other polysaccharides to remove nonspecific reactivity, especially common in unvaccinated individuals (Marchese et al., 2006). Modern updates to this method, using microarray printing and reading technology (Pickering et al., 2007), for example, have greatly improved the reliability of these assays; yet until this study, one could not be definite whether observed cross-reactivity is due to actual cross-reactive individual antibodies, or the polyclonal nature of serum antibodies.

This study, focusing on cross-reactivity in monoclonal antibodies, has addressed such ambiguities. Park et al. (2009) describes cross-serotype monoclonal antibodies, deducing the common linear carbohydrate structure to which the antibodies were binding. Other reports (Baxendale et al., 2006; Baxendale et al., 2000; Zhou et al., 2004) do not specify cross-reactive antibodies, although those produced from Fab libraries were only panned with the serotype of interest. These experiments are the first, however, that characterize a large number of anti-pneumococcal human monoclonal antibodies, and although most of the antibodies are serotype specific, 15% were not. Unlike the above report, explaining the cross-reactivity of several of the monoclonal antibodies the inventor characterized is clearly not as simple as finding similar primary polysaccharide structures. While 9N/9V and 19A/19F are quite similar, 17F and 33F, and 14 and 15B do not have similar primary structures. Pickering et al. (2007), found that 9V could inhibit 9N binding, 15B inhibited 14 binding, 19F strongly inhibited 19A binding and 33F strongly inhibited 17F binding, all matching the observed results (FIGS. 3A-D and 4A-C). Interestingly, the converse is not typically the case (14 does not inhibit 15B and 17F does not inhibit 33F), but this is likely an affinity issue. Using these results to illustrate this, it is unlikely that Con1p4B03 binding to 9N could be inhibited by adding 9V polysaccharide because its affinity for 9N is over an order of magnitude higher. Overall, the inventor can say with confidence that the serum cross-reactivity observed in these studies is indeed due to individual monoclonal antibodies that bind to at least two different serotypes.

The observation that each of the donors produced a unique panel of antibodies to each of the serotypes is quite interesting. One explanation of this phenomenon is that one is seeing an "anamnestic fingerprint," or that the memory response being observed is a product of the serotypes that each of the subjects had been exposed to in the past. It is difficult to approximate how many of the 23 strains someone has been exposed to up to the time when they receive the Pneumovax®23 vaccine. The four donors whose serum was carefully examined by Pickering et al. (2007) had appreciable IgG concentrations (higher than 1 μg/ml) for 5-12 of the 22 serotypes (the samples were depleted with CWPS and 22F) indicating active plasma cells and subsequently previous exposure to those serotypes. The donors here showed antibodies to just over an average of 11 (13, 13, 9, and 10) serotypes, matching the serology in this previous study. Thus, one is observing that antibodies from the reactivation of memory cells seven days after vaccination is similar to those observed in the sera, likely from long-lived plasma cells.

While the generation of these human monoclonal antibodies elucidates basic anamnestic response, it may also serve a therapeutic purpose. As many current treatments can become ineffective due to antibiotic resistance, it is important to consider passive immunotherapeutics that can safely target pathogens. Several previous reports (Casal et al., 2002; Yuste et al., 2002) have explored the effects of specific antibodies in a mouse sepsis model. Remarkably, administering hyperimmune serum after infection was able to reduce the amount of antibiotic required for the mouse to recover by eight-fold. In addition, this synergistic effect might be effectively used in treating difficult or invasive infections, such as empyema, as well as bacteremia in immunocompromised individuals. In addition to the myriad of treatment options of fully human monoclonal antibodies, the drastically decreased risk of anaphylactic shock and of anti-treatment immune responses suggests that they will become as important in infectious diseases as they are currently in autoimmune settings.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

VIII. References

The following references, to the extent that they provide exemplary procedural or other details supplementary to those set forth herein, are specifically incorporated herein by reference.

U.S. Pat. No. 2,653,899
U.S. Pat. No. 3,817,837
U.S. Pat. No. 3,850,752
U.S. Pat. No. 3,939,350
U.S. Pat. No. 3,996,345
U.S. Pat. No. 4,196,265
U.S. Pat. No. 4,275,149
U.S. Pat. No. 4,277,437
U.S. Pat. No. 4,366,241
U.S. Pat. No. 4,472,509
U.S. Pat. No. 4,554,101
U.S. Pat. No. 4,680,338
U.S. Pat. No. 4,816,567
U.S. Pat. No. 4,867,973
U.S. Pat. No. 4,938,948
U.S. Pat. No. 5,021,236
U.S. Pat. No. 5,141,648
U.S. Pat. No. 5,196,066
U.S. Pat. No. 5,563,250
U.S. Pat. No. 5,565,332
U.S. Pat. No. 5,856,456
U.S. Pat. No. 5,880,270
"Antibodies: A Laboratory Manual," Cold Spring Harbor Press, Cold Spring Harbor, N.Y., 1988.
Anttila et al., *Clin. Exp. Immunol.*, 118:402-407, 1999.
Atherton et al., *Biol. of Reproduction*, 32:155-171, 1985.
Baxendale et al., *Eur. J. Immunol.*, 30:1214-1223, 2000.
Baxendale et al., *Infect. Immun.*, 74:1025-1031, 2006.
Campbell, In: *Monoclonal Antibody Technology, Laboratory Techniques in Biochemistry and Molecular Biology*, Vol. 13, Burden and Von Knippenberg, Eds. pp. 75-83, Amsterdam, Elsevier, 1984.
Capaldi et al., *Biochem. Biophys. Res. Comm.*, 74(2):425-433, 1977.
Casal et al., *Antimicrob. Agents Chemother.*, 46: 1340-1344, 2002.
Chowdhry et al., *Arthritis Rheum.*, 52:2403-10, 2005.
Clutterbuck et al., *Immunol.*, 119:328-337, 2006.
Crowe et al., *J. Infect. Dis.*, 202:251-60, 2010.
De Jager et al., *Semin. Nucl. Med.* 23(2):165-179, 1993.
Dholakia et al., *J. Biol. Chem.*, 264:20638-20642, 1989.
Doolittle and Ben-Zeev, *Methods Mol. Biol.*, 109:215-237, 1999.
Elkayam et al., *Autoimmunity*, 38:493-496, 2005.

Gefter et al., *Somatic Cell Genet.,* 3:231-236, 1977.
Goding, *In: Monoclonal Antibodies: Principles and Practice,* 2d ed., Orlando, Fla., Academic Press, 60-61, 65-66, 71-74, 1986.
Gulbis and Galand, *Hum. Pathol.* 24(12):1271-1285, 1993.
Harris et al., *Clin. Vacc. Immunol.,* 14:397-403, 2007.
Khatoon et al., *Ann. of Neurology,* 26:210-219, 1989.
King et al., *J. Biol. Chem.,* 269:10210-10218, 1989.
Kobasa et al., *Nature,* 445:319-323, 2007.
Kohler and Milstein, *Eur. J. Immunol.,* 6:511-519, 1976.
Kohler and Milstein, *Nature,* 256:495-497, 1975.
Kyte and Doolittle, *J. Mol. Biol.,* 157(1):105-132, 1982.
Lee et al., *J. Immunol.,* 133:2706-2711, 1984.
Marchese et al., *Clin. Vacc. Immunol.,* 13:905-912, 2006.
Morrison, *Science,* 229(4719): 1202-1207, 1985.
Nakamura et al., *In: Enzyme Immunoassays: Heterogeneous and Homogeneous Systems,* Chapter 27, 1987.
Nieminen et al., *Vaccine,* 16:313-319, 1998.
Nieminen et al., *Vaccine,* 16:630-636, 1998.
O'Shannessy et al., *J. Immun. Meth.,* 99:153-161, 1987.
Owens and Haley, *J. Biol. Chem.,* 259:14843-14848, 1987.
Park et al., *Infect. Immun.,* 77:3374-3379, 2009.
Persic et al., *Gene,* 187(1): 1-8, 1997.
Pickering et al., *Am. J. Clin. Pathol.,* 128:23-31, 2007.
Posner et al., *Hybridoma,* 6:611-625, 1987.
Potter and Haley, *Meth. Enzymol.,* 91:613-633, 1983.
Smith et al., *Nat. Protoc.,* 4:372-384, 2009.
Soininen et al., *Clin. Diagn. Lab. Immunol.,* 7:468-476, 2000.
Tang et al., *J. Biol. Chem.,* 271:28324-28330, 1996.
Usinger et al., *Infect. Immun.,* 67:2366-2370, 1999.
Wawrzynczak & Thorpe, *In: Immumoconjugates, Antibody Conuugates In Radioimaging And Therapy Of Cancer,* Vogel (Ed.), NY, Oxford University Press, 28, 1987.
Wrammert et al., *Nature,* 453:667-671, 2008.
Xu et al., *Anal. Biochem.,* 336:262-272, 2005.
Yuste et al., *Clin. Exp. Immunol.,* 128:411-415, 2002.
Zhou et al., *Infect. Immun.,* 70:4083-4091, 2002.
Zhou et al., *Infect. Immun.,* 72:3505-3514, 2004.

What is claimed is:

1. A method of treating a *Streptococcus pneumoniae* infection in a subject comprising administering to said subject at least one antibody that binds selectively to Streptococcus pneumonia, wherein said antibody comprise
   i) a heavy chain [CDR] selected from the group consisting of the nucleotide sequence set forth in SEQ ID NOS: 127, 122, 129, 130, 131, 132, 133, 134, 135, 136, 137, 138, 139, 140, 141, 142, 143, 161, 162, 164, 165, 166, 167, 168, 169, 170, 171, 172, 173, 174, 175, 176, 177, 178, 179, 199, 200, 201, 202, 203, 204, 205, 206, 207, 208, 209, 210, 211, 225, 226, 227, 228, 229, 230, 231, 232, 233, 234, 235, 236, 237, and 238; and
   ii) a light chain [CDR] selected from the group consisting of the nucleotide sequence set forth SEQ ID NOS: 144, 145, 146, 147, 148, 149, 150, 151, 152, 153, 154, 155, 156, 157, 158, 159, 160, 180, 181, 182, 183, 184, 185, 186, 187, 188, 189, 190, 191, 192, 193, 194, 195, 196, 197, 198, 212, 213, 214, 215, 216, 217, 218, 219, 220, 221, 222, 223, 224, 239, 240, 241, 242, 243, 244, 245, 246, 247, 248, 249, 250, 251, and 252.

2. The method of claim 1, further comprising administering to said subject a second anti-*Streptococcus pneumoniae* treatment.

3. The method of claim 2, wherein said second anti-*Streptococcus pneumoniae* treatment is given at the same time as said antibody.

4. The method of claim 2, wherein said second anti-*Streptococcus pneumoniae* treatment is given before and/or after said antibody.

5. The method of claim 1, wherein said antibody is a single chain antibody.

6. The method of claim 1, wherein said antibody is a single domain antibody.

7. The method of claim 1, wherein said antibody is a chimeric antibody.

8. The method of claim 1, wherein said antibody a Fab fragment.

9. The method of claim 1, wherein said antibody is an IgG.

10. The method of claim 1, wherein said antibody further comprises a linker, said linker is linked to an antibiotic.

11. The method of claim 10, wherein said linker is a photo labile linker.

12. The method of claim 10, wherein said linker is an enzymatically-cleaved linker.

13. The method of claim 1, wherein said antibody is conjugated to a liposome or nanoparticle.

14. The method of claim 1, wherein multiple anti-*Streptococcus pneumonia* antibodies are administered.

15. The method of claim 14, wherein said multiple anti-*Streptococcus pneumonia* antibodies bind to 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95 or 100 *Streptococcus pneumonia* serotypes.

* * * * *

SEQUENCE LISTING

```
<160> NUMBER OF SEQ ID NOS: 252

<210> SEQ ID NO 1
<211> LENGTH: 9
<212> TYPE: PRT
<213> ORGANISM: Streptococcus pneumoniae

<400> SEQUENCE: 1

Ala Lys Gly Val Thr Ser Phe Asp Tyr
1               5

<210> SEQ ID NO 2
<211> LENGTH: 10
<212> TYPE: PRT
<213> ORGANISM: Streptococcus pneumoniae

<400> SEQUENCE: 2

Gln Gln Phe Gly Ser Ser Pro Pro Asp Thr
1               5                   10

<210> SEQ ID NO 3
<211> LENGTH: 12
<212> TYPE: PRT
<213> ORGANISM: Streptococcus pneumoniae

<400> SEQUENCE: 3

Ala Arg Asp Pro Gly Ile Arg Asn Gly Met Gly Val
1               5                   10

<210> SEQ ID NO 4
<211> LENGTH: 9
<212> TYPE: PRT
<213> ORGANISM: Streptococcus pneumoniae

<400> SEQUENCE: 4

Met Gln Val Thr His Trp Pro Arg Thr
1               5

<210> SEQ ID NO 5
<211> LENGTH: 14
<212> TYPE: PRT
<213> ORGANISM: Streptococcus pneumoniae
```

```
<400> SEQUENCE: 5

Ala Lys Ala His Arg Gly Asp Trp Asn Asn Phe Phe Asp Tyr
1               5                   10

<210> SEQ ID NO 6
<211> LENGTH: 9
<212> TYPE: PRT
<213> ORGANISM: Streptococcus pneumoniae

<400> SEQUENCE: 6

Gln Gln Ser Gly Asp Trp Pro Leu Thr
1               5

<210> SEQ ID NO 7
<211> LENGTH: 9
<212> TYPE: PRT
<213> ORGANISM: Streptococcus pneumoniae

<400> SEQUENCE: 7

Ala Arg Glu Trp Ser Gly Phe Asp Phe
1               5

<210> SEQ ID NO 8
<211> LENGTH: 9
<212> TYPE: PRT
<213> ORGANISM: Streptococcus pneumoniae

<400> SEQUENCE: 8

Gln Gln Tyr Gly Ser Leu Pro Arg Thr
1               5

<210> SEQ ID NO 9
<211> LENGTH: 8
<212> TYPE: PRT
<213> ORGANISM: Streptococcus pneumoniae

<400> SEQUENCE: 9

Ala Arg Gly Gln Trp Leu Ala Phe
1               5

<210> SEQ ID NO 10
<211> LENGTH: 9
<212> TYPE: PRT
<213> ORGANISM: Streptococcus pneumoniae

<400> SEQUENCE: 10

Met Gln Gly Thr His Trp Pro Tyr Thr
1               5

<210> SEQ ID NO 11
<211> LENGTH: 9
<212> TYPE: PRT
<213> ORGANISM: Streptococcus pneumoniae

<400> SEQUENCE: 11

Ala Arg Gly Arg Asn Asn Phe Arg His
1               5

<210> SEQ ID NO 12
<211> LENGTH: 9
<212> TYPE: PRT
<213> ORGANISM: Streptococcus pneumoniae
```

```
<400> SEQUENCE: 12

Gln Gln Phe Glu Ser Phe Pro Arg Thr
1               5

<210> SEQ ID NO 13
<211> LENGTH: 20
<212> TYPE: PRT
<213> ORGANISM: Streptococcus pneumoniae

<400> SEQUENCE: 13

Ala Arg Glu Leu Gly Val Phe His Ser Gly Gly Asp Gln Trp Leu Gly
1               5                   10                  15

Pro Leu Asp Cys
            20

<210> SEQ ID NO 14
<211> LENGTH: 11
<212> TYPE: PRT
<213> ORGANISM: Streptococcus pneumoniae

<400> SEQUENCE: 14

His Gln Tyr Lys Asn Trp Pro Pro Met Gly Thr
1               5                   10

<210> SEQ ID NO 15
<211> LENGTH: 11
<212> TYPE: PRT
<213> ORGANISM: Streptococcus pneumoniae

<400> SEQUENCE: 15

Arg Trp Thr Gly Gly Val Ser Phe Gly Ala Tyr
1               5                   10

<210> SEQ ID NO 16
<211> LENGTH: 8
<212> TYPE: PRT
<213> ORGANISM: Streptococcus pneumoniae

<400> SEQUENCE: 16

Gln Gln Tyr Asp Ile Tyr Leu Thr
1               5

<210> SEQ ID NO 17
<211> LENGTH: 10
<212> TYPE: PRT
<213> ORGANISM: Streptococcus pneumoniae

<400> SEQUENCE: 17

Ala Arg Asp Tyr Tyr His Ser Val Asp Tyr
1               5                   10

<210> SEQ ID NO 18
<211> LENGTH: 9
<212> TYPE: PRT
<213> ORGANISM: Streptococcus pneumoniae

<400> SEQUENCE: 18

Met Gln Gly Thr His Trp Pro Tyr Thr
1               5

<210> SEQ ID NO 19
<211> LENGTH: 11
<212> TYPE: PRT
<213> ORGANISM: Streptococcus pneumoniae
```

<400> SEQUENCE: 19

Ala Arg Gly Pro Asp Ala His Lys Thr Gly Tyr
1               5                   10

<210> SEQ ID NO 20
<211> LENGTH: 9
<212> TYPE: PRT
<213> ORGANISM: Streptococcus pneumoniae

<400> SEQUENCE: 20

Gln Gln Tyr Ala Ala Thr Pro Trp Thr
1               5

<210> SEQ ID NO 21
<211> LENGTH: 10
<212> TYPE: PRT
<213> ORGANISM: Streptococcus pneumoniae

<400> SEQUENCE: 21

Ala Arg Asp Ser Tyr Thr Ser Pro Asp Tyr
1               5                   10

<210> SEQ ID NO 22
<211> LENGTH: 9
<212> TYPE: PRT
<213> ORGANISM: Streptococcus pneumoniae

<400> SEQUENCE: 22

Met Gln Gly Ser His Trp Pro Leu Thr
1               5

<210> SEQ ID NO 23
<211> LENGTH: 11
<212> TYPE: PRT
<213> ORGANISM: Streptococcus pneumoniae

<400> SEQUENCE: 23

Thr Thr Asp Asn Gly Val Lys Ala Phe Asp Ile
1               5                   10

<210> SEQ ID NO 24
<211> LENGTH: 9
<212> TYPE: PRT
<213> ORGANISM: Streptococcus pneumoniae

<400> SEQUENCE: 24

His Gln Tyr Tyr Thr Thr Pro Phe Ala
1               5

<210> SEQ ID NO 25
<211> LENGTH: 11
<212> TYPE: PRT
<213> ORGANISM: Streptococcus pneumoniae

<400> SEQUENCE: 25

Thr Arg Gly Gly Ser Gly Ala Thr Ile Asn Tyr
1               5                   10

<210> SEQ ID NO 26
<211> LENGTH: 9
<212> TYPE: PRT
<213> ORGANISM: Streptococcus pneumoniae

<400> SEQUENCE: 26

Gln Gln Ser His Ser Ser Pro Leu Thr
1               5

<210> SEQ ID NO 27
<211> LENGTH: 16
<212> TYPE: PRT
<213> ORGANISM: Streptococcus pneumoniae

<400> SEQUENCE: 27

Ala Arg Asp Arg Ala Gly Ile Asp Gly Tyr Asn Tyr Tyr Phe Asp Tyr
1               5                   10                  15

<210> SEQ ID NO 28
<211> LENGTH: 8
<212> TYPE: PRT
<213> ORGANISM: Streptococcus pneumoniae

<400> SEQUENCE: 28

Gln Gln Tyr Tyr Ser Phe Tyr Thr
1               5

<210> SEQ ID NO 29
<211> LENGTH: 13
<212> TYPE: PRT
<213> ORGANISM: Streptococcus pneumoniae

<400> SEQUENCE: 29

Ala Arg Glu Val Ala Ala Glu Gly Lys Ala Phe Asp Tyr
1               5                   10

<210> SEQ ID NO 30
<211> LENGTH: 9
<212> TYPE: PRT
<213> ORGANISM: Streptococcus pneumoniae

<400> SEQUENCE: 30

Gln Gln Tyr Tyr Thr Pro Pro Leu Thr
1               5

<210> SEQ ID NO 31
<211> LENGTH: 9
<212> TYPE: PRT
<213> ORGANISM: Streptococcus pneumoniae

<400> SEQUENCE: 31

Ala Arg Gly Gln Ser Tyr Pro Gly Ile
1               5

<210> SEQ ID NO 32
<211> LENGTH: 9
<212> TYPE: PRT
<213> ORGANISM: Streptococcus pneumoniae

<400> SEQUENCE: 32

Gln Gln Tyr Asn Asn Trp Pro Arg Thr
1               5

<210> SEQ ID NO 33
<211> LENGTH: 15
<212> TYPE: PRT
<213> ORGANISM: Streptococcus pneumoniae

<400> SEQUENCE: 33

Ala Gly Arg Ala Tyr Ser Ser Gly Tyr Tyr Tyr Leu Ile Asp Tyr

```
1               5                   10                  15
```

<210> SEQ ID NO 34
<211> LENGTH: 9
<212> TYPE: PRT
<213> ORGANISM: Streptococcus pneumoniae

<400> SEQUENCE: 34

```
Gln His Tyr His Asn Trp Pro Pro Thr
1               5
```

<210> SEQ ID NO 35
<211> LENGTH: 15
<212> TYPE: PRT
<213> ORGANISM: Streptococcus pneumoniae

<400> SEQUENCE: 35

```
Ala Lys Gly Cys Ser Asn Gly Gly Asn Cys Phe Leu Ile Asp Tyr
1               5                   10                  15
```

<210> SEQ ID NO 36
<211> LENGTH: 9
<212> TYPE: PRT
<213> ORGANISM: Streptococcus pneumoniae

<400> SEQUENCE: 36

```
Gln Gln Tyr Tyr Asn Ala Pro Leu Thr
1               5
```

<210> SEQ ID NO 37
<211> LENGTH: 16
<212> TYPE: PRT
<213> ORGANISM: Streptococcus pneumoniae

<400> SEQUENCE: 37

```
Ala Lys Gly Gly Tyr Tyr Glu Ser Gly Thr Met Arg Ala Phe Asp Ile
1               5                   10                  15
```

<210> SEQ ID NO 38
<211> LENGTH: 9
<212> TYPE: PRT
<213> ORGANISM: Streptococcus pneumoniae

<400> SEQUENCE: 38

```
Gln Gln Arg Ser Asn Trp Pro Ala Thr
1               5
```

<210> SEQ ID NO 39
<211> LENGTH: 9
<212> TYPE: PRT
<213> ORGANISM: Streptococcus pneumoniae

<400> SEQUENCE: 39

```
Ala Arg Gly Glu Ser Asn Phe Arg Tyr
1               5
```

<210> SEQ ID NO 40
<211> LENGTH: 9
<212> TYPE: PRT
<213> ORGANISM: Streptococcus pneumoniae

<400> SEQUENCE: 40

```
Gln Gln Phe Val Ser Phe Pro Arg Thr
1               5
```

<210> SEQ ID NO 41
<211> LENGTH: 12
<212> TYPE: PRT
<213> ORGANISM: Streptococcus pneumoniae

<400> SEQUENCE: 41

Ala Arg Asp Ser Thr Ser Pro Ala Arg Phe Gly Tyr
1               5                   10

<210> SEQ ID NO 42
<211> LENGTH: 11
<212> TYPE: PRT
<213> ORGANISM: Streptococcus pneumoniae

<400> SEQUENCE: 42

Gln His Tyr Gly Thr Ser Pro Pro Arg Tyr Thr
1               5                   10

<210> SEQ ID NO 43
<211> LENGTH: 12
<212> TYPE: PRT
<213> ORGANISM: Streptococcus pneumoniae

<400> SEQUENCE: 43

Ala Thr Gly Gly Met Thr Ser Ser Trp Tyr Gly Tyr
1               5                   10

<210> SEQ ID NO 44
<211> LENGTH: 9
<212> TYPE: PRT
<213> ORGANISM: Streptococcus pneumoniae

<400> SEQUENCE: 44

Gln Gln Tyr Tyr Ser Thr Pro Tyr Thr
1               5

<210> SEQ ID NO 45
<211> LENGTH: 18
<212> TYPE: PRT
<213> ORGANISM: Streptococcus pneumoniae

<400> SEQUENCE: 45

Ser Met Gly Pro Pro Tyr Cys Thr Gly Gly Ser Cys Tyr Ser Ala Cys
1               5                   10                  15

Asp Phe

<210> SEQ ID NO 46
<211> LENGTH: 10
<212> TYPE: PRT
<213> ORGANISM: Streptococcus pneumoniae

<400> SEQUENCE: 46

Gln Arg Tyr Gly Asn Ser Pro Pro Tyr Thr
1               5                   10

<210> SEQ ID NO 47
<211> LENGTH: 15
<212> TYPE: PRT
<213> ORGANISM: Streptococcus pneumoniae

<400> SEQUENCE: 47

Thr Thr Asp Ile Gly Lys Gly Trp Tyr Thr His Tyr Pro Asp Leu
1               5                   10                  15

<210> SEQ ID NO 48
<211> LENGTH: 9
<212> TYPE: PRT
<213> ORGANISM: Streptococcus pneumoniae

<400> SEQUENCE: 48

Leu Gln Tyr Arg Ser Ala Pro Phe Thr
1               5

<210> SEQ ID NO 49
<211> LENGTH: 14
<212> TYPE: PRT
<213> ORGANISM: Streptococcus pneumoniae

<400> SEQUENCE: 49

Val Lys Glu Tyr Ser Trp Gly Tyr Tyr Arg Thr Ala Asp Tyr
1               5                   10

<210> SEQ ID NO 50
<211> LENGTH: 9
<212> TYPE: PRT
<213> ORGANISM: Streptococcus pneumoniae

<400> SEQUENCE: 50

Gln Gln Tyr Ser Thr Tyr Pro Trp Thr
1               5

<210> SEQ ID NO 51
<211> LENGTH: 10
<212> TYPE: PRT
<213> ORGANISM: Streptococcus pneumoniae

<400> SEQUENCE: 51

Ala Arg Ser Pro Gly Gly Tyr Phe Asp Tyr
1               5                   10

<210> SEQ ID NO 52
<211> LENGTH: 9
<212> TYPE: PRT
<213> ORGANISM: Streptococcus pneumoniae

<400> SEQUENCE: 52

Gln Gln Tyr Ser Thr Trp Leu Trp Thr
1               5

<210> SEQ ID NO 53
<211> LENGTH: 7
<212> TYPE: PRT
<213> ORGANISM: Streptococcus pneumoniae

<400> SEQUENCE: 53

Thr Thr Asp Asp Leu Lys Asn
1               5

<210> SEQ ID NO 54
<211> LENGTH: 9
<212> TYPE: PRT
<213> ORGANISM: Streptococcus pneumoniae

<400> SEQUENCE: 54

Gln Gln Arg Tyr Arg Ile Pro Tyr Ser
1               5

<210> SEQ ID NO 55

```
<211> LENGTH: 22
<212> TYPE: PRT
<213> ORGANISM: Streptococcus pneumoniae

<400> SEQUENCE: 55

Ala Arg Gly Arg Asp Cys Tyr Gly Gly Asn Cys Val Ile Tyr Phe His
1               5                   10                  15

Tyr Tyr Gly Leu Asp Val
            20

<210> SEQ ID NO 56
<211> LENGTH: 9
<212> TYPE: PRT
<213> ORGANISM: Streptococcus pneumoniae

<400> SEQUENCE: 56

Met Arg Ala Leu Gln Thr Pro Tyr Thr
1               5

<210> SEQ ID NO 57
<211> LENGTH: 14
<212> TYPE: PRT
<213> ORGANISM: Streptococcus pneumoniae

<400> SEQUENCE: 57

Val Lys Glu Ser Ala Thr Gly Trp Tyr Arg Thr Ala Asp Tyr
1               5                   10

<210> SEQ ID NO 58
<211> LENGTH: 9
<212> TYPE: PRT
<213> ORGANISM: Streptococcus pneumoniae

<400> SEQUENCE: 58

His Gln Tyr Asn Lys Tyr Pro Trp Thr
1               5

<210> SEQ ID NO 59
<211> LENGTH: 16
<212> TYPE: PRT
<213> ORGANISM: Streptococcus pneumoniae

<400> SEQUENCE: 59

Ala Arg Asp Ile Pro Thr Thr Phe Gly Ile Gly Glu Ala Phe Asp Ile
1               5                   10                  15

<210> SEQ ID NO 60
<211> LENGTH: 8
<212> TYPE: PRT
<213> ORGANISM: Streptococcus pneumoniae

<400> SEQUENCE: 60

Gln Gln Tyr Tyr Ser Trp Gly Thr
1               5

<210> SEQ ID NO 61
<211> LENGTH: 9
<212> TYPE: PRT
<213> ORGANISM: Streptococcus pneumoniae

<400> SEQUENCE: 61

Ala Arg Asp Asp Ser Ala Phe Asp Tyr
1               5
```

<210> SEQ ID NO 62
<211> LENGTH: 9
<212> TYPE: PRT
<213> ORGANISM: Streptococcus pneumoniae

<400> SEQUENCE: 62

Met Gln Ala Ser Gln Ser Thr Trp Thr
1               5

<210> SEQ ID NO 63
<211> LENGTH: 14
<212> TYPE: PRT
<213> ORGANISM: Streptococcus pneumoniae

<400> SEQUENCE: 63

Ala Lys Gly Cys Ser Gly Glu Asn Cys Phe Tyr Met Asp Asp
1               5                   10

<210> SEQ ID NO 64
<211> LENGTH: 9
<212> TYPE: PRT
<213> ORGANISM: Streptococcus pneumoniae

<400> SEQUENCE: 64

Gln Gln Cys Tyr Asn Ala Pro Leu Thr
1               5

<210> SEQ ID NO 65
<211> LENGTH: 22
<212> TYPE: PRT
<213> ORGANISM: Streptococcus pneumoniae

<400> SEQUENCE: 65

Thr Arg Glu Ile Gly Ala Val Val Val Asp Ala Thr Ser Leu Gly Trp
1               5                   10                  15

Leu Gly Tyr Phe Asp Tyr
            20

<210> SEQ ID NO 66
<211> LENGTH: 10
<212> TYPE: PRT
<213> ORGANISM: Streptococcus pneumoniae

<400> SEQUENCE: 66

Gln Gln Tyr Asn Asn Trp Pro Pro Val Thr
1               5                   10

<210> SEQ ID NO 67
<211> LENGTH: 8
<212> TYPE: PRT
<213> ORGANISM: Streptococcus pneumoniae

<400> SEQUENCE: 67

Ala Gly Trp Gly Arg Thr Gln Asp
1               5

<210> SEQ ID NO 68
<211> LENGTH: 9
<212> TYPE: PRT
<213> ORGANISM: Streptococcus pneumoniae

<400> SEQUENCE: 68

Met Gln Tyr Thr Phe Trp Pro His Thr
1               5

<210> SEQ ID NO 69
<211> LENGTH: 14
<212> TYPE: PRT
<213> ORGANISM: Streptococcus pneumoniae

<400> SEQUENCE: 69

Thr Lys Glu Gly Ala Pro Pro Gly Lys Tyr Ala Phe Asp Ile
1               5                   10

<210> SEQ ID NO 70
<211> LENGTH: 11
<212> TYPE: PRT
<213> ORGANISM: Streptococcus pneumoniae

<400> SEQUENCE: 70

Gln His Arg Gly Glu Trp Pro Pro Gly Ala Thr
1               5                   10

<210> SEQ ID NO 71
<211> LENGTH: 11
<212> TYPE: PRT
<213> ORGANISM: Streptococcus pneumoniae

<400> SEQUENCE: 71

Leu Lys Asp Ser Ser Gln Tyr Ser Phe Asp Ala
1               5                   10

<210> SEQ ID NO 72
<211> LENGTH: 9
<212> TYPE: PRT
<213> ORGANISM: Streptococcus pneumoniae

<400> SEQUENCE: 72

Gln Gln Phe Lys Gly Tyr Pro Leu Thr
1               5

<210> SEQ ID NO 73
<211> LENGTH: 9
<212> TYPE: PRT
<213> ORGANISM: Streptococcus pneumoniae

<400> SEQUENCE: 73

Ala Arg Gly Asp Gly Tyr Asn Phe Phe
1               5

<210> SEQ ID NO 74
<211> LENGTH: 9
<212> TYPE: PRT
<213> ORGANISM: Streptococcus pneumoniae

<400> SEQUENCE: 74

Gln Gln Ile Asn Ser Tyr Pro Arg Thr
1               5

<210> SEQ ID NO 75
<211> LENGTH: 18
<212> TYPE: PRT
<213> ORGANISM: Streptococcus pneumoniae

<400> SEQUENCE: 75

Ala Lys Cys Gly Ala Glu Asp Ser Thr Thr Val Trp Leu Asn Trp Phe
1               5                   10                  15

Asp Pro

<210> SEQ ID NO 76
<211> LENGTH: 9
<212> TYPE: PRT
<213> ORGANISM: Streptococcus pneumoniae

<400> SEQUENCE: 76

Gln Gln Arg Ala Asp Trp Pro Leu Thr
1               5

<210> SEQ ID NO 77
<211> LENGTH: 13
<212> TYPE: PRT
<213> ORGANISM: Streptococcus pneumoniae

<400> SEQUENCE: 77

Ala Lys Pro Asn Tyr Phe Gly Ser Gly Ser Pro Asp Tyr
1               5                   10

<210> SEQ ID NO 78
<211> LENGTH: 10
<212> TYPE: PRT
<213> ORGANISM: Streptococcus pneumoniae

<400> SEQUENCE: 78

Leu Gln Cys Ser Asn Trp Pro Met Tyr Thr
1               5                   10

<210> SEQ ID NO 79
<211> LENGTH: 14
<212> TYPE: PRT
<213> ORGANISM: Streptococcus pneumoniae

<400> SEQUENCE: 79

Val Lys Glu Gln Asp Tyr Gly Tyr Tyr Arg Thr Ala Asp His
1               5                   10

<210> SEQ ID NO 80
<211> LENGTH: 9
<212> TYPE: PRT
<213> ORGANISM: Streptococcus pneumoniae

<400> SEQUENCE: 80

Gln Gln Tyr Asp Lys Tyr Pro Trp Thr
1               5

<210> SEQ ID NO 81
<211> LENGTH: 19
<212> TYPE: PRT
<213> ORGANISM: Streptococcus pneumoniae

<400> SEQUENCE: 81

Val Arg Val Ala Val Pro Ala Ala Thr Tyr Thr Arg Gly Asn Asp Ala
1               5                   10                  15

Phe Asp Ile

<210> SEQ ID NO 82
<211> LENGTH: 9
<212> TYPE: PRT
<213> ORGANISM: Streptococcus pneumoniae

<400> SEQUENCE: 82

Leu Gln His Ser Ser Phe Pro Trp Thr
1               5

```
<210> SEQ ID NO 83
<211> LENGTH: 10
<212> TYPE: PRT
<213> ORGANISM: Streptococcus pneumoniae

<400> SEQUENCE: 83

Thr Thr Ala His Gly Pro Val Gly Asp His
1               5                   10

<210> SEQ ID NO 84
<211> LENGTH: 10
<212> TYPE: PRT
<213> ORGANISM: Streptococcus pneumoniae

<400> SEQUENCE: 84

Gln Gln Tyr Tyr Thr Thr Pro Ser Ile Thr
1               5                   10

<210> SEQ ID NO 85
<211> LENGTH: 19
<212> TYPE: PRT
<213> ORGANISM: Streptococcus pneumoniae

<400> SEQUENCE: 85

Ala Arg Ala Gly Gly Cys Ser Ser Thr Arg Cys His Thr Thr Pro Gly
1               5                   10                  15

Phe Asp Tyr

<210> SEQ ID NO 86
<211> LENGTH: 10
<212> TYPE: PRT
<213> ORGANISM: Streptococcus pneumoniae

<400> SEQUENCE: 86

Gln Gln Tyr Tyr Thr Thr Pro Pro Ile Thr
1               5                   10

<210> SEQ ID NO 87
<211> LENGTH: 11
<212> TYPE: PRT
<213> ORGANISM: Streptococcus pneumoniae

<400> SEQUENCE: 87

Ala Ser Leu Ser Gly Thr Asn Ala Phe Asp Ile
1               5                   10

<210> SEQ ID NO 88
<211> LENGTH: 8
<212> TYPE: PRT
<213> ORGANISM: Streptococcus pneumoniae

<400> SEQUENCE: 88

Gln Gln Arg Ser Ser Gly Arg Thr
1               5

<210> SEQ ID NO 89
<211> LENGTH: 13
<212> TYPE: PRT
<213> ORGANISM: Streptococcus pneumoniae

<400> SEQUENCE: 89

Ala Lys Pro Arg Gly Tyr Ser Tyr Gly Tyr Phe Asp Tyr
1               5                   10
```

```
<210> SEQ ID NO 90
<211> LENGTH: 9
<212> TYPE: PRT
<213> ORGANISM: Streptococcus pneumoniae

<400> SEQUENCE: 90

Gln Gln Tyr Gly Ile Ser Pro Arg Thr
1               5

<210> SEQ ID NO 91
<211> LENGTH: 9
<212> TYPE: PRT
<213> ORGANISM: Streptococcus pneumoniae

<400> SEQUENCE: 91

Ala Pro Pro Ala Arg Arg Leu Asp Tyr
1               5

<210> SEQ ID NO 92
<211> LENGTH: 9
<212> TYPE: PRT
<213> ORGANISM: Streptococcus pneumoniae

<400> SEQUENCE: 92

Met Gln Gly Thr His His Pro Trp Thr
1               5

<210> SEQ ID NO 93
<211> LENGTH: 9
<212> TYPE: PRT
<213> ORGANISM: Streptococcus pneumoniae

<400> SEQUENCE: 93

Ala Arg Ser Asn Ala Gly His Glu Ala
1               5

<210> SEQ ID NO 94
<211> LENGTH: 9
<212> TYPE: PRT
<213> ORGANISM: Streptococcus pneumoniae

<400> SEQUENCE: 94

Gln Gln Tyr Tyr Ser Thr Pro Leu Thr
1               5

<210> SEQ ID NO 95
<211> LENGTH: 11
<212> TYPE: PRT
<213> ORGANISM: Streptococcus pneumoniae

<400> SEQUENCE: 95

Ala Arg Asp Ile Pro His Ala Asn Leu Asp Tyr
1               5                   10

<210> SEQ ID NO 96
<211> LENGTH: 9
<212> TYPE: PRT
<213> ORGANISM: Streptococcus pneumoniae

<400> SEQUENCE: 96

Leu Gln His Thr Thr Phe Pro Trp Thr
1               5

<210> SEQ ID NO 97
```

```
<211> LENGTH: 14
<212> TYPE: PRT
<213> ORGANISM: Streptococcus pneumoniae

<400> SEQUENCE: 97

Val Lys Asp Arg Val Pro Pro Gly Asp Val Pro Gly Asp Phe
1               5                   10

<210> SEQ ID NO 98
<211> LENGTH: 10
<212> TYPE: PRT
<213> ORGANISM: Streptococcus pneumoniae

<400> SEQUENCE: 98

Gln Gln Arg Arg Thr Trp Pro Pro Leu Thr
1               5                   10

<210> SEQ ID NO 99
<211> LENGTH: 12
<212> TYPE: PRT
<213> ORGANISM: Streptococcus pneumoniae

<400> SEQUENCE: 99

Ala Thr Leu Leu Leu Arg Asp Asn Gln Leu Asp Val
1               5                   10

<210> SEQ ID NO 100
<211> LENGTH: 8
<212> TYPE: PRT
<213> ORGANISM: Streptococcus pneumoniae

<400> SEQUENCE: 100

Met Gln Gly Thr His Trp Arg Thr
1               5

<210> SEQ ID NO 101
<211> LENGTH: 14
<212> TYPE: PRT
<213> ORGANISM: Streptococcus pneumoniae

<400> SEQUENCE: 101

Val Lys Glu Gln Gly Phe Gly Tyr Tyr Arg Thr Ala Asp Tyr
1               5                   10

<210> SEQ ID NO 102
<211> LENGTH: 9
<212> TYPE: PRT
<213> ORGANISM: Streptococcus pneumoniae

<400> SEQUENCE: 102

His Gln Tyr Asp Lys Tyr Pro Trp Thr
1               5

<210> SEQ ID NO 103
<211> LENGTH: 8
<212> TYPE: PRT
<213> ORGANISM: Streptococcus pneumoniae

<400> SEQUENCE: 103

Ala Arg Arg Asn Asp Phe Asn Ile
1               5

<210> SEQ ID NO 104
<211> LENGTH: 9
<212> TYPE: PRT
```

<213> ORGANISM: Streptococcus pneumoniae

<400> SEQUENCE: 104

Gln Gln Tyr Gly Ser Ser Pro Phe Thr
1               5

<210> SEQ ID NO 105
<211> LENGTH: 16
<212> TYPE: PRT
<213> ORGANISM: Streptococcus pneumoniae

<400> SEQUENCE: 105

Ser Ile Trp Trp Gly Thr Ser Val Gln Tyr Pro Leu Val Leu Asp Tyr
1               5                   10                  15

<210> SEQ ID NO 106
<211> LENGTH: 10
<212> TYPE: PRT
<213> ORGANISM: Streptococcus pneumoniae

<400> SEQUENCE: 106

Gln Gln Tyr Ser Lys Trp Pro Pro Ile Thr
1               5                   10

<210> SEQ ID NO 107
<211> LENGTH: 14
<212> TYPE: PRT
<213> ORGANISM: Streptococcus pneumoniae

<400> SEQUENCE: 107

Val Lys Glu Gln Asp Tyr Gly Tyr Tyr Arg Thr Ala Asp His
1               5                   10

<210> SEQ ID NO 108
<211> LENGTH: 9
<212> TYPE: PRT
<213> ORGANISM: Streptococcus pneumoniae

<400> SEQUENCE: 108

Gln Gln Tyr Asp Lys Tyr Pro Trp Thr
1               5

<210> SEQ ID NO 109
<211> LENGTH: 9
<212> TYPE: PRT
<213> ORGANISM: Streptococcus pneumoniae

<400> SEQUENCE: 109

Ala Arg Gly His Gly Phe Asn Ala Tyr
1               5

<210> SEQ ID NO 110
<211> LENGTH: 9
<212> TYPE: PRT
<213> ORGANISM: Streptococcus pneumoniae

<400> SEQUENCE: 110

Gln Gln Tyr Gly Asn Ser Pro Arg Thr
1               5

<210> SEQ ID NO 111
<211> LENGTH: 13
<212> TYPE: PRT
<213> ORGANISM: Streptococcus pneumoniae

<400> SEQUENCE: 111

Thr Thr Val Arg Asn Met Ala Asp Leu Ser Leu Asn His
1               5                   10

<210> SEQ ID NO 112
<211> LENGTH: 9
<212> TYPE: PRT
<213> ORGANISM: Streptococcus pneumoniae

<400> SEQUENCE: 112

Gln Gln Tyr Asp Asp Ser Arg Trp Thr
1               5

<210> SEQ ID NO 113
<211> LENGTH: 11
<212> TYPE: PRT
<213> ORGANISM: Streptococcus pneumoniae

<400> SEQUENCE: 113

Ala Thr Gly Asn Arg Gly Ser Leu Pro Arg Arg
1               5                   10

<210> SEQ ID NO 114
<211> LENGTH: 9
<212> TYPE: PRT
<213> ORGANISM: Streptococcus pneumoniae

<400> SEQUENCE: 114

Met Gln Ala Leu Arg Ser Pro Tyr Thr
1               5

<210> SEQ ID NO 115
<211> LENGTH: 11
<212> TYPE: PRT
<213> ORGANISM: Streptococcus pneumoniae

<400> SEQUENCE: 115

Val Arg Asp Gly Trp Asp Thr Phe Phe Asp Ser
1               5                   10

<210> SEQ ID NO 116
<211> LENGTH: 9
<212> TYPE: PRT
<213> ORGANISM: Streptococcus pneumoniae

<400> SEQUENCE: 116

Met Gln Gly Arg Tyr Trp Pro Tyr Thr
1               5

<210> SEQ ID NO 117
<211> LENGTH: 6
<212> TYPE: PRT
<213> ORGANISM: Streptococcus pneumoniae

<400> SEQUENCE: 117

Val Asn Phe Gln Leu Gly
1               5

<210> SEQ ID NO 118
<211> LENGTH: 9
<212> TYPE: PRT
<213> ORGANISM: Streptococcus pneumoniae

<400> SEQUENCE: 118

```
Gln Gln Tyr Gly Asn Ser Pro Arg Thr
 1               5
```

<210> SEQ ID NO 119
<211> LENGTH: 16
<212> TYPE: PRT
<213> ORGANISM: Streptococcus pneumoniae

<400> SEQUENCE: 119

```
Ala Arg Ala Glu Tyr Cys Ser Pro Gly Asp Cys Phe Leu Ile Asp Thr
 1               5                  10                  15
```

<210> SEQ ID NO 120
<211> LENGTH: 8
<212> TYPE: PRT
<213> ORGANISM: Streptococcus pneumoniae

<400> SEQUENCE: 120

```
Met Gln Gly Thr His Trp Arg Thr
 1               5
```

<210> SEQ ID NO 121
<211> LENGTH: 12
<212> TYPE: PRT
<213> ORGANISM: Streptococcus pneumoniae

<400> SEQUENCE: 121

```
Leu Arg Gly Asn Pro Pro Ser Ser Pro Thr Asp Tyr
 1               5                  10
```

<210> SEQ ID NO 122
<211> LENGTH: 9
<212> TYPE: PRT
<213> ORGANISM: Streptococcus pneumoniae

<400> SEQUENCE: 122

```
Gln Gln Tyr Asn Ser Tyr Pro Leu Thr
 1               5
```

<210> SEQ ID NO 123
<211> LENGTH: 12
<212> TYPE: PRT
<213> ORGANISM: Streptococcus pneumoniae

<400> SEQUENCE: 123

```
Ala Lys Val Val Tyr Ser Arg Pro Pro Met Asp Val
 1               5                  10
```

<210> SEQ ID NO 124
<211> LENGTH: 9
<212> TYPE: PRT
<213> ORGANISM: Streptococcus pneumoniae

<400> SEQUENCE: 124

```
Gln Gln Ser Tyr Ser Thr Pro Trp Thr
 1               5
```

<210> SEQ ID NO 125
<211> LENGTH: 11
<212> TYPE: PRT
<213> ORGANISM: Streptococcus pneumoniae

<400> SEQUENCE: 125

```
Ala Arg Ala Ser Arg Glu Thr Gly Glu Pro Tyr
 1               5                  10
```

<210> SEQ ID NO 126
<211> LENGTH: 9
<212> TYPE: PRT
<213> ORGANISM: Streptococcus pneumoniae

<400> SEQUENCE: 126

Met Gln Ala Thr His Trp Pro Trp Thr
1               5

<210> SEQ ID NO 127
<211> LENGTH: 348
<212> TYPE: DNA
<213> ORGANISM: Streptococcus pneumoniae

<400> SEQUENCE: 127

```
gaggtgcagc tgttggagtc ggggggaggc ttggtacagc ctggggggtc cctgagagtc      60
tcctgtgcag cctctggatt cacctttagc aactctggca tgagttgggt ccgccaggct     120
ccagggaagg ggctggagtg ggtctcaggt attggtggtg gtggtggtag tgcatactac     180
gcagactccg tgaagggccg gttcaccatc tccagagaca attccaagaa cacgctgtat     240
ctacaaatga acaatttgag agccgaggac acggccgtat actactgtgc gaaaggagtt     300
accagttttg actactgggg ccagggaatc ctggtcaccg tctcctca                 348
```

<210> SEQ ID NO 128
<211> LENGTH: 354
<212> TYPE: DNA
<213> ORGANISM: Streptococcus pneumoniae

<400> SEQUENCE: 128

```
gaggtgcagc tggtggagtc tgggggaggc ttggtccagc ctggggggtc cctgagactc      60
tcctgtgcag cctctggatt caccgtcagt agcgactata tgagttgggt ccgccaggct     120
ccagggaagg ggctggagtg ggtctcagtt atgtatagcg ggggtagcac atactacgca     180
gacgccgtga aggacagatt caccatctcc agagacaatt ccaagaatat actgtatctt     240
caaatgaaca gcctgagagc cgaggacacg gcggtttatt actgtgcgag agatcccggg     300
ataaggaacg gtatgggcgt ctggggccaa gggaccacgg tcaccgtctc ctca          354
```

<210> SEQ ID NO 129
<211> LENGTH: 363
<212> TYPE: DNA
<213> ORGANISM: Streptococcus pneumoniae

<400> SEQUENCE: 129

```
gaggtgcagc tgttggagtc tgggggagcc ttggtacagc cggggggtc cctgagactt       60
tcctgtgcag cctctggatt cacctttacc agctttgcca tgggctgggt ccgccaggct     120
ccagggaagg ggctggagtg ggtctcagct gtgactggca gtggttatta caaaaactat     180
gcagactccg tgaagggccg gttcaccatc tccagagaca attccgacaa tactctctat     240
ctgcaaatga acagcctgag aggcgacgac acggccctat attactgtgc gaaagcacat     300
agaggtgact ggaataactt ctttgactat tggggccagg gaaccctggt caccgtctcc     360
tca                                                                  363
```

<210> SEQ ID NO 130
<211> LENGTH: 345
<212> TYPE: DNA
<213> ORGANISM: Streptococcus pneumoniae

```
<400> SEQUENCE: 130
caggtgcagc tgcaggagtc gggcccagga ctagtgaagc cttcggagac cctgtccctc    60
acctgctctg tgtctgctga ctccttcagt ccttacaagt ggagctggat ccggcagccc   120
ccagggaagg gactggaatg gattggatat atctattcca gtgggaacac caactacaac   180
ccccccctca agagtcgagt caccatatca ctggacacgt ccaagaatca ggtctccctg   240
aggctgagct ctgtggccgc tgcggacacg gccatgtatt actgtgcgag agagtggagt   300
ggttttgatt tctggggcca aggaacaatg gtcaccgtct cttca                    345

<210> SEQ ID NO 131
<211> LENGTH: 345
<212> TYPE: DNA
<213> ORGANISM: Streptococcus pneumoniae

<400> SEQUENCE: 131
gaggtgcagc tggtggagtc tgggggaggc ttggtccagc ctgggggtc cctgagactc     60 tcctgtgcag cctctggatt cacctttact aactattgga tgagctgggt ccgccaggct   120
ccagggaagg ggctggagtg ggtggccaac ataaagcaag atggacgtga gacatactat   180
gtggactctg tgaagggccg attcaccatc tccagagaca cgccaagaa ctcagtgtct    240 ctacagatga gtagcctgag agccgaggac acggccgtgt attactgtgc gcagggcag    300 tggctggcct ccggggccca gggaaccctg gtcaccgtct cctca                    345

<210> SEQ ID NO 132
<211> LENGTH: 348
<212> TYPE: DNA
<213> ORGANISM: Streptococcus pneumoniae

<400> SEQUENCE: 132
gaggtgcagc tggtggagtc tgggggaggc ttggtccaga ttgggggtc cctgagactc     60 tcctgtgcag cctctggatt cacctttagt acctattgga tgagctgggt ccgccaggct   120
ccagggaagg ggctggagtg cgtggccagc ataaaggagg atggaagtga gagatactat   180
gtggactctg tgaagggccg attcaccatc tccagagaca cgccaagaa ctcactgcat    240 ctgcagatgg acagcctgag agccgcggac acggctgtgt atttctgtgc gagaggccgg   300
aacaacttcc gacactgggg ccagggaacc ctggtcaccg tctcctca                 348

<210> SEQ ID NO 133
<211> LENGTH: 378
<212> TYPE: DNA
<213> ORGANISM: Streptococcus pneumoniae

<400> SEQUENCE: 133
gaggtgcagc tggtggagtc tgggggaggc ttggtccagc ctgggggtc cctgagactc     60 tcctgtgcag cctctggatt cgccatcagt ggtaactaca tgagttgggt ccgccaggct   120
ccagggaagg gcctggagtg ggtctcactt atttattgga ctgatgacac agtctacgca   180
gactccgtga agggcagatt caccatctcc agggacgtct ccaagaacat ggtgcatctt   240
caaatgagca gcctgagagt cgaggacacg gctgtttatt actgtgcgag agaattaggt   300 gttttttcatt caggggggga ccagtggctg ggccctttag actgctgggg ccagggaacc   360
ctggtcaccg tctcctca                                                 378

<210> SEQ ID NO 134
```

<211> LENGTH: 360
<212> TYPE: DNA
<213> ORGANISM: Streptococcus pneumoniae

<400> SEQUENCE: 134

| | | | | | |
|---|---|---|---|---|---|
| gaggtgcagc | tggtggagtc | tggggggaggc | ttggtgcagc | cagggcagtc | cctgagactt | 60 |
| tcctgtacag | tttctggatt | cagcgtagaa | gaccatggtc | tgaactgggt | ccgccaggct | 120 |
| ccagggaagg | ggctggagtg | ggtagggttc | attagaagga | aaagttctgg | tgggacagaa | 180 |
| tacgccgcgt | ctgtgaaagg | ccgattcacc | atctcaagag | atgattccaa | gagcgccgtc | 240 |
| tatctgcaaa | tgaacagcct | gaagatgag | gacacaggcg | tatattattg | tcttcgctgg | 300 |
| acgggtggag | tgagttttgg | tgcctactgg | ggccaggaa | ccctggtcac | cgtctcctca | 360 |

<210> SEQ ID NO 135
<211> LENGTH: 348
<212> TYPE: DNA
<213> ORGANISM: Streptococcus pneumoniae

<400> SEQUENCE: 135

| | | | | | |
|---|---|---|---|---|---|
| gaggtgcagc | tggtggagtc | cgggggaggc | ttagttcagc | ctgggggtc | cctgagactc | 60 |
| tcctgtgcag | cctctggatt | caccttcact | agctggatgc | actgggtccg | ccaagctcca | 120 |
| gggaagggc | tggtgtgggt | ctcacatatt | aatactgatg | ggagtagcac | aagctacgcg | 180 |
| gactccgtga | agggccgatt | caccatctcc | agagacaacg | ccaagaacac | gctgtatctg | 240 |
| caaatgaaca | gtctgagagc | cgaggacacg | gctgtgtatt | actgtgcaag | agattattac | 300 |
| cactccgttg | actactgggg | ccagggaacc | ctggtcaccg | tctcctca | | 348 |

<210> SEQ ID NO 136
<211> LENGTH: 351
<212> TYPE: DNA
<213> ORGANISM: Streptococcus pneumoniae

<400> SEQUENCE: 136

| | | | | | |
|---|---|---|---|---|---|
| caggtgcagc | tgcaggagtc | gggcccagga | atggtgaagc | cttcggagac | cctgtccctc | 60 |
| atctgcagtg | tctctggtgc | ctccgtcagt | cgtgaccact | ggagctggat | ccgccagtcc | 120 |
| ccagggaagg | gactggagtg | gattgtctat | atatataaca | gtgagagcat | cgaatacaat | 180 |
| ccctccctca | agagtcgagt | caccatatcc | gtagacacgt | ccaagaacca | ggtctccctg | 240 |
| acagtgactt | ctgtgaccgc | tgcagacacg | gccttctatt | actgtgcgcg | agggccagat | 300 |
| gcccacaaaa | ctggctactg | ggcccggga | accctggtca | ccgtctcctc | a | 351 |

<210> SEQ ID NO 137
<211> LENGTH: 351
<212> TYPE: DNA
<213> ORGANISM: Streptococcus pneumoniae

<400> SEQUENCE: 137

| | | | | | |
|---|---|---|---|---|---|
| gaggtgcagc | tggtggagtc | cggggagggc | ttagttcagc | ctgggggtc | gctgagactc | 60 |
| tcctgcgcag | cctctggatt | caccttcagt | aacttctgga | tgtactgggt | ccgccaagtt | 120 |
| ccagggaagg | ggctggtgtg | cgtctcacgt | attaatagag | atgggagtat | cacattgtac | 180 |
| gcggactccg | tgagggggccg | attcaccatc | tccagagaca | acgccaagaa | cacgctgtat | 240 |
| ctgcaaatga | acagtctgag | agtcgaggac | acggctgtgt | attactgtgc | aagagattcc | 300 |
| tataccagcc | ctgactactg | gggccagggg | accctggtca | ccgtctcctc | a | 351 |

-continued

```
<210> SEQ ID NO 138
<211> LENGTH: 360
<212> TYPE: DNA
<213> ORGANISM: Streptococcus pneumoniae

<400> SEQUENCE: 138
gaggtgcagc tggtggagtc tgggggaggc ttggtaaagc cggggagtc ccttagactc      60 tcctgtgcga cctcaggatt aactttcagt aacgtatgga tgagctgggt ccgccaggct    120
ccagggaagg ggctggagtg ggttgggcgt cttaaaaaca agcctgatgg tggaacaaca    180
gactacgcag cacccgtgaa gggcagattc accatctcaa gagatgattc aaaaaccacg    240
ctgtatctgg aaatgaacag cctgaaagtc gaggacacag ccgtgtatta ctgtaccaca    300
gataacggag tcaaggcttt tgatatctgg ggccaaggga caatggtcac cgtctcttca    360

<210> SEQ ID NO 139
<211> LENGTH: 354
<212> TYPE: DNA
<213> ORGANISM: Streptococcus pneumoniae

<400> SEQUENCE: 139
gaggtgcagc tggtggagtc cggggggaggc ttagttcagc ctgggggtc cctgagactc     60 tcctgtgcag cctctggatt caccttcagt acctactgga tgcactgggt ccgccaaact    120
ccggagaagg ggctggtatg ggtctcacgt attcatcctg atgggagtaa cacagcctac    180
gcggactccg tgaagggccg attcaccatc tccagagaca acgccaagaa cacgctgtat    240
ctgcaaatga atagtctgag agtcgaggac acggcttttt attattgtac aagaggggt    300 tccggggcta cgatcaatta ctggggccag ggaatcctgg tcaccgtctc ctca          354

<210> SEQ ID NO 140
<211> LENGTH: 372
<212> TYPE: DNA
<213> ORGANISM: Streptococcus pneumoniae

<400> SEQUENCE: 140
caggtgcagc tgcaggagtc gggcccaggg ctggtgaagc cttcacagac cctgtccctc     60
acctgcactg tctctggtgg ctccatcagc ggtggtactt actcctggac ctggatccgg    120
cagcccgccg ggaagggact ggagtggatt gggcgtatt ttgctagtgg gagcaccaac    180
tacaattcct ccctcaagag tcgagtcacc attttagtag acacgtccaa gaacctgttc    240
tccctgagcc tgagctctgt gaccgccgca gacacggcca tgtattactg tgcgagagat    300
cgagccggta tagatggcta caattactac tttgactact ggggccaggg aaccctggtc    360
accgtctcct ca                                                         372

<210> SEQ ID NO 141
<211> LENGTH: 359
<212> TYPE: DNA
<213> ORGANISM: Streptococcus pneumoniae

<400> SEQUENCE: 141
aggtgcagct ggtgcagtct ggggctgagg tgaagaagcc tggggcctca gtgaaggttt     60
cctgcaagac atctggatac acccctcacca gttactatat gcactgggtg cgacaggccc   120
ctggacaagg gcttgagtgg ctgggagtga tcaggcctac ggacgctagc acaaggtccg    180
cacagaagtt ccagggcaga atcaccatga ccagggacac gtccacgagc acactctaca    240
tggagctgag tagcctgaga tctgaagaca cggccgtgta ctattgtgcg agagaagtgg    300
```
cagcagaagg taaagctttc gactactggg gccagggaac cctggtcacc gtctcctca    359

<210> SEQ ID NO 142
<211> LENGTH: 348
<212> TYPE: DNA
<213> ORGANISM: Streptococcus pneumoniae

<400> SEQUENCE: 142
gaggtgcagc tggtggagtc tgggggaggc ttggtccagc ctgggggtc cctgagactc     60 tcctgtgcag cctctggatt cacctttagt agctattgga tgagctgggt ccgccaggct    120
ccagggaagg gactggagtg ggtgggcaaa ataaaggaag acggaagtga aaatactat     180 gtggactctg tgaagggccg attcgccatc tccagagaca cgccaagaa ctccctgtct    240 ctgcaaatga acagcctgag agccgaggac acggccgtgt attactgtgc gagaggtcaa    300
tcatatccgg gaatttgggg ccaagggaca atggtcaccg tctcttca                 348

<210> SEQ ID NO 143
<211> LENGTH: 363
<212> TYPE: DNA
<213> ORGANISM: Streptococcus pneumoniae

<400> SEQUENCE: 143
caggtgcagc tgcaggagtc gggcccagga ctggtgaagc cttcggagac cctgtccctc     60
acctgcactg tctctggtgg ctccatcact aattactact ggggctggat ccggcagccc    120
ccaggggagg gactggagtg gattggctat atctattaca gtggaagcac caactacaac    180
ccctccctca agagtcgagt caccatatca gtagacacgt ccaagaacca gttctcccta    240
aagctgacct ctgtaaccgc cgcagacacg gccgtgtatt actgtgcggg tcgggcttac    300
agtagtggtt actactacct aattgactac tggggccagg gaaccctggt caccgtctcc    360
tca                                                                  363

<210> SEQ ID NO 144
<211> LENGTH: 321
<212> TYPE: DNA
<213> ORGANISM: Streptococcus pneumoniae

<400> SEQUENCE: 144
gaaattgtgt tgacgcagtc tccaggcacc ctgtctttgt ctccagggga aagagccacc     60
ctctcctgca gggccagtca gagtgttacc tacttagcct ggtaccagca gaaacctggc    120
caggctccca ggctcctctt ctatggtaca tccagcaggg ccactggcat cccagacagg    180
ttcagtggca gtgggtctgg gacagacttc actctcacca tcagcagagt ggagcctgaa    240
gattttgcag tgtattactg tcagcagttt ggcagctcac ctccggacac tttcggcgga    300
gggaccaagg tggaaatcaa a                                              321

<210> SEQ ID NO 145
<211> LENGTH: 332
<212> TYPE: DNA
<213> ORGANISM: Streptococcus pneumoniae

<400> SEQUENCE: 145
ttgtgatgac tcagtctcca ctctccctgc ccgtcaccct tggacagccg gcctccatct     60
cctgcagggc tagtcaaggc ctcgaacaca gtgatggaaa cacctacttg agttggtttc    120
agcagaggcc aggccgatct ccccggcgcc taatttataa ggtttctaac cgggactctg    180
ggtcccgaga cagattcagt ggcagtgggt caggcactga tttcacactg aaatcacca    240

```
gggtggaggc tgaggatgtt ggagtttatt actgcatgca agttacacac tggccgagga    300
cgttcggcca agggaccaag gtggaaatca aa                                  332
```

<210> SEQ ID NO 146
<211> LENGTH: 321
<212> TYPE: DNA
<213> ORGANISM: Streptococcus pneumoniae

<400> SEQUENCE: 146

```
gaaattgtgt tgacacagtc tccaggcacc ctgtcgttgt ctccagggga aagagccacc    60
ctctcctgca gggccagtca gagtattagt ccccacttgg cctggtacca acagaaacct    120
ggccagtctc ccaggctcct catatatgat gcatccaaca gggccactgg catcccagcc    180
aggttcagtg gcagtgagtc tgggacagac ttcactctca gcatcagcag cctagagcct    240
gaagattttg cagtttatta ctgtcagcag agtggcgact ggcctctcac tttcggcgga    300
gggaccaagg tggagatcaa a                                              321
```

<210> SEQ ID NO 147
<211> LENGTH: 324
<212> TYPE: DNA
<213> ORGANISM: Streptococcus pneumoniae

<400> SEQUENCE: 147

```
gaaattgtgt tgacgcagtc tccaggcacc ctgtctttgt ctccagggga aagagccacc    60
ctctcctgca gggccagtca gagtgtttac agcatctact cgcctggta ccagcagaaa     120 cccggccagg ctcccaggcc cctcatttat ggtgtctcca cagggccac tggcatccca     180 gacaggttca gtggcagtgg gtctgggaca gacttcactc tcaccatcag cagactggag    240
ccagaagatt ttgcagtgta ttactgtcag cagtatggta gtttacctcg gacgttcggc    300
caagggacca ggtggaaat caaa                                            324
```

<210> SEQ ID NO 148
<211> LENGTH: 332
<212> TYPE: DNA
<213> ORGANISM: Streptococcus pneumoniae

<400> SEQUENCE: 148

```
ttgtgatgac tcagtctcca ctctccctgc ccgtcaccct tggacagccg gcctccatct    60
cctgcaggtc tagtcgaagc ctcgtataca gtgatggagg cacctacttg aattggtttc    120
agcagaggcc aggccaatct ccaaggcgcc taatttggca cgtttctaac cgggactctg    180
gggtcccaga cagattcagc ggcagtgggt caggcactga tttcacactg aaaatcagca    240
gggtggaggc tgaggatgtt ggggtttatt actgcatgca agtacacac tggccttaca     300 cttttggcca ggggaccaag gtggaaatca aa                                  332
```

<210> SEQ ID NO 149
<211> LENGTH: 321
<212> TYPE: DNA
<213> ORGANISM: Streptococcus pneumoniae

<400> SEQUENCE: 149

```
gacatccaga tgacccagtc tccatcttcc ctgtctgcat ctgtaggaga cagagtcacc    60
atcacttgcc aggcgagtca ggacattagg aagcttttaa attggtatca gcagagacca    120
gggaaagccc ctaacctcct gatctacgat gcatccaatt tggaaacagg ggtcccatca    180
```

```
aggttcagtg aagtggatc tgggacacat tttagtttca ccatcaccag cctgcagcct      240
gaagatattg caacatatta ctgtcaacag tttgaaagtt tccctcgcac cttcggccct      300
gggaccaaag tggatatcaa a                                                321

<210> SEQ ID NO 150
<211> LENGTH: 327
<212> TYPE: DNA
<213> ORGANISM: Streptococcus pneumoniae

<400> SEQUENCE: 150
gaaatagtga tgacgcagtc tccagccacc ctgtctgtgt ctccagggga aacagccacc       60
ctctcctgca gggccagtca gagtgttaac agcttcttag cctggtacca gcagaaacct      120
ggccaggctc ccaggctcct catctatgct gcatccacca gggccactgg tgtcccagcc      180
aggttcagtg gcagtgggtc tgggacagag ttcactctca ccatcagcag cctgcagtct      240
gaagattttg cagtttacta ctgtcaccag tataaaaact ggcctccgat gggcactttc      300
ggccctggga ccaaagtgga tatcaaa                                           327

<210> SEQ ID NO 151
<211> LENGTH: 318
<212> TYPE: DNA
<213> ORGANISM: Streptococcus pneumoniae

<400> SEQUENCE: 151
gacatccaga tgacccagtc tccttccacc ctgtcttctt ctgtcggaga cagagtcact       60
atcacttgcc gggccagtca gaatattggt gtctccttgg cctggtatca gcagaaacca      120
gggaaagccc ctaacctcct gatctataag gcgtcttatt tagaaacggg ggtcccatca      180
aggttcagcg gcagtggatc tgggacagaa ttcactctca ccatcagcag cctacagcct      240
gatgattttg caacttatta ttgccaacag tatgatattt atttgacatt cggccaaggg      300
accaaggtgg aaatcaaa                                                     318

<210> SEQ ID NO 152
<211> LENGTH: 332
<212> TYPE: DNA
<213> ORGANISM: Streptococcus pneumoniae

<400> SEQUENCE: 152
ttgtgatgac tcagtctcca ctctccctgc ccgtcaccct tggacagccg gcctccatct       60
cctgcaggtc tagtcaaagt ctcgcacaca gtgatggaaa tacctacttg aattggtttc      120
agcagaggcc aggccaatct ccaaggcgcc taatttataa ggtttctaac cgggactctg      180
ggtcccagaa cagattcagc ggcagtgggt caggcactga tttcacactg aaaatcagca      240
gggtggaggc tgaggatgtt ggggtttatt actgcatgca aggtacacac tggccgtaca      300
cttttggcca ggggaccaag gtggaaatca aa                                    332

<210> SEQ ID NO 153
<211> LENGTH: 339
<212> TYPE: DNA
<213> ORGANISM: Streptococcus pneumoniae

<400> SEQUENCE: 153
gacatcgtga tgacccagtc tccagactcc ctggctgtgt ctctgggcga gagggccacc       60
atcaactgca agtccagcca gagtgtttta tacagcccca caataagaa ttacttagct      120 tggttccagc agaagccagg acagcctcct aaattactca tttactgggc atctatccgg      180
```

```
gactccgggg tccctgaccg attcagtggc agcgggtctg ggacagattt cactctcacc    240
gtcagcagtc tgcaggctga cgatgtggca gtttattact gtcagcaata tgctgctact    300
ccgtggacgt tcggccaagg gaccaaggtg aaatcaaa                            339
```

<210> SEQ ID NO 154
<211> LENGTH: 332
<212> TYPE: DNA
<213> ORGANISM: Streptococcus pneumoniae

<400> SEQUENCE: 154

```
ttgtgatgac tcagtctcca ctctccctgc ccgtcaccct ggacagccg gcctccatct     60 cctgcagttc tagtcaaagc ctcgtataca gtgatggaaa cacctacttg agttggtttc    120
agcagaggcc aggccaatct ccccggcgcc taatttataa ggtttctaac cgggactctg    180
gggtcccaga cagattcagc ggcagtgggt caggcactga tttcacactg agaatcagca    240
gggtggaggc tgaggatgtt gggtttatt actgcatgca aggttcacac tggccgctca    300
ctttcggcgg agggaccaag gtggagatca aa                                  332
```

<210> SEQ ID NO 155
<211> LENGTH: 339
<212> TYPE: DNA
<213> ORGANISM: Streptococcus pneumoniae

<400> SEQUENCE: 155

```
gacatcgtga tgacccagtc tccagactcc ctggctgtgt ctctgggcga gagggccacc    60
atcaactgca agtccagcct gagtgtttta tccagctcca ataatgagaa ctacttagct    120
tggtaccagc agaaaccagg acagcctcct aagctgctca tttactgggc atctacccgg    180
ggatccgggg tccctggccg attcagtggc agcgggtctg ggacagattt cactctcacc    240
atcagcagcc tgcaggctga agatgtggca gtttattact gtcaccaata ttatactact    300
cccttcgctt tcggccctgg gaccaaagtg gatatcaaa                           339
```

<210> SEQ ID NO 156
<211> LENGTH: 321
<212> TYPE: DNA
<213> ORGANISM: Streptococcus pneumoniae

<400> SEQUENCE: 156

```
gacatccaga tgacccagtc tccgtcctcc ctgtctgcat ctgtgggaga cagtgtcacc    60
atcacttgcc gggcaagtca gagcattagc agctatttaa attggtatca ccaaaaacca    120
gggaaagccc ctaaactcct gatctatggt gcatccactt gcaaagtgg gtcccatca     180 aggttcggtg gcagtggatc tgggacagat ttcactctca ccatcagcag tctgcaacct    240
gacgattttg caacttacta ctgtcaacag agtcacagtt cccctctcac tttcggcgga    300
gggaccaagg tggagatcaa a                                              321
```

<210> SEQ ID NO 157
<211> LENGTH: 318
<212> TYPE: DNA
<213> ORGANISM: Streptococcus pneumoniae

<400> SEQUENCE: 157

```
gacatccaga tgacccagtc tccttccacc ctgtctgcct ctgtaggaga cagagtcacc    60
atcacttgtc gggccagtcg gagtcttggt agctggttgg cctggtatca gcagagccca    120
```

```
gggaaagccc ctaagctcct gatctataag gcgtctactt tagaaagtgg ggtcccatca    180
cggttcagcg gcagtggatc tgggacagaa ttcactctca ccatcagcag cctgcagcct    240
gatgattttg caacttatta ctgccaacag tattatagct tctcacttt tggccagggg    300 accaaggtgg aaatcaaa                                                  318

<210> SEQ ID NO 158
<211> LENGTH: 339
<212> TYPE: DNA
<213> ORGANISM: Streptococcus pneumoniae

<400> SEQUENCE: 158
gacatcgtga tgacccagtc tgcagactcc ctggctgtgt ctctgggcga gagggccacc    60
atcaactgca agtccagcca gagtctttc tacagttcca acaagaagaa ctacttagct    120
tggtaccagc agaagccagg acagcctcct aaactgatca tttactgggc atctacccgg    180
gaatccgggg tccctgaccg attcagtggc agcgggtctg ggacagattt cactctcacc    240
atcaccagcc tgcgggctga agatgtggca gtttattact gtcagcaata ttatactcct    300
cctctcacat tcggcggagg gaccaaggtg gaaatcaaa                           339

<210> SEQ ID NO 159
<211> LENGTH: 321
<212> TYPE: DNA
<213> ORGANISM: Streptococcus pneumoniae

<400> SEQUENCE: 159
gaaatagtga tgacgcagtc tccagccacc ctgtctgtgt ctccagggga aagagccacc    60
ctctcctgca gggccagtca gagtgttagc ggcgacttag tctggtacca gcagaaacct    120
ggccaggctc ccaggctcct catctatggt gccaccacca gggcctctgg tgtcccagcc    180
aggttcagtg gcagtgggtc tgggacagag ttcactctca ccatcagcag cctgcagtct    240
gaagattttg caatttatta ctgtcagcag tataataact ggccccggac gttcggccaa    300
gggaccaagg tggaaatcaa a                                              321

<210> SEQ ID NO 160
<211> LENGTH: 321
<212> TYPE: DNA
<213> ORGANISM: Streptococcus pneumoniae

<400> SEQUENCE: 160
gaaatagtga tgacgcagtc tccagccacc ctgtctgtgt ctccagggga aagagccacc    60
ctctcctgca gggccagtca gagtgttggc aacaacttag cctggtttca gcagaaacct    120
ggccaggctc ccaggctcct catctatggt gcatccacca gggccactgg tatcccagcc    180
aggttcagtg gcagtgggtc tgggacagag ttcactctca ccatcagcag cctgcagtct    240
gaagattttg cagtttatca ctgtcaacac tatcataact ggcctccac ttttggccag    300 gggaccaagg tggaaatcaa a                                              321

<210> SEQ ID NO 161
<211> LENGTH: 366
<212> TYPE: DNA
<213> ORGANISM: Streptococcus pneumoniae

<400> SEQUENCE: 161
caggtgcagc tggtggagtc tgggggaggc gtggtccagc ctgggaggtc cctgagactc    60
tcctgtgcag cctctggatt caccttcagc aaccatggca tgcactggct ccgccagact    120
```

```
ccaggcaagg ggctggagtg ggtggcagtc atttcatatg atggaagtac caaatactat    180
gcagactccg tgaagggccg atgcaccctc tccagagaca attccaagga aacggtgttt    240
ctgcaaatga acagcctgag acctgaggac acggctgtgt attattgtgc gaaagggtgt    300
tctaatggtg gtaactgctt tttgattgac tactggggcc cgggaaccct ggtcaccgtc    360
tcctca                                                               366
```

<210> SEQ ID NO 162
<211> LENGTH: 369
<212> TYPE: DNA
<213> ORGANISM: Streptococcus pneumoniae

<400> SEQUENCE: 162

```
gaggtgcagc tgttggagtc ggggggagac ttggtgcagc ctggggggtc cctgagactc     60
tcctgtgcag cctctggatt cgacttcagt atttatggca tgaactgggt ccgccaggct    120
ccagggaagg ggcttgaatg ggtctcagtt attagtggtg atggcactat catatactac    180
gcagactccg tgaagggccg gttcactatc tccagagaca attccaagaa cacactgttt    240
ttgcaagtga acagcgtgag agccgaggac acggccgtat attactgtgc gaaggggggc    300
tactatgaat cggggactat gcgggctttt gatatctggg gccaagggac aatggtcacc    360
gtctcttca                                                           369
```

<210> SEQ ID NO 163
<211> LENGTH: 351
<212> TYPE: DNA
<213> ORGANISM: Streptococcus pneumoniae

<400> SEQUENCE: 163

```
gaggtgcagc tggtggagga gtctggggga ggcttggtcc agcctggggg gtccctgaga     60
ctctcctgtg cagcctctgg atacaccttt agtagttatt caatgagttg ggtccgccag    120
gctccaggga aggggctgga gtgggtggcc agcattaagc agaaggaagt gagaaattc     180 tatgtggact ctgtgaaggg ccgattcact atctccagag acaacgccaa gaactcactg    240
tatctgcaaa tgaacagcct gagaggcgag gacacggctg tctactactg tgcgagaggg    300
gaatctaatt tccgatactg gcaccaggga accctggtca ccgtctcctc a             351
```

<210> SEQ ID NO 164
<211> LENGTH: 357
<212> TYPE: DNA
<213> ORGANISM: Streptococcus pneumoniae

<400> SEQUENCE: 164

```
gaggtgcagc tggtggagtc tgggggagcc ttggtccagc ctggggggtc cctgagactc     60
tcctgtgcag cctctggatt catcttcagt aactcttgga tgggctggtt ccgccaggct    120
ccagggaagc ggccggagtt cgtggccaac ataaaaccag atggaagtga aaattccat     180 gtggactctg tgaagggccg attcaccatc tccagagaca cgccgagaa ctcactgtat    240 ctgctgatga acagcctgag agccgaggac acggctgtct attactgcgc gagagatagc    300
acttccccgg cccgttttgg gtactggggc agggaaccc tggtcaccgt ctcctca       357
```

<210> SEQ ID NO 165
<211> LENGTH: 354
<212> TYPE: DNA
<213> ORGANISM: Streptococcus pneumoniae

<400> SEQUENCE: 165

```
gaggtgcagc tggtggagac tggaggaggc ttgatccagc ctggggggtc cctgaggctc    60
tcctgtgcag cctctgggtt aaacgtcaat agttactaca tgaactgggt ccgccaggct   120
ccagggaagg ggctggagtg ggtctcagtt atttatagcg gtggtggcac aaactacgca   180
gactccgtga ggggccgatt catcatctcc agagacaatt ccaggaacgc gctttatctt   240
caaatgaaca gcctgagagc cgaggacacg gccgtgtatt actgtgcgac gggcgggatg   300
accagtagtt ggtacggcta ctggggccag ggaaccctgg tcaccgtctc ctca          354
```

<210> SEQ ID NO 166
<211> LENGTH: 374
<212> TYPE: DNA
<213> ORGANISM: Streptococcus pneumoniae

<400> SEQUENCE: 166

```
aggtgcagct ggtgcagtct ggggccgagg tgaagaagcc tggggcctca gtgaaggttt    60
cctgcaaggc atctgaatac actttcatca actaccttgt gttctgggtg cgacaggccc   120
ctggacaagg gcttgagtgg atgggagaaa tgaaccccac tcgtgggagc acaagctacg   180
cacagaagtt ccagggcaga gtcaccatga ccagggacac gtccacgagc acagtctaca   240
tggagttgag cagcctgaga tctgacgaca cggccgttta ttactgctcc atgggtccgc   300
cctattgtac tggtggaagc tgttactccg cctgtgattt ctggggccgg gaaccctgg    360
tcaccgtctc ctca                                                     374
```

<210> SEQ ID NO 167
<211> LENGTH: 372
<212> TYPE: DNA
<213> ORGANISM: Streptococcus pneumoniae

<400> SEQUENCE: 167

```
gaggtgcagc tggtggagtc tgggggaggc ttgatgaaac ctggggggtc ccttagactc    60
tcctgtgcag tctctgggtt cactttcact aacgcctggc tgagctgggt ccgccagcct   120
ccagggaagg ggctggagtg ggttggccgt gcttacagca gttctggcgg ttggacaatg   180
gactactctt cacccgtgag gggcagattc accatcacaa gagacgattc aaaaaacaca   240
ctgtatctgc aaatgaacaa cctgaaaacc gaggacacag ccgtgtatta ctgtaccaca   300
gatattggca aaggctggta cacgcactat cctgacctct ggggccaggg aaccctggtc   360
accgtctcct ca                                                       372
```

<210> SEQ ID NO 168
<211> LENGTH: 363
<212> TYPE: DNA
<213> ORGANISM: Streptococcus pneumoniae

<400> SEQUENCE: 168

```
caggtgcagc tggtggagtc tggggagcc gtggtccagc ctgggaagtc cctcagactc    60
tcctgtgtag cctctggatt caccttaagt acctgtggca tgcactgggt ccgccaggct   120
ccaggcaagg ggctggagtg ggtggcagtt acaacatatg atggagatcg taaatataat   180
gtagactccg tgaagggccg attcaccatc tccagagaca attccaagaa cacggtgtat   240
ctgcaaatgg acggcctcaa agccgaggac acggctgtgt atcactgtgt gaaagaatat   300
agttgggggtt actacagaac tgcggactac tggggccagg gaaccctggt caccgtctcc   360
tca                                                                 363
```

<210> SEQ ID NO 169
<211> LENGTH: 351
<212> TYPE: DNA
<213> ORGANISM: Streptococcus pneumoniae

<400> SEQUENCE: 169

| | | |
|---|---|---|
| gaggtgcagc tggtggagtc cggggggaggc ttagttcagc cggggggtc cctgagactc | 60 |
| tcctgtgtag cctctggatt caccttcagt acttactgga tgcactgggt ccgccaacct | 120 |
| ccggggaagg ggctggtgtg ggtctcacgt attaatcctg atggcagtag cacaaactac | 180 |
| gcggactccg tgaacggccg attcaccatc tccagagaca acgccaagaa cacgctgtat | 240 |
| cttgaaatga acagtttgag agtcgaggac acagctctct attactgtgc aagaagtcct | 300 |
| gggggttact ttgactactg gggccacagc accctggtca ccgtctcctc a | 351 |

<210> SEQ ID NO 170
<211> LENGTH: 348
<212> TYPE: DNA
<213> ORGANISM: Streptococcus pneumoniae

<400> SEQUENCE: 170

| | | |
|---|---|---|
| gaggtgcagc tggtggagtc tggggggaggc ttggtgaagc ctggggggtc ccttacactc | 60 |
| tcctgtgcag tctctggatt cactttcagt accggctgga tgagctgggt ccgccaggct | 120 |
| ccagggaagg ggctggactg ggttggccgt attaaaagca aaactgctgg tgggacaaca | 180 |
| gactatgctg cacccgtgaa agacagattc accatctcaa gagatgattc aaaaaacacg | 240 |
| ctgtatctgc aactgagcag ccttaaaacc gaggacacag ccgtgtatta ctgtaccaca | 300 |
| gatgacctga aaaactgggg ccagggaacc ctggtcaccg tctcctca | 348 |

<210> SEQ ID NO 171
<211> LENGTH: 387
<212> TYPE: DNA
<213> ORGANISM: Streptococcus pneumoniae

<400> SEQUENCE: 171

| | | |
|---|---|---|
| gaggtgcagc tggtggagtc tggggggaggc ttggtgcagc cggggggtc cctgagactc | 60 |
| tcctgtgcag cctctggatt caccttcagt agttatagca tgaactgggt ccgccaggtc | 120 |
| ccgggaaagg ggctggagtg ggtctcatac acaagtacta aaagtgatat caaatactac | 180 |
| gcggactctg tggaaggccg attcaccatt tccagagaca atgccaagaa ctcattgtat | 240 |
| ctgcaaatga acagcctgag agacgaagac acggctgtct attattgtgc gagaggacga | 300 |
| gattgttatg ggggtaactg cgtcatctac ttccactact acggtttgga cgtctggggc | 360 |
| caagggacca cggtcaccgt ctcctca | 387 |

<210> SEQ ID NO 172
<211> LENGTH: 369
<212> TYPE: DNA
<213> ORGANISM: Streptococcus pneumoniae

<400> SEQUENCE: 172

| | | |
|---|---|---|
| caggtgcagc tggtggagtc tggggggaggc gtggtccagc ctggggggtc cctgagactc | 60 |
| tcctgtgtag tctctggatt caccctcagt tcctgtggca tgcattgggt ccgccagtct | 120 |
| ccaggcaagg ggctggagtg gctgtcagtt agcacctatg atggagatgg caatcagaaa | 180 |
| tactatgcgg cctccgtgaa gggccgattc ctcatctcca gagacacttc gaagaacacg | 240 |

| | |
|---|---|
| gtgtatctcc atatgaacag cctgacagct gaggacacgg ctctatatta ttgtgtgaaa | 300 |
| gagagtgcca ctggctggta tcgcaccgct gattactggg gccagggaac cctggtcacc | 360 |
| gtctcctca | 369 |

<210> SEQ ID NO 173
<211> LENGTH: 366
<212> TYPE: DNA
<213> ORGANISM: Streptococcus pneumoniae

<400> SEQUENCE: 173

| | |
|---|---|
| gaggtgcagc tggtggagtc tgggggaggc ttggtccagc ctgggggtc cttgagactc | 60 |
| tcctgtgcag cctctggatt caccgtcagt agcatattca tgagctgggt ccgccaggct | 120 |
| ccagggcagg gctggagtg gtctcagtc atctataccg atggaaaaac atattatgca | 180 |
| cactccgtgg agggccgatt caccatctcc agagacgatt ccaagaatat ggtgtatctt | 240 |
| caattgagca gcctgagaac tgaggacacg gctgtttatt actgtgcgag agatattcca | 300 |
| acgacatttg aataggtga agcttttgat atctggggcc aggggacaat ggtcaccgtc | 360 |
| tcttca | 366 |

<210> SEQ ID NO 174
<211> LENGTH: 347
<212> TYPE: DNA
<213> ORGANISM: Streptococcus pneumoniae

<400> SEQUENCE: 174

| | |
|---|---|
| aggtgcagct ggtgcagtct ggggctgagg tgaagaagcc tggggcctca gtgaagcttt | 60 |
| cctgcaagac atctggatac tccttcacca gcaactattt gcactgggtg cgacaggccc | 120 |
| ctggacaagg acttgagtgg atgggaatgg tctacccaaa tgatggtact acaacctacg | 180 |
| ctcagaagtt tcagggcaga gtcaccatga ccagtgagac gtccacaacc acaatctaca | 240 |
| tggacctgag cggcctgaca tctgaggaca cggccatata ttactgtgct agagacgatt | 300 |
| cggcctttga ctactggggc cagggaaccc tggtcaccgt ctcctca | 347 |

<210> SEQ ID NO 175
<211> LENGTH: 363
<212> TYPE: DNA
<213> ORGANISM: Streptococcus pneumoniae

<400> SEQUENCE: 175

| | |
|---|---|
| caggtgcagc tggtggagtc tgggggaggc gtggtccagc ctggggagtc cctgagactc | 60 |
| tcctgtgaag cctctggatt catcttcagt agcaatggca tgcactgggt ccgccaggct | 120 |
| ccaggcaagg gctggagtg gtggcagtt atatcatctg atggaagtag gagatactat | 180 |
| gcagactcaa tgaagggccg attcaccatc tccagagaca actccaagaa cacgctgtat | 240 |
| ctgcaattga acagcctgag agctgacgac acggctgtct attactgtgc gaaaggctgt | 300 |
| agtggtgaaa attgcttcta tatggacgac tggggcaaag gaccacggt caccgtctcc | 360 |
| tca | 363 |

<210> SEQ ID NO 176
<211> LENGTH: 386
<212> TYPE: DNA
<213> ORGANISM: Streptococcus pneumoniae

<400> SEQUENCE: 176

| | |
|---|---|
| aggtgcagct ggtgcagtct ggggctgagg tgaagaagcc tggggcctca ctgaaggtct | 60 |

```
cctgcaaggc atctggatac accttcagac agaactattt ccactgggtg cgacaggccc    120
ctggacaagg gcttgagtgg atgggagtaa tcaacccgag tgatggtagt acaaagttcg    180
cacagaagtt ccagggcaga gtcagcatga ccagggacac gtccacgagc acagtttaca    240
tggacctgag cagtctgaca tctgaggaca cggccgtcta ttattgtacg agagagatcg    300
gcgcagtggt agtagatgct acgtcgttgg ggtggttggg ctactttgac tactggggcc    360
agggaaccct ggtcaccgtc tcctca                                         386

<210> SEQ ID NO 177
<211> LENGTH: 345
<212> TYPE: DNA
<213> ORGANISM: Streptococcus pneumoniae

<400> SEQUENCE: 177
gaggtgcagc tggtggagtc tgggggaggc ttggtccagc cggggggttc cctgagtctc     60
tcctgtgaag cctctggatt aaccttcagt ggctactgga tgaactgggt ccgccaggct    120
ccagggaagg ggctggagtg ggtggccaac ataaatccag aaggaagtga gaggagatac    180
gtggagtctg tgcagggccg attcaccgtc tccagagaca cccgaagaa caccctgtat     240 ttgcaaatga acagcctgag agtcgaggac acggctctgt attactgtgc gggctggggg    300
agaacccagg actggggcca gggagccctg gtcaccgtct cctca                   345

<210> SEQ ID NO 178
<211> LENGTH: 363
<212> TYPE: DNA
<213> ORGANISM: Streptococcus pneumoniae

<400> SEQUENCE: 178
caggtgcagc tggtggagtc tgggggaggc gtggtccagc ctgggaggtc cctgagactc     60
tcctgtgcag cctctggact caccttcagc aattatggca tgcactgggt ccgccaggct    120
ccagggaagg ggctggagtg ggttgcagtt gtgtcggcaa ggggaggaac tacatattat    180
gcagactccg tgaagggccg attcaccatc tccagagaca attccaagaa cacgatgtct    240
ctgcaaatga acggcctgag acctgacgac acggctgtgt attttttgtac gaaagaagga    300 gcaccacctg gaaaatatgc ttttgatatc tggggccaag ggacaatggt caccgtctct    360
tca                                                                   363

<210> SEQ ID NO 179
<211> LENGTH: 360
<212> TYPE: DNA
<213> ORGANISM: Streptococcus pneumoniae

<400> SEQUENCE: 179
gaggtgcagc tggtggagtc tgggggaggc ttggtccagc ctggaggatc cctgagactc     60
tcctgcgcag cctccggatt caccttcagt gactaccgca tggactgggt ccgccaggct    120
ccagggaggg ggctggagtg gattgcccgt attagacaca gagatgcagg ctatagcaca    180
gaatacgccg cgtctgtgag gggcagattc accgtctcaa gagatgactc acagagtaca    240
ctgtacctgc agatgaacag cttgaaagcc gacgacacgg ccgtgtatat ttgtcttaaa    300
gattcttcgc aatactcttt tgatgcgtgg ggccaaggga caatggtcac cgtctcttca    360

<210> SEQ ID NO 180
<211> LENGTH: 339
<212> TYPE: DNA
```

<213> ORGANISM: Streptococcus pneumoniae

<400> SEQUENCE: 180

| gacatcgtga tgacccagtc tccagactcc ctggctgtgt ctctgggcga gagggccacc | 60 |
| atcaactgca agtccagtca gagtatttta tccagatcca acaataagaa ctacttagcc | 120 |
| tggtaccagc agaaaccagg acagcctcct aaattgctcc tttattgggc atctacccgg | 180 |
| gaatccgggg tccctgaccg attcagtgtc agcgggtctg ggtcagattt cactctcacc | 240 |
| atcagtagcc tgcaggctga ggatgtggca gtttattact gtcagcagta ttataatgct | 300 |
| cccctcactt tcggcggagg gaccaaggtg gagatcaaa | 339 |

<210> SEQ ID NO 181
<211> LENGTH: 321
<212> TYPE: DNA
<213> ORGANISM: Streptococcus pneumoniae

<400> SEQUENCE: 181

| gaaattgtgt tgacacagtc tccagccacc ctgtctttgt ctccagggga aagggccacc | 60 |
| ctctcctgca gggccagtca gactgttagc aggtacttag cctggtacca acaaaagcct | 120 |
| ggccaggctc ccaggctcct catctatgct gcatccaaca gggccactgg catcccaacc | 180 |
| aggttcagtg gcagtgggtc tgggacagac ttcactctca ccatcagcag cctagagcct | 240 |
| gaagattttg catttattta ctgtcagcag cgtagcaact ggcctgccac tttcggcgga | 300 |
| gggaccaagg tggagatcaa a | 321 |

<210> SEQ ID NO 182
<211> LENGTH: 321
<212> TYPE: DNA
<213> ORGANISM: Streptococcus pneumoniae

<400> SEQUENCE: 182

| gacatccaga tgacccagtc tccttcctcc ctgtctgcat ctgtaggaga cagtgtcacc | 60 |
| atcacttgcc aggcgagtca ggacattaga gaccgtttaa attggtatca gcagaagcca | 120 |
| gggaaagccc ctaacctcct gatctacgat gcatcaagtt tggaaacagg ggtcccatca | 180 |
| aggttcagag gaagtggatc tgggacagat tttactttca ccatcagcag cctgcagcct | 240 |
| gaagatattg caacatatta ctgtcaacag tttgttagtt ccctcgaac tttcggcccg | 300 |
| gggaccaaag tggatatcaa a | 321 |

<210> SEQ ID NO 183
<211> LENGTH: 330
<212> TYPE: DNA
<213> ORGANISM: Streptococcus pneumoniae

<400> SEQUENCE: 183

| gaaattgtgt tgacgcagtc tccaggcatc ctgtctttgt ctccagggga aagagccacc | 60 |
| ctctcctgca gggccagtca gagtgttagc agcaggtcct tgtcctggta ccagcagaga | 120 |
| cctggcctgg ctcccaggct cctcatctat gctgcatcca gcagggccgc tgtcaccccca | 180 |
| gacaggttca ctgccagcgg gtctgggaca gacttcactc tcaccatcag cagtctggag | 240 |
| cctgaagatt ttgcagtgta ttactgtcag cactatggta cctcacctcc gaggtacact | 300 |
| tttgggcagg ggaccaaggt ggagatcaaa | 330 |

<210> SEQ ID NO 184
<211> LENGTH: 339

```
<212> TYPE: DNA
<213> ORGANISM: Streptococcus pneumoniae

<400> SEQUENCE: 184
gacatcgtga tgacccagtc cccagactcc ctggctgtgt ctctgggcga gagggccacc    60
atcaactgca gtccagcca gagtgtttta cacagctcca acaataagaa ctactttgct   120
tggtaccagc agaaaccagg acagcctcct aagctgctca ttcactgggc atctacccgg   180
gcatccgggg tccctgaccg attcagtggc agcgggtctg ggacagattt cactctcacc   240
atcagcagcc tgcaggctga agatgtgaca atttattact gtcagcaata ttatagtact   300
ccgtacactt ttggccaggg gaccaaggtg gaaatcaaa                          339

<210> SEQ ID NO 185
<211> LENGTH: 327
<212> TYPE: DNA
<213> ORGANISM: Streptococcus pneumoniae

<400> SEQUENCE: 185
gaaattgtgt tgacgcagtc tccaggcacc ctgtctttgt ctccagggga aagagccacc    60
ctctcctgca gggccagtcc gagtcttgac agcgcctact tagcctggta ccagcagaag   120
cctggccagg ctcccaggct cctcatctat ggtgcatcct ccagggtcac tggcatccca   180
gataggttca gtggcagtgc gtcagggaca gacttcactc tcaccatcag cagactggag   240
cctgaagatt ttgcagtgta ctactgtcag cggtatggta actcacctcc gtacactttt   300
ggccagggga ccaaggtgga gatcaaa                                       327

<210> SEQ ID NO 186
<211> LENGTH: 339
<212> TYPE: DNA
<213> ORGANISM: Streptococcus pneumoniae

<400> SEQUENCE: 186
gacatcgtga tgacccagtc tccagactcc ctggctgtgt ctctgggcga gagggccacc    60
atcagctgca gtccagcca gagtctttta tacagttcca gcaataagaa ctacctagct   120
tggttccagc agaaaccagg acaggctcct aagttgctca tttactgggc atctacccgg   180
gaatccgggg tccctgaccg attcagtggc agcgggtctg ggacagattt cactctcacc   240
atcagcagcc tgcagactga agatgtggca gtttattatt gtctgcaata tcgtagtgct   300
ccgttcactt tcggcggagg gaccaaggtg gagatcaaa                          339

<210> SEQ ID NO 187
<211> LENGTH: 321
<212> TYPE: DNA
<213> ORGANISM: Streptococcus pneumoniae

<400> SEQUENCE: 187
gacatccaga tgacccagtc tccttccacc cagtctgcat ctgtaggaga cagagtcacc    60
atcacttgcc gggccagtca gagtattagt agttggttgg cctggtatca gcagaaacca   120
gggaaagccc ctaaggtcct gatctatgcg gtgtctagtt tagaaagtgg ggtcccatca   180
aggttcagcg gcagtggatc tgggacagaa ttcactctca ccatcagcag cctgcagcct   240
gaggattttg caacttatta ctgccaacaa tatagtactt atccctggac gttcggccca   300
gggaccaagg tggaaatcaa a                                             321

<210> SEQ ID NO 188
```

```
<211> LENGTH: 321
<212> TYPE: DNA
<213> ORGANISM: Streptococcus pneumoniae

<400> SEQUENCE: 188
gaaatagtga tgacgcagtc tccagcctcc ctgtctgtgt ctccagggga aacagccacc      60
ctctcctgca gggccagtca gagtgttggc agcacctag cctggtacca gcagaagccc     120
ggccaggctc ccaggctcct catctataat gtattcacca gggccgctgg tgtcccagcc    180
aggttcagtg gcagtgggtc taggacggag ttcactctca ccatcagcag cctgcagtct    240
gaagattttg cagtttatta ctgtcagcag tatagtacct ggctgtggac gttcggccaa    300
gggaccaagg tggaaatcaa a                                              321

<210> SEQ ID NO 189
<211> LENGTH: 321
<212> TYPE: DNA
<213> ORGANISM: Streptococcus pneumoniae

<400> SEQUENCE: 189
gacatccaga tgacccagtc tccatcctcc ctgtctgcat ctgtaggaga cagagtcacc      60
atcacttgcc gggcaagtca gcgcattagc agctacttga attggtatca gcagaaacca    120
gggaaagccc ctaacctcct gatctacgct gcagccagtt tgcatgatgg ggtcccatca    180
aggttcagtg gcagtggatc tgggacagat ttcactctca ccatcagcag tctgcaacct    240
gaagattttg caacttatta ttgtcaacag cgttacagaa tcccgtacag ttttggcccg    300
gggaccaagg tggagatcaa a                                              321

<210> SEQ ID NO 190
<211> LENGTH: 336
<212> TYPE: DNA
<213> ORGANISM: Streptococcus pneumoniae

<400> SEQUENCE: 190
gatattgtga tgactcagtc tccactctcc ctgtccgtca cccctggaga gccggcctcc      60
atctcctgca ggtctagtca gagcctcctt cagggtaatg gacacaacta tttggattgg    120
tacctgcaga agccaggaca gtctccacaa ctcctgatct atttgggttc tattcgggcc    180
tccggggtcc ctgacaggtt cagtggcagt ggatcaggca cagattttat actgaaaatc    240
agcagagtgg aggctgagga tgttggggtt tattactgca tgcgagctct acaaactccg    300
tacacttttg gccaggggac caaggtggaa atcaaa                              336

<210> SEQ ID NO 191
<211> LENGTH: 321
<212> TYPE: DNA
<213> ORGANISM: Streptococcus pneumoniae

<400> SEQUENCE: 191
gacatccaga tgacccagtc gccttccacc ctgtctgcat ctgttggaga cagagtcacc      60
ctcacttgtc gggccagtga gactcttaat aactggttgg cctggtttca gcaaaagcca    120
gggaaagccc ctaccctcct gatctatgag cgtctagtt tagaaagtgg agtcccatca    180
aggttcagcg gcagtggatc tgggacagac ttcgctctca ccatcagcag cctgcagccc    240
gatgattttg caacttatta ttgccaccag tataataaat accgtggac gttcggccaa     300 gggaccaagg tggagatcaa a                                              321
```

<210> SEQ ID NO 192
<211> LENGTH: 318
<212> TYPE: DNA
<213> ORGANISM: Streptococcus pneumoniae

<400> SEQUENCE: 192

```
gacatccaga tgacccagtc tccttccacc ttgtctgcat ctgtaggaga cagagtcacc      60
atcacttgtc gggccagtca gagtattagt ggctggttgg cctggtatca gcagaaagca     120
gggaaagccc ctaagctcct gatctataag gcgtctagtt tagaaagtgg ggtcccatca     180
aggttcagcg gcagtggatc tgggacagag ttcactctca ccatcagcag cctgcagcct     240
gatgattttg caacttatta ctgccagcag tattatagtt ggggaacgtt cggccaaggg     300
accaaggtgg agatcaaa                                                   318
```

<210> SEQ ID NO 193
<211> LENGTH: 336
<212> TYPE: DNA
<213> ORGANISM: Streptococcus pneumoniae

<400> SEQUENCE: 193

```
gatattgtga tgacccagac tccactctcc ttacctgtca cccttggaca gccggcctcc      60
atctcctgca tatctagtca agcctcgta cacagtgatg gaaacaccta cttgagttgg     120
cttcagcaga ggccaggcca gcctccaaga ctcctgattt ataagatttc taaccggttc     180
tctggggtcc cagacagatt cagtggcagt ggggcaggga cagatttcac actgaaaatc     240
agcagggtgg aagctgagga tgtcggggtt tattactgca tgcaagcttc acaatctacg     300
tggacgctcg gccaagggac caaggtggag atcaaa                              336
```

<210> SEQ ID NO 194
<211> LENGTH: 339
<212> TYPE: DNA
<213> ORGANISM: Streptococcus pneumoniae

<400> SEQUENCE: 194

```
gacatcgtga tgacccagtc tccagactcc ctggctgtgc ctctgggcga gagggccacc      60
atcaactgca cgtccagcca gactgtttta tccagttcca acaataagaa ctacttagtt     120
tggtaccagc agaaaccagg acagcctcct aagttgctcc tttactgggc gtctacccgg     180
gcatccgggg tccctgaccg attcagtggg agcgggtctg ggacagattt cactctcacc     240
attagcagtc tgcaggctga agatgtggca gtttattact gtcagcaatg ttataatgct     300
ccgctcactt tcggccgagg gaccaaggtg gagatcaaa                            339
```

<210> SEQ ID NO 195
<211> LENGTH: 324
<212> TYPE: DNA
<213> ORGANISM: Streptococcus pneumoniae

<400> SEQUENCE: 195

```
gaaatagtga tgacgcagtc tccagccacc ctgtctgtgt ttccagggga aggagtcacc      60
ctctcctgca gggccagtca gagtattagc aacaacttgg cctggtacca gcagaaacct     120
ggccaggctc ccaggctcct catgtatgat gcatccacca gggccactgg tatcccagcc     180
aggttcagtg gcagtgggtc tgggacagag ttcactctca ccatcagcag cctgcagtct     240
gaagatttcg cagtttatta ctgtcagcag tataataact ggcctccggt cacgttcggc     300
caagggacca aggtggaaat caaa                                            324
```

<210> SEQ ID NO 196
<211> LENGTH: 332
<212> TYPE: DNA
<213> ORGANISM: Streptococcus pneumoniae

<400> SEQUENCE: 196

| | | | | | |
|---|---|---|---|---|---|
| ttgtgatgac | tcagtctcca | ctctccctgc | ccgtcaccct | tggacagtcg | gcctccgtct | 60 |
| cctgcaggtc | aagtcaaagc | ctcggcccca | gtgacggaag | cacccgcttg | gattggtttc | 120 |
| aacagaggcc | aggccaatct | ccaaggcgcc | taatttatgc | ggtttctaac | cgggactctg | 180 |
| gggtcccaga | cagattcagc | ggcagcgggt | caggcagtga | tttcacactg | agaatcagca | 240 |
| gagtggaggc | tgaggatgtt | ggggtttatt | actgcatgca | atatacatac | tggcctcaca | 300 |
| cttttggcca | ggggaccaag | gtggaaatca | aa | | | 332 |

<210> SEQ ID NO 197
<211> LENGTH: 327
<212> TYPE: DNA
<213> ORGANISM: Streptococcus pneumoniae

<400> SEQUENCE: 197

| | | | | | |
|---|---|---|---|---|---|
| gaaattgtgt | tgacacagtc | tccagccacc | ctgtctttgt | ctccagggga | aagagccacc | 60 |
| ctctcctgca | gggccagtca | gagtgttagc | agttccttag | cctggtacca | acaaaaacct | 120 |
| ggccaggctc | ccaggctcct | catctatgat | gcatccaaga | gggccactga | catcccagcc | 180 |
| aggttcagtg | gcagtgggtc | tgggacagac | ttcactctca | ccatcagcag | cctagagcct | 240 |
| gaagattttg | cggtttatta | ctgtcagcac | cgggggggagt | ggcctccggg | ggccactttc | 300 |
| ggccctggga | ccaaagtgga | tatcaaa | | | | 327 |

<210> SEQ ID NO 198
<211> LENGTH: 321
<212> TYPE: DNA
<213> ORGANISM: Streptococcus pneumoniae

<400> SEQUENCE: 198

| | | | | | |
|---|---|---|---|---|---|
| gacatccagt | tgacccagtc | tccatccttc | ctgtctgcat | ctgtaggaga | cagagtcacc | 60 |
| atcacttgcc | gggccagtca | gggcattgat | actcgtttga | tctggtatca | acagaagcca | 120 |
| ggggaagccc | ctaagctcct | gatctatgaa | gcatccactt | tgcaaagtgg | ggccccatca | 180 |
| aggttcagcg | gcagtggatt | cgggacagaa | ttcactctca | caatcagcag | tctgcagcct | 240 |
| gaagactttg | caacttatta | ctgtcaacag | tttaaaggtt | acccgctcac | tttcggcggg | 300 |
| gggaccaagg | tggagatcaa | a | | | | 321 |

<210> SEQ ID NO 199
<211> LENGTH: 345
<212> TYPE: DNA
<213> ORGANISM: Streptococcus pneumoniae

<400> SEQUENCE: 199

| | | | | | |
|---|---|---|---|---|---|
| caggtgcagc | tgcaggagtc | gggcccagga | ctggtgaagc | cttcggagac | cctgtccctc | 60 |
| acctgcactg | tctctggtgg | ctccatcagt | agtcactact | ggagctggat | ccggcagccc | 120 |
| ccagcgaagg | gactggagtg | gattgggtat | atctatcaca | gtgggatgac | caactacaac | 180 |
| ccctccctca | agagtcgagt | caccatatca | atagacacgt | ccaagaacca | gttctccctg | 240 |
| aagttgagct | ctgtgaccgc | tgcggacacg | gccgtgtatt | actgtgcgag | aggtgatggc | 300 |
| tacaatttct | tctggggcca | gggaacgctg | gtcaccgtct | cctca | | 345 |

```
<210> SEQ ID NO 200
<211> LENGTH: 375
<212> TYPE: DNA
<213> ORGANISM: Streptococcus pneumoniae

<400> SEQUENCE: 200
caggtgcagc tggtggagtc tgggggaggc gtggtccagc ctgggggtc cctgagactc      60 tcctgtgcag cgtctggact cacgttcagt aaccaagatt ccactgggt ccgccaggct     120 ccaggcaagg ggctggaatg ggtggcattt atacgttatg atggaggttt taaaaactat    180
gcagactccg tgaagggccg attcaccatc tccagagaca attcccagaa aatgctgtat    240
ctgcaaatgg acagcctgag agttgaagac acggctgtgt attactgtgc gaagtgcggc    300
gcagaggact ctactactgt ctggctgaat tggttcgacc cctggggcca gggaaccctg    360
gtcaccgtct cctca                                                    375

<210> SEQ ID NO 201
<211> LENGTH: 360
<212> TYPE: DNA
<213> ORGANISM: Streptococcus pneumoniae

<400> SEQUENCE: 201
gaggtgcagc tgttggagtc tgggggaggc ttggtagagc ctgggggtc cctgagactc      60 tcctgtgcag cctctggatt caccttagc agctatgcca tgagctgggt ccgccaggct    120
ccagggaagg ggctggagtg ggtctcagct attagtgaca gtggtggtag cacatactac    180
gcagactccg tgaagggccg gttcaccatc tccagagaca agtccaagaa cacgctgtat    240
ctgcaaatga acagcctgag agccgaggac acggccgtat attactgtgc gaaaccgaat    300
tactttggtt cggggagtcc cgactactgg ggccagggaa cgctggtcac cgtctcctca    360

<210> SEQ ID NO 202
<211> LENGTH: 345
<212> TYPE: DNA
<213> ORGANISM: Streptococcus pneumoniae

<400> SEQUENCE: 202
caggtgcagc tgcaggagtc gggcccagga ctggtgaagc cttcggagac cctgtccctc      60
acctgcactg tctctggtgc ctccatcagt agtcactact ggagctggat ccggcagccc    120
ccagggaagg gactggagtg gattgggtat atctatcaca gtgggattac caactacaac    180
ccctccctca agagtcgagt caccatatca atagacacg ccaagaacca gtactccctg    240
aagctgagct ctgtgaccgc tgcggacacg gccgtgtatt actgtgcgag aggtgatggc    300
tacaatttct actggggcca gggaacgctg gtcaccgtct cctca                    345

<210> SEQ ID NO 203
<211> LENGTH: 378
<212> TYPE: DNA
<213> ORGANISM: Streptococcus pneumoniae

<400> SEQUENCE: 203
gaggtgcagc tggtggagtc tgggggaggt gtggtacggc ctgggggtc cctgagactc      60 tcctgtgcag cctctggatt caccttgat gattatggca tgacctgggt ccgccaagct    120
ccagggaagg ggctggagtg gatctctggt atttgttgca acgtggttg ctcaggttat    180 gcagactctg tgaagggccg attcaccatc tccagagaca acgccaagaa gtccctgttt    240
```

```
ctggtcatga acagtctgag agccgaggac acggccttgt attactgtgt gagagtggca    300
gtaccagctg ctacatacac ccagggaatt gatgcttttg atatttgggg ccaagggaca    360
atggtcaccg tctcttca                                                  378

<210> SEQ ID NO 204
<211> LENGTH: 357
<212> TYPE: DNA
<213> ORGANISM: Streptococcus pneumoniae

<400> SEQUENCE: 204
gaggtgcagc tggtggagtc tgggggaggc ttggtagagc ctgggggtc cctcagactc      60 tcctgtgcag tctctggttt cactttcact gacgcctgga tgacctgggt ccgccaggct    120
ccagggaagg ggctagattg ggttggccat gtaaaaagta aatatgatgg tgcgacaaca    180
gagtacgctg cacccgtgca aggcagattc accatctcaa gagatgattc aaagaagaca    240
atatatctgc aaatgaacag cctgaacacc gaggacacag gcgtctattt ttgtaccaca    300
gctcatggcc cggtgggtga ccattgggc cagggaacac tggtcaccgt ctcctca        357

<210> SEQ ID NO 205
<211> LENGTH: 378
<212> TYPE: DNA
<213> ORGANISM: Streptococcus pneumoniae

<400> SEQUENCE: 205
gaggtgcagc tggtggagtc tgggggaggc ttggtccagc cggggggtc cctgagactc      60 tcctgtgcag cctctggatt cagctttgat acctcttgga tgacctgggt ccgccaggct    120
ccagggaagg ggctggagtg ggtggccacc ataaaccagg gtggaagtga caaatactat    180
gtggactctg tgaagggccg attcaccatc tccagagaca cgccaagaa ctcactgtat     240 ctgcaaatga acagcctgcg agccgaggac acggctgtat attactgtgc gagagcgggc    300
gggtgtagct ctaccagatg ccatacaacc ccgggatttg actactgggg ccagggagcg    360
ctggtcaccg tctcctca                                                  378

<210> SEQ ID NO 206
<211> LENGTH: 353
<212> TYPE: DNA
<213> ORGANISM: Streptococcus pneumoniae

<400> SEQUENCE: 206
tgcagctgca ggagtcgggc ccaggactgg tgaagccttc ggagaccctg tccctcacct     60
gcactgtctc tggtagctcc atcagcagta gtagttacta ctggggctgg gtccgccagt    120
ccccagggaa gggactggag tggattggga gtatctatca cagtgggacc atctactaca    180
acccgtccct caggagtcga gtcaccatat ccgtagacac gtccaagaac cagttctccc    240
tgaagctgaa ctctgtgacc gccgcagaca cggctgttta ttactgtgcg agtcttagtg    300
gcacaaatgc ttttgatatc tggggccaag ggacaatggt caccgtctct tca           353

<210> SEQ ID NO 207
<211> LENGTH: 360
<212> TYPE: DNA
<213> ORGANISM: Streptococcus pneumoniae

<400> SEQUENCE: 207
gaggtgcagc tgttggagtc tggggggggc ttggtacagc ctgggggtc cctgagactc      60 tcctgtgcag cctctggatt caccttagc agccatgaca tgagttgggt ccgcctggct    120
```

```
ccagggaagg ggccggagtg ggtctcagct cttggtgctg gagatgcttg gacacactac    180
gcaaactccg tgaggggccg gttcaccatc tccagagacg attccaagaa cacgctgtat    240
ctgcaaatga acagcctgag agccgaagac acggccgtgt atttctgtgc gaaacccgt     300 ggatactcct atggctactt tgactactgg ggccaaggaa cgctggtcac cgtctcctca    360
```

<210> SEQ ID NO 208
<211> LENGTH: 351
<212> TYPE: DNA
<213> ORGANISM: Streptococcus pneumoniae

<400> SEQUENCE: 208

```
gaggtgcagc tggtggagtc tgggggaggc ttggtccagc ctggggggtc cctgagactc    60
tcctgtggag cctctggatt cacctttagt acctattgga tgacctgggt ccgccaggct   120
ccagggaagg gcctggagtg ggtggccaat ataaaccaag atggaagtga aaacaatat   180 gtggactctg tgaagggccg attcaccatc tccagagaca cgccaagaa ctcactgtat    240 ctgcagatga acagcctgag agtcgaggat acggctattt attactgtgc gagaccccca    300
gctcgccgac ttgactactg gggccaggga tcgctggtca ccgtctcctc a             351
```

<210> SEQ ID NO 209
<211> LENGTH: 348
<212> TYPE: DNA
<213> ORGANISM: Streptococcus pneumoniae

<400> SEQUENCE: 209

```
gaggtgcagc tggtggagtc cggggggaggc ttagttcagc ctggggggtc cctgagactc    60
tcctgtgcag cctctgaatt cacccttcagt gactactgga tgcactgggt ccgccaagct   120
ccagggaagg ggctggtctg ggtctcacgt attaatactg acgggagtac cacaacctac    180
gcggactccg tgaagggccg attcaccatc tccagagaca cgccaagaa cacgctgtat     240 ctacaaatga acagtctgag ggccgaggac acggctgtgt attactgtgc aagatctaat    300
gcggggcacg aagcgtgggg ccagggaacg ctggtcaccg tctcctca                 348
```

<210> SEQ ID NO 210
<211> LENGTH: 353
<212> TYPE: DNA
<213> ORGANISM: Streptococcus pneumoniae

<400> SEQUENCE: 210

```
aggtgcagct ggtgcagtct ggggctgagg tgaagaagcc tggggcctca gtgagggttt    60
cctgcaaggc atctggatac accttcacca actactggat acactgggtg cgacaggccc   120
ctggacaagg gcttgagtgg atgggaatga tcgcccctaa ggaaggttac acattctacg    180
cacagcaatt cacagggcaga gtcaccgtga ccagggacac gtcgacgagc gcggtttaca   240
tggagctgaa cagcctgaga tctgaggaca cggccgtata tttctgtgcg agagacattc    300
cccacgctaa tttggactat tggggccagg ggacgctggt caccgtctcc tca           353
```

<210> SEQ ID NO 211
<211> LENGTH: 363
<212> TYPE: DNA
<213> ORGANISM: Streptococcus pneumoniae

<400> SEQUENCE: 211

```
gaggtgcagc tgttggagtc tgggggagga ttggtacagc ctggggggtc cctgagactc    60
```

-continued

| | |
|---|---|
| tcctgtgcag cctctggatt cacctttagc gattatacca tgaattgggc ccgccaggct | 120 |
| ccagggaagg ggctggagtg ggtctcagct attagagaga gtggtgacag cacatactac | 180 |
| gcagactccg tgacgggccg gttcaccatc tccagggaca attccagaaa cacactttat | 240 |
| ctgcacatga acagcctgag agccgaggac acggccatgt attttgtgt gaaagacagg | 300 |
| gtgccgccgg gtgacgtgcc gggtgacttc tggggcccgg aacgctggt caccgtctcc | 360 |
| tca | 363 |

<210> SEQ ID NO 212
<211> LENGTH: 321
<212> TYPE: DNA
<213> ORGANISM: Streptococcus pneumoniae

<400> SEQUENCE: 212

| | |
|---|---|
| gacatccagt tgacccagtc tccatccttc ctgtctgcat ctgtaggaga cagagtcacc | 60 |
| atcacttgcc gggccagtca ggacatgacc cattctttag cctggtatca gcaaaaacca | 120 |
| gggaaagccc ctaacctcct gatctataat gcatacactt tgcaaagtgg ggtcccatca | 180 |
| aggttcagcg gcagtggatc tgggacagaa ttcactctca caatcagcag cctgcagcct | 240 |
| gaagattttg caacttatta ctgtcaacag attaatagtt accctcgaac ttttggccag | 300 |
| gggaccaagg tggagatcaa a | 321 |

<210> SEQ ID NO 213
<211> LENGTH: 321
<212> TYPE: DNA
<213> ORGANISM: Streptococcus pneumoniae

<400> SEQUENCE: 213

| | |
|---|---|
| gaaattgtgt tgacacagtc tccaggcacc ctgtctttgt ctccagggga aagagccact | 60 |
| ctctcctgca gggccagtca gaatattggc accgcttag cctggtacca acagaaacct | 120 |
| ggccaggctc ccagactcat catctatgaa acatccaaca gggccactga cgtcccagcc | 180 |
| aggttcagtg gcagtgggtc tgggacagac ttcactctca ccatcagcag cctggagcgt | 240 |
| gaagattttg ccctttatta ctgtcaacag cgtgccgact ggccgctcac tttcggcgga | 300 |
| gggaccaagg tggagatcaa a | 321 |

<210> SEQ ID NO 214
<211> LENGTH: 324
<212> TYPE: DNA
<213> ORGANISM: Streptococcus pneumoniae

<400> SEQUENCE: 214

| | |
|---|---|
| gaaattgtgt tgacacagtc tccagccacc ctgtctttgt ctccagggga aagagccacc | 60 |
| ctctcctgca gggccagtca gagtgttagc agctacttag cctggtacca acagagacct | 120 |
| ggccaggctc ccaggctcgt catctatgct gcatccaaca gggccactgg catcccagcc | 180 |
| aggttcagtg gcagtgggtc tgggacagac ttcactctca ccatcagcag cctagagcct | 240 |
| gaagattttg cagtttatta ctgtctgcag tgtagcaact ggcccatgta cacttttggc | 300 |
| caggggacca aggtggagat caaa | 324 |

<210> SEQ ID NO 215
<211> LENGTH: 321
<212> TYPE: DNA
<213> ORGANISM: Streptococcus pneumoniae

<400> SEQUENCE: 215

```
gacatccagt tgacccagtc tccatccttc ctgtctgcat ctgtagggga cagagtcacc      60
atcacttgcc gggccagtca ggacattacc gattctttag cctggtatca gcaaaaacca     120
gggaaagccc ctaacctcct gatctatact gcatccactt tgcaaagtgg ggtcccatca     180
aggttcagcg gcagtggatc tgggacagaa ttcactctca caatcagcag cctgcagcct     240
gaagatttta caacttatta ctgtcaacag attaatagtt accctcgaac ttttggccag     300
gggaccaagg tggagatcaa a                                                321

<210> SEQ ID NO 216
<211> LENGTH: 321
<212> TYPE: DNA
<213> ORGANISM: Streptococcus pneumoniae

<400> SEQUENCE: 216
gacatccaga tgacccagtc tccatcctcc ctgtctgcat ctgtaggaga cagagtcacc      60
atcacttgcc gggcaagtca gggcattaga aatgatttag gctggtatca gcagaaacca    120
gggaaagccc ctaagcgcct gatctatgct gcatccagtt tgcaaagtgg ggtcccatca    180
aggttcagcg gcagtggatc tgggacagaa ttcactctca caatcagcag cctgcagcct    240
gaagattttg caagttatta ctgtctacag catagtagtt cccgtggac gttcggccag     300 gggaccaagg tggaaatcaa a                                                321

<210> SEQ ID NO 217
<211> LENGTH: 342
<212> TYPE: DNA
<213> ORGANISM: Streptococcus pneumoniae

<400> SEQUENCE: 217
gacatcgtga tgacccagtc tccagactcc ctggctgtgt ctctgggcga gagggccgcc     60
atcaactgca gtccagcca gagtgtctta gacagctcca acatgaagag gtacttagcc    120
tggtatcagc tgaaagcagg acagcctcct aggttgctca tttacttggc ttccacccgg    180
gaatccgggg tcccggaccg attcagtggc agcgggtccg ggacagattt caatctcact    240
atcagcagcc tgcaggctga agatgtggca gtttattact gtcagcaata ttatacaacc    300
ccttcgatca ccttcggcca agggacacga ctggagatta aa                        342

<210> SEQ ID NO 218
<211> LENGTH: 342
<212> TYPE: DNA
<213> ORGANISM: Streptococcus pneumoniae

<400> SEQUENCE: 218
gacatcgtga tgacccagtc tccagactcc ctggctgtgt ctctgggcga gagggccacc     60
atcaactgca agtccagcca gagtgtttta tacagctcca acaataagaa ctacttagct    120
tggtaccagc agaaaccagg tcagcctcct aagatgctca tttactgggc atctacccgg    180
gagtccgggg tccctgaccg attcagtggc agcgggtctg ggacagattt cactctcacc    240
atcagcagcc tgcaggctga agatgtggca gtttattact gtcagcaata ttatactact    300
cctcccatca ccttcggcca agggacacga ctggagatta aa                        342

<210> SEQ ID NO 219
<211> LENGTH: 318
<212> TYPE: DNA
<213> ORGANISM: Streptococcus pneumoniae
```

<400> SEQUENCE: 219

```
gaaattgtgt tgacacagtc tccagccacc ctgtctttgt ctccagggga aagagccacc    60
ctctcctgca gggccagtca gagtgttagt atctacttag cctggtacca acagaaacct   120
ggccaggctc ccaggctcct catctatgat tcatccaaca gggccactgg catcccagcc   180
aggttcagtg gcagtgggtc tgggacagac ttcactctca ccatcagcag cctagagccc   240
gaagattttg cggtttatta ctgtcagcag cgtagcagcg ggcgaacgtt cggccaaggg   300
accaaggtgg agatcaaa                                                 318
```

<210> SEQ ID NO 220
<211> LENGTH: 324
<212> TYPE: DNA
<213> ORGANISM: Streptococcus pneumoniae

<400> SEQUENCE: 220

```
gaaattgtgt tgacgcagtc tccaggcacc ctgtctttgt ctccagggga aagagccacc    60
ctctcctgca gggccagtca gactgttacc aacaactact agcctggta ccaacacaaa   120
cctggcctgg cgcccaggct cctcatcttt gatgcatcca tcagggccac tggcatccca   180
gacaggttca gtggcagtgg gtctggggca gacttcactc tcaccatcag cagactggag   240
cctgaagatt ttacattcta ttactgtcag caatatggta tttcacctcg aacttttggc   300
caggggacca aggtggagat caaa                                          324
```

<210> SEQ ID NO 221
<211> LENGTH: 336
<212> TYPE: DNA
<213> ORGANISM: Streptococcus pneumoniae

<400> SEQUENCE: 221

```
gatattgtga tgacccagac tccactctct ctgtccgtca cccctggaca gccggcctcc    60
atctcctgca gtctagtca gagtctcctg gatagtgatg aaggaccta tttcttttgg   120
tatttgcaga agccaggcca gtctccacaa ctcctgatct atgaagtttc caaccggttc   180
tctggagtgc cagataggtt cagtggcagc gggtcaggga cagatttcac actgaaaatc   240
agccgggtgg agtctgaaga tgttggggtt tattactgca tgcaaggtac acaccatccg   300
tggacgttcg gccaagggac caaggtggaa atcaaa                             336
```

<210> SEQ ID NO 222
<211> LENGTH: 340
<212> TYPE: DNA
<213> ORGANISM: Streptococcus pneumoniae

<400> SEQUENCE: 222

```
gacatcgtga tgacccagtc tccagactcc ctggctgtgt ctctgggcga gagggccacc    60
gtcaactgca gtccagcca gagtgtttta tacagctcca acagtaagaa ctacttagct   120
tggtaccagc agaaaccagg acagcctcct aagctgctca tttactgggc atctacccgg   180
gaatccgggg tccctgaccg attcagtggc agcgggtctg ggacagattt cactctcacc   240
atcagcagcc tgcaggctga agatgtggca gtgtattact gtcagcaata ttatagtact   300
cctctcactt tcggcggagg gaccaaggtg gagatcaaac                         340
```

<210> SEQ ID NO 223
<211> LENGTH: 322
<212> TYPE: DNA

<400> SEQUENCE: 223

```
gacatccaga tgacccagtc tccatcctcc ctgtctgcat ctgtgggaga cagagtcacc        60
atcacttgcc gggcaagtca gggcattggg aatgatttag ctggtatca gcatgaacca       120
gggaaagccc ctaagcgcct gatctatgca gcatccagtt tgcaaagtgg ggtcccatcg       180
aggttcagcg gcagtgcatc tgggacagaa ttcactctca caatcaccag cctgcagcct       240
gaagattttg caacttatta ctgtctacaa catactactt tcccgtggac gttcggccaa       300
gggaccaagg tggaaatcaa ac                                                322
```

<210> SEQ ID NO 224
<211> LENGTH: 325
<212> TYPE: DNA
<213> ORGANISM: Streptococcus pneumoniae

<400> SEQUENCE: 224

```
gaaattgtgt tgacacagtc tccagccacc ctgtctttgt ctccagggga aagagccacc        60
ctctcctgca gggccagtca gagtgttggc agtcacttcg cctggtacca acagaaacct       120
ggccaggctc ccaggctcct catctatggt gcatccaaca gggcccctgg catcccacct       180
aggttcagtg ccagtggatc tgggacagac ttcactctca ccatcagcag cctagagcct       240
gaagattttg caatttatta ctgtcaacag cgtaggacct ggcctccgct aaccttcggc       300
caagggacac gactggagat taaac                                             325
```

<210> SEQ ID NO 225
<211> LENGTH: 357
<212> TYPE: DNA
<213> ORGANISM: Streptococcus pneumoniae

<400> SEQUENCE: 225

```
gaggtgcagc tggtggagtc tgggggaggc ttggtacagc ctggagggtc cctgagactc        60
tcctgtgtag cctctggatt cagtttcagt ggtcatgaaa tgaactgggt ccgccagcct       120
ccagggaagg ggctggagtg ggtttcacac attggcagtg gtggtgatta tataggttac       180
gcagactctg tgaagggccg attcaccgtc tctagagaca cgccaagaa tttactctat       240
ctgcaaatga acagcctgag agccgacgac acggctgttt attactgtgc gaccttgctt       300
ttgcgagaca accaactgga cgtctggggc caagggacca cggtcaccgt ctcctca          357
```

<210> SEQ ID NO 226
<211> LENGTH: 363
<212> TYPE: DNA
<213> ORGANISM: Streptococcus pneumoniae

<400> SEQUENCE: 226

```
caggtgcagc tggtggagtc tgggggaggc gtggtccagc cagggaggtc cctaagactc        60
tcctgtgcag cctctggatt caccctcagt agttgtggca tgcactggat ccgccaggct       120
ccaggcaagg ggctggagtg ggtggcagtt ataacatatg atggacgaag tcacttcaac       180
gcagacgccg tgaagggccg attcaccatc tccagagaca gatccatgaa cacggtgtct       240
ctgcaaatgg acagcctgag acccgaggac acggctgttt attactgtgt caagaacaa       300
ggctttggtt actaccggac cgccgactac tggggccagg gaaccctggt caccgtctcc       360
tca                                                                    363
```

<210> SEQ ID NO 227

```
<211> LENGTH: 342
<212> TYPE: DNA
<213> ORGANISM: Streptococcus pneumoniae

<400> SEQUENCE: 227
caggtgcagc tgcaggagtc gggcccagga ctggtgaggc cttcggagac cctgtccctc      60
acctgcactg tctctggtgg ctccatcagt agtgaccact ggagttggat ccggcagccc     120 ccagggcaagg gactggagtg gattgggaat gtctattaca gtgggcgcac ctactacaac    180
ccctccttca agagtcgagt caccatatca gtagccacgt ccaagaacca gttctccctg     240
aaggtgacct ctgtgaccgc cgcagacacg gccatttatt actgtgcgag gcgaaatgat     300
tttaatatct ggggccaggg gacaatggtc accgtctctt ca                        342

<210> SEQ ID NO 228
<211> LENGTH: 369
<212> TYPE: DNA
<213> ORGANISM: Streptococcus pneumoniae

<400> SEQUENCE: 228
gaggtgcagc tgttggagtc tgggggaggc ttggtacagc ctgggggtc cctgagactc       60 tcctgtgcag cctctggatt cacctttagt aaatatgccg tgagctgggt ccgccaggct     120
ccagggaagg ggctggagtg ggtctcagct gtcagtggta atggtgactc cacatactac     180
gcagaccccg tgaggggccg gttcaccatc tccagagaca attccaagaa cacccctgtat     240 ctgcaaatga acagcctgag agccgaggac acggccctat attactgttc gatctggtgg     300
gggacttcag tacagtaccc attggtgctc gactactggg gcctgggaac cctggtcacc    360
gtctcctca                                                              369

<210> SEQ ID NO 229
<211> LENGTH: 363
<212> TYPE: DNA
<213> ORGANISM: Streptococcus pneumoniae

<400> SEQUENCE: 229
caggtgcagc tggtggagtc ggggggaggc gtggtccagc ctgggaggtc cctaagactc       60
ctgtgtgcag cctctggatt caccctcagt acttgtggca tgcactggat ccgccagact     120
cctggcaagg ggctggagtg ggtggcagtt aaaacatatg acggaagaga ggagttctac    180
gcagactccg tgaagggccg attcaccatt tccagagacg agtccatgaa cacgctgtct     240
ttgcagatga acagcctgag acctgaagac acggctgtat attactgtgt caaagaacaa    300
gactacggtt actaccggac cgccgaccac tggggccagg gaaccctggt caccgtctcc    360
tca                                                                    363

<210> SEQ ID NO 230
<211> LENGTH: 351
<212> TYPE: DNA
<213> ORGANISM: Streptococcus pneumoniae

<400> SEQUENCE: 230
caggtgcagc tgcaggaggc gggcccagga ctggtgaagc cttcacagac cctgtccctc       60
acctgcactg tctctggtgg ctccatcagc agtggtggtt actactggag ctggatccgc     120
cagcacccag ggaagggcct ggagtggatt gggtacatct attacagtgg gagcacctac    180
tacaacccgt ccctcaagag tcgagtcacc atatcagtag acacgtccaa gaaccagtat    240
tccctgaagc tgagttctgt gaccgccgca gacacggccg tatattactg tgcgagaggg    300
```

```
catggcttca acgcctactg gggccaggga accctggtca ccgtctcctc a        351
```

<210> SEQ ID NO 231
<211> LENGTH: 366
<212> TYPE: DNA
<213> ORGANISM: Streptococcus pneumoniae

<400> SEQUENCE: 231

```
gaggtgcagc tggtggagtc cgggggaggc ttggtaaagc cgggggagtc ccttagactc    60
tcgtgtgcaa cctctggagt caacttcaac atcgcctgga tgacctgggt ccgccaggct   120
ccagggaagg gactgagtg gttggccgt attaaaagca aaattggtgg tgggacaaca    180
gactatgctg cacccgtgaa aggcagattc accatgtcaa tagatgattc aaaaaatacc   240
ctatatctgc aaatgaacag cctgaaaacc gaggacacag ccgtgtatta ttgtaccaca   300
gtccgcaata tggccgactt gtcccttaat cactggggcc agggaaccct ggtcaccgtc   360
tcctca                                                             366
```

<210> SEQ ID NO 232
<211> LENGTH: 354
<212> TYPE: DNA
<213> ORGANISM: Streptococcus pneumoniae

<400> SEQUENCE: 232

```
gaggtgcagc tggtggagtc tgggggaggc ttggtacagc ctggagcgtc cctgacactg    60
tcatgtgtag tctctggatt caccttcatt ggcactgaaa tgacctggat tcgccaggct   120
ccagggaagg ggctggaggg actttcgtac atcagtggga gtgcgggac aacatactac    180
gcagagtctg tgaggggccg attcaccatc tccagagaca acgccaagaa gtcactgttt   240
ctgcaaatga ccagcctgac agccgaggac acggctgttt actactgtgc gacaggcaac   300
cggggatcac ttcctcgccg ctggggccag ggaaccctgg tcaccgtctc ctca         354
```

<210> SEQ ID NO 233
<211> LENGTH: 354
<212> TYPE: DNA
<213> ORGANISM: Streptococcus pneumoniae

<400> SEQUENCE: 233

```
gaggtgcagc tggtggagtt tgggggaggc ttggtccagc ctgggggtc cctgagactc     60
tcctgtgtag cctctggatt cacctttagt tcctcttgga tgagttgggt ccgccaggct   120
ccagggaagg ggctggagtg cgtgggcaac ataaagccgg atgcaagttt ggtgtcctat   180
gtggactctg tgaagggccg agtcaccatc tccagagaca acgccaagaa ttcactgttt   240
ctggatatga gcagcctgag agtcgaggac acggccgtct actactgtgt gagagacggg   300
tgggacaccct tctttgactc ctggggccag ggaaccctgg tcaccgtctc ctca        354
```

<210> SEQ ID NO 234
<211> LENGTH: 339
<212> TYPE: DNA
<213> ORGANISM: Streptococcus pneumoniae

<400> SEQUENCE: 234

```
gaggtgcagc tggtggagtc cggggggaggc ttagttcagc cggggggtc cctgagactc    60
tcctgtgcag cctctggatt cacctttagt aactactgga tgaggtgggt ccgccaatct  120
ccagggaagg ggctggtgtg gtctcacat attaaccctg atgggagttt tacaaactac   180
```

```
gcggactccg tgaagggccg attcaccatc tccagagaca acaccaagaa cacactgtat    240
ctgcaaatga acagtctgag agccgaggac acggctgtgt attactgtgt gaattttcaa    300
ctggggtggg gccagggaac cctggtcacc gtctcctca                           339

<210> SEQ ID NO 235
<211> LENGTH: 369
<212> TYPE: DNA
<213> ORGANISM: Streptococcus pneumoniae

<400> SEQUENCE: 235
caggtgcagc tggtggagtc tgggggaggc gtagtccagc ctgggaggtc cctgaaactc    60
tcctgtgcag tcgctggatt caccttcagg acctatgcta tgcactgggt ccgccaggct    120
ccaggcaggg ggctggagtg ggtggcactt atatcaaatg atggaaccaa aaaatactcc    180
gcagactccg tgaggggcca cttcaccatc tccagagaca attccaagga cacgctgtat    240
ctgcaaatga acagcctgcg acctgacgac acggctgtct attactgtgc gagagcggag    300
tattgtagtc ctggtgactg cttccttatt gacacctggg gccagggaac cctggtcacc    360
gtctcctca                                                            369

<210> SEQ ID NO 236
<211> LENGTH: 357
<212> TYPE: DNA
<213> ORGANISM: Streptococcus pneumoniae

<400> SEQUENCE: 236
caggtgcagc tggtggagtc tgggggaggc gtggtccagc ctgggaggtc cctgagactc    60
tcctgtgcag tgtctggatt caccttcagt agatacggca tgcactgggt ccgccaggct    120
ccaggcaagg ggctggagtg ggtggtagtt atatggcatg atggaagtaa tacatactat    180
gcagactccg tgaagggccg attcaccatc tccagagacg actccaagaa cacggtgtat    240
ctgcaaatga acagcctcag agtcgaggac acggctatgt attactgtct gagaggcaac    300
ccacctagca gccccaccga ctactggggc cagggaaccc tggtcaccgt ctcctca      357

<210> SEQ ID NO 237
<211> LENGTH: 357
<212> TYPE: DNA
<213> ORGANISM: Streptococcus pneumoniae

<400> SEQUENCE: 237
gaggtgcagc tgttggagtc tgggggaggc ttggtacagc ctggggggtc cctgagactc    60
tcctgtgaag tctctggatt catctttagc aactatgcca tgacctgggt ccgccaggct    120
ccagggaagg ggctgcagtg ggtctcagct attggcacta gtggtggtga cacacactac    180
gcagactccg tgaagggccg gttcaccatc tccagacaca attcccagaa caccctgtat    240
ctgcagatga acagcctgag agccgaggac acggccatat attactgtgc gaaagtcgtt    300
tatagcaggc ctcctatgga cgtctggggc caagggacca cggtcaccgt ctcctca      357

<210> SEQ ID NO 238
<211> LENGTH: 354
<212> TYPE: DNA
<213> ORGANISM: Streptococcus pneumoniae

<400> SEQUENCE: 238
gaggtgcagc tggtggagtc tgggggaggc ttggtccagc ctgggggtc cctgagactc     60 tcctgtgcag cctctggatt cacctttagt aatcgttgga tgagttgggt ccgccaggct    120
```

```
ccagggaagg ggctggaatg ggtggccaac ataaacgaag atggaagtca gaaacactat    180
gtggactctg tgaggggccg attcaccatc tccagagaca cgccaagaa ctcactgtct     240 ctgcaaatgg acagcctgag agtcgaggat acggccgtgt attattgcgc gagagcatcg   300
agggagaccg gtgaaccta ctggggccag ggaaccctgg tcaccgtctc ctca           354
```

<210> SEQ ID NO 239
<211> LENGTH: 329
<212> TYPE: DNA
<213> ORGANISM: Streptococcus pneumoniae

<400> SEQUENCE: 239

```
ttgtgatgac tcagtctcca ctctccctgc ccgtcaccct tggacagtcg gcctccatct    60
cctgcaggtc tagtcgaagc ctcgtattca gtgatggaaa cacctacttg aattggtttc   120
agcagaggcc aggccgatct ccaaggcgcc taatttataa ggtttctaag cgggactctg   180
gggtcccaga cagattcagc ggcagtggg cagacactga tttcacactg aaaatcagca   240
gggtggaggc tgaggatgtt ggggtttatt actgcatgca aggtacacac tggcggacgt   300
tcggccaagg gaccaaggtg gagatcaaa                                      329
```

<210> SEQ ID NO 240
<211> LENGTH: 321
<212> TYPE: DNA
<213> ORGANISM: Streptococcus pneumoniae

<400> SEQUENCE: 240

```
gacatccaga tgacccagtc tccttccaca ctgtctgcat ctgtgggaga cagagtcacc    60
atcacttgcc gggccagtca gagtattaat tcctggttgg cctggtatca gcggaaacca   120
gggaaaaccc ctaaactcct catctatgag gcgtccagtt tagaaagtgg ggtcccatca   180
aggttcagcg gcagtagatc tgggacagag ttcaccctca ccatcagcag cctgcaggct   240
gatgattttg caacttatta ctgccaccag tatgataaat atccgtggac gttcggccaa   300
gggaccaagg tggagatcaa a                                              321
```

<210> SEQ ID NO 241
<211> LENGTH: 324
<212> TYPE: DNA
<213> ORGANISM: Streptococcus pneumoniae

<400> SEQUENCE: 241

```
gaaattgtgt tgacgcagtc tccaggcacc ctgtctttgt ctccagggga aagagccacc    60
ctctcctgca gggccagtca gagtgtgacc aacaactatt tggtctggca ccagcagaaa   120
cctggccagc tcccaggct cctcatttct gatgcatcca acagggccac tggcatccca   180
gacaggttca gtggcagtgg gtctgggaca gacttcactc tcaccatcaa cagactggag   240
cctgaagatt tcgcagtgta ttactgtcag caatacggta gctcaccttt cactttcggc   300
cctgggacca aagtggatat caaa                                           324
```

<210> SEQ ID NO 242
<211> LENGTH: 324
<212> TYPE: DNA
<213> ORGANISM: Streptococcus pneumoniae

<400> SEQUENCE: 242

```
gaaatagtga tgacgcagtc tccagccacc ctgtctgtgt ctccagggga aagagtcacc    60
```

```
ctctcctgca gggccagtca gagtattggc agcagcttag cctggtacct gcagaaacct    120
ggccaggctc ccagagtcct catctatggt gcatccacca ggaccctgg caccccagcc    180 aggttcagtg gcagtgggtc tgggacagag ttcactctca ccatcagcag cctgcagtct    240
gaagatcttg cgatttatta ttgtcaacag tatagtaagt ggcctccgat caccttcggc    300
caagggacac gactggagat taaa                                          324
```

<210> SEQ ID NO 243
<211> LENGTH: 321
<212> TYPE: DNA
<213> ORGANISM: Streptococcus pneumoniae

<400> SEQUENCE: 243

```
gacatccaga tgacccagtc tccctccatc ctgtctgcat ctgtaggaga cagagtcacc     60
atcaattgcc gggccagtca gagtattaat gcctggttgg cctggtatca gcagaaacca    120
gggaaagccc ctaaattcct aatttataag gcgtctagtt tagaaagtgg ggtctcgtca    180
aggttcagcg gcagtggatc tgggacagaa ttcaccctca tcatcagcag cctgcagcct    240
gatgattttg caacttatta ctgccaacag tatgataaat accgtggac gttcggccgg    300 gggaccaagg tggagatcaa a                                             321
```

<210> SEQ ID NO 244
<211> LENGTH: 324
<212> TYPE: DNA
<213> ORGANISM: Streptococcus pneumoniae

<400> SEQUENCE: 244

```
gaaattgtgt tgacgcagtc tccaggcacc ctgtctttct ctccagggga tagagccacc     60
ctctcctgca gggccagtca gagtgttagc agcagctcct agcctggta ccagcagaga    120 cctggccagg ctcccagcct cctcatctat ggtgcatcca gcagggccac tggcatccca    180
gacaggttca gtggcagtgg gtctgggaca gacttcactc tcaccatcag cagactggag    240
cctgaagatt ttgcagtgta ttactgtcag cagtatggta actcacctcg gacgttcggc    300
caagggacca ggtggagat caaa                                           324
```

<210> SEQ ID NO 245
<211> LENGTH: 324
<212> TYPE: DNA
<213> ORGANISM: Streptococcus pneumoniae

<400> SEQUENCE: 245

```
gaaattgtgt tgacgcagtc tccaggcacc ctgtctttgt ctccagggga aagagccacc     60
ctctcctgca gggccagtca gagtgtcagc agcacctact aaactggta ccagcagaag    120 cctggccagg ctcccaggct cctcatctat ggtgcgtcca ccagggccac tggcatccca    180
dacaggttca gtggcagtgg gtctgggca gacttcactc taaccatcag cagactggag    240
cctgaagact ttgcagtgta ctactgtcag caatatgatg actcacggtg gacgttcggc    300
caagggacca ggtggaaat caaa                                           324
```

<210> SEQ ID NO 246
<211> LENGTH: 336
<212> TYPE: DNA
<213> ORGANISM: Streptococcus pneumoniae

<400> SEQUENCE: 246

```
gatattgtga tgactcagtc tccactctcc ctgcccgtca cccctggaga gccggcctcc     60
```

```
atctcctgca ggtctggtca gagcctcctg tatagtgatg aaacaacta tttggattgg      120 tatctgcaga agccagggca gtctccacag ctcctgatct atttgggttc taatcgggcc     180
tccggggtcc ctgacaggtt cagtggcagt gaatcaggca cagattttac actgaaaatc    240
agcagagtgg aggctgggga tgttgggatt tattactgca tgcaagctct acgaagtccg    300 tacactttg gccaggggac caaggtggag atcaaa                               336
```

```
<210> SEQ ID NO 247
<211> LENGTH: 332
<212> TYPE: DNA
<213> ORGANISM: Streptococcus pneumoniae

<400> SEQUENCE: 247
ttgtgatgac tcagtctcca ctctccctgc ccgtcaccct ggacagccg gcctccatct       60 cctgcaggtc tagtcaaagc cccgtataca gtgatggaaa cacctacctg aattggtttc    120
agcagaggcc aggccaatct ccaaggcgcc taatttataa ggtttctaac cgggactccg    180 ggtcccaga cagattcagc ggcagtgggt caggcactga tttcacactg aatatcagcg     240
gggtggaggc tgaggacgtt ggggtttatt actgcatgca aggtagatac tggccgtaca    300
cttttggcca ggggaccaag gtggagatca aa                                  332
```

```
<210> SEQ ID NO 248
<211> LENGTH: 324
<212> TYPE: DNA
<213> ORGANISM: Streptococcus pneumoniae

<400> SEQUENCE: 248
gaaattgtgt tgacgcagtc tccaggcacc ctgtctttct ctccagggga tagagccacc     60
ctctcctgca gggccagtca gagtgtaagc agcagcgcct tagcctggta ccagcagaaa    120
cctggccagg ctcccagcct cctcatctat ggtgcatcca gcaggccac tggcatccca     180 gacaggttca gtggcagtgg gtctgggaca gacttcactc tcaccatcag cagactggag    240
cctgaagatt ttgcagtgta ttactgtcag cagtatggta actcacctcg gacgttcggc    300
caagggacca aggtggaaat caaa                                           324
```

```
<210> SEQ ID NO 249
<211> LENGTH: 330
<212> TYPE: DNA
<213> ORGANISM: Streptococcus pneumoniae

<400> SEQUENCE: 249
ttgtgatgac tcagtctcca ctctccctgc ccgtcaccct ggacagtcg gcctccatct       60 cctgcaggtc tagtcgaagc ctcgtattca gtgatggaaa cacctacttg aattggtttc    120
agcagaggcc aggccgatct ccaaggcgcc taatttataa ggtttctaag cgggactctg    180 ggtcccaga cagattcagc ggcagtgggt cagacactga tttcacactg aaaatcagca    240
gggtggaggc tgaggatgtt ggggtttatt actgcatgca aggtacacac tggcggacgt    300
tcggccaagg gaccaaggtg aaatcaaac                                      330
```

```
<210> SEQ ID NO 250
<211> LENGTH: 321
<212> TYPE: DNA
<213> ORGANISM: Streptococcus pneumoniae

<400> SEQUENCE: 250
```

```
gacatccaga tgacccagtc tccttcctca ctgtctgcat ctgtagggga cagaatcacc      60
atcacttgtc gggcgagtca ggcattaac  aattatttag cctggtttca gcagaagcca    120
gggaaagccc ctaagaccct gatctactct acatccactt tgcaaagtgg ggtcccatca    180
aagttcagcg gcagtggatc tgggacagtt ttcactctca ccatcagcaa cctgcagcct    240
gaagattttg caacttatta ctgtcaacaa tataatagtt acccgctcac tttcggcgga    300
gggaccaagg tggagatcaa a                                              321

<210> SEQ ID NO 251
<211> LENGTH: 321
<212> TYPE: DNA
<213> ORGANISM: Streptococcus pneumoniae

<400> SEQUENCE: 251
gacatccaga tgacccagtc tccatcctcc ctgtctgcat ctgtaggaga cagagtcacc      60
atcacttgcc gggcaagtca gaccattagc aactatttaa attggtttca gcagaaacca    120
gggaaagccc ctaggctcct gatctatgct gcatcgagtt tgcaaagtgg ggtcccatca    180
aggttcagtg gcagtggatc tgtgacagat ttcactctca ccatcagcag tctgcaacct    240
gaagattttg caacttactt ctgtcaacag agttacagca ccccgtggac gttcggccaa    300
gggaccaagg tggaaatcaa a                                              321

<210> SEQ ID NO 252
<211> LENGTH: 332
<212> TYPE: DNA
<213> ORGANISM: Streptococcus pneumoniae

<400> SEQUENCE: 252
ttgtgatgac tcagtctcca ttctccctgc ccgtcaccct tggacagccg gcctccatct      60
cctgcaggtc tagtcaaagc ctcgtataca gtgatggaaa cacctacttg aattggtttc    120
agcagaggcc aggccaatct ccaaggcgcc tgatttataa gctttctaac cgggactctg    180
gggtcccaga cagattcagc ggcagtgggt caggcactga tttcacactg aaaatcagca    240
gggtggaggc tgaggatgtt ggggtttatt actgcatgca agctacacac tggccttgga    300
cgttcggcca agggaccaag gtggaaatca aa                                  332
```